United States Patent
Choi

(10) Patent No.: US 11,896,593 B2
(45) Date of Patent: Feb. 13, 2024

(54) SULFAMATE DERIVATIVE COMPOUNDS FOR USE IN TREATING OR ALLEVIATING A PSYCHIATRIC DISORDER

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/980,822

(22) PCT Filed: Sep. 10, 2020

(86) PCT No.: PCT/KR2020/012237
§ 371 (c)(1),
(2) Date: Sep. 14, 2020

(87) PCT Pub. No.: WO2022/054987
PCT Pub. Date: Mar. 17, 2022

(65) Prior Publication Data
US 2022/0218702 A1    Jul. 14, 2022

(51) Int. Cl.
| | | |
|---|---|---|
| A61K 31/506 | (2006.01) | |
| A61K 31/357 | (2006.01) | |
| A61K 31/381 | (2006.01) | |
| A61K 31/427 | (2006.01) | |
| A61K 31/445 | (2006.01) | |
| A61P 25/24 | (2006.01) | |
| A61K 31/443 | (2006.01) | |

(52) U.S. Cl.
CPC .......... *A61K 31/506* (2013.01); *A61K 31/357* (2013.01); *A61K 31/381* (2013.01); *A61K 31/427* (2013.01); *A61K 31/443* (2013.01); *A61P 25/24* (2018.01)

(58) Field of Classification Search
CPC .. A61K 31/506; A61K 31/357; A61K 31/381; A61K 31/427; A61K 31/443
USPC ........................................................ 514/256
See application file for complete search history.

(56) References Cited

U.S. PATENT DOCUMENTS

| | | | |
|---|---|---|---|
| 6,762,205 B1 | 7/2004 | Koizumi et al. | |
| 9,221,783 B2 * | 12/2015 | Choi | A61P 21/02 |
| 9,834,545 B2 * | 12/2017 | Chen | A61K 31/341 |
| 9,937,145 B2 * | 4/2018 | Choi | A61K 31/505 |
| 9,956,197 B2 | 5/2018 | Choi | |
| 2003/0078213 A1 | 4/2003 | Ehrenberg et al. | |
| 2009/0247616 A1 | 10/2009 | Smith-Swintowsky | |
| 2016/0310461 A1 | 10/2016 | Choi | |
| 2018/0230090 A1 | 8/2018 | Choi | |
| 2022/0062220 A1 | 3/2022 | Choi | |

FOREIGN PATENT DOCUMENTS

| | | |
|---|---|---|
| WO | WO 2001/002349 | 1/2001 |
| WO | WO 2002/067925 | 9/2002 |
| WO | WO 2006/044472 | 4/2006 |
| WO | WO 2010/011548 | 1/2010 |
| WO | WO 2014/097137 | 6/2014 |
| WO | WO 2014/142547 | 9/2014 |
| WO | WO 2016/190638 | 12/2016 |
| WO | WO 2022/045824 | 3/2022 |

OTHER PUBLICATIONS

Bourin et al., "The mouse light/dark box test," Eur J Pharm (2003) 463:55-65.
Bourwknecht et al., "Behavioral and physiological mouse assays for anxiety: a survey in nine mouse strains," Behavioural Brian Research (2002) 136:489-501.
Brummelte et al., "Chronic corticosterone during pregnancy and postpartum affects maternal care, cell proliferation and depressive-like behavior in the dam," Hormones and Behavior (2010) 58:769-779.
Porsolt et al., "Depression: a new animal model sensitive to anti-depressant treatements," Nature (1997) 266(5604):730-732.
Prut et al., "The open field as a paradigm to measure the effects of drugs on anxiety-like behaviors: a review," Eur J Pharm (2003) 463:3-33.

* cited by examiner

*Primary Examiner* — Yevgeny Valenrod
(74) *Attorney, Agent, or Firm* — MORRISON & FOERSTER LLP

(57) ABSTRACT

The present invention relates to a pharmaceutical composition for treating and/or alleviating a psychiatric disorder comprising a sulfamate derivative compound and/or a pharmaceutically acceptable salt thereof as an active ingredient. Furthermore, the present invention relates to a pharmaceutical composition for inducing anti-stress, anti-anxiety and/or anti-depressant activities comprising a sulfamate derivative compound and/or a pharmaceutically acceptable salt thereof as an active ingredient.

13 Claims, No Drawings

SULFAMATE DERIVATIVE COMPOUNDS FOR USE IN TREATING OR ALLEVIATING A PSYCHIATRIC DISORDER

CROSS REFERENCE TO RELATED APPLICATIONS

This application is a national stage application under 35 U.S.C. § 371 of International Application No. PCT/KR2020/012237, filed internationally on Sep. 10, 2020.

TECHNICAL FIELD

The present invention relates to a pharmaceutical composition for treating and/or alleviating a psychiatric disorder comprising a sulfamate derivative compound and/or a pharmaceutically acceptable salt thereof as an active ingredient. Furthermore, the present invention relates to a pharmaceutical composition for inducing anti-stress, anti-anxiety and/or anti-depressant activities comprising a sulfamate derivative compound and/or a pharmaceutically acceptable salt thereof as an active ingredient.

BACKGROUND ART

Psychiatry is the medical specialty devoted to the study, diagnosis, treatment, and prevention of mental disorders. These include various affective, behavioural, cognitive and perceptual abnormalities. A number of psychiatric syndromes feature depressed mood as a main symptom. Depression is a state of low mood and aversion to activity that can affect a person's thoughts, behavior, feelings and sense of well-being. Depressed people may feel sad, anxious, empty, hopeless, worried, helpless, worthless, guilty, irritable, hurt, or restless. The mood disorders are a group of disorders considered to be primary disturbances of mood. These include major depressive disorder (MDD; commonly called major depression or clinical depression) where a person has at least two weeks of depressed mood or a loss of interest or pleasure in nearly all activities; and dysthymia, a state of chronic depressed mood, the symptoms of which do not meet the severity of a major depressive episode.

Another mood disorder, bipolar disorder, features one or more episodes of abnormally elevated mood, cognition and energy levels, but may also involve one or more depressive episodes. When the course of depressive episodes follows a seasonal pattern, the disorder (major depressive disorder, bipolar disorder, etc.) may be described as a seasonal affective disorder. Outside the mood disorders: borderline personality disorder commonly features depressed mood; adjustment disorder with depressed mood is a mood disturbance appearing as a psychological response to an identifiable event or stressor, in which the resulting emotional or behavioral symptoms are significant but do not meet the criteria for a major depressive episode and post-traumatic stress disorder, an anxiety disorder that sometimes follows trauma, is commonly accompanied by depressed mood. Bipolar disorder has been known for decades as a chronic mental disorder, with high relapse rates, most of times incapacitating, supposedly having a neurobiological substrate.

Anxiety is a broad range of very unpleasant or vaguely anxious feelings, as well as including physical symptoms related thereto, and it is the most basic reaction pattern that is shown when a body tries to adapt to an unfamiliar environment. The reaction pattern includes physical symptoms, behavioral symptoms and the like. While stimulating the autonomic nervous system, anxiety is a normal psychological response corresponding to one type of the defense system for protecting the human body. However, when a person feels anxiety too frequently, he or she becomes tired, and when frequent anxiety due to stress, overwork and the like is repeated, the sympathetic nerves become overactivated, causing disruption in life or developing into anxiety disorder. The anxiety disorder includes post-traumatic depression, stress disorder, obsessive-compulsive disorder, social phobia, generalized anxiety disorder and the like, and anxiety may be involved in other psychiatric diseases such as depression and drug abuse. In particular, since social phobia and generalized anxiety disorder are not well-known but cause pain in many people, these are accepted as one type of psychiatric disorders. In case of patients having anxiety disorder, depression is commonly accompanied, and the patients frequently drink alcohol in order to reduce anxiety, thereby causing addiction disorder such as alcohol dependence.

Representative anti-anxiety agents that are currently used include benzodiazepine drugs such as diazepam, oxazepan, prazepam, lorazepam, alprazolam, helazepam, clonazepam and the like, but these drugs are mainly used for sedation and sleep induction.

However, problems such as side effects have been pointed out for most anti-anxiety agents. In particular, problems regarding various side effects have been raised for benzodiazepine drugs which are most commonly prescribed in Korea due to an advantage that their effects appear quickly. Since benzodiazepin drugs are highly habitual and addictive, symptoms recur or withdrawal symptoms appear when drug administration is stopped, and it has been reported to have problems of side effects such as drowsiness, ataxia, orthostatic hypotension, respiratory depression, headache, chronic sleep disorder, liver disease and the like.

Among anxieties, depressive disorder refers to a condition in which the inner emotional status of a person is abnormally depressed and reduced. The depressive disorder, that is, depression has decreased motivation and depressive feelings as main symptoms and is defined as a disease that brings about a decrease in daily functions by causing various cognitive, psychological, and psychical symptoms.

In addition, about 80% of depression patients report sleep disorder, and particularly, it has been reported to exhibit symptoms in which the patients cannot sleep enough until the morning and wake up early or frequently wake up during the night. In addition, many patients show decreased appetite and weight loss, but some patients show an atypical pattern of increased appetite and prolonged sleep. In addition, it is known that about 90% of depression patents show symptoms associated with anxiety. Other than the above, symptoms of a decline in cognitive functions such as decreased libido or decreased concentration also appear.

With regard to depression treatment, while various treatment methods have been proposed such as psychotherapeutic approaches, electroconvulsion therapy, phototherapy or the like, the situation is that it is still mainly dependent on drug therapy. However, various antidepressants that are proposed according to the neurotransmitter system generally take a few days to several weeks for their efficacy to be exerted, and it is necessary to take at least 4 to 6 weeks to confirm the effect of the drug, and various side effects have been reported.

Meanwhile, mental stress is not only a cause of psychiatric disorder such as anxiety and depression, but also it is considered to be a trigger for various diseases such as tension headache, migraine, pain, various neuroses, high blood pressure, diabetes, indigestion, gastrointestinal ulcer, decreases in physiological activity and immune activity of the body, weakened resistance of the body, emotional anxiety, menopausal disorder, decreased sexual function and the like. In particular, it is considered to be a representative cause of factors that cause disorders such as anxiety and depression by acting on the central nervous system, endocrine system and various metabolic systems in the body.

In the research of stress, several methods have been proposed as methods of inducing acute stress, and among these methods, the forced swimming stress method has been proposed with regard to methods using experimental animals. The forced swimming stress method is a form that can give both physical and mental stress at once, and it has been reported that the secretion of adrenocorticotropic hormone is increased by the stress, the level of corticosterone in the blood is increased, and it acts on the autonomic nervous system such that the level of catecholamine is increased, thereby activating the sympathetic nervous system. Therefore, the stress relief effect, as well as the effects of treating, alleviating or preventing anxiety or depression, can be confirmed through an enhancement effect by the forced swimming stress method.

While WO 2001/02349 discloses phenylsulfamate derivatives that are effective in preventing or treating diseases involving steroids such as estrogen, etc., for example, breast cancer, uterine cancer, endometrial hyperplasia, infertility, endometriosis, adenomysis and the like, the structure and use of the sulfamate derivative compounds of the present invention are different therefrom.

DISCLOSURE OF INVENTION

Technical Problem

Under such circumstances, the present inventors completed the present invention by confirming that sulfamate derivatives exhibited excellent anti-stress, anti-anxiety or anti-depressant activity through the forced swim test.

Accordingly, it is an object of the present invention to provide a pharmaceutical composition for preventing and/or treating a psychiatric disorder using a sulfamate derivative, and a method for preventing and/or treating a psychiatric disorder.

It is another object of the present invention to provide a pharmaceutical composition having anti-stress, anti-anxiety and/or anti-depressant activities using a sulfamate derivative, and a method for inducing anti-stress, anti-anxiety and/or anti-depressant activities.

Solution to Problem

In order to solve the above problems, the present invention provides a pharmaceutical composition for preventing or treating a psychiatric disorder, comprising a compound of Chemical Formula I below or a pharmaceutically acceptable salt thereof as an active ingredient:

[Chemical Formula I]

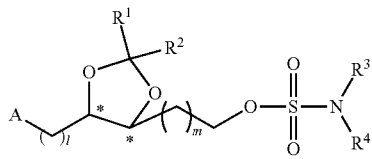

wherein $R^1$ and $R^2$ are each independently selected from the group consisting of hydrogen. $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is an aryl moiety or a heterocyclic moiety optionally substituted by one or more substituents selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; $R^3$ and $R^4$ are each independently hydrogen or $C_1$-$C_3$ alkyl; and l and m are each independently an integer of 0~4.

The present invention also provides a method for preventing or treating a psychiatric disorder, including administering the above-mentioned pharmaceutical composition to a subject in need thereof at a pharmaceutically effective amount.

Furthermore, the present invention provides a use of the above-mentioned pharmaceutical composition in the manufacture of a medicament for preventing or treating a psychiatric disorder.

In another aspect, the present invention provides a pharmaceutical composition having anti-stress, anti-anxiety or anti-depressant activites, including a compound of Chemical Formula I below or a pharmaceutically acceptable salt thereof as an active ingredient.

[Chemical Formula I]

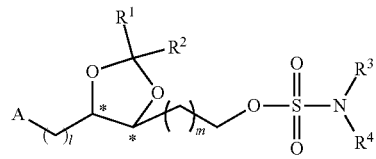

wherein $R^1$ and $R^2$ are each independently selected from the group consisting of hydrogen. $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is an aryl moiety or a heterocyclic moiety optionally substituted by one or more substituents selected from the group consisting of hydrogen, hydroxyl, $C_1$-$C_5$ alkoxy, $C_1$-$C_5$alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$alkylthio, cyano, nitro, amine. $C_1$-$C_5$ alkylamine and halogen; $R^3$ and $R^4$ are each independently hydrogen or $C_1$-$C_5$ alkyl; and l and m are each independently an integer of 0~4.

The present invention also provides a method for inducing anti-stress, anti-anxiety or anti-depressant activity, including administering the above-mentioned pharmaceutical composition to a subject in need thereof at a pharmaceutically effective amount.

Furthermore, the present invention provides a use of the above-mentioned pharmaceutical composition in the manufacture of a medicament for inducing anti-stress, anti-anxiety or anti-depressant activity.

Advantageous Effects of Invention

Since the sulfamate derivative of Chemical Formula I of the present invention exhibits excellent anti-stress, anti-anxiety or anti-depressant activity, it is effective for treating various psychiatric disorders due to stress, anxiety or depression.

BEST MODE FOR CARRYING OUT THE INVENTION

Hereinafter, the present invention will be described in more detail.

All technical terms used in the present invention, unless otherwise defined, are used in the same sense as those of ordinary skill in the art generally understand in the related field of the present invention. In addition, although preferred methods or samples are described in the present specification, those similar or equivalent are included in the scope of the present invention.

A first aspect of the present invention is a pharmaceutical composition for preventing or treating a psychiatric disorder, including a compound of Chemical Formula I below or a pharmaceutically acceptable salt thereof as an active ingredient, and a method for preventing or treating a psychiatric disorder including administering the same to a subject in need thereof at a pharmaceutically effective amount:

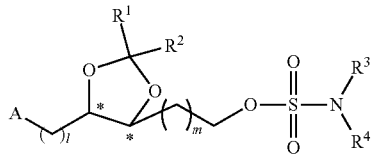

[Chemical Formula I]

wherein $R^1$ and $R^2$ are each independently selected from the group consisting of hydrogen, $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is an aryl moiety or a heterocyclic moiety optionally substituted by one or more substituents selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine. $C_1$-$C_5$ alkylamine and halogen; $R^3$ and $R^4$ are each independently hydrogen or $C_1$-$C_3$ alkyl; and l and m are each independently an integer of 0~4.

According to a concrete embodiment, $R^1$ and $R^2$ are each independently selected from the group consisting of hydrogen, $C_1$-$C_3$ alkyl and phenyl or $R^1$ and $R^2$ together with the carbon atom to which they attach form a $C_3$-$C_6$ cycloalkyl group.

In a preferred embodiment according to the invention, an aryl moiety represents a $C_6$-$C_{10}$ aryl group.

In a preferred embodiment according to the invention, a heterocyclic moiety represents a $C_3$-$C_{10}$ heterocyclic group.

In a preferred embodiment according to the invention. A is a phenyl optionally substituted by one or more substituents selected from the group consisting of hydrogen, halogen, $C_1$-$C_5$ alkyl, nitro, amine and $C_1$-$C_5$ alkylamine or $C_3$-$C_{10}$ heterocyclic group optionally substituted by one or more substituents selected from the group consisting of hydrogen, halogen, $C_1$-$C_5$ alkyl, and $C_6$-$C_{10}$ aryl.

According to a concrete embodiment, $R^3$ and $R^4$ are each independently hydrogen or methyl.

In a preferred embodiment according to the invention, l and m are each independently an integer of 0~2.

In a more preferred embodiment according to the invention, l and m are each independently an integer of 0~1.

Particular examples of the substituents represented by A in Chemical Formula I include the following:

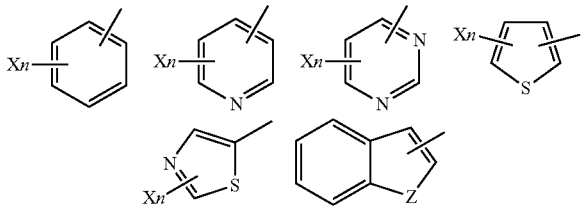

wherein X is each independently selected from the group consisting of hydrogen, halogen, nitro, amine, and $C_1$-$C_5$ alkyl; n is an integer of 0~5; and Z is selected from S, O or NH.

In a preferred embodiment according to the invention, n is an integer of 0~2.

In a more preferred embodiment according to the invention, n is an integer of 0~1.

In a preferred embodiment according to the invention, $R^1$ and $R^2$ are each independently selected from the group consisting of hydrogen and $C_1$-$C_5$ alkyl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is $C_6$-$C_{10}$ aryl or 5- or 6-membered heterocyclic ring containing one or two sulfur atoms, optionally substituted by one or more substituents selected from the group consisting of hydrogen, $C_1$-$C_5$ alkyl, nitro, amine, and halogen; $R^3$ and $R^4$ are each independently hydrogen or $C_1$-$C_3$ alkyl; and l and m are each independently an integer of 0~1.

In a more preferred embodiment according to the invention, $R^1$ and $R^2$ are each independently $C_1$-$C_3$ alkyl, $R^1$ and $R^2$ together with the carbon atom to which they attach form a $C_5$-$C_6$ cycloalkyl group, or $R^1$ and $R^2$ are bond and they together with the oxygen atom to which they attach form a carbonyl group; A is $C_6$-$C_{10}$ aryl optionally substituted by one or more substituents selected from the group consisting of hydrogen, $C_1$-$C_5$ alkyl, nitro, amine, and halogen, or 5-membered heterocyclic ring containing one sulfur atom, optionally substituted by one or more substituents selected from the group consisting of hydrogen, and halogen; $R^3$ and $R^4$ are each independently hydrogen or $C_1$-$C_3$ alkyl; and l and m are each independently an integer of 0~1.

The term "alkyl" as used herein, refers to a linear or branched chain of a saturated hydrocarbon group, e.g., methyl, ethyl, propyl, butyl, isobutyl, tert-butyl and pentyl. "$C_1$-$C_5$ alkyl group" as used herein, refers to an alkyl group with a carbon number of 1-5.

The term "alkenyl", as used herein, unless otherwise indicated, includes alkyl moieties having at least one carbon-carbon double bond wherein alkyl is as defined above.

The term "alkoxy", as used herein, unless otherwise indicated, includes O-alkyl groups wherein alkyl is as defined above.

The term "alkylthio", as used herein, unless otherwise indicated, includes S-alkyl groups wherein alkyl is as defined above.

The term "alkoxycarbonyl", as used herein, unless otherwise indicated, includes —C(O)O-alkyl groups wherein alkyl is as defined above.

The term "acyl", as used herein, unless otherwise indicated, includes —C(O)-alkyl groups wherein alkyl is as defined above.

The term "aryl" or "aryl group" as used herein, refers to totally or partially unsaturated monocyclic or polycyclic carbon rings having aromaticity. The aryl group of the present invention is preferably monoaryl or biaryl, such as phenyl or naphthyl. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

The term "cycloalkyl" or "cycloalkyl group" as used herein, refers' to a monocyclic or polycyclic saturated ring comprising carbon and hydrogen atoms.

The term "heterocyclic" or "heterocyclic group", as used herein, unless otherwise indicated, means aromatic and non-aromatic heterocyclic groups (including saturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or polycyclic, for example bicyclic (which may comprise non-aromatic and/or aromatic rings).

According to more concrete embodiment, the compound is selected from the group consisting of:
(1) (5-(2-chlorophenyl)-2,2-dimethyl-1,3-dioxolan-4-yl) methyl sulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl) methyl sulfamate;
(4) (3-(2-chlorophenyl)-1,4-dioxaspiro[4,4]nonan-2-yl) methyl sulfamate;
(5) (3-(2-chlorophenyl)-1,4-dioxaspiro[4,5]decan-2-yl) methyl sulfamate;
(6) (5-(2-chlorophenyl)-2-phenyl-1,3-dioxolan-4-yl)methyl sulfamate;
(7) (5-(2-fluorophenyl)-2,2-dimethyl-1,3-dioxolan-4-yl) methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl) methyl sulfamate;
(10) (3-(2-fluorophenyl)-1,4-dioxaspiro[4,4]nonan-2-yl) methyl sulfamate;
(11) (3-(2-fluorophenyl)-1,4-dioxaspiro[4,5]decan-2-yl) methyl sulfamate;
(12) (5-(2-fluorophenyl)-2-phenyl-1,3-dioxolan-4-yl)methyl sulfamate;
(13) (5-(2-iodophenyl)-2,2-dimethyl-1,3-dioxolan-4-yl) methyl sulfamate;
(14) (5-(2-iodophenyl)-2-methyl-1,3-dioxolan-4-yl) methyl sulfamate;
(15) (5-(2-iodophenyl)-2,2-diethyl-1,3-dioxolan-4-yl) methyl sulfamate;
(16) (3-(2-iodophenyl)-1,4-dioxaspiro[4,4]nonan-2-yl) methyl sulfamate;
(17) (3-(2-iodophenyl)-1,4-dioxaspiro[4,5]decan-2-yl) methyl sulfamate;
(18) (5-(2-iodophenyl)-2-phenyl-1,3-dioxolan-4-yl)methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl) methyl sulfamate;
(21) (5-(2,4-dichlorophenyl)-2,2-diethyl-1,3-dioxolan-4-yl) methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl) methyl sulfamate;
(24) (5-(2,4-dichlorophenyl)-2-phenyl-1,3-dioxolan-4-yl) methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl) methyl sulfamate;
(27) (5-(2,6-dichlorophenyl)-2,2-diethyl-1,3-dioxolan-4-yl) methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl) methyl sulfamate;
(30) (5-(2,6-dichlorophenyl)-2-phenyl-1,3-dioxolan-4-yl) methyl sulfamate;
(31) (5-(2-aminophenyl)-2,2-dimethyl-1,3-dioxolan-4-yl) methyl sulfamate;
(32) (5-(2-aminophenyl)-2-methyl-1,3-dioxolan-4-yl) methyl sulfamate;
(33) (5-(2-aminophenyl)-2,2-diethyl-1,3-dioxolan-4-yl) methyl sulfamate;
(34) (3-(2-aminophenyl)-1,4-dioxaspiro[4,4]nonan-2-yl) methyl sulfamate;
(35) (3-(2-aminophenyl)-1,4-dioxaspiro[4,5]decan-2-yl) methyl sulfamate;
(36) (5-(2-aminophenyl)-2-phenyl-1,3-dioxolan-4-yl) methyl sulfamate;
(37) (5-(2-nitrophenyl)-2,2-dimethyl-1,3-dioxolan-4-yl) methyl sulfamate;
(38) (5-(2-nitrophenyl)-2-methyl-1,3-dioxolan-4-yl) methyl sulfamate;
(39) (5-(2-nitrophenyl)-2,2-diethyl-1,3-dioxolan-4-yl) methyl sulfamate;
(40) (3-(2-nitrophenyl)-1,4-dioxaspiro[4,4]nonan-2-yl) methyl sulfamate;
(41) (3-(2-nitrophenyl)-1,4-dioxaspiro[4,5]decan-2-yl) methyl sulfamate;
(42) (5-(2-nitrophenyl)-2-phenyl-1,3-dioxolan-4-yl)methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl) methyl sulfamate;
(45) (5-(2-methylphenyl)-2-methyl-1,3-dioxolan-4-yl) methyl sulfamate;
(46) (5-(2-methylphenyl)-2,2-diethyl-1,3-dioxolan-4-yl) methyl sulfamate;
(47) (3-(2-methylphenyl)-1,4-dioxaspiro[4,4]nonan-2-yl) methyl sulfamate;
(48) (3-(2-methylphenyl)-1,4-dioxaspiro[4,5]decan-2-yl) methyl sulfamate:
(49) (5-(2-methylphenyl)-2-phenyl-1,3-dioxolan-4-yl) methyl sulfamate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;

(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;
(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 2-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl) ethyl sulfamate;
(68) 2-(5-(2-chlorobenzyl)-2,2-diethyl-1,3-dioxolan-4-yl) ethyl sulfamate;
(69) 2-(3-(2-chlorobenzyl)-1,4-dioxaspiro[4,4]nonan-2-yl) ethyl sulfamate;
(70) 2-(3-(2-chlorobenzyl)-1,4-dioxaspiro[4,5]decan-2-yl) ethyl sulfamate;
(71) (5-(2-chlorbenzyl)-2,2-dimethyl-1,3-dioxolan-4-yl) methyl sulfamate;
(72) (5-(2-chlorobenzyl)-2,2-diethyl-1,3-dioxolan-4-yl) methyl sulfamate;
(73) (3-(2-chlorobenzyl)-1,4-dioxaspiro[4,4]nonan-2-yl) methyl sulfamate;
(74) (3-(2-chlorobenzyl)-1,4-dioxaspiro[4,5]decan-2-yl) methyl sulfamate;
(75) 2-(5-(2-chlorophenyl)-2,2-dimethyl-1,3-dioxolan-4-yl) ethyl sulfamate;
(76) 2-(5-(2-chlorophenyl)-2,2-diethyl-1,3-dioxolan-4-yl) ethyl sulfamate;
(77) 2-(3-(2-chlorophenyl)-1,4-dioxaspiro[4,4]nonan-2-yl) ethyl sulfamate;
(78) 2-(3-(2-chlorophenyl)-1,4-dioxaspiro[4,5]decan-2-yl) ethyl sulfamate;
(79) (5-(2,4-dichlorothiazol-5-yl)-2,2-dimethyl-1,3-dioxolan-4-yl)methyl sulfamate;
(80) (5-(2-chlorothiazol-5-yl)-2,2-dimethyl-1,3-dioxolan-4-yl)methyl sulfamate;
(81) (2,2-dimethyl-5-(4-methylthiazol-5-yl)-1,3-dioxolan-4-yl)methylsulfamate;
(82) (2,2-dimethyl-5-(2-chloro-4-methylthiazol-5-yl)-1,3-dioxolan-4-yl)methylsulfamate;
(83) (2,2-dimethyl-5-(thiophen-3-yl)-1,3-dioxolan-4-yl) methylsulfamate;
(84) (2,2-dimethyl-5-(5-chlorothiophen-2-yl)-1,3-dioxolan-4-yl)methylsulfamate;
(85) (5-(3-chloropyridin-4-yl)-2,2-dimethyl-1,3-dioxolan-4-yl)methylsulfamate;
(86) (5-(4-chloropyridin-3-yl)-2,2-dimethyl-1,3-dioxolan-4-yl)methylsulfamate;
(87) (2,2-dimethyl-5-(pyrimidin-5-yl)-1,3-dioxolan-4-yl) methylsulfamate; and
(88) (2,2-dimethyl-5-(2-chloropyrimidin-5-yl)-1,3-dioxolan-4-yl)methylsulfamate.

According to more concrete embodiment, the compound is selected from the group consisting of:
(1) (5-(2-chlorophenyl)-2,2-dimethyl-1,3-dioxolan-4-yl) methyl sulfamate;
(4) (3-(2-chlorophenyl)-1,4-dioxaspiro[4,4]nonan-2-yl) methyl sulfamate;
(19) (5-(2,4-dichlorophenyl)-2,2-dimethyl-1,3-dioxolan-4-yl)methyl sulfamate;
(25) (5-(2,6-dichlorophenyl)-2,2-dimethyl-1,3-dioxolan-4-yl)methyl sulfamate;
(34) (3-(2-aminophenyl)-1,4-dioxaspiro[4,4]nonan-2-yl) methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl) methyl sulfamate;
(51) (5-phenyl-2,2-dimethyl-1,3-dioxolan-4-yl)methyl sulfamate;
(53) (3-phenyl-1,4-dioxaspiro[4,4]nonan-2-yl)methyl sulfamate;
(55) 2-(5-benzyl-2,2-dimethyl-1,3-dioxolan-4-yl)ethyl sulfamate;
(57) 2-(3-benzyl-1,4-dioxaspiro[4,4]nonan-2-yl)ethyl sulfamate;
(59) (5-benzyl-2,2-dimethyl-1,3-dioxolan-4-yl)methyl sulfamate;
(61) (3-benzyl-1,4-dioxaspiro[4.4]nonan-2-yl)methyl sulfamate;
(63) 2-(5-phenyl-2,2-dimethyl-1,3-dioxolan-4-yl)ethyl sulfamate;
(65) 2-(3-phenyl-1,4-dioxaspiro[4,4]nonan-2-yl)ethyl sulfamate;
(67) 2-(5-(2-chlorobenzyl)-2,2-dimethyl-1,3-dioxolan-4-yl) ethyl sulfamate;
(69) 2-(3-(2-chlorobenzyl)-1,4-dioxaspiro[4,4]nonan-2-yl) ethyl sulfamate;
(71) (5-(2-chlorobenzyl)-2,2-dimethyl-1,3-dioxolan-4-yl) methyl sulfamate;
(73) (3-(2-chlorobenzyl)-1,4-dioxaspiro[4,4]nonan-2-yl) methyl sulfamate;
(75) 2-(5-(2-chlorophenyl)-2,2-dimethyl-1,3-dioxolan-4-yl) ethyl sulfamate;
(77) 2-(3-(2-chlorophenyl)-1,4-dioxaspiro[4,4]nonan-2-yl) ethyl sulfamate;
(79) (5-(2,4-dichlorothiazol-5-yl)-2,2-dimethyl-1,3-dioxolan-4-yl)methyl sulfamate; and
(80) (5-(2-chlorothiazol-5-yl)-2,2-dimethyl-1,3-dioxolan-4-yl)methyl sulfamate.

According to a concrete embodiment, the compound is in the form of a racemate, an enantiomer, a diastereomer, a mixture of enantiomers or a mixture of diastereomers.

According to more concrete embodiment, a configuration of each chiral center in the compound is (S).

According to more concrete embodiment, the compound is selected from the group consisting of:
((4R,5R)-5-(2-chlorophenyl)-2,2-dimethyl-1,3-dioxolan-4-yl)methyl sulfamate;
((4S,5S)-5-(2-chlorophenyl)-2,2-dimethyl-1,3-dioxolan-4-yl)methyl sulfamate;
(5-(2-chlorophenyl)-2,2-dimethyl-1,3-dioxolan-4-yl)methyl sulfamate (SS & RR mixture);

(5-(2-chlorophenyl)-2,2-dimethyl-1,3-dioxolan-4-yl)methyl sulfamate (SR & RS mixture);
((4R,5R)-5-(2-chlorophenyl)-2-methyl-1,3-dioxolan-4-yl) methyl sulfamate;
((4S,5S)-5-(2-chlorophenyl)-2-methyl-1,3-dioxolan-4-yl) methyl sulfamate;
((4R,5R)-5-(2-chlorophenyl)-2,2-diethyl-1,3-dioxolan-4-yl) methyl sulfamate;
((4S,5S)-5-(2-chlorophenyl)-2,2-diethyl-1,3-dioxolan-4-yl) methyl sulfamate;
((2R,3R)-3-(2-chlorophenyl)-1,4-dioxaspiro[4,4]nonan-2-yl)methyl sulfamate:
((2S,3S)-3-(2-chlorophenyl)-1,4-dioxaspiro[4,4]nonan-2-yl)methyl sulfamate;
((2R,3R)-3-(2-chlorophenyl)-1,4-dioxaspiro[4,5]decan-2-yl)methyl sulfamate;
((2S,3S)-3-(2-chlorophenyl)-1,4-dioxaspiro[4,5]decan-2-yl) methyl sulfamate;
((4R,5R)-5-(2-chlorophenyl)-2-phenyl-1,3-dioxolan-4-yl) methyl sulfamate;
((4S,5S)-5-(2-chlorophenyl)-2-phenyl-1,3-dioxolan-4-yl) methyl sulfamate;
((4R,5R)-5-(2-fluorophenyl)-2,2-dimethyl-1,3-dioxolan-4-yl)methyl sulfamate;
((4S,5S)-5-(2-fluorophenyl)-2,2-dimethyl-1,3-dioxolan-4-yl)methyl sulfamate;
((4R,5R)-5-(2-fluorophenyl)-2-methyl-1,3-dioxolan-4-yl) methyl sulfamate;
((4S,5S)-5-(2-fluorophenyl)-2-methyl-1,3-dioxolan-4-yl) methyl sulfamate;
((4R,5R)-5-(2-fluorophenyl)-2,2-diethyl-1,3-dioxolan-4-yl) methyl sulfamate;
((4S,5S)-5-(2-fluorophenyl)-2,2-diethyl-1,3-dioxolan-4-yl) methyl sulfamate;
((2R,3R)-3-(2-fluorophenyl)-1,4-dioxaspiro[4,4]nonan-2-yl)methyl sulfamate;
((2S,3S)-3-(2-fluorophenyl)-1,4-dioxaspiro[4,4]nonan-2-yl) methyl sulfamate;
((2R,3R)-3-(2-fluorophenyl)-1,4-dioxaspiro[4,5]decan-2-yl)methyl sulfamate;
((2S,3S)-3-(2-fluorophenyl)-1,4-dioxaspiro[4,5]decan-2-yl) methyl sulfamate;
((4R,5R)-5-(2-fluorophenyl)-2-phenyl-1,3-dioxolan-4-yl) methyl sulfamate;
((4S,5S)-5-(2-fluorophenyl)-2-phenyl-1,3-dioxolan-4-yl) methyl sulfamate;
((4R,5R)-5-(2-iodophenyl)-2,2-dimethyl-1,3-dioxolan-4-yl) methyl sulfamate;
((4S,5S)-5-(2-iodophenyl)-2,2-dimethyl-1,3-dioxolan-4-yl) methyl sulfamate;
((4R,5R)-5-(2-iodophenyl)-2-methyl-1,3-dioxolan-4-yl) methyl sulfamate;
((4S,5S)-5-(2-iodophenyl)-2-methyl-1,3-dioxolan-4-yl) methyl sulfamate;
((4R,5R)-5-(2-iodophenyl)-2,2-diethyl-1,3-dioxolan-4-yl) methyl sulfamate;
((4S,5S)-5-(2-iodophenyl)-2,2-diethyl-1,3-dioxolan-4-yl) methyl sulfamate;
((2R,3R)-3-(2-iodophenyl)-1,4-dioxaspiro[4,4]nonan-2-yl) methyl sulfamate:
((2S,3S)-3-(2-iodophenyl)-1,4-dioxaspiro[4,4]nonan-2-yl) methyl sulfamate;
((2R,3R)-3-(2-iodophenyl)-1,4-dioxaspiro[4,5]decan-2-yl) methyl sulfamate;
((2S,3S)-3-(2-iodophenyl)-1,4-dioxaspiro[4,5]decan-2-yl) methyl sulfamate;
((4R,5R)-5-(2-iodophenyl)-2-phenyl-1,3-dioxolan-4-yl) methyl sulfamate;
((4S,5S)-5-(2-iodophenyl)-2-phenyl-1,3-dioxolan-4-yl) methyl sulfamate;
((4R,5R)-5-(2,4-dichlorophenyl)-2,2-dimethyl-1,3-dioxolan-4-yl)methyl sulfamate;
((4S,5S)-5-(2,4-dichlorophenyl)-2,2-dimethyl-1,3-dioxolan-4-yl)methyl sulfamate;
((4R,5R)-5-(2,4-dichlorophenyl)-2-methyl-1,3-dioxolan-4-yl)methyl sulfamate;
((4S,5S)-5-(2,4-dichlorophenyl)-2-methyl-1,3-dioxolan-4-yl)methyl sulfamate;
((4R,5R)-5-(2,4-dichlorophenyl)-2,2-diethyl-1,3-dioxolan-4-yl)methyl sulfamate;
((4S,5S)-5-(2,4-dichlorophenyl)-2,2-diethyl-1,3-dioxolan-4-yl)methyl sulfamate:
((2R,3R)-3-(2,4-dichlorophenyl)-1,4-dioxaspiro[4,4]nonan-2-yl)methyl sulfamate;
((2S,3S)-3-(2,4-dichlorophenyl)-1,4-dioxaspiro[4,4]nonan-2-yl)methyl sulfamate;
((2R,3R)-3-(2,4-dichlorophenyl)-1,4-dioxaspiro[4,5]decan-2-yl)methyl sulfamate;
((2S,3S)-3-(2,4-dichlorophenyl)-1,4-dioxaspiro[4,5]decan-2-yl)methyl sulfamate;
((4R,5R)-5-(2,4-dichlorophenyl)-2-phenyl-1,3-dioxolan-4-yl)methyl sulfamate;
((4S,5S)-5-(2,4-dichlorophenyl)-2-phenyl-1,3-dioxolan-4-yl)methyl sulfamate;
((4R,5R)-5-(2,6-dichlorophenyl)-2,2-dimethyl-1,3-dioxolan-4-yl)methyl sulfamate;
((4S,5S)-5-(2,6-dichlorophenyl)-2,2-dimethyl-1,3-dioxolan-4-yl)methyl sulfamate:
((4R,5R)-5-(2,6-dichlorophenyl)-2-methyl-1,3-dioxolan-4-yl)methyl sulfamate;
((4S,5S)-5-(2,6-dichlorophenyl)-2-methyl-1,3-dioxolan-4-yl)methyl sulfamate;
((4R,5R)-5-(2,6-dichlorophenyl)-2,2-diethyl-1,3-dioxolan-4-yl)methyl sulfamate;
((4S,5S)-5-(2,6-dichlorophenyl)-2,2-diethyl-1,3-dioxolan-4-yl)methyl sulfamate;
((2R,3R)-3-(2,6-dichlorophenyl)-1,4-dioxaspiro[4,4]nonan-2-yl)methyl sulfamate;
((2S,3S)-3-(2,6-dichlorophenyl)-1,4-dioxaspiro[4,4]nonan-2-yl)methyl sulfamate;
((2R,3R)-3-(2,6-dichlorophenyl)-1,4-dioxaspiro[4,5]decan-2-yl)methyl sulfamate;
((2S,3S)-3-(2,6-dichlorophenyl)-1,4-dioxaspiro[4,5]decan-2-yl)methyl sulfamate;
((4R,5R)-5-(2,6-dichlorophenyl)-2-phenyl-1,3-dioxolan-4-yl)methyl sulfamate;
((4S,5S)-5-(2,6-dichlorophenyl)-2-phenyl-1,3-dioxolan-4-yl)methyl sulfamate;
((4R,5R)-5-(2-aminophenyl)-2,2-dimethyl-1,3-dioxolan-4-yl)methyl sulfamate:
((4S,5S)-5-(2-aminophenyl)-2,2-dimethyl-1,3-dioxolan-4-yl)methyl sulfamate;
((4R,5R)-5-(2-aminophenyl)-2-methyl-1,3-dioxolan-4-yl) methyl sulfamate;
((4S,5S)-5-(2-aminophenyl)-2-methyl-1,3-dioxolan-4-yl) methyl sulfamate;
((4R,5R)-5-(2-aminophenyl)-2,2-diethyl-1,3-dioxolan-4-yl) methyl sulfamate;
((4S,5S)-5-(2-aminophenyl)-2,2-diethyl-1,3-dioxolan-4-yl) methyl sulfamate;
((2R,3R)-3-(2-aminophenyl)-1,4-dioxaspiro[4,4]nonan-2-yl)methyl sulfamate;

((2S,3S)-3-(2-aminophenyl)-1,4-dioxaspiro[4,4]nonan-2-yl)methyl sulfamate;
((2R,3R)-3-(2-aminophenyl)-1,4-dioxaspiro[4,5]decan-2-yl)methyl sulfamate;
((2S,3S)-3-(2-aminophenyl)-1,4-dioxaspiro[4,5]decan-2-yl)methyl sulfamate;
((4R,5R)-5-(2-aminophenyl)-2-phenyl-1,3-dioxolan-4-yl)methyl sulfamate;
((4S,5S)-5-(2-aminophenyl)-2-phenyl-1,3-dioxolan-4-yl)methyl sulfamate;
((4R,5R)-5-(2-nitrophenyl)-2,2-dimethyl-1,3-dioxolan-4-yl)methyl sulfamate;
((4S,5S)-5-(2-nitrophenyl)-2,2-dimethyl-1,3-dioxolan-4-yl)methyl sulfamate;
((4R,5R)-5-(2-nitrophenyl)-2-methyl-1,3-dioxolan-4-yl)methyl sulfamate;
((4S,5S)-5-(2-nitrophenyl)-2-methyl-1,3-dioxolan-4-yl)methyl sulfamate;
((4R,5R)-5-(2-nitrophenyl)-2,2-diethyl-1,3-dioxolan-4-yl)methyl sulfamate;
((4S,5S)-5-(2-nitrophenyl)-2,2-diethyl-1,3-dioxolan-4-yl)methyl sulfamate;
((2R,3R)-3-(2-nitrophenyl)-1,4-dioxaspiro[4,4]nonan-2-yl)methyl sulfamate;
((2S,3S)-3-(2-nitrophenyl)-1,4-dioxaspiro[4,4]nonan-2-yl)methyl sulfamate;
((2R,3R)-3-(2-nitrophenyl)-1,4-dioxaspiro[4,5]decan-2-yl)methyl sulfamate;
((2S,3S)-3-(2-nitrophenyl)-1,4-dioxaspiro[4,5]decan-2-yl)methyl sulfamate;
((4R,5R)-5-(2-nitrophenyl)-2-phenyl-1,3-dioxolan-4-yl)methyl sulfamate;
((4S,5S)-5-(2-nitrophenyl)-2-phenyl-1,3-dioxolan-4-yl)methyl sulfamate;
((4R,5R)-5-(2-nitrophenyl)-2-oxo-1,3-dioxolan-4-yl)methyl sulfamate;
((4S,5S)-5-(2-nitrophenyl)-2-oxo-1,3-dioxolan-4-yl)methyl sulfamate;
((4R,5R)-5-(2-methylphenyl)-2,2-dimethyl-1,3-dioxolan-4-yl)methyl sulfamate;
((4S,5S)-5-(2-methylphenyl)-2,2-dimethyl-1,3-dioxolan-4-yl)methyl sulfamate;
((4R,5R)-5-(2-methylphenyl)-2-methyl-1,3-dioxolan-4-yl)methyl sulfamate;
((4S,5S)-5-(2-methylphenyl)-2-methyl-1,3-dioxolan-4-yl)methyl sulfamate;
((4R,5R)-5-(2-methylphenyl)-2,2-diethyl-1,3-dioxolan-4-yl)methyl sulfamate;
((4S,5S)-5-(2-methylphenyl)-2,2-diethyl-1,3-dioxolan-4-yl)methyl sulfamate;
((2R,3R)-3-(2-methylphenyl)-1,4-dioxaspiro[4,4]nonan-2-yl)methyl sulfamate;
((2S,3S)-3-(2-methylphenyl)-1,4-dioxaspiro[4,4]nonan-2-yl)methyl sulfamate;
((2R,3R)-3-(2-methylphenyl)-1,4-dioxaspiro[4,5]decan-2-yl)methyl sulfamate;
((2S,3S)-3-(2-methylphenyl)-1,4-dioxaspiro[4,5]decan-2-yl)methyl sulfamate;
((4R,5R)-5-(2-methylphenyl)-2-phenyl-1,3-dioxolan-4-yl)methyl sulfamate;
((4S,5S)-5-(2-methylphenyl)-2-phenyl-1,3-dioxolan-4-yl)methyl sulfamate;
((4R,5R)-5-(2-methylaminophenyl)-2,2-dimethyl-1,3-dioxolan-4-yl)methyl sulfamate;
((4S,5S)-5-(2-methylaminophenyl)-2,2-dimethyl-1,3-dioxolan-4-yl)methyl sulfamate;
((4R,5R)-5-phenyl-2,2-dimethyl-1,3-dioxolan-4-yl)methyl sulfamate;
((4S,5S)-5-phenyl-2,2-dimethyl-1,3-dioxolan-4-yl)methyl sulfamate;
((4R,5R)-5-phenyl-2,2-diethyl-1,3-dioxolan-4-yl)methyl sulfamate;
((4S,5S)-5-phenyl-2,2-diethyl-1,3-dioxolan-4-yl)methyl sulfamate;
((2R,3R)-3-phenyl-1,4-dioxaspiro[4,4]nonan-2-yl)methyl sulfamate;
((2S,3S)-3-phenyl-1,4-dioxaspiro[4,4]nonan-2-yl)methyl sulfamate;
((2R,3R)-3-phenyl-1,4-dioxaspiro[4,5]decan-2-yl)methyl sulfamate;
((2S,3S)-3-phenyl-1,4-dioxaspiro[4,5]decan-2-yl)methyl sulfamate;
2-((4S,5S)-5-benzyl-2,2-dimethyl-1,3-dioxolan-4-yl)ethyl sulfamate;
2-((4R,5R)-5-benzyl-2,2-dimethyl-1,3-dioxolan-4-yl)ethyl sulfamate:
2-((4S,5S)-5-benzyl-2,2-diethyl-1,3-dioxolan-4-yl)ethyl sulfamate;
2-((4R,5R)-5-benzyl-2,2-diethyl-1,3-dioxolan-4-yl)ethyl sulfamate;
2-((2S,3S)-3-benzyl-1,4-dioxaspiro[4,4]nonan-2-yl)ethyl sulfamate;
2-((2R,3R)-3-benzyl-1,4-dioxaspiro[4,4]nonan-2-yl)ethyl sulfamate;
2-((2S,3S)-3-benzyl-1,4-dioxaspiro[4,5]decan-2-yl)ethyl sulfamate;
2-((2R,3R)-3-benzyl-1,4-dioxaspiro[4,5]decan-2-yl)ethyl sulfamate;
((4S,5S)-5-benzyl-2,2-dimethyl-1,3-dioxolan-4-yl)methyl sulfamate;
((4R,5R)-5-benzyl-2,2-dimethyl-1,3-dioxolan-4-yl)methyl sulfamate;
((4S,5S)-5-benzyl-2,2-diethyl-1,3-dioxolan-4-yl)methyl sulfamate;
((4R,5R)-5-benzyl-2,2-diethyl-1,3-dioxolan-4-yl)methyl sulfamate;
2-((4R,5R)-5-phenyl-2,2-dimethyl-1,3-dioxolan-4-yl)ethyl sulfamate;
2-((4S,5S)-5-phenyl-2,2-dimethyl-1,3-dioxolan-4-yl)ethyl sulfamate;
2-((4R,5R)-5-phenyl-2,2-diethyl-1,3-dioxolan-4-yl)ethyl sulfamate;
2-((4S,5S)-5-phenyl-2,2-diethyl-1,3-dioxolan-4-yl)ethyl sulfamate;
2-((2R,3R)-3-phenyl-1,4-dioxaspiro[4,4]nonan-2-yl)ethyl sulfamate;
2-((2S,3S)-3-phenyl-1,4-dioxaspiro[4,4]nonan-2-yl)ethyl sulfamate;
2-((2R,3R)-3-phenyl-1,4-dioxaspiro[4,5]decan-2-yl)ethyl sulfamate;
2-((2S,3S)-3-phenyl-1,4-dioxaspiro[4,5]decan-2-yl)ethyl sulfamate;
2-((4S,5S)-5-(2-chlorobenzyl)-2,2-dimethyl-1,3-dioxolan-4-yl)ethyl sulfamate;
2-((4R,5R)-5-(2-chlorobenzyl)-2,2-dimethyl-1,3-dioxolan-4-yl)ethyl sulfamate;
2-((4S,5S)-5-(2-chlorobenzyl)-2,2-diethyl-1,3-dioxolan-4-yl)ethyl sulfamate;
2-((4R,5R)-5-(2-chlorobenzyl)-2,2-diethyl-1,3-dioxolan-4-yl)ethyl sulfamate;
2-((2S,3S)-3-(2-chlorobenzyl)-1,4-dioxaspiro[4,4]nonan-2-yl)ethyl sulfamate;

2-((2R,3R)-3-(2-chlorobenzyl)-1,4-dioxaspiro[4.4]nonan-2-yl)ethyl sulfamate;
2-((2S,3S)-3-(2-chlorobenzyl)-1,4-dioxaspiro[4,5]decan-2-yl)ethyl sulfamate;
2-((2R,3R)-3-(2-chlorobenzyl)-1,4-dioxaspiro[4,5]decan-2-yl)ethyl sulfamate;
((4S,5S)-5-(2-chlorobenzyl)-2,2-diethyl-1,3-dioxolan-4-yl)methyl sulfamate;
((4R,5R)-5-(2-chlorobenzyl)-2,2-diethyl-1,3-dioxolan-4-yl)methyl sulfamate;
((2S,3S)-3-(2-chlorobenzyl)-1,4-dioxaspiro[4,4]nonan-2-yl)methyl sulfamate;
((2R,3R)-3-(2-chlorobenzyl)-1,4-dioxaspiro[4,4]nonan-2-yl)methyl sulfamate;
((2S,3S)-3-(2-chlorobenzyl)-1,4-dioxaspiro[4,5]decan-2-yl)methyl sulfamate;
((2R,3R)-3-(2-chlorobenzyl)-1,4-dioxaspiro[4,5]decan-2-yl)methyl sulfamate;
2-((4R,5R)-5-(2-chlorophenyl)-2,2-dimethyl-1,3-dioxolan-4-yl)ethyl sulfamate;
2-((4S,5S)-5-(2-chlorophenyl)-2,2-dimethyl-1,3-dioxolan-4-yl)ethyl sulfamate;
2-((4R,5R)-5-(2-chlorophenyl)-2,2-diethyl-1,3-dioxolan-4-yl)ethyl sulfamate;
2-((4S,5S)-5-(2-chlorophenyl)-2,2-diethyl-1,3-dioxolan-4-yl)ethyl sulfamate;
2-((2R,3R)-3-(2-chlorophenyl)-1,4-dioxaspiro[4,4]nonan-2-yl)ethyl sulfamate;
2-((2S,3S)-3-(2-chlorophenyl)-1,4-dioxaspiro[4,4]nonan-2-yl)ethyl sulfamate;
2-((2R,3R)-3-(2-chlorophenyl)-1,4-dioxaspiro[4,5]decan-2-yl)ethyl sulfamate;
2-((2S,3S)-3-(2-chlorophenyl)-1,4-dioxaspiro[4,5]decan-2-yl)ethyl sulfamate;
((4S,5R)-5-(2-chlorophenyl)-2,2-dimethyl-1,3-dioxolan-4-yl)methyl sulfamate;
((4R,5S)-5-(2-chlorophenyl)-2,2-dimethyl-1,3-dioxolan-4-yl)methyl sulfamate;
((4R,5S)-5-(2,4-dichlorothiazol-5-yl)-2,2-dimethyl-1,3-dioxolan-4-yl)methyl sulfamate;
((4S,5R)-5-(2,4-dichlorothiazol-5-yl)-2,2-dimethyl-1,3-dioxolan-4-yl)methyl sulfamate;
((4R,5S)-5-(2-chlorothiazol-5-yl)-2,2-dimethyl-1,3-dioxolan-4-yl)methyl sulfamate;
((4S,5R)-5-(2-chlorothiazol-5-yl)-2,2-dimethyl-1,3-dioxolan-4-yl)methyl sulfamate;
((4R,5S)-2,2-dimethyl-5-(4-methylthiazol-5-yl)-1,3-dioxolan-4-yl)methyl sulfamate;
((4S,5R)-2,2-dimethyl-5-(4-methylthiazol-5-yl)-1,3-dioxolan-4-yl)methyl sulfamate;
((4R,5S)-2,2-dimethyl-5-(2-chloro-4-methylthiazol-5-yl)-1,3-dioxolan-4-yl)methyl sulfamate;
((4S,5R)-2,2-dimethyl-5-(2-chloro-4-methylthiazol-5-yl)-1,3-dioxolan-4-yl)methyl sulfamate;
((4S,5S)-2,2-dimethyl-5-(thiophen-3-yl)-1,3-dioxolan-4-yl)methyl sulfamate;
((4S,5R)-2,2-dimethyl-5-(5-chlorothiophen-2-yl)-1,3-dioxolan-4-yl)methyl sulfamate;
Sodium (((4R,5R)-5-(2-aminophenyl)-2,2-dimethyl-1,3-dioxolan-4-yl)methyl sulfonyl)amide;
Sodium (((4S,5S)-5-(2-aminophenyl)-2,2-dimethyl-1,3-dioxolan-4-yl)methyl sulfonyl)amide; and
Sodium (((4S,5S)-5-(2-chlorophenyl)-2,2-dimethyl-1,3-dioxolan-4-yl)methoxy)sulfonyl)amide.

According to more concrete embodiment, the compound is selected from the group consisting of:

((4S,5S)-5-(2-chlorophenyl)-2,2-dimethyl-1,3-dioxolan-4-yl)methyl sulfamate;
((2S,3S)-3-(2-chlorophenyl)-1,4-dioxaspiro[4,4]nonan-2-yl)methyl sulfamate;
((4S,5S)-5-(2,4-dichlorophenyl)-2,2-dimethyl-1,3-dioxolan-4-yl)methyl sulfamate;
((4S,5S)-5-(2,6-dichlorophenyl)-2,2-dimethyl-1,3-dioxolan-4-yl)methyl sulfamate;
((2S,3S)-3-(2-aminophenyl)-1,4-dioxaspiro[4,4]nonan-2-yl)methyl sulfamate;
((4S,5S)-5-(2-nitrophenyl)-2-oxo-1,3-dioxolan-4-yl)methyl sulfamate;
((4S,5S)-5-(2-methylphenyl)-2,2-dimethyl-1,3-dioxolan-4-yl)methyl sulfamate;
((4S,5S)-5-phenyl-2,2-dimethyl-1,3-dioxolan-4-yl)methyl sulfamate;
((2S,3S)-3-phenyl-1,4-dioxaspiro[4,4]nonan-2-yl)methyl sulfamate;
2-((4S,5S)-5-benzyl-2,2-dimethyl-1,3-dioxolan-4-yl)ethyl sulfamate;
2-((2S,3S)-3-benzyl-1,4-dioxaspiro[4,4]nonan-2-yl)ethyl sulfamate;
((4S,5S)-5-benzyl-2,2-dimethyl-1,3-dioxolan-4-yl)methyl sulfamate;
((2S,3S)-3-benzyl-1,4-dioxaspiro[4,4]nonan-2-yl)methyl sulfamate;
((4S,5S)-5-phenyl-2,2-dimethyl-1,3-dioxolan-4-yl)ethyl sulfamate;
2-((2S,3S)-3-phenyl-1,4-dioxaspiro[4,4]nonan-2-yl)ethyl sulfamate;
2-((4S,5S)-5-(2-chlorobenzyl)-2,2-dimethyl-1,3-dioxolan-4-yl)ethyl sulfamate;
2-((2S,3S)-3-(2-chlorobenzyl)-1,4-dioxaspiro[4,4]nonan-2-yl)ethyl sulfamate;
((4S,5S)-5-(2-chlorobenzyl)-2,2-dimethyl-1,3-dioxolan-4-yl)methyl sulfamate;
((2S,3S)-3-(2-chlorobenzyl)-1,4-dioxaspiro[4,4]nonan-2-yl)methyl sulfamate;
2-((4S,5S)-5-(2-chlorophenyl)-2,2-dimethyl-1,3-dioxolan-4-yl)ethyl sulfamate;
2-((2S,3S)-3-(2-chlorophenyl)-1,4-dioxaspiro[4,4]nonan-2-yl)ethyl sulfamate;
((4S,5R)-5-(2,4-dichlorothiazol-5-yl)-2,2-dimethyl-1,3-dioxolan-4-yl)methyl sulfamate; and
((4S,5R)-5-(2-chlorothiazol-5-yl)-2,2-dimethyl-1,3-dioxolan-4-yl)methyl sulfamate.

As seen in the Examples, the present inventors have synthesized the compounds of various stereochemistries, and investigated their anti-stress, anti-anxiety and/or anti-depressant activity by multilateral experiments.

The term "enantiomer" as used herein, refers to one of two stereoisomers that are mirror images of each other which are non-superposable due to existence of one or more chiral carbons. According to a concrete embodiment, the enantiomer of the present invention is one in which chiral carbons of $C_4$ and $C_5$ are diverse in stereo-configuration.

The term "diastereomer" as used herein, refers to stereoisomers that are not enantiomers, which occurs when two or more stereoisomers of a compound have different configurations at one or more (but not all) of the equivalent chiral centers thus are not mirror images of each other.

According to a concrete embodiment, a configuration of each chiral center in the compound is (S).

The term "racemate" as used herein, refers to one that has equal amounts of two enantiomers of different stereo-configuration, and lack in optical activity.

It would be obvious to the skilled artisan from the Examples below that the compounds of this invention are not limited to those with specific stereochemistry.

According to a concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethane sulfonate, benzene sulfonate and toluene sulfonate; metal salts by reaction with an alkali metal such as sodium and potassium; or salts with ammonium ion.

In first aspect of the invention, the term "pharmaceutically effective amount" as used herein, refers to an amount enough to show and accomplish efficacies and activities for preventing, alleviating, treating psychiatric disease and/or symptoms associated therewith.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Nonlimiting examples of the formulations include, but are not limited to, a solution, a suspension or an emulsion in oil or aqueous medium, an elixir, a powder, a granule, a tablet and a capsule, and may further comprise a dispersion agent or a stabilizer.

The term "psychiatric disorder" as used herein is used interchangeably with "mental disorder" and is a symptom associated with mental health, affecting mood, thinking and behavior, and it usually occurs as a problem in the brain and is largely divided into psychosis and neurosis. Examples of the former may be schizophrenia, depression and the like, and examples of the latter may be conversion disorder and obsessive-compulsive disorder. Examples of such psychiatric disorders include anxiety disorder including generalized anxiety disorder, phobia (specific phobia, social phobia and agoraphobia), panic disorder, obsessive-compulsive disorder and post traumatic stress disorder (PTSD); mood disorder including depressive disorder and bipolar disorder, somatoform disorder including somatization disorder, conversion disorder, pain disorder, hypochondria and body dysmorphic disorder; dissociative disorder including dissociative amnesia and dissociative identity disorder; psychotic disorder including schizophrenia, schizoaffective disorder and delusional disorder, personality disorder including schizoid personality disorder, borderline personality disorder and obsessive-compulsive personality disorder; sexual disorder and sexual identity disorder; substance-related disorder resulting in addiction to addictive substances including alcohol, tobacco, or drugs; eating disorder including anorexia nervosa and bulimia nervosa; sleep disorder including sleep disturbance and dyssomnia; impulse-control disorder including intermittent explosive disorder, gambling disorder, arsonism and trichotillomania; and adjustment disorder, but are not limited thereto.

According to a preferred embodiment of the present invention, examples of the depressive disorder include major depressive disorder, dysthymic disorder, persistent depressive disorder, premenstrual dysphoric disorder or postpartum depression, but are not limited thereto.

The term "bipolar disorder" as used herein refers to mental disorder that includes an episode of elevated or agitated mood, known as mania, alternating with an episode of depression.

The term "anxiety disorder" as used herein refers to mental disorder characterized by excessive rumination, apprehension, fear, anxiety and worry about future uncertainties based on real or imaginary events.

The term "postpartum depression (PPD)" as used herein is a type of mood disorder associated with childbirth, which can affect both sexes. Symptoms may include extreme sadness, low energy, anxiety, crying episodes, irritability, and changes in sleeping or eating patterns. Onset is typically between one week and one month following childbirth. PPD can also negatively affect the newborn child.

Preferably, the pharmaceutical composition of the present invention has a use in preventing or treating a psychiatric disorder selected from the group consisting of anxiety disorder, depressive disorder, bipolar disorder and schizophrenia, and the depressive disorder includes generalized anxiety disorder, phobia, panic disorder, obsessive-compulsive disorder and post traumatic stress disorder, and the depressive disorder includes postpartum depression.

In the method of the present invention, the term "subject" includes any animal (e.g. humans, horses, pigs, rabbits, dogs, sheep, goats, non-human primates, cows, cats, guinea pigs or rodents), but is not limited thereto. These terms do not refer to a particular age or gender. Accordingly, it is intended to include women/female, men/male, adult/adulthood and newborn subjects, as well as fetuses.

In the method of the present invention, since descriptions regarding the effect of the pharmaceutical composition including the compound of Chemical Formula I or a pharmaceutically acceptable salt thereof, the administration route thereof, the number of times of administration, the administration dosage and the like are the same as described above, the description thereof will be omitted herein.

A first aspect of the present invention also relates to a use of the compound of Chemical Formula I above or a pharmaceutically acceptable salt thereof in the manufacture of a medicament for preventing or treating a psychiatric disorder.

In the use of the present invention, since descriptions regarding the compound of Chemical Formula I or a pharmaceutically acceptable salt thereof and the effect thereof are the same as described above, the description thereof will be omitted herein.

In the use of the present invention, since description regarding psychiatric disorders is the same as described above, the description thereof will be omitted herein.

A second aspect of the present invention relates to a pharmaceutical composition having anti-stress, anti-anxiety or anti-depressant activity, including a compound of Chemical Formula I below or a pharmaceutically acceptable salt thereof as an active ingredient, and a method for inducing anti-stress, anti-anxiety or anti-depressant activity including administering the same to a subject in need thereof at a pharmaceutically effective amount:

[Chemical Formula I]

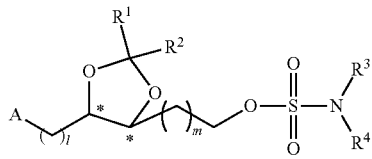

wherein $R^1$ and $R^2$ are each independently selected from the group consisting of hydrogen. $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is an aryl moiety or a heterocyclic moiety optionally substituted by one or more substituents selected from the group consisting of hydrogen, hydroxyl, $C_1$-$C_5$ alkoxy, $C_1$-$C_5$alkyl, $C_2$-$C_5$ alkenyl, $C_1$-$C_{10}$ aryl, $C_1$-$C_5$ alkoxycarbonyl, carboxyl, $C_2$-$C_5$ acyl, $C_1$-$C_5$ alkylthio, cyano, nitro, amine. $C_1$-$C_5$ alkylamine and halogen; $R^3$ and $R^4$ are each independently hydrogen or $C_1$-$C_3$ alkyl; and l and m are each independently an integer of 0~4.

The second aspect of the present invention also relates to a use of the compound of Chemical Formula I above or a pharmaceutically acceptable salt thereof in the manufacture of a medicament for inducing anti-stress, anti-anxiety or anti-depressant activity.

In the second aspect of the present invention, since description regarding the compound of Chemical Formula I above or a pharmaceutically acceptable salt thereof is the same as described in the first aspect, the description thereof will be omitted herein.

In the second aspect of the invention, the term "pharmaceutically effective amount" as used herein refers to an amount enough to show and accomplish anti-stress, anti-anxiety, and/or anti-depressant activities.

In the pharmaceutical composition of the second aspect of the present invention, since pharmaceutically acceptable carriers, administration routes, suitable dosages and the formulation forms are the same as those described in the first aspect, the description thereof will be omitted herein.

In addition, in the method of the second aspect, description regarding the term "subject" is the same as described in the first aspect, and since descriptions regarding the administration route, the number of times of administration, the administration dosage and the like of a pharmaceutical composition including the compound of Chemical Formula I or a pharmaceutically acceptable salt thereof are the same as described in the first aspect, the description thereof will be omitted herein.

The term "anti-stress" as used herein refers to a relief of excessive physical reactions caused by internal or external stimuli of the body or recovery from mental/physical fatigue, and specifically refers to relaxation of tension, relief of anxiety or improvement of concentration.

The terms "anti-anxiety" and "anti-depressant" as used herein refer to activities that are effective for the prevention or treatment of a psychiatric disorder such as anxiety disorder, mood disorder (depressive disorder, bipolar disorder, etc.) and the like. Since mental stress is the cause of a psychiatric disorder such as anxiety or depression, the sulfamate derivative of the present invention that exhibits excellent anti-stress, anti-anxiety and/or anti-depressant activities is effective for the prevention or treatment of various psychiatric disorders. Since the types of various psychiatric disorders are the same as those described in the first aspect, the description thereof will be omitted herein.

The sulfamate derivatives compound of the present invention may be prepared by the following reaction scheme.

[Reaction scheme 1] Synthesis of dioxolan-alcohol compound

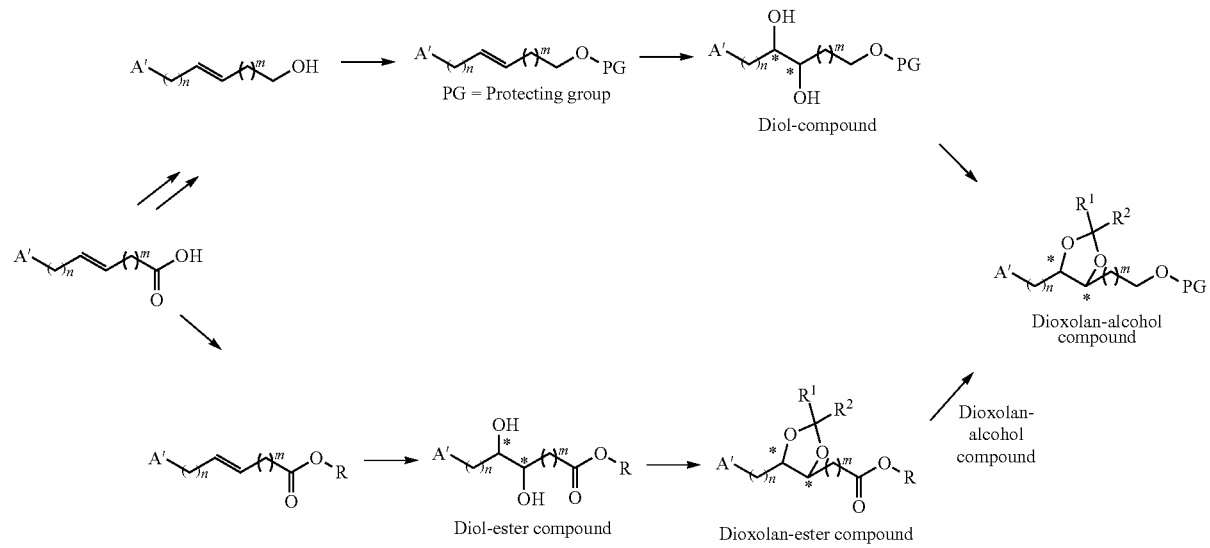

A dioxolan-alcohol compound used in the synthesis of a sulfamate compound is synthesized by dihydroxylation, condensation and a deprotection reaction.

[Reaction scheme 2] Synthesis of alcohol compound

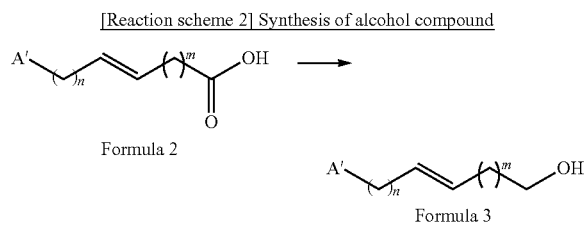

Formula 2

Formula 3

An alcohol compound of formula 3 is synthesized by a reduction reaction using a reducing agent, including but not limited to, LiAlH$_4$(Lithium aluminum hydride), NaBH$_4$ (Sodium borohydride), Zn(BH$_4$)$_2$ (Zincborohydride), NaH (Sodium hydride), KH (Potassium hydride), AlH$_3$ (Aluminum hydride), and NaOMe (Sodiummethoxyde) in a basic condition from the Carboxylic acid compound of formula 2.

[Reaction scheme 3] Synthesis of protected alcohol compound

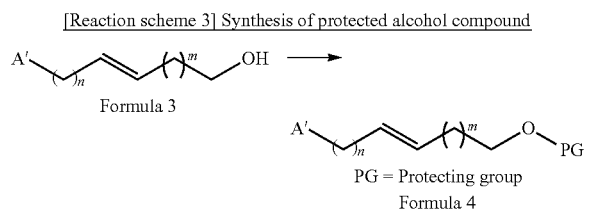

Formula 3

PG = Protecting group
Formula 4

OH of an alcohol compound of formula 3 is protected by a protecting group, including but not limited to, TMS (Trimethyl silyl), TES (Triethyl silyl). TIPS (Triisopropyl silyl), TBDMS (tert-butyldimethyl silyl), TBDPS (tert-butyldiphenyl silyl), Piv (Pivaloyl), MOM (Methoxymethyl). Acetyl, Benzoyl, and Tityl (Triphenylmethyl) in a basic condition for using in a next reaction.

[Reaction scheme 4] Synthesis of diol compound

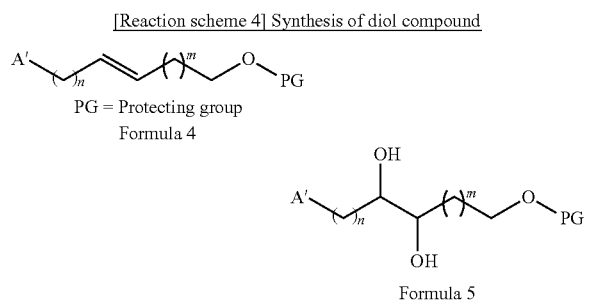

PG = Protecting group
Formula 4

Formula 5

The asymmetric dihydroxylation catalyst may be one or more selected from the group consisting of a chiral ligand (e.g., (DHQD)$_2$PHAL, (DHQ)$_2$PHAL, etc.), an osmium catalyst (e.g., OsO$_4$, K$_2$OsO$_2$(OH)$_4$, etc.), K$_2$CO$_3$, K$_3$Fe(CN)$_6$, N-methylmorpholine oxide (NMO), methane sulfone amide (CH$_3$SO$_2$NH$_2$), and the like. For example, the asymmetric dihydroxylation catalyst may be AD-mix-α (K$_2$OsO$_2$(OH)$_4$(cat), K$_2$CO$_3$, K$_3$Fe(CN)$_6$, (DHQ)$_2$PHAL(cat)) and methane sulfone amide (CH$_3$SO$_2$NH$_2$), or OsO$_4$ and N-methylmorpholine oxide (NMO), it is not limited thereto and may be appropriately selected depending on the intended purpose.

[Reaction scheme 5] Synthesis of dioxolan-alcohol compound

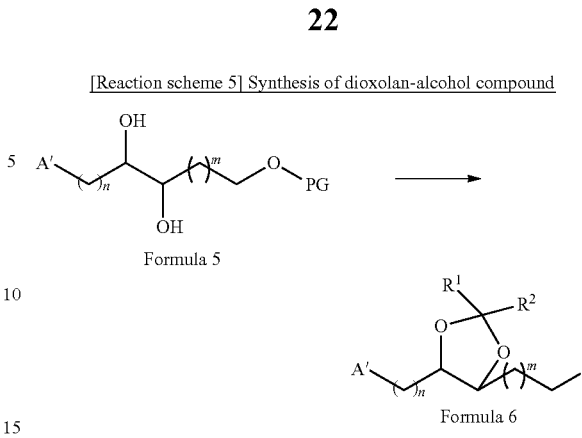

Formula 5

Formula 6

A diol compound of formula 5 is reacted with a ketone compound (such as acetone, 3-pentanone, cyclopentanone, or cyclohexanone), an alkoxy compound (such as dimethoxypropan, diethoxyethane, or methoxy propene), or an aldehyde compound (such as benzaldyde, cyclopentanecarboxaldehyde, or cyclohexaecarboxaldehyde) in an acidic condition, for example, a solution dissolved with an acid such as p-TsOH (p-toluenesulfonic acid), H$_2$SO$_4$ (Sulfuric acid), HNO$_3$ (Nitric acid), followed by removing a protecting group to afford the Dioxolan-alcohol compound of formula 6. But while we have described several examples of the ketone compound, the alkoxy compound, the aldehyde compound and the acid for the above reaction, it is not limited thereto and may be appropriately selected depending on the intended purpose.

[Reaction scheme 6] Synthesis of ester compound

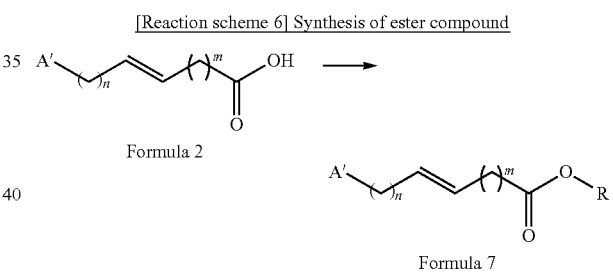

Formula 2

Formula 7

An ester compound of formula 7 having R selected from the group consisting of linear or branched C$_1$-C$_{10}$ alkyl, or cyclic C$_3$-C$_{10}$ alkyl, allyl and benzyl is synthesized by an esterification reaction in an acidic condition from the carboxylic acid compound of formula 2.

[Reaction scheme 7] Synthesis of ester-diol compound

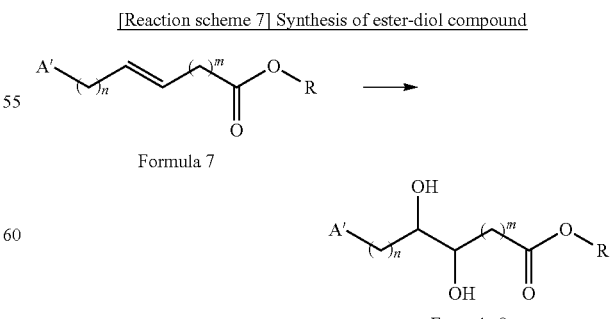

Formula 7

Formula 8

The asymmetric dihydroxylation catalyst may be one or more selected from the group consisting of a chiral ligand (e.g., (DHQD)$_2$PHAL, (DHQ)$_2$PHAL, etc.), an osmium catalyst (e.g., OsO$_4$, K$_2$OsO$_2$(OH)$_4$, etc.). K$_2$CO$_3$, K$_3$Fe(CN)$_6$, N-methylmorpholine oxide (NMO), methane sulfone amide (CH$_3$SO$_2$NH$_2$), and the like. For example, the asymmetric dihydroxylation catalyst may be AD-mix-α (K$_2$OsO$_2$(OH)$_4$(cat), K$_2$CO$_3$, K$_3$Fe(CN)$_6$, (DHQ)$_2$PHAL(cat)) and methane sulfone amide (CH$_3$SO$_2$NH$_2$), or OsO$_4$ and N-methylmorpholine oxide (NMO), it is not limited thereto and may be appropriately selected depending on the intended purpose.

[Reaction scheme 8] Synthesis of dioxolan-ester compound

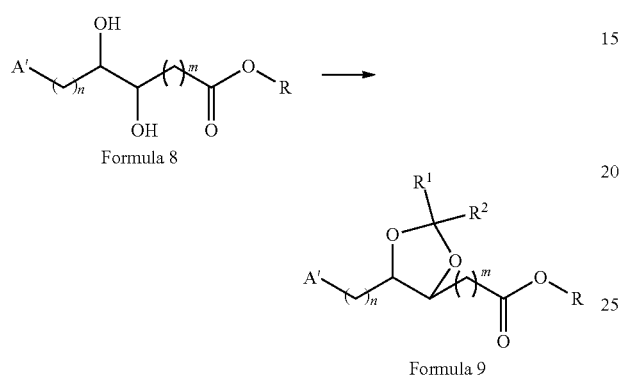

Formula 9

A diol compound of formula 8 is reacted with a ketone compound (such as acetone, 3-pentanone, cyclopentanone, or cyclohexanone), an alkoxy compound (such as dimethoxypropan, diethoxyethane, 3-methoxypente-2-ene, 1-methoxycyclopent-1-ene, 1-methoxycyclohex-1-ene or methoxy propene), or an aldehyde compound (such as benzaldyde, cyclopentanecarboxaldehyde, or cyclohexaecarboxaldehyde) in an acidic condition, for example, a solution dissolved with an acid such as pTsOH (p-toluenesulfonic acid), H$_2$SO$_4$(Sulfuric acid), HNO$_3$(Nitric acid) to afford the Dioxolan-alcohol compound of formula 9. But while we have described several examples of the ketone compound, the alkoxy compound, the aldehyde compound and the acid for the above reaction, it is not limited thereto and may be appropriately selected depending on the intended purpose.

[Reaction scheme 9] Synthesis of dioxolan-alcohol compound

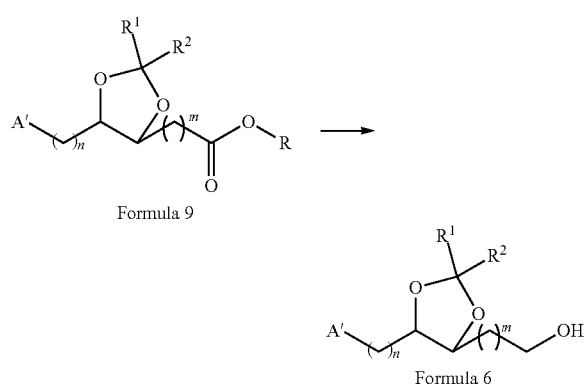

Formula 6

A dioxolan-alcohol compound of formula 6 is synthesized by a reduction reaction using a reducing agent, including but not limited to, LiAlH$_4$(Lithium aluminum hydride), NaBH$_4$ (Sodium borohydride), Zn(BH$_4$)$_2$ (Zincborohydride), NaH (Sodium hydride), KH (Potassium hydride), AlH$_3$ (Aluminum hydride), and NaOMe (Sodiummethoxyde) in a basic condition from the dioxolan-ester compound of formula 9.

[Reaction scheme 10] Synthesis of Sulfamate compound

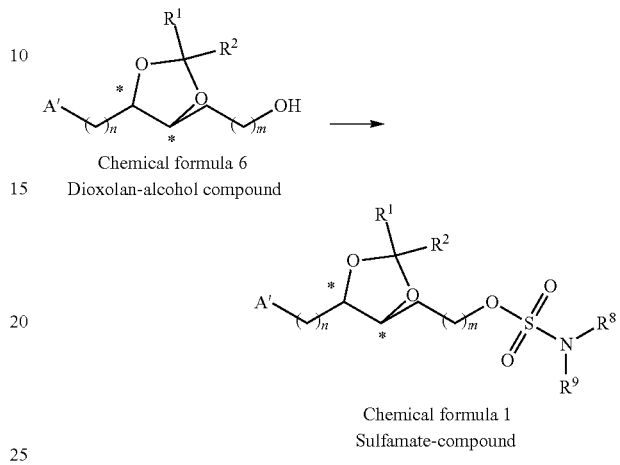

Chemical formula 1
Sulfamate-compound

A dioxolan-alcohol compound of formula 6 is reacted with sulfamide or sulfamoyl chloride in a basic condition using a base, including but not limited to, pyridine, piperidine, and piperazine to produce the sulfamate compound of formula 1.

Hereinafter, the present invention will be described in detail through examples. However, since the present invention can be modified in various ways and have various forms, specific examples and descriptions described below are only to help understanding the present invention, and do not limit the present invention to specific disclosure forms. It is to be understood that the scope of the present invention includes all modifications, equivalents and substitutes included in the spirit and scope of the present invention.

MODE FOR THE INVENTION

Preparation Example 1: (E)-3-(2-chlorophenyl)prop-2-en-1-ol

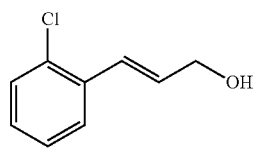 [SMILES: OC/C=C/c1ccccc1Cl]

To a 100 mL round-bottomed flask, 2-Chlorocinnamic acid (5.0 g, 7.3 mmol) and THF (20 mL) were added and the reaction mixture was cooled to 0° C. Triethylamine (4.2 mL, 30.1 mmol) and Ethyl chloroformate (2.88 mL, 30.1 mmol) were added. The reaction mixture was precipitated as a white solid during stirring. After 2 hr, the reaction mixture was filtered with THF (white solid+yellow solution).

The yellow solution was added dropwise to Sodium borohydride (2.68 g, 142.3 mmol) in H$_2$O at 0° C. and stirred for 2 hrs, quenched with 1 N HCl solution. The reaction mixture was extracted by EtOAc and washed with H$_2$O. The combined organic extracts were dried over anhydrous magnesium sulfate (MgSO$_4$), filtered and concentrated under vacuum. The crude compound was purified by a silica gel column to produce the title compound (2.96 g, 60~70%).

$^1$H NMR (400 MHz, CDCl$_3$) δ 1.67 (s, 1H), 4.39 (t, J=4.0 Hz, 2H), 6.37 (dt J=5.6, 16.0 Hz, 1H), 7.03 (d, J=16.0 Hz, 1H), 7.18~7.38 (m, 4H).

Preparation Example 2: (E)-1-chloro-2-(3-(methoxymethoxy)prop-1-enyl)benzene

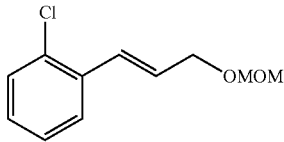

To a 250 mL round-bottomed flask, (E)-3-(2-chlorophenyl)prop-2-en-1-ol (2.96 g, 17.5 mmol, Preparation example 1) and Dichloromethane (17.5 mL) were added and the reaction mixture was cooled to 0° C. Diisopropylethylamine (6.1 mL, 35.1 mmol) was added and stirred at 0° C. Methyl chloromethyl ether (2.77 mL, 35.1 mmol) was added dropwise and stirred for overnight. The reaction mixture was quenched with 1 N NaOH solution, extracted by dichloromethane. The combined organic extracts were dried over anhydrous magnesium sulfate (MgSO$_4$), filtered and concentrated under vacuum. The crude compound was purified by a silica gel column to produce the title compound (3.43 g, 85~95%).

$^1$H NMR (400 MHz, CDCl$_3$) δ 3.44 (s, 3H), 4.30 (dd, J=1.6, 8.0 Hz, 1H), 4.73 (s, 2H), 6.30 (1H, dt, J=6.0, 16.0 Hz), 7.04 (d, J=16.0 Hz, 1H), 7.20~7.57 (m, 4H).

Preparation Example 3: (1R,2R)-1-(2-chlorophenyl)-3-(methoxymethoxy)propane-1,2-diol

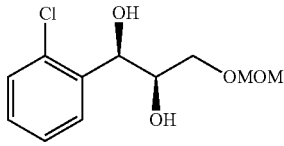

A 250 mL round-bottomed flask, equipped with a magnetic stirrer, was filled with 80 mL of tert-butyl alcohol, 80 mL of water, and K$_3$Fe(CN)$_6$ (15.93 g, 48.3 mmol), K$_2$CO$_3$ (6.7 g, 48.3 mmol), (DHQD)$_2$-PHAL (0.12 g, 0.16 mmol), K$_2$OsO$_2$(OH)$_4$, (11.8 mg, 0.03 mmol), and Methanesulfonamide (1.53 g, 16.1 mmol). Stirring at 0° C. (E)-1-chloro-2-(3-(methoxymethoxy)prop-1-enyl)benzene (3.43 g, 16.1 mmol, Preparation example 2) was added at once, and the mixture was stirred vigorously at 0° C. overnight. While the mixture was stirred at 0° C., solid sodium sulfite (Na$_2$SO$_3$, 24.4 g, 193.5 mmol) was added and the mixture was allowed to warm to room temperature. Ethyl acetate was added to the reaction mixture, and after the separation of the layers, the aqueous phase was further extracted with the organic solvent. The combined organic layers were washed with 2 N KOH. The combined organic extracts were dried over anhydrous magnesium sulfate (MgSO$_4$), filtered and concentrated under vacuum.

The crude compound was purified by a silica gel column to produce the title compound (3.31 g, 75~90%).

$^1$H NMR (400 MHz, CDCl$_3$) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 1H).

Preparation Example 4: (1S,2S)-1-(2-chlorophenyl)-3-(methoxymethoxy)propane-1,2-diol

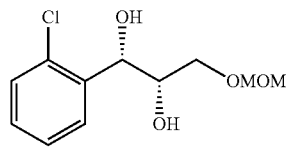

The substantially same method as described in Preparation Example 3 was conducted, except that (DHQ)?-PHAL was used instead of (DHQD)$_2$-PHAL, to obtain the title compound. 3.1 g (75~90%).

$^1$H NMR (400 MHz, CDCl$_3$) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 4H).

Preparation Example 5: 1-(2-chlorophenyl)-3-(methoxymethoxy)propane-1,2-diol

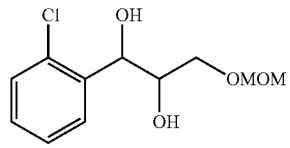

(E)-1-chloro-2-(3-(methoxymethoxy)prop-1-enyl)benzene (9.1 g. Preparation Example 2) was dissolved in 45 mL of a mixture of acetone/t-BuOH/H$_2$O (5:1:1 V/V).

At room temperature, N-methylmorpholine-N-oxide (7.51 g) and OsO$_4$ (0.54 g) were added thereto and stirred for 2~3 hours. When the reaction was completed, the obtained product was washed with water and methylenechloride (MC). Then, the organic layer was dehydrated with anhydrous magnesium sulfate (MgSO$_4$), filtrated, and concentrated under reduced pressure. The crude compound was purified by a silica gel column to produce the title compound (7.42 g, 70~90%).

$^1$H NMR (400 MHz, CDCl$_3$) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t. J=4.4, 1H), 7.23~7.61 (m, 4H).

Preparation Example 6: ((4R,5R)-5-(2-chlorophenyl)-2,2-dimethyl-1,3-dioxolan-4-yl)methanol

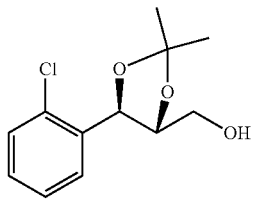 [SMILES: CC1(C)O[C@H](c2ccccc2Cl)[C@@H](CO)O1]

To (1R,2R)-1-(2-chlorophenyl)-3-(methoxymethoxy)propane-1,2-diol (3.31 g, 13.4 mmol, Preparation example 3). Dichloromethane was added and cooled to 0° C. 2,2-Dimethoxypropane (3.3 mL, 26.8 mmol) and p-toluenesulfonic acid (2.0 g, 10.7 mmol) was added and stirred at room temperature for 5 hrs. The reaction mixture was quenched with H$_2$O, extracted with DCM, and washed with H$_2$O. The organic layer was dried over anhydrous magnesium sulfate (MgSO$_4$), filtered and concentrated. The crude compound was purified by a silica gel column to produce the title compound (1.05 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 7: ((4S,5S)-5-(2-chlorophenyl)-2,2-dimethyl-1,3-dioxolan-4-yl)methanol

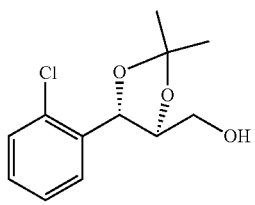 [SMILES: CC1(C)O[C@@H](CO)[C@H](c2ccccc2Cl)O1]

The substantially same method as described in Preparation Example 6 was conducted, except that (1S,2S)-1-(2-chlorophenyl)-3-(methoxymethoxy)propane-1,2-diol (Preparation example 4) was used instead of (1R,2R)-1-(2-chlorophenyl)-3-(methoxymethoxy)propane-1,2-diol (Preparation example 3), to obtain the title compound (1.1 g, 30~40%).

$^1$H NMR (400 MHz, CDCl$_3$) δ 1.57 (s, 3H), 1.64 (s, 3H), 1.98 (m, 1H), 3.76~3.83 (m, 1H), 3.88~3.90 (m, 2H), 5.41 (d, J=8.4 Hz, 1H), 7.25~7.66 (m, 4H).

Preparation Example 8: (5-(2-chlorophenyl)-2,2-dimethyl-1,3-dioxolan-4-yl)methanol

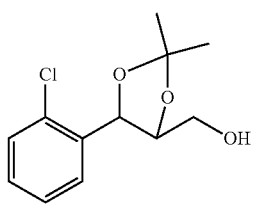 [SMILES: CC1(C)OC(CO)C(c2ccccc2Cl)O1]

The substantially same method as described in Preparation Example 6 was conducted, except that 1-(2-chlorophenyl)-3-(methoxymethoxy)propane-1,2-diol (Preparation example 5) was used instead of (1R,2R)-1-(2-chlorophenyl)-3-(methoxymethoxy)propane-1,2-diol (Preparation example 3), to obtain the title compound (2.1 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 9: (E)-3-(2-fluorophenyl)-acrylic Acid

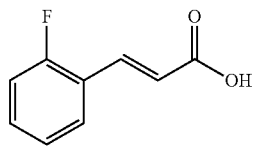

Piperidine (247 mg, 2.90 mmol) was added to a stirred solution of malonic acid (3.1 g, 29.0 mmol) and 2-fluoroaldehyde (3.0 g, 24.17 mmol) in pyridine at room temperature under N$_2$ condition. The solution was cooled to room temperature, then quenched with HCl solution. The residue was treated with EA and H$_2$O. The organic layer was separated and the aqueous layer was extracted further with EA. The combined extracts were washed with brine. The organic layer was dried over Na$_2$SO$_4$, filtered and concentrated. The crude compound was purified by a silica gel column to produce the title compound (3.66 g, 70~90%).

$^1$H NMR (400 MHz, CDCl$_3$) δ 6.60 (d, J=16.0 Hz, 1H), 7.24~7.50 (m, 3H), 7.66 (d, J=16.0 Hz, 1H), 7.84 (t, J=8.0 Hz, 1H).

Preparation Example 10: (E)-3-(2-fluorophenyl)-prop-2-en-1-ol

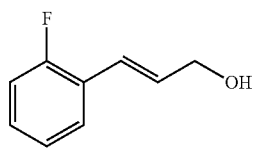

The substantially same method as described in Preparation Example 1 was conducted, except that (E)-3-(2-fluorophenyl)-acrylic acid (Preparation example 9) was used instead of 2-Chlorocinnamic acid, to obtain the title compound (1.6 g, 30~40%).

$^1$H NMR (400 MHz, CDCl$_3$) δ 1.67 (s, 1H), 4.39 (t, J=4.0 Hz, 2H), 6.34~6.41 (m, 1H), 7.00~7.38 (m, 4H).

Preparation Example 11: (E)-1-Fluoro-2-(3-(methoxymethoxy)prop-1-enyl)benzene

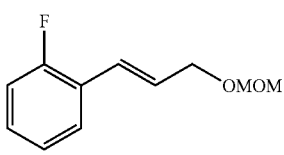

The substantially same method as described in Preparation Example 2 was conducted, except that (E)-3-(2-fluorophenyl)-prop-2-en-1-ol (Preparation example 10) was used instead of (E)-3-(2-chlorophenyl)-prop-2-en-1-ol (Preparation example 1), to obtain the title compound (2.23 g, 85~95%).

¹H NMR (400 MHz, CDCl₃) δ 3.44 (s, 3H), 4.30 (dd, J=1.6, 8.0 Hz, 1H), 4.73 (s, 2H), 6.27~6.37 (m, 1H), 7.02~7.57 (m, 4H).

Preparation Example 12: (1R,2R)-1-(2-fluorophenyl)-3-(methoxymethoxy)propane-1,2-diol

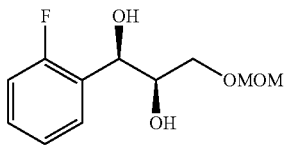

The substantially same method as described in Preparation Example 3 was conducted, except that (E)-1-Fluoro-2-(3-(methoxymethoxy)prop-1-enyl)benzene (Preparation example 11) was used instead of (E)-1-chloro-2-(3-(methoxymethoxy) prop-1-enyl)benzene (Preparation example 2), to obtain the title compound (2.13 g, 75~90%).

¹H NMR (400 MHz, CDCl₃) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 4H).

Preparation Example 13: ((4R,5R)-5-(2-fluorophenyl)-2,2-dimethyl-1,3-dioxolan-4-yl)methanol

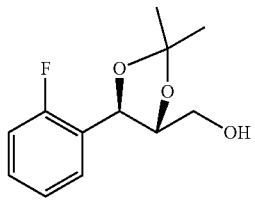

The substantially same method as described in Preparation Example 6 was conducted, except that (1R,2R)-1-(2-fluorophenyl)-3-(methoxymethoxy)propane-1,2-diol (Preparation example 12) was used instead of (1R,2R)-1-(2-chlorophenyl)-3-(methoxymethoxy)propane-1,2-diol (Preparation example 3), to obtain the title compound (1.73 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 14: (1S,2S)-1-(2-fluorophenyl)-3-(methoxymethoxy)propane-1,2-diol

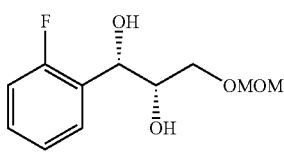

The substantially same method as described in Preparation Example 4 was conducted, except that (E)-1-Fluoro-2-(3-(methoxymethoxy)prop-1-enyl)benzene (Preparation example 11) was used instead of (E)-1-chloro-2-(3-(methoxymethoxy)prop-1-enyl)benzene (Preparation example 2), to obtain the title compound (2.13 g, 75~90%).

¹H NMR (400 MHz, CDCl₃) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 4H).

Preparation Example 15: ((4S,5S)-5-(2-fluorophenyl)-2,2-dimethyl-1,3-dioxolan-4-yl)methanol

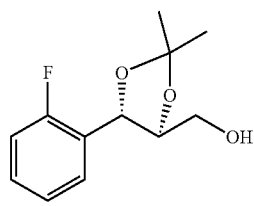

The substantially same method as described in Preparation Example 6 was conducted, except that (1S,2S)-1-(2-fluorophenyl)-3-(methoxymethoxy)propane-1,2-diol (Preparation example 14) was used instead of (1R,2R)-1-(2-chlorophenyl)-3-(methoxymethoxy)propane-1,2-diol (Preparation example 3), to obtain the title compound (1.73 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 16: 2-Iodobenzenealdehyde

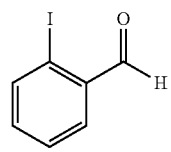

in a flask, 2-iodobenzyl alcohol (4.0 g, 17.09 mmol) was dissolved in dichloromethane (MC, 85 mL), and then, manganese oxide (MnO₂, 14.86 g, 170.92 mmol) was added thereto. The obtained reaction product was stirred under reflux. When the reaction was completed, the obtained reaction product was cooled to room temperature, and then, filtered and concentrated using celite, to obtain the title compound (3.6 g, yield 75~90%).

¹H NMR (400 MHz, CDCl₃) δ 7.30~7.99 (m, 4H), 10.10 (s, 1H).

Preparation Example 17: (E)-3-(2-iodophenyl)-acrylic Acid

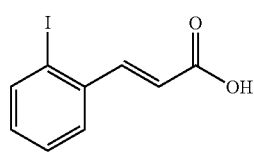 [SMILES: O=C(O)/C=C/c1ccccc1I]

The substantially same method as described in Preparation Example 9 was conducted, except that 2-Iodobenzenealdehyde (Preparation example 16) was used instead of 2-Fluoroaldehyde, to obtain the title compound (2.06 g, 70~90%).

¹H NMR (400 MHz, CDCl₃) δ 6.60 (d, J=16.0 Hz, 1H), 7.24~7.50 (m, 3H), 7.66 (d, J=16.0 Hz, 1H), 7.84 (t, J=8.0 Hz, 1H).

Preparation Example 18: (E)-3-(2-iodophenyl)-prop-2-en-1-ol

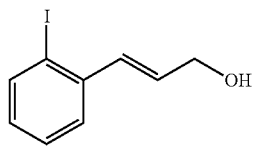 [SMILES: OC/C=C/c1ccccc1I]

The substantially same method as described in Preparation Example 1 was conducted, except that (E)-3-(2-iodophenyl)-acrylic acid (Preparation example 17) was used instead of 2-Chlorocinnamic acid, to obtain the title compound (1.08 g, 30~40%).

¹H NMR (400 MHz, CDCl₃) δ 1.67 (s, 1H), 4.39 (t, J=4.0 Hz, 2H), 6.34~6.41 (m, 1H), 7.00~7.38 (m, 4H).

Preparation Example 19: (E)-1-Iodo-2-(3-(methoxymethoxy)prop-1-enyl)benzene

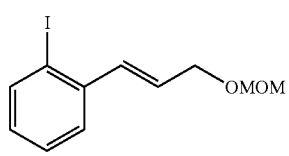

The substantially same method as described in Preparation Example 2 was conducted, except that (E)-3-(2-iodophenyl)-prop-2-en-1-ol (Preparation example 18) was used instead of (E)-3-(2-chlorophenyl)-prop-2-en-1-ol (Preparation example 1), to obtain the title compound (1.37 g, 85~95%).

¹H NMR (400 MHz, CDCl₃) δ 3.44 (s, 3H), 4.30 (dd, J=1.6, 8.0 Hz, 1H), 4.73 (s, 2H), 6.27~6.34 (m, 1H), 7.02~7.57 (m, 4H).

Preparation Example 20: (1R,2R)-1-(2-Iodophenyl)-3-(methoxymethoxy)propane-1,2-diol

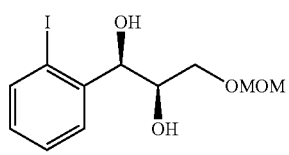

The substantially same method as described in Preparation Example 3 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).

¹H NMR (400 MHz, CDCl₃) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 4H).

Preparation Example 21: ((4R,5R)-5-(2-iodophenyl)-2,2-dimethyl-1,3-dioxolan-4-yl)methanol

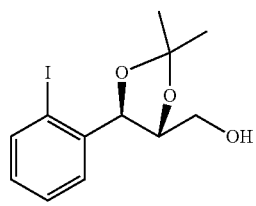 [SMILES: CC1(C)O[C@H](c2ccccc2I)[C@@H](CO)O1]

The substantially same method as described in Preparation Example 6 was conducted, except that (1R,2R)-1-(2-iodophenyl)-3-(methoxymethoxy)propane-1,2-diol (Preparation example 20) was used instead of (1R,2R)-1-(2-chlorophenyl)-3-(methoxymethoxy)propane-1,2-diol (Preparation example 3), to obtain the title compound (1.33 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 22: (1S,2S)-1-(2-iodophenyl)-3-(methoxymethoxy)propane-1,2-diol

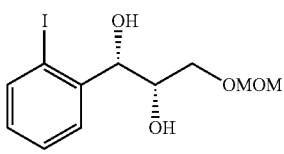

The substantially same method as described in Preparation Example 4 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).

¹H NMR (400 MHz, CDCl₃) δ 3.09 (d, J=5.6 Hz, 1H), 3.27 (d, J=4.4 Hz, 1H), 3.41 (s, 3H), 3.69~3.77 (m, 2H), 3.96~3.99 (m, 1H), 4.69 (s, 2H), 5.19 (t, J=4.4 Hz, 1H), 7.23~7.61 (m, 4H).

Preparation Example 23: ((4S,5S)-5-(2-iodophenyl)-2,2-dimethyl-1,3-dioxolan-4-yl)methanol

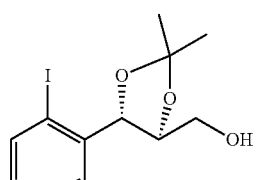

The substantially same method as described in Preparation Example 6 was conducted, except that (1S,2S)-1-(2-iodophenyl)-3-(methoxymethoxy)propane-1,2-diol (Preparation example 22) was used instead of (1R,2R)-1-(2-chlorophenyl)-3-(methoxymethoxy)propane-1,2-diol (Preparation example 3), to obtain the title compound (1.33 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4 Hz, 1H), 7.25~7.66 (m, 4H).

Preparation Example 24:
(E)-Methyl-3-(2-chlorophenyl)acrylate

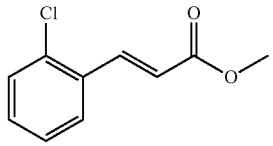

To a 250 mL round-bottomed flask, 2-Chlorocinnamic acid (25.0 g, 136.9 mmol) and MeOH (56 mL) were added. POCl$_3$ (1.27 mL, 13.6 mmol) was added dropwise. The reaction mixture was stirred under reflux for 3~4 h. The reaction mixture was cooled to room temperature, quenched with 1 N NaOH solution. The mixture was extracted by EtOAc and washed with H$_2$O. The aqueous layer was further extracted with EtOAc. The combined organic layer was dried over anhydrous magnesium sulfate (MgSO$_4$), filtered and concentrated under vacuum (26.98 g, 85~97%).

$^1$H NMR (400 MHz, CDCl$_3$) δ 3.84 (s, 3H), 6.45 (d, J=16.0 Hz, 1H), 7.28~7.65 (m, 4H), 8.12 (d, J=16.0 Hz, 1H).

Preparation Example 25: (2R,3S)-methyl-3-(2-chlorophenyl)-2,3-dihydroxypropanoate

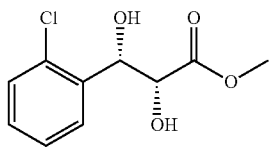

A 1000 mL round-bottomed flask, equipped with a magnetic stirrer, was filled with 362 mL of tert-butyl alcohol, 362 mL of water, K$_3$Fe(CN)$_6$ (135.53 g, 411.63 mmol), K$_2$CO$_3$ (56.89 g, 411.63 mmol), (DHQ)$_2$PHAL (1.06 g, 1.37 mmol), K$_2$OsO$_2$(OH)$_4$ (0.1 g, 0.27 mmol), and Methanesulfonamide (13.05 g, 137.21 mmol) and stirred at 0° C. (E)-Methyl-3-(2-chlorophenyl)acrylate (26.98 g, Preparation example 24) was added at once, and the mixture was stirred vigorously at 0° C. overnight. While the mixture was stirred at 0° C., solid sodium sulfite (Na$_2$SO$_3$, 24.4 g, 193.5 mmol), EtOAc and water was added and the mixture was allowed to warm to room temperature and stirred. After the separation of the layer, the aqueous layer was added to EtOAc, and the aqueous layer was separated. The combined organic layers were washed with 0.3 M H$_2$SO$_4$/Na$_2$SO$_4$ solution (H$_2$SO$_4$ 76 mL, H$_2$O 2 L, Na$_2$SO$_4$ 360.0 g) twice. After separation of the organic layer, the organic layer was washed with H$_2$O. After separating of the layer, the organic layer were dried over anhydrous MgSO$_4$, filtered and concentrated under vacuum. The crude compound was purified by a silica gel column to produce the title compound (24.42 g, 70~90%).

$^1$H NMR (400 MHz, CDCl$_3$) δ 7.62~7.26 (4H, m), 5.51 (1H, dd, J=2.4, 7.2 Hz), 4.50 (1H dd, J=2.4, 5.6 Hz), 3.86 (3H, s), 3.13 (1H, d, J=6.0 Hz), 2.79 (1H, d, J=7.2 Hz).

Preparation Example 26: (4R,5S)-methyl-5-(2-chlorophenyl)-2,2-dimethyl-1,3-dioxolane-4-carboxylate

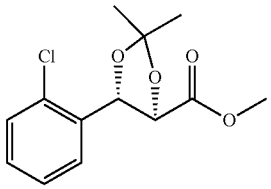 [SMILES: COC(=O)[C@@H]1OC(C)(C)O[C@H]1c1ccccc1Cl]

Dichloromethane (DMC) was added to (2R,3S)-methyl-3-(2-chlorophenyl)-2,3-dihydroxypropanoate (24.4 g, Preparation example 25) and cooled to 0°. 2,2-Dimethoxypropane (26 mL, 211.77 mmol) and p-toluenesulfonic acid (2.0 g, 10.58 mmol) was added and stirred at room temperature. The reaction mixture was quenched with H$_2$O, extracted with DCM, washed with H$_2$O, dried over anhydrous magnesium sulfate, filtered and concentrated. The crude compound was purified by a silica gel column to produce the title compound (23.6 g, 70~95%).

$^1$H NMR (400 MHz, CDCl$_3$) δ 1.63 (s, 3H), 1.65 (s, 3H), 3.78 (s, 3H), 4.30 (d, J=7.6 Hz, 1H), 5.62 (d, J=7.6 Hz, 1H), 7.28~7.64 (m, 4H).

Preparation Example 27: ((4S,5S)-5-(2-chlorophenyl)-2,2-dimethyl-1,3-dioxolane-4-yl)methanol

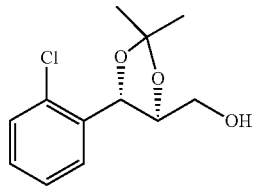 [SMILES: CC1(C)O[C@@H](CO)[C@H](c2ccccc2Cl)O1]

A solution of To a solution LAH (LiAlH$_4$ 3.31 g, 87.25 mmol) in THF was added dropwise to a solution of (4R, 5S)-methyl 5-(2-chlorophenyl)-2,2-dimethyl-1,3-dioxolane-4-carboxylate (23.6 g, Preparation 26) in THF at 0° C., and the mixture stirred at room temp. The reaction mixture was quenched with H$_2$O at 0° C., celite filtered with EtOAc, washed with EtOAc, dried over anhydrous magnesium sulfate (MgSO$_4$), filtered and concentrated. The crude compound was purified by a silica gel column to produce the title compound (21.13 g 70~95%).

$^1$H NMR (400 MHz, CDCl$_3$) δ 1.57 (s, 3H), 1.64 (s, 3H), 1.98 (m, 1H), 3.76~3.83 (m, 1H), 3.88~3.90 (m, 2H), 5.41 (d, J=8.4 Hz, 1H), 7.25~7.66 (m, 4H).

Preparation Example 28:
(E)-Methyl-3-(2,4-dichlorophenyl)acrylate

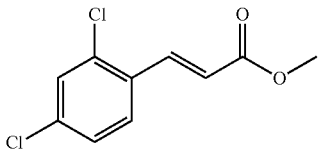

The substantially same method as described in Preparation Example 24 was conducted, except that 2,4-dichlorocinnamic acid was used instead of 2-chlorocinnamic acid, to obtain the title compound (9.7 g, 70~90%).
$^1$H NMR (400 MHz, CDCl$_3$) δ 3.84 (s, 3H), 6.44 (d, J=16.0 Hz, 1H), 7.28~7.33 (m, 1H), 7.41 (d, J=2.0 Hz, 1H), 7.55 (d, J=8.4 Hz, 1H), 8.04 (d, J=16.0 Hz, 1H).

Preparation Example 29: (2R,3S)-methyl-3-(2,4-dichlorophenyl)-2,3-dihydroxypropanoate

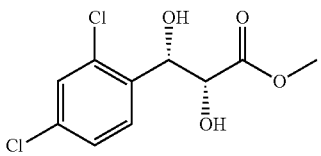 [SMILES: COC(=O)[C@H](O)[C@@H](O)c1ccc(Cl)cc1Cl]

The substantially same method as described in Preparation Example 25 was conducted, except that (E)-Methyl-3-(2,4-dichlorophenyl)acrylate (Preparation example 28) was used instead of (E)-Methyl-3-(2-chlorophenyl)acrylate (Preparation example 24), to obtain the title compound (3.8 g, 60~80%).
$^1$H NMR (400 MHz, CDCl$_3$) δ 3.11 (s, 1H), 3.88 (s, 3H), 4.42 (d, J=2.4 Hz, 1H), 5.43 (d, J=2.0 Hz, 1H), 7.28~7.33 (m, 1H), 7.41 (d, J=2.0 Hz, 1H), 7.55 (d, J=8.4 Hz, 1H).

Preparation Example 30: (4R,5S)-methyl-5-(2,4-dichlorophenyl)-2,2-dimethyl-1,3-dioxolane-4-carboxylate

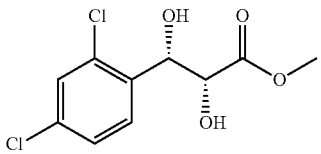 [SMILES: COC(=O)[C@H](O)[C@@H](O)c1ccc(Cl)cc1Cl]

The substantially same method as described in Preparation Example 26 was conducted, except that (2R,3S)-methyl-3-(2,4-dichlorophenyl)-2,3-dihydroxypropanoate (Preparation example 29) was used instead of (2S,3R)-methyl-3-(2-chlorophenyl)-2,3-dihydroxypropanoate (Preparation example 25), to obtain the title compound (3.5 g, 60~80%).
$^1$H NMR (400 MHz, CDCl$_3$) δ 1.59 (s, 3H), 1.63 (d, J=8.8 Hz, 3H), 3.78 (s, 3H), 4.25 (d, J=7.6 Hz, 1H), 5.56 (d, J=8.0 Hz, 1H), 7.28~7.33 (m, 1H), 7.41 (d, J=2.0 Hz, 1H), 7.56 (d, J=8.4 Hz, 1H).

Preparation Example 31: ((4S,5S)-5-(2,4-dichlorophenyl)-2,2-dimethyl-1,3-dioxolane-4-yl)methanol

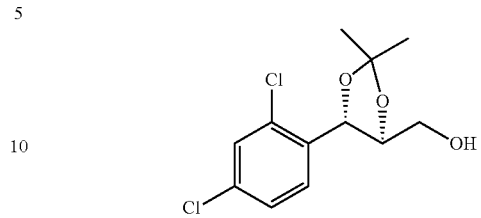

The substantially same method as described in Preparation Example 27 was conducted, except that (4R,5S)-methyl-5-(2,4-dichlorophenyl)-2,2-dimethyl-1,3-dioxolane-4-carboxylate (Preparation example 30) was used instead of (4S,5R)-methyl-5-(2-chlorophenyl)-2,2-dimethyl-1,3-dioxolane-4-carboxylate (Preparation example 26), to obtain the title compound (3.2 g, 70~95%).
$^1$H NMR (400 MHz, CDCl$_3$) δ 1.56 (s, 3H), 1.62 (d, J=4.8 Hz, 6H), 1.97 (dd, J=7.2, 7.6 Hz, 1H), 3.75~3.80 (m, 1H), 3.82~3.86 (m, 1H), 3.89~3.94 (m, 1H), 5.36 (d, J=8.4 Hz, 1H), 7.28~7.33 (m, 1H), 7.41 (d, J=2.0 Hz, 1H), 7.56 (d, J=8.4 Hz, 1H).

Preparation Example 32:
(E)-Ethyl-3-(2,6-dichlorophenyl)acrylate

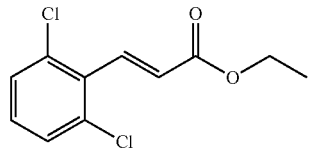

To a stirred solution of 2,6-dichlorobenzaldehyde (5.0 g, 28.56 mmol) in THF was added triethyl phosphono acetate (6.4 g, 28.56 mmol) at 0° C. The reaction mixture was added t-BuOK (3.2 g, 28.56 mmol) at room temperature. The mixture was stirred for 10 h then the resulting mixture was quenched with 1 N HCl, diluted with ether, washed with water, dried over MgSO$_4$, filtered, and concentrated under reduced pressure. The crude product was purified by SiO$_2$ gel column chromatography (4.3 g, 40~60%).
$^1$H NMR (400 MHz, CDCl$_3$) δ 1.36 (t, J=3.6 Hz, 3H), 4.31 (q, J=3.7 Hz, 2H), 6.61 (d, J=16.0 Hz, 1H), 7.21 (t, J=4.2 Hz, 1H), 7.38 (d, J=5.2 Hz, 1H), 7.81 (d, J=16.0 Hz, 1H).

Preparation Example 33: (2R,3S)-ethyl-3-(2,6-dichlorophenyl)-2,3-dihydroxypropanoate

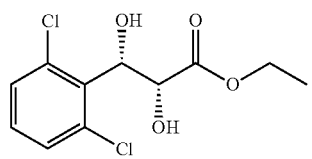 [SMILES: CCOC(=O)[C@H](O)[C@@H](O)c1c(Cl)cccc1Cl]

The substantially same method as described in Preparation Example 25 was conducted, except that (E)-ethyl-3-(2, 6-dichlorophenyl)acrylate (Preparation example 32) was used instead of (E)-Methyl-3-(2-chlorophenyl)acrylate (Preparation example 24), to obtain the title compound (3.9 g, 60~80%).

$^1$H NMR (400 MHz, CDCl$_3$) δ 1.21 (t, J=7.2 Hz, 3H), 3.22 (s, 1H), 3.69 (s, 1H), 4.20~4.28 (m, 1H), 4.70 (d, J=5.2 Hz, 1H), 5.62 (d, J=5.6 Hz, 1H), 7.19~7.36 (m, 3H).

Preparation Example 34: (4R,5S)-ethyl-5-(2,4-dichlorophenyl)-2,2-dimethyl-1.3-dioxolane-4-carboxylate

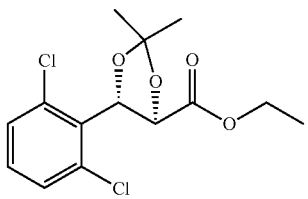 [SMILES: CCOC(=O)[C@@H]1OC(C)(C)O[C@H]1c1c(Cl)cccc1Cl]

The substantially same method as described in Preparation Example 26 was conducted, except that (2R,3S)-ethyl-3-(2,6-dichlorophenyl)-2,3-dihydroxypropanoate (Preparation example 29) was used instead of (2R,3S)-methyl-3-(2-chlorophenyl)-2,3-dihydroxypropanoate (Preparation example 25), to obtain the title compound (4.1 g, 60~90%).

$^1$H NMR (400 MHz, CDCl$_3$) δ 1.26 (t, J=7.2 Hz, 3H), 1.58 (s, 3H), 1.70 (s, 3H), 3.77 (s, 3H), 4.24 (q, J=7.2 Hz, 1H), 4.95 (q, J=4.4 Hz, 1H), 5.95 (q, J=3.0 Hz, 1H), 7.20~7.39 (m, 3H).

Preparation Example 35: ((4S,5S)-5-(2,6-dichlorophenyl)-2,2-dimethyl-1.3-dioxolane-4-yl)methanol

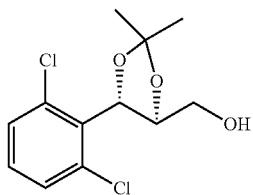 [SMILES: CC1(C)O[C@@H](CO)[C@H](c2c(Cl)cccc2Cl)O1]

The substantially same method as described in Preparation Example 27 was conducted, except that (4R,5S)-ethyl-5-(2,6-dichlorophenyl)-2,2-dimethyl-1.3-dioxolane-4-carboxylate (Preparation example 33) was used instead of (4R,5S)-methyl-5-(2-chlorophenyl)-2,2-dimethyl-1.3-dioxolane-4-carboxylate (Preparation example 26), to obtain the title compound (3.5 g, 70~95%).

$^1$H NMR (400 MHz, CDCl$_3$) δ 1.55 (s, 3H), 1.68 (s, 3H), 3.66 (q, J=5.5 Hz, 1H), 3.85 (q, J=5.1 Hz, 1H), 4.56~4.61 (m, 1H), 5.78 (d, J=9.2 Hz, 1H), 7.19~7.37 (m, 3H).

Preparation Example 36: (2S,3R)-methyl-3-(2,4-dichlorophenyl)-2,3-dihydroxypropanoate

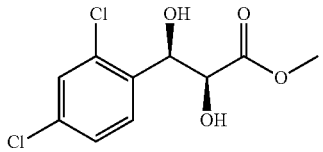 [SMILES: COC(=O)[C@@H](O)[C@H](O)c1ccc(Cl)cc1Cl]

The substantially same method as described in Preparation Example 3 was conducted, except that (E)-Methyl-3-(2,4-dichlorophenyl)acrylate (Preparation example 28) was used instead of (E)-1-chloro-2-(3-(methoxymethoxy)prop-1-enyl)benzene (Preparation example 2), to obtain the title compound (2.4 g, 75~90%).

$^1$H NMR (400 MHz, CDCl$_3$) δ 3.11 (s, 1H), 3.88 (s, 3H), 4.42 (d, J=2.4 Hz, 1H), 5.43 (d, J=2.0 Hz, 1H), 7.28~7.33 (m, 1H), 7.41 (d, J=2.0 Hz, 1H), 7.55 (d, J=8.4 Hz, 1H).

Preparation Example 37: (4S,5R)-methyl-5-(2,4-dichlorophenyl)-2,2-dimethyl-1.3-dioxolane-4-carboxylate

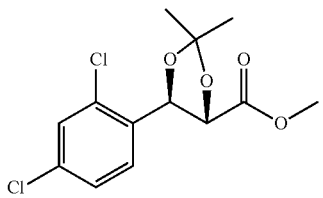 [SMILES: COC(=O)[C@H]1OC(C)(C)O[C@@H]1c1ccc(Cl)cc1Cl]

The substantially same method as described in Preparation Example 26 was conducted, except that (2S,3R)-methyl-3-(2,4-dichlorophenyl)-2,3-dihydroxypropanoate (Preparation example 36) was used instead of (2R,3S)-methyl-3-(2-chlorophenyl)-2,3-dihydroxypropanoate (Preparation example 25), to obtain the title compound (3.2 g, 60~80%).

$^1$H NMR (400 MHz, CDCl$_3$) δ 1.59 (s, 3H), 1.63 (d, J=8.8 Hz, 3H), 3.78 (s, 3H), 4.25 (d, J=7.6 Hz, 1H), 5.56 (d, J=8.0 Hz, 1H), 7.28~7.33 (m, 1H), 7.41 (d, J=2.0 Hz, 1H), 7.56 (d, J=8.4 Hz, 1H).

Preparation Example 38: ((4R,5R)-5-(2,4-dichlorophenyl)-2,2-dimethyl-1.3-dioxolane-4-yl)methanol

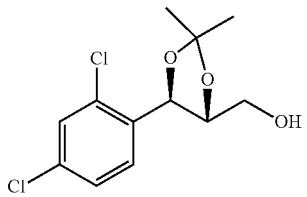 [SMILES: CC1(C)O[C@H](c2ccc(Cl)cc2Cl)[C@@H](CO)O1]

The substantially same method as described in Preparation Example 27 was conducted, except that (4S,5R)-methyl-5-(2,4-dichlorophenyl)-2,2-dimethyl-1.3-dioxolane-4-carboxylate (Preparation example 37) was used instead of (4S,5R)-methyl-5-(2-chlorophenyl)-2,2-dimethyl-1.3-dioxolane-4-carboxylate (Preparation example 26), to obtain the title compound (3.5 g, 70~95%).

¹H NMR (400 MHz, CDCl₃) δ 1.56 (s, 3H), 1.62 (d, J=4.8 Hz, 6H), 1.97 (dd, J=7.2, 7.6 Hz, 1H), 3.75~3.80 (m, 1H), 3.82~3.86 (m, 1H), 3.89~3.94 (m, 1H), 5.36 (d, J=8.4 Hz, 1H), 7.28~7.33 (m, 1H), 7.41 (d, J=2.0 Hz, 1H), 7.56 (d, J=8.4 Hz, 1H).

Preparation Example 39: (2S,3R)-ethyl-3-(2,6-dichlorophenyl)-2,3-dihydroxypropanoate

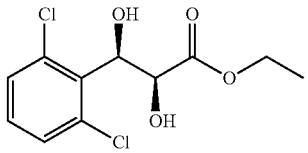 [SMILES: CCOC(=O)[C@@H](O)[C@H](O)c1c(Cl)cccc1Cl]

The substantially same method as described in Preparation Example 3 was conducted, except that (E)-ethyl-3-(2,6-dichlorophenyl)acrylate (Preparation example 32) was used instead of (E)-1-chloro-2-(3-(methoxymethoxy)prop-1-enyl)benzene (Preparation example 2), to obtain the title compound (2.8 g, 75~90%).

¹H NMR (400 MHz, CDCl₃) δ 3.11 (s, 1H), 3.88 (s, 3H), 4.42 (d, J=2.4 Hz, 1H), 5.43 (d, J=2.0 Hz, 1H), 7.28~7.33 (m, 1H), 7.41 (d, J=2.0 Hz, 1H), 7.55 (d, J=8.4 Hz, 1H).

¹H NMR (400 MHz, CDCl₃) δ 1.21 (t, J=7.2 Hz, 3H), 3.22 (s, 1H), 3.69 (s, 1H), 4.20~4.28 (m, 1H), 4.70 (d, J=5.2 Hz, 1H), 5.62 (d, J=5.6 Hz, 1H), 7.19~7.36 (m, 3H).

Preparation Example 40: (4S,5R)-ethyl-5-(2,4-dichlorophenyl)-2,2-dimethyl-1.3-dioxolane-4-carboxylate

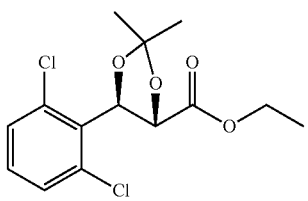 [SMILES: CCOC(=O)[C@H]1OC(C)(C)O[C@@H]1c1c(Cl)cccc1Cl]

The substantially same method as described in Preparation Example 26 was conducted, except that (2S,3R)-ethyl-3-(2,6-dichlorophenyl)-2,3-dihydroxypropanoate (Preparation example 39) was used instead of (2R,3S)-methyl-3-(2-chlorophenyl)-2,3-dihydroxypropanoate (Preparation example 25), to obtain the title compound (4.1 g, 60~90%).

¹H NMR (400 MHz, CDCl₃) δ 1.26 (t, J=7.2 Hz, 3H), 1.58 (s, 3H), 1.70 (s, 3H), 3.77 (s, 3H), 4.24 (q, J=7.2 Hz, 1H), 4.95 (q, J=4.4 Hz, 1H), 5.95 (q, J=3.0 Hz, 1H), 7.20~7.39 (m, 3H).

Preparation Example 41: ((4R,5R)-5-(2,6-dichlorophenyl)-2,2-dimethyl-1.3-dioxolane-4-yl)methanol

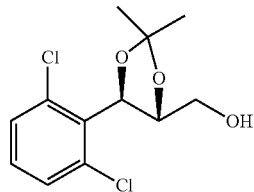 [SMILES: CC1(C)O[C@H](c2c(Cl)cccc2Cl)[C@@H](CO)O1]

The substantially same method as described in Preparation Example 27 was conducted, except that (4S,5R)-ethyl-5-(2,6-dichlorophenyl)-2,2-dimethyl-1.3-dioxolane-4-carboxylate (Preparation example 40) was used instead of (4R,5S)-methyl-5-(2-chlorophenyl)-2,2-dimethyl-1.3-dioxolane-4-carboxylate (Preparation example 26), to obtain the title compound (5.2 g, 70~95%).

¹H NMR (400 MHz, CDCl₃) δ 1.55 (s, 3H), 1.68 (s, 3H), 3.66 (q, J=5.5 Hz, 1H), 3.85 (q, J=5.1 Hz, 1H), 4.56~4.61 (m, 1H), 5.78 (d, J=9.2 Hz, 1H), 7.19~7.37 (m, 3H).

Preparation Example 42: (E)-3-(2-nitrophenyl)-acrylic Acid

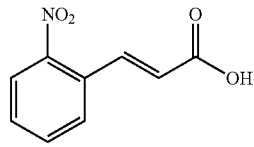 [SMILES: O=C(O)/C=C/c1ccccc1[N+](=O)[O-]]

The substantially same method as described in Preparation Example 9 was conducted, except that 2-nitrobenzeneldehyde was used instead of 2-Fluoroaldehyde, to obtain the title compound (2.06 g, 70~90%).

¹H NMR (400 MHz, DMSO-d₆) δ 6.52 (d, J=15.6 Hz, 1H), 7.65 (t, J=8.1 Hz, 1H), 7.75 (t, J=7.4 Hz, 1H), 7.83 (d, J=15.8 Hz, 1H), 7.92 (dd, J=1.1, 7.6 Hz, 1H), 8.05 (dd. J=1.2, 8.1 Hz, 1H).

Preparation Example 43: (E)-Methyl-3-(2-nitrophenyl)acrylate

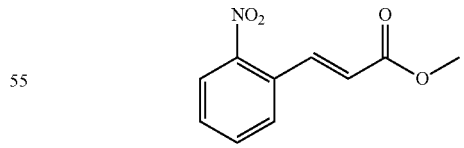

The substantially same method as described in Preparation Example 24 was conducted, except that (E)-3-(2-nitrophenyl)-acrylic acid (Preparation example 42) was used instead of 2-chlorocinnamic acid, to obtain the title compound (15.8 g, 70~90%).

¹H NMR (400 MHz, CDCl₃) δ 3.80 (s, 3H), 6.34 (d, J=15.9 Hz, 1H), 7.49~7.68 (m, 4H), 8.01 (d, J=7.9 Hz, 1H), 8.08 (d, J=15.9 Hz, 1H).

Preparation Example 44: (2S,3R)-methyl-3-(2-nitrophenyl)-2,3-dihydroxypropanoate

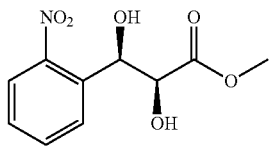 [SMILES: COC(=O)[C@@H](O)[C@H](O)c1ccccc1[N+](=O)[O-]]

The substantially same method as described in Preparation Example 3 was conducted, except that (E)-Methyl-3-(2-nitrophenyl)acrylate (Preparation example 43) was used instead of (E)-1-chloro-2-(3-(methoxymethoxy)prop-1-enyl)benzene (Preparation example 2), to obtain the title compound (12.5 g, 75~90%).

$^1$H NMR (400 MHz, CDCl$_3$) δ 4.31 (s, 3H), 5.44 (m, 4H), 5.89 (s, 1H), 7.53~7.90 (m, 4H).

Preparation Example 45: (4S,5R)-methyl-5-(2-nitrophenyl)-2,2-dimethyl-1.3-dioxolane-4-carboxylate

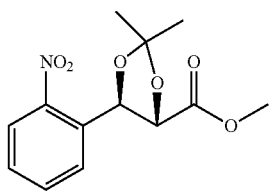 [SMILES: COC(=O)[C@H]1OC(C)(C)O[C@@H]1c1ccccc1[N+](=O)[O-]]

The substantially same method as described in Preparation Example 26 was conducted, except that (2S,3R)-methyl-3-(2-nitrophenyl)-2,3-dihydroxypropanoate (Preparation example 44) was used instead of (2R,3S)-methyl-3-(2-chlorophenyl)-2,3-dihydroxypropanoate (Preparation example 25), to obtain the title compound (11.0 g, 60~80%).

$^1$H NMR (400 MHz, CDCl$_3$) δ 1.38 (s, 3H), 1.40 (s, 3H), 3.75 (s, 3H), 4.49 (d, J=7.4 Hz, 1H), 5.25 (d, J=7.4 Hz, 1H), 7.48~7.77 (m, 3H), 8.08 (m, 1H).

Preparation Example 46: ((4R,5R)-5-(2-nitrophenyl)-2,2-dimethyl-1.3-dioxolane-4-yl)methanol

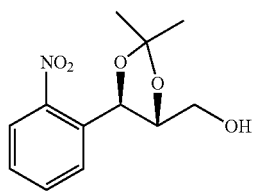 [SMILES: CC1(C)O[C@H](c2ccccc2[N+](=O)[O-])[C@@H](CO)O1]

The substantially same method as described in Preparation Example 27 was conducted, except that (4S,5R)-methyl-5-(2-nitrophenyl)-2,2-dimethyl-1.3-dioxolane-4-carboxylate (Preparation example 45) was used instead of (4S,5R)-methyl-5-(2-chlorophenyl)-2,2-dimethyl-1.3-dioxolane-4-carboxylate (Preparation example 26), to obtain the title compound (13.1 g, 70~95%).

$^1$H NMR (400 MHz, CDCl$_3$) δ 1.38 (s, 3H), 1.40 (s, 3H), 3.89 (d, J=4.1 Hz, 2H), 4.26 (dt, J=4.1, 7.0 Hz, 1H), 5.26 (d, J=7.0 Hz, 1H), 7.55~7.86 (m, 3H), 8.08 (m, 1H).

Preparation Example 47: ((4R,5R)-5-(2-aminophenyl)-2,2-dimethyl-1.3-dioxolane-4-yl)methanol

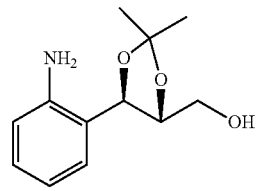 [SMILES: CC1(C)O[C@H](c2ccccc2N)[C@@H](CO)O1]

To a stirred solution of ((4R,5R)-5-(2-nitrophenyl)-2,2-dimethyl-1.3-dioxolane-4-yl)methanol (Preparation example 46, 14.0 g) in EtOAc was added Pd(OH)$_2$ (20 wt %, 2.8 g) under hydrogen gas (balloon). The mixture was stirred for 6 h then the resulting mixture was filtered through celite and concentrated under reduced pressure. The crude product was purified by SiO$_2$ gel column chromatography to give title compound (7.5 g 65~85%).

$^1$H NMR (400 MHz, CDCl$_3$) δ 1.39 (s, 3H), 1.40 (s, 3H), 3.88 (d, J=4.27 Hz, 2H), 3.99 (dt, J=4.3, 7.02 Hz, 1H), 4.74 (d, J=7.02 Hz, 1H), 6.65~6.72 (m, 2H), 6.98 (m, 1H), 7.25 (m, 1H).

Preparation Example 48: (2R,3S)-methyl-3-(2-nitrophenyl)-2,3-dihydroxypropanoate

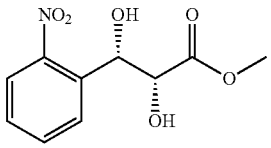

The substantially same method as described in Preparation Example 25 was conducted, except that (E)-methyl-3-(2-nitrophenyl)acrylate (Preparation example 43) was used instead of (E)-Methyl-3-(2-chlorophenyl)acrylate (Preparation example 24), to obtain the title compound (21.7 g, 60~80%).

$^1$H NMR (400 MHz, CDCl$_3$) δ 4.31 (s, 3H), 5.44 (m, 4H), 5.89 (s, 1H), 7.53~7.90 (m, 4H).

Preparation Example 49: (4R,5S)-methyl-5-(2-nitrophenyl)-2,2-dimethyl-1.3-dioxolane-4-carboxylate

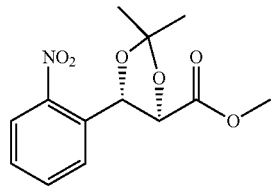

The substantially same method as described in Preparation Example 26 was conducted, except that (2R,3S)- methyl-3-(2-nitrophenyl)-2,3-dihydroxypropanoate (Preparation example 48) was used instead of (2S,3R)-methyl-3-(2-chlorophenyl)-2,3-dihydroxypropanoate (Preparation example 25), to obtain the title compound (21.0 g, 60~90%).

¹H NMR (400 MHz, CDCl₃) δ 1.38 (s, 3H), 1.40 (s, 3H), 3.75 (s, 3H), 4.49 (d, J=7.4 Hz, 1H), 5.25 (d, J=7.4 Hz, 1H), 7.48~7.77 (m, 3H), 8.08 (m, 1H).

Preparation Example 50: ((4S,5S)-5-(2-nitrophenyl)-2,2-dimethyl-1.3-dioxolane-4-yl)methanol

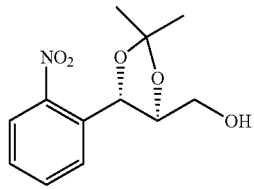 [SMILES: CC1(C)O[C@@H](CO)[C@H](c2ccccc2[N+](=O)[O-])O1]

The substantially same method as described in Preparation Example 27 was conducted, except that (4R,5S)-methyl-5-(2-nitrophenyl)-2,2-dimethyl-1.3-dioxolane-4-carboxylate (Preparation example 48) was used instead of (4R,5S)-methyl-5-(2-chlorophenyl)-2,2-dimethyl-1.3-dioxolane-4-carboxylate (Preparation example 26), to obtain the title compound (14.0 g, 70~95%).

¹H NMR (400 MHz, CDCl₃) δ 1.38 (s, 3H), 1.40 (s, 3H), 3.89 (d, J=4.1 Hz, 2H), 4.26 (dt, J=4.1, 7.0 Hz, 1H), 5.26 (d, J=7.0 Hz, 1H), 7.55~7.86 (m, 3H), 8.08 (m, 1H).

Preparation Example 51: ((4S,5S)-5-(2-aminophenyl)-2,2-dimethyl-1.3-dioxolane-4-yl)methanol

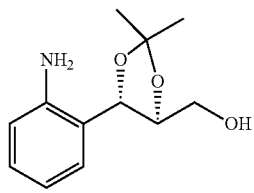

The substantially same method as described in Preparation Example 47 was conducted, except that (4S,5S)-methyl-5-(2-nitrophenyl)-2,2-dimethyl-1.3-dioxolane-4-carboxylate (Preparation example 50) was used instead of (4R,5R)-5-(2-nitrophenyl)-2,2-dimethyl-1.3-dioxolane-4-yl)methanol (Preparation example 46), to obtain the title compound (11.0 g, 70~95%).

¹H NMR (400 MHz, CDCl₃) δ 1.38 (s, 3H), 1.40 (s, 3H), 3.89 (d, J=4.1 Hz, 2H), 4.26 (dt, J=4.1, 7.0 Hz, 1H), 5.26 (d, J=7.0 Hz, 1H), 7.55~7.86 (m, 3H), 8.08 (m, 1H).

Preparation Example 52: (E)-3-o-tolyacrylic Acid

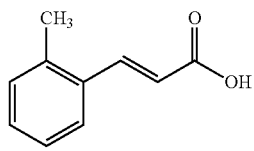

The substantially same method as described in Preparation Example 9 was conducted, except that 2-methylbenzenealdehyde was used instead of 2-Fluoroaldehyde, to obtain the title compound (1.5 g, 70~90%).

¹H NMR (400 MHz, CDCl₃) δ 2.48 (s, 3H), 6.16 (d, J=15.1 Hz, 1H), 7.00~7.10 (m, 1H), 7.21~7.26 (m, 3H), 8.04 (d, J=15.1 Hz, 1H), 11.0 (s, 1H).

Preparation Example 53: (E)-Methyl-3-o-tolyacrylate

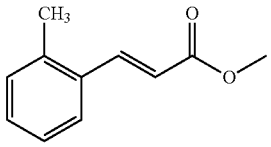

The substantially same method as described in Preparation Example 24 was conducted, except that (E)-3-o-tolyacrylic acid (Preparation example 52) was used instead of 2-chlorocinnamic acid, to obtain the title compound (1.5 g, 70~90%).

¹H NMR (400 MHz, CDCl₃) δ 2.48 (s, 3H), 3.77 (s, 3H), 6.14 (d, J=15.1 Hz, 1H), 7.00~7.10 (m, 1H), 7.21~7.26 (m, 3H), 8.07 (d, J=15.1 Hz, 1H).

Preparation Example 54: (2S,3R)-methyl-3-(2-methylphenyl)-2,3-dihydroxypropanoate

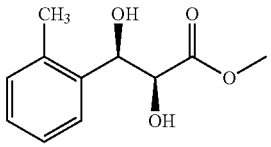

The substantially same method as described in Preparation Example 3 was conducted, except that (E)-Methyl-3-o-tolyacrylate (Preparation example 53) was used instead of (E)-1-chloro-2-(3-(methoxymethoxy)prop-1-enyl)benzene (Preparation example 2), to obtain the title compound (1.3 g, 75~90%).

¹H NMR (400 MHz, CDCl₃) δ 2.34 (s, 3H), 2.80 (s, 1H), 3.65 (s, 1H), 3.68 (s, 3H), 4.52 (d, J=7.0 Hz, 1H), 5.22 (d, J=7.0 Hz, 1H), 7.19~7.39 (m, 4H).

Preparation Example 55: (4S,5R)-methyl-5-(2-methylphenyl)-2,2-dimethyl-1.3-dioxolane-4-carboxylate

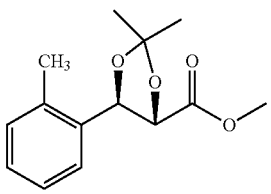 [SMILES: COC(=O)[C@H]1OC(C)(C)O[C@@H]1c1ccccc1C]

The substantially same method as described in Preparation Example 26 was conducted, except that (2S,3R)- methyl-3-(2-methylphenyl)-2,3-dihydroxypropanoate (Preparation example 54) was used instead of (2R,3S)-methyl-3-(2-chlorophenyl)-2,3-dihydroxypropanoate (Preparation example 25), to obtain the title compound (1.7 g, 60~80%).

$^1$H NMR (400 MHz, CDCl$_3$) δ 1.27 (s, 6H), 2.34 (s, 3H), 3.68 (s, 3H), 5.11 (d, J=7.0 Hz, 1H), 5.81 (d, J=7.0 Hz, 1H), 7.19~7.26 (m, 3H), 7.37~7.39 (m, 1H).

Preparation Example 56: ((4R,5R)-5-(2-methylphenyl)-2,2-dimethyl-1.3-dioxolane-4-yl)methanol

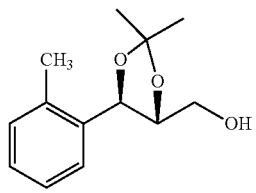 [SMILES: Cc1ccccc1[C@H]1OC(C)(C)O[C@@H]1CO]

The substantially same method as described in Preparation Example 27 was conducted, except that (4S,5R)-methyl-5-(2-methylphenyl)-2,2-dimethyl-1.3-dioxolane-4-carboxylate (Preparation example 55) was used instead of (4R,5S)-methyl-5-(2-chlorophenyl)-2,2-dimethyl-1.3-dioxolane-4-carboxylate (Preparation example 26), to obtain the title compound (1.3 g, 70~95%).

$^1$H NMR (400 MHz, CDCl$_3$) δ 1.27 (s, 6H), 2.34 (s, 3H), 3.52~3.60 (m, 2H), 3.65 (s, 1H), 4.36 (dd, J=7.0, 7.0 Hz, 1H), 5.17 (d, J=7.0 Hz, 1H), 7.19~7.26 (m, 3H), 7.37~7.39 (m, 1H).

Preparation Example 57: (2R,3S)-methyl-3-(2-methylphenyl)-2,3-dihydroxypropanoate

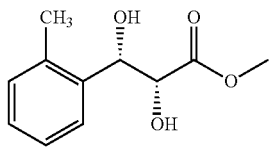

The substantially same method as described in Preparation Example 25 was conducted, except that (E)-methyl-3-o-tolyacrylate (Preparation example 53) was used instead of (E)-Methyl-3-(2-chlorophenyl)acrylate (Preparation example 24), to obtain the title compound (1.7 g, 60~80%).

$^1$H NMR (400 MHz, CDCl$_3$) δ 2.34 (s, 3H), 2.80 (s, 1H), 3.65 (s, 1H), 3.68 (s, 3H), 4.52 (d, J=7.0 Hz, 1H), 5.22 (d, J=7.0 Hz, 1H), 7.19~7.39 (m, 4H).

Preparation Example 58: (4R,5S)-methyl-5-(2-methylphenyl)-2,2-dimethyl-1.3-dioxolane-4-carboxylate

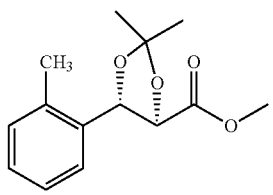 [SMILES: COC(=O)[C@@H]1OC(C)(C)O[C@H]1c1ccccc1C]

The substantially same method as described in Preparation Example 26 was conducted, except that (2R,3S)-methyl-3-(2-methylphenyl)-2,3-dihydroxypropanoate (Preparation example 57) was used instead of (2R,3S)-methyl-3-(2-chlorophenyl)-2,3-dihydroxypropanoate (Preparation example 25), to obtain the title compound (1.9 g, 60~90%).

$^1$H NMR (400 MHz, CDCl$_3$) δ 1.27 (s, 6H), 2.34 (s, 3H), 3.68 (s, 3H), 5.11 (d, J=7.0 Hz, 1H), 5.81 (d, J=7.0 Hz, 1H), 7.19~7.26 (m, 3H), 7.37~7.39 (m, 1H).

Preparation Example 59: ((4S,5S)-5-(2-methylphenyl)-2,2-dimethyl-1.3-dioxolane-4-yl)methanol

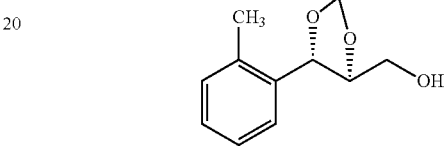

The substantially same method as described in Preparation Example 27 was conducted, except that (4R,5S)-methyl-5-(2-methylphenyl)-2,2-dimethyl-1.3-dioxolane-4-carboxylate (Preparation example 58) was used instead of (4R,5S)-methyl-5-(2-chlorophenyl)-2,2-dimethyl-1.3-dioxolane-4-carboxylate (Preparation example 26), to obtain the title compound (1.5 g, 70~95%).

$^1$H NMR (400 MHz, CDCl$_3$) δ 1.27 (s, 6H), 2.34 (s, 3H), 3.52~3.60 (m, 2H), 3.65 (s, 1H), 4.36 (dd, J=7.0, 7.0 Hz, 1H), 5.17 (d, J=7.0 Hz, 1H), 7.19~7.26 (m, 3H), 7.37~7.39 (m, 1H).

Preparation Example 60: ((4S,5R)-methyl-5-(2-chlorophenyl)-2-methyl-1.3-dioxolane-4-carboxylate

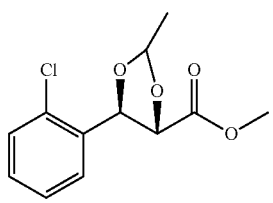

Dichloromethane (MC) was added to (2S,3R)-methyl-3-(2-chlorophenyl)-2,3-dihydroxypropanoate (Preparation example 433) at room temperature. 1,1-Diethoxyethane (8 mL) and p-toluenesulfonic acid (0.27 g) was added and stirred at room temperature. The reaction mixture was quenched with H$_2$O, extracted with MC, washed with H$_2$O, dried over anhydrous magnesium sulfate (MgSO$_4$), filtered and concentrated. The crude compound was purified by a silica gel column to produce the title compound (3.6 g, 70~95%).

$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.28~7.64 (m, 4H).

Preparation Example 61: ((4R,5R)-5-(2-chlorophenyl)-2-methyl-1.3-dioxolane-4-yl)methanol

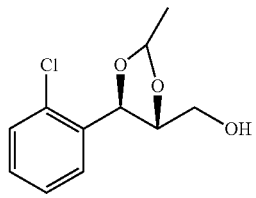

The substantially same method as described in Preparation Example 27 was conducted, except that (4S,5R)-methyl-5-(2-chlorophenyl)-2-methyl-1.3-dioxolane-4-carboxylate (Preparation example 60) was used instead of (4R,5S)-methyl-5-(2-chlorophenyl)-2,2-dimethyl-1.3-dioxolane-4-carboxylate (Preparation example 26), to obtain the title compound (3.1 g, 70~95%).
$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.19~7.26 (m, 3H), 7.37~7.39 (m, 1H).

Preparation Example 62: ((4R,5S)-methyl-5-(2-chlorophenyl)-2-methyl-1.3-dioxolane-4-carboxylate

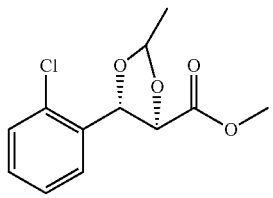

The substantially same method as described in Preparation Example 60 was conducted, except that (2R,3S)-methyl-3-(2-chlorophenyl)-2.3-dihydroxypropanoate (Preparation example 25) was used instead of (2S,3R)-methyl-3-(2-chlorophenyl)-2.3-dihydroxypropanoate (Preparation example 54), to obtain the title compound (2.1 g, 70~9 5%).
$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.28~7.64 (m, 4H).

Preparation Example 63: ((4S,5S)-5-(2-chlorophenyl)-2-methyl-1.3-dioxolane-4-yl)methanol

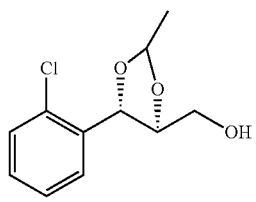

The substantially same method as described in Preparation Example 27 was conducted, except that (4R,5S)-methyl-5-(2-chlorophenyl)-2-methyl-1.3-dioxolane-4-carboxylate (Preparation example 62) was used instead of (4R,5S)-methyl-5-(2-chlorophenyl)-2,2-dimethyl-1.3-dioxolane-4-carboxylate (Preparation example 26), to obtain the title compound (3.1 g, 70~95%).
$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.19~7.26 (m, 3H), 7.37~7.39 (m, 1H).

Preparation Example 64: (4S,5R)-methyl-5-(2-chlorophenyl)-2,2-diethyl-1.3-dioxolane-4-carboxylate

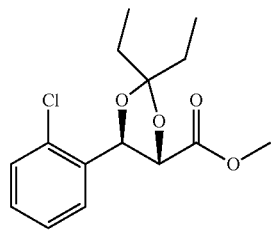 [SMILES: CCC1(CC)O[C@H](C(=O)OC)[C@@H](c2ccccc2Cl)O1]

3-pentanone was added to (2S,3R)-methyl-3-(2-chlorophenyl)-2,3-dihydroxypropanoate (Preparation example 433) at room temperature. Sulfuric acid (H$_2$SO$_4$) was added and stirred at room temperature. The reaction mixture was quenched with H$_2$O, extracted with EA, washed with H$_2$O, dried over anhydrous sodium sulfate (Na$_2$SO$_4$), filtered and concentrated. The crude compound was purified by a silica gel column to produce the title compound (1.6 g, 60~85%).
$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.22~7.60 (m, 4H).

Preparation Example 65: ((4R,5R)-5-(2-chlorophenyl)-2,2-diethyl-1.3-dioxolane-4-yl)methanol

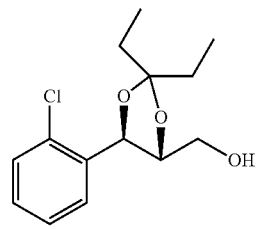 [SMILES: CCC1(CC)O[C@H](c2ccccc2Cl)[C@@H](CO)O1]

The substantially same method as described in Preparation Example 27 was conducted, except that (4S,5R)-methyl-5-(2-chlorophenyl)-2,2-diethyl-1.3-dioxolane-4-carboxylate (Preparation example 64) was used instead of (4R,5S)-methyl-5-(2-chlorophenyl)-2,2-dimethyl-1.3-dioxolane-4-carboxylate (Preparation example 26), to obtain the title compound (2.0 g, 70~95%).
$^1$H NMR (400 MHz, CDCl$_3$) δ 0.96 (m, 6H), 1.59 (m, 4H), 3.66 (d, J=8.0 Hz, 2H), 5.09 (d, J=7.6 Hz, 1H), 5.88 (d, J=7.6 Hz, 1H), 7.26~7.62 (m, 4H).

Preparation Example 66: (4R,5S)-methyl-5-(2-chlorophenyl)-2,2-diethyl-1,3-dioxolane-4-carboxylate

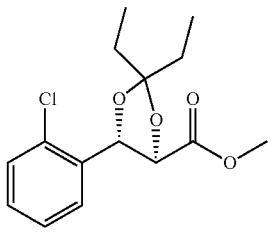 [SMILES: CCC1(CC)O[C@@H](C(=O)OC)[C@H](c2ccccc2Cl)O1]

The substantially same method as described in Preparation Example 64 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate (Preparation example 54), to obtain the title compound (1.4 g, 70~95%).

$^{1}$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.22~7.60 (m, 4H).

Preparation Example 67: ((4S,5S)-5-(2-chlorophenyl)-2,2-diethyl-1,3-dioxolane-4-yl)methanol

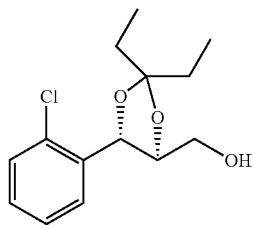

The substantially same method as described in Preparation Example 65 was conducted, except that (4R,5S)-methyl-5-(2-chlorophenyl)-2,2-diethyl-1,3-dioxolane-4-carboxylate (Preparation example 66) was used instead of (4R,5S)-methyl-5-(2-chlorophenyl)-2,2-diethyl-1,3-dioxolane-4-carboxylate (Preparation example 64), to obtain the title compound (2.2 g, 70~95%).

$^{1}$H NMR (400 MHz, CDCl$_3$) δ 0.96 (m, 6H), 1.59 (m, 4H), 3.66 (d, J=8.0 Hz, 2H), 5.09 (d, J=7.6 Hz, 1H), 5.88 (d, J=7.6 Hz, 1H), 7.26~7.62 (m, 4H).

Preparation Example 68: (2S,3R)-methyl-3-(2-chlorophenyl)-1,4-dioxaspiro[4,4]nonane-2-carboxylate

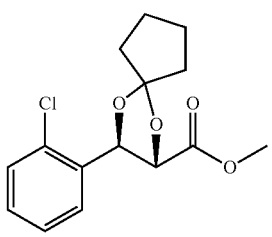 [SMILES: COC(=O)[C@H]1OC2(CCCC2)O[C@@H]1c1ccccc1Cl]

The substantially same method as described in Preparation Example 64 was conducted, except that cyclopentanone was used instead of 3-pentanone, to obtain the title compound (2.2 g, 70~95%).

$^{1}$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.39~7.61 (m, 4H).

Preparation Example 69: ((2R,3R)-3-(2-chlorophenyl)-1,4-dioxaspiro[4,4]nonane-2-yl)methanol

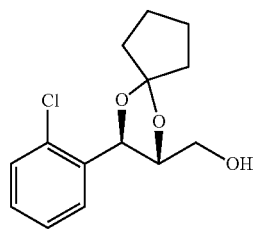 [SMILES: OC[C@H]1OC2(CCCC2)O[C@@H]1c1ccccc1Cl]

The substantially same method as described in Preparation Example 65 was conducted, except that (2S,3R)-methyl-3-(2-chlorophenyl)-1,4-dioxaspiro[4,4]nonane-2-carboxylate (Preparation example 68) was used instead of (4S,5R)-methyl-5-(2-chlorophenyl)-2,2-diethyl-1,3-dioxolane-4-carboxylate (Preparation example 64), to obtain the title compound (1.7 g, 70~95%).

$^{1}$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.34~7.58 (m, 4H).

Preparation Example 70: (2R,3S)-methyl-3-(2-chlorophenyl)-1,4-dioxaspiro[4,4]nonane-2-carboxylate

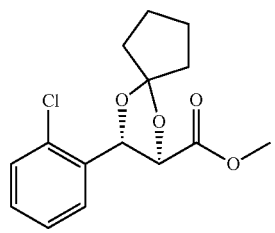 [SMILES: COC(=O)[C@@H]1OC2(CCCC2)O[C@H]1c1ccccc1Cl]

The substantially same method as described in Preparation Example 68 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate (Preparation example 433), to obtain the title compound (1.5 g, 70~95%).

$^{1}$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.39~7.61 (m, 4H).

Preparation Example 71: ((2R,3R)-3-(2-chlorophenyl)-1,4-dioxaspiro[4,4]nonane-2-yl)methanol

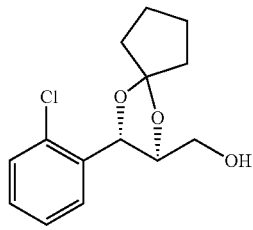

The substantially same method as described in Preparation Example 69 was conducted, except that (2R,3S)-methyl-3-(2-chlorophenyl)-1,4-dioxaspiro[4,4]nonane-2-carboxylate (Preparation example 70) was used instead of (2S,3R)-methyl-3-(2-chlorophenyl)-1,4-dioxaspiro[4,4]nonane-2-carboxylate (Preparation example 68), to obtain the title compound (1.8 g, 70~95%).

$^1$H NMR (400 MHz, DMSO-$d_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.34~7.58 (m, 4H).

Preparation Example 72: (2S,3R)-methyl-3-(2-chlorophenyl)-1,4-dioxaspiro[4,5]decane-2-carboxylate

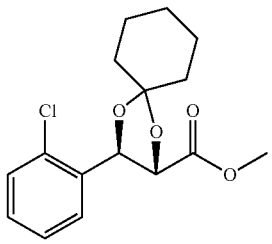 [SMILES: COC(=O)[C@H]1OC2(CCCCC2)O[C@@H]1c1ccccc1Cl]

The substantially same method as described in Preparation Example 64 was conducted, except that cyclohexanone was used instead of 3-pentanone, to obtain the title compound (1.2 g, 70~95%).

$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.35~7.63 (m, 4H).

Preparation Example 73: ((2R,3R)-3-(2-chlorophenyl)-1,4-dioxaspiro[4,5]decane-2-yl)methanol

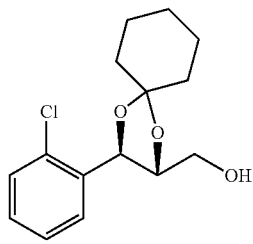 [SMILES: OC[C@H]1OC2(CCCCC2)O[C@@H]1c1ccccc1Cl]

The substantially same method as described in Preparation Example 65 was conducted, except that (2S,3R)-methyl-3-(2-chlorophenyl)-1,4-dioxaspiro[4,5]decane-2-carboxylate (Preparation example 72) was used instead of (4S,5R)-methyl-5-(2-chlorophenyl)-2,2-diethyl-1,3-dioxolane-4-carboxylate (Preparation example 64), to obtain the title compound (1.8 g, 70~95%).

$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.48~7.87 (m, 4H).

Preparation Example 74: (2R,3S)-methyl-3-(2-chlorophenyl)-1,4-dioxaspiro[4,5]decane-2-carboxylate

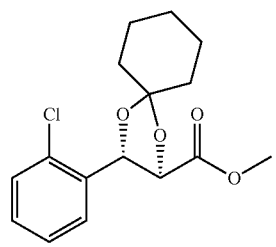 [SMILES: COC(=O)[C@@H]1OC2(CCCCC2)O[C@H]1c1ccccc1Cl]

The substantially same method as described in Preparation Example 72 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate (Preparation example 433), to obtain the title compound (2.1 g, 70~95%).

$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.35~7.63 (m, 4H).

Preparation Example 75: ((2S,3S)-3-(2-chlorophenyl)-1,4-dioxaspiro[4,5]decane-2-yl)methanol

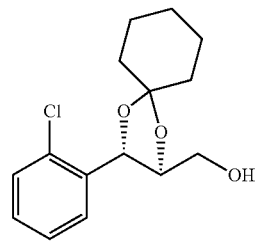 [SMILES: OC[C@@H]1OC2(CCCCC2)O[C@H]1c1ccccc1Cl]

The substantially same method as described in Preparation Example 65 was conducted, except that (2R,3S)-methyl-3-(2-chlorophenyl)-1,4-dioxaspiro[4,5]decane-2-carboxylate (Preparation example 74) was used instead of (4S,5R)-methyl-5-(2-chlorophenyl)-2,2-diethyl-1,3-dioxolane-4-carboxylate (Preparation example 64), to obtain the title compound (1.6 g, 70~95%).

$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.48~7.87 (m, 4H).

Preparation Example 76: (4S,5R)-methyl-5-(2-chlorophenyl)-2-phenyl-1,3-dioxolane-4-carboxylate

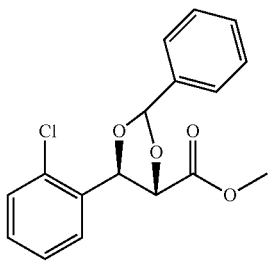

The substantially same method as described in Preparation Example 64 was conducted, except that benzaldehyde was used instead of 3-pentanone, to obtain the title compound (1.1 g, 50~70%).
$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.35~7.63 (m, 4H).

Preparation Example 77: ((4R,5R)-5-(2-chlorophenyl)-2-phenyl-1,3-dioxolane-4-yl)methanol

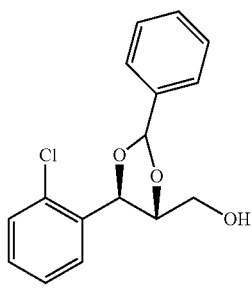

The substantially same method as described in Preparation Example 65 was conducted, except that (2S,3R)-methyl-3-(2-chlorophenyl)-2-phenyl-1,3-dioxolane-4-carboxylate (Preparation example 76) was used instead of (4S,5R)-methyl-5-(2-chlorophenyl)-2,2-diethyl-1.3-dioxolane-4-carboxylate (Preparation example 64), to obtain the title compound (0.7 g, 70~95%).
$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.48~7.87 (m, 4H).

Preparation Example 78: (4R,5S)-methyl-5-(2-chlorophenyl)-2-phenyl-1,3-dioxolane-4-carboxylate

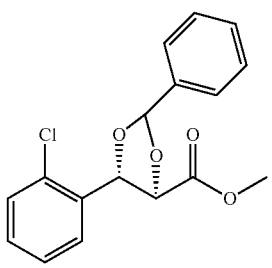

The substantially same method as described in Preparation Example 66 was conducted, except that benzaldehyde was used instead of 3-pentanone, to obtain the title compound (1.9 g, 50~70%).
$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.35~7.63 (m, 4H).

Preparation Example 79: ((4S,5S)-5-(2-chlorophenyl)-2-phenyl-1,3-dioxolane-4-yl)methanol

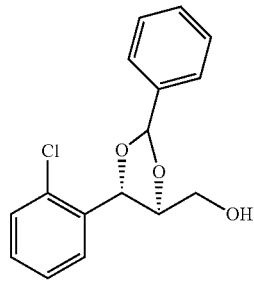

The substantially same method as described in Preparation Example 65 was conducted, except that (2R,3S)-methyl-3-(2-chlorophenyl)-2-phenyl-1,3-dioxolane-4-carboxylate (Preparation example 78) was used instead of (4S,5R)-methyl-5-(2-chlorophenyl)-2,2-diethyl-1.3-dioxolane-4-carboxylate (Preparation example 64), to obtain the title compound (1.3 g, 70~95%).
$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.48~7.87 (m, 4H).

Preparation Example 80: (E)-Methyl-3-(2-fluorophenyl)acrylate

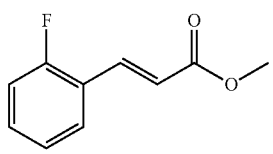

The substantially same method as described in Preparation Example 24 was conducted, except that (E)-3-(2-fluorophenyl)-acrylic acid (Preparation example 9) was used instead of 2-chlorocinnamic acid, to obtain the title compound (6.98 g, 70~90%).
$^1$H NMR (400 MHz, CDCl$_3$) δ 3.84 (s, 3H), 6.45 (d, J=16.0 Hz, 1H), 7.24~7.62 (m, 4H), 8.12 (d, J=16.0 Hz, 1H).

Preparation Example 81: (2S,3R)-methyl-3-(2-fluorophenyl)-2,3-dihydroxypropanoate

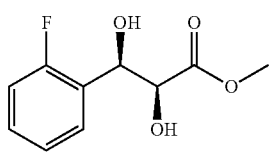

The substantially same method as described in Preparation Example 3 was conducted, except that (E)-Methyl-3-(2-fluorophenyl)acrylate (Preparation example 80) was used instead of (E)-1-chloro-2-(3-(methoxymethoxy)prop-1-enyl) benzene (Preparation example 2), to obtain the title compound (7.5 g, 75~90%).

¹H NMR (400 MHz, CDCl₃) δ 4.31 (s, 3H), 5.44 (m, 4H), 5.89 (s, 1H), 7.32~7.70 (m, 4H).

Preparation Example 82: (2R,3S)-methyl-3-(2-fluorophenyl)-2,3-dihydroxypropanoate

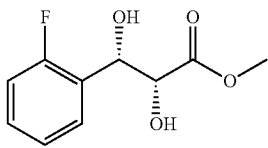

The substantially same method as described in Preparation Example 25 was conducted, except that (E)-methyl-3-(2-fluorophenyl)acrylate (Preparation example 80) was used instead of (E)-Methyl-3-(2-chlorophenyl)acrylate (Preparation example 24), to obtain the title compound (7.2 g, 60~80%).

¹H NMR (400 MHz, CDCl₃) δ 4.31 (s, 3H), 5.44 (m, 4H), 5.89 (s, 1H), 7.32~7.70 (m, 4H).

Preparation Example 83: ((4S,5R)-methyl-5-(2-fluorophenyl)-2-methyl-1.3-dioxolane-4-carboxylate

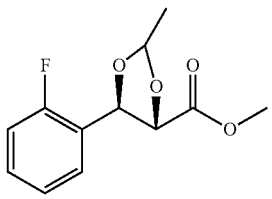

The substantially same method as described in Preparation Example 60 was conducted, except that (2S,3R)-methyl-3-(2-fluorophenyl)-2,3-dihydroxypropanoate (Preparation example 81) was used instead of ((2S,3R)-methyl-3-(2-chlorophenyl)-2,3-dihydroxypropanoate (Preparation example 433), to obtain the title compound ((3.1 g, 70~95%).

¹H NMR (400 MHz, CDCl₃) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.29~7.67 (m, 4H).

Preparation Example 84: ((4R,5R)-5-(2-fluorophenyl)-2-methyl-1.3-dioxolane-4-yl)methanol

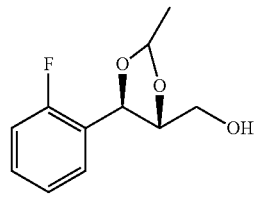

The substantially same method as described in Preparation Example 27 was conducted, except that (4S,5R)-methyl-5-(2-fluorophenyl)-2-methyl-1.3-dioxolane-4-carboxylate (Preparation example 83) was used instead of (4R,5S)-methyl-5-(2-chlorophenyl)-2,2-dimethyl-1.3-dioxolane-4-carboxylate (Preparation example 26), to obtain the title compound (3.3 g, 70~95%).

¹H NMR (400 MHz, CDCl₃) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.19~7.39 (m, 4H).

Preparation Example 85: ((4R,5S)-methyl-5-(2-fluorophenyl)-2-methyl-1.3-dioxolane-4-carboxylate

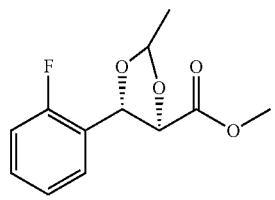

The substantially same method as described in Preparation Example 60 was conducted, except that (2R,3S)-methyl-3-(2-fluorophenyl)-2.3-dihydroxypropanoate (Preparation example 82) was used instead of (2S,3R)-methyl-3-(2-chlorophenyl)-2.3-dihydroxypropanoate (Preparation example 433), to obtain the title compound (2.9 g, 70~95%).

¹H NMR (400 MHz, CDCl₃) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.29~7.69 (m, 4H).

Preparation Example 86: ((4S,5S)-5-(2-fluorophenyl)-2-methyl-1.3-dioxolane-4-yl)methanol

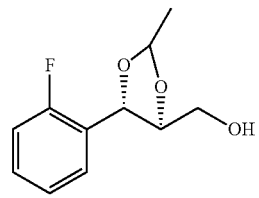

The substantially same method as described in Preparation Example 27 was conducted, except that (4R,5S)-methyl-5-(2-fluorophenyl)-2-methyl-1.3-dioxolane-4-carboxylate (Preparation example 85) was used instead of (4R,5S)-methyl-5-(2-chlorophenyl)-2,2-dimethyl-1.3-dioxolane-4-carboxylate (Preparation example 26), to obtain the title compound (3.8 g, 70~95%).

¹H NMR (400 MHz, CDCl₃) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.19~7.42 (m, 4H).

Preparation Example 87: (4S,5R)-methyl-5-(2-fluorophenyl)-2,2-diethyl-1,3-dioxolane-4-carboxylate

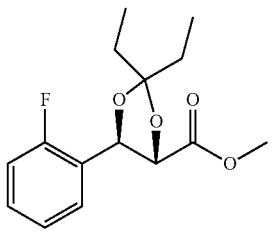 [SMILES: CCC1(CC)O[C@H](C(=O)OC)[C@@H](c2ccccc2I)O1]

The substantially same method as described in Preparation Example 64 was conducted, except that (2S,3R)-methyl-3-(2-fluorophenyl)-2,3-dihydroxypropanoate (Preparation example 81) was used instead of (2S,3R)-methyl-3-(2-chlorophenyl)-2,3-dihydroxypropanoate (Preparation example 433), to obtain the title compound (2.1 g, 60~85%).

$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.20~7.61 (m, 4H).

Preparation Example 88: ((4R,5R)-5-(2-fluorophenyl)-2,2-diethyl-1,3-dioxolane-4-yl)methanol

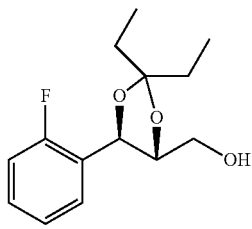

The substantially same method as described in Preparation Example 27 was conducted, except that (4S,5R)-methyl-5-(2-fluorophenyl)-2,2-diethyl-1,3-dioxolane-4-carboxylate (Preparation example 87) was used instead of (4R,5S)-methyl-5-(2-chlorophenyl)-2,2-dimethyl-1,3-dioxolane-4-carboxylate (Preparation example 26), to obtain the title compound (2.2 g, 70~95%).

$^1$H NMR (400 MHz, CDCl$_3$) δ 0.96 (m, 6H), 1.59 (m, 4H), 3.66 (d, J=8.0 Hz, 2H), 5.09 (d, J=7.6 Hz, 1H), 5.88 (d, J=7.6 Hz, 1H), 7.23~7.60 (m, 4H).

Preparation Example 89: (4R,5S)-methyl-5-(2-fluorophenyl)-2,2-diethyl-1,3-dioxolane-4-carboxylate

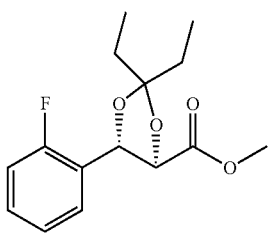

The substantially same method as described in Preparation Example 87 was conducted, except that (2R,3S)-methyl-3-(2-fluorophenyl)-2,3-dihydroxypropanoate (Preparation example 82) was used instead of (2S,3R)-methyl-3-(2-fluorophenyl)-2,3-dihydroxypropanoate (Preparation example 81), to obtain the title compound (2.3 g, 70~95%).

$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.20~7.61 (m, 4H).

Preparation Example 90: ((4S,5S)-5-(2-fluorophenyl)-2,2-diethyl-1,3-dioxolane-4-yl)methanol

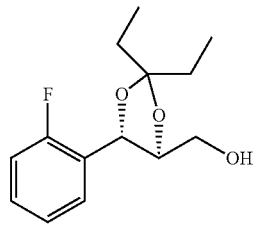 [SMILES: CCC1(CC)O[C@@H](CO)[C@H](c2ccccc2I)O1]

The substantially same method as described in Preparation Example 88 was conducted, except that (4R,5S)-methyl-5-(2-fluorophenyl)-2,2-diethyl-1,3-dioxolane-4-carboxylate (Preparation example 89) was used instead of (4S,5R)-methyl-5-(2-fluorophenyl)-2,2-diethyl-1,3-dioxolane-4-carboxylate (Preparation example 87), to obtain the title compound (2.2 g, 70~95%).

$^1$H NMR (400 MHz, CDCl$_3$) δ 0.96 (m, 6H), 1.59 (m, 4H), 3.66 (d, J=8.0 Hz, 2H), 5.09 (d, J=7.6 Hz, 1H), 5.88 (d, J=7.6 Hz, 1H), 7.23~7.62 (m, 4H).

Preparation Example 91: (2S,3R)-methyl-3-(2-fluorophenyl)-1,4-dioxaspiro[4,4]nonane-2-carboxylate

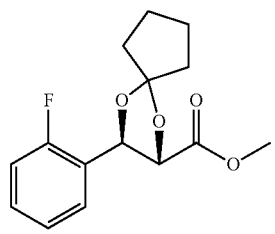 [SMILES: COC(=O)[C@H]1OC2(CCCC2)O[C@@H]1c1ccccc1I]

The substantially same method as described in Preparation Example 87 was conducted, except that cyclopentanone was used instead of 3-pentanone, to obtain the title compound (2.1 g, 70~95%).

$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.33~7.62 (m, 4H).

Preparation Example 92: ((2R,3R)-3-(2-fluorophenyl)-1,4-dioxaspiro[4,4]nonane-2-yl)methanol

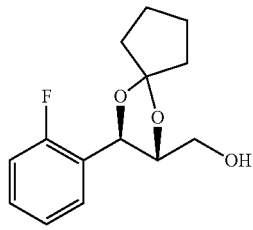

The substantially same method as described in Preparation Example 65 was conducted, except that (2S,3R)-methyl-3-(2-fluorophenyl)-1,4-dioxaspiro[4,4]nonane-2-carboxylate (Preparation example 91) was used instead of (4S,5R)-methyl-5-(2-chlorophenyl)-2,2-diethyl-1,3-dioxolane-4-carboxylate (Preparation example 64), to obtain the title compound (1.9 g, 70~95%).

$^1$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.32~7.57 (m, 4H).

Preparation Example 93: (2R,3S)-methyl-3-(2-fluorophenyl)-1,4-dioxaspiro[4,4]nonane-2-carboxylate

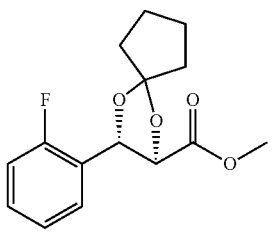 [SMILES: COC(=O)[C@@H]1OC2(CCCC2)O[C@H]1c1ccccc1I]

The substantially same method as described in Preparation Example 91 was conducted, except that (2R,3S)-methyl-3-(2-fluorophenyl)-2,3-dihydroxypropanoate (Preparation example 82) was used instead of (2S,3R)-methyl-3-(2-fluorophenyl)-2,3-dihydroxypropanoate (Preparation example 81), to obtain the title compound (1.5 g, 70~95%).

$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.39~7.61 (m, 4H).

Preparation Example 94: ((2R,3R)-3-(2-fluorophenyl)-1,4-dioxaspiro[4,4]nonane-2-yl)methanol

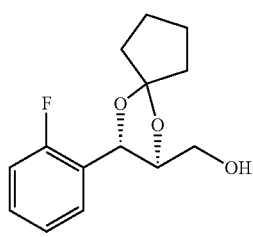 [SMILES: OC[C@@H]1OC2(CCCC2)O[C@H]1c1ccccc1I]

The substantially same method as described in Preparation Example 88 was conducted, except that (2R,3S)-methyl-3-(2-fluorophenyl)-1,4-dioxaspiro[4,4]nonane-2-carboxylate (Preparation example 93) was used instead of (4S,5R)-methyl-5-(2-fluorophenyl)-2,2-diethyl-1,3-dioxolane-4-carboxylate (Preparation example 87), to obtain the title compound (1.2 g, 70~95%).

$^1$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.38~7.63 (m, 4H).

Preparation Example 95: (2S,3R)-methyl-3-(2-fluorophenyl)-1,4-dioxaspiro[4,5]decane-2-carboxylate

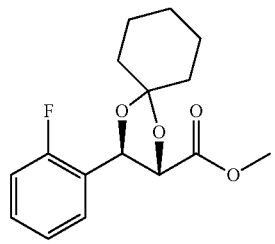 [SMILES: COC(=O)[C@H]1OC2(CCCCC2)O[C@@H]1c1ccccc1I]

The substantially same method as described in Preparation Example 91 was conducted, except that cyclohexanone was used instead of cyclopentanone, to obtain the title compound (1.7 g, 70~95%).

$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.37~7.63 (m, 4H).

Preparation Example 96

((2R,3R)-3-(2-fluorophenyl)-1,4-dioxaspiro[4,5]decane-2-yl)methanol

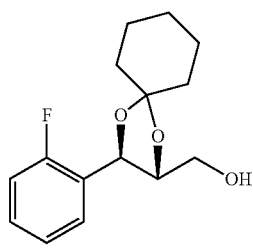 [SMILES: OC[C@H]1OC2(CCCCC2)O[C@@H]1c1ccccc1I]

The substantially same method as described in Preparation Example 73 was conducted, except that (2S,3R)-methyl-3-(2-fluorophenyl)-1,4-dioxaspiro[4,5]decane-2-carboxylate (Preparation example 95) was used instead of (2S,3R)-methyl-3-(2-chlorophenyl)-1,4-dioxaspiro[4,5]decane-2-carboxylate (Preparation example 72), to obtain the title compound (1.4 g, 70~95%).

$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.42~7.89 (m, 4H).

Preparation Example 97: (2R,3S)-methyl-3-(2-fluorophenyl)-1,4-dioxaspiro[4,5]decane-2-carboxylate

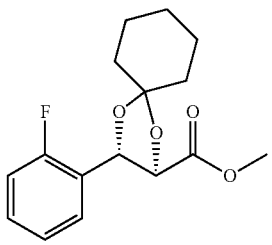 [SMILES: COC(=O)[C@@H]1OC2(CCCCC2)O[C@H]1c1ccccc1I]

The substantially same method as described in Preparation Example 95 was conducted, except that (2R,3S)-methyl-3-(2-fluorophenyl)-2,3-dihydroxypropanoate (Preparation example 82) was used instead of (2S,3R)-methyl-3-(2-fluorophenyl)-2,3-dihydroxypropanoate (Preparation example 81), to obtain the title compound (1.8 g, 70~95%).
¹H NMR (400 MHz, DMSO-d₆) δ 1.61~1.69 (m, 10H), 3.79 (s, 3H), 4.33 (d, J=8.0 Hz, 1H), 5.85 (d, J=8.0 Hz, 1H), 7.32~7.64 (m, 4H).

Preparation Example 98: ((2S,3S)-3-(2-fluorophenyl)-1,4-dioxaspiro[4,5]decane-2-yl)methanol

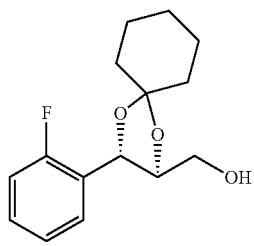

The substantially same method as described in Preparation Example 96 was conducted, except that (2R,3S)-methyl-3-(2-fluorophenyl)-1,4-dioxaspiro[4,5]decane-2-carboxylate (Preparation example 97) was used instead of (2S,3R)-methyl-3-(2-fluorophenyl)-1,4-dioxaspiro[4,5]decane-2-carboxylate (Preparation example 95), to obtain the title compound (1.5 g, 70~95%).
¹H NMR (400 MHz, DMSO-d₆) δ 1.63~1.75 (m, 10H), 3.52~3.81 (m, 2H), 3.95 (t, J=8.0 Hz, 1H), 5.43 (d, J=7.6 Hz, 1H), 7.33~7.67 (m, 4H).

Preparation Example 99: (4S,5R)-methyl-5-(2-fluorophenyl)-2-phenyl-1,3-dioxolane-4-carboxylate

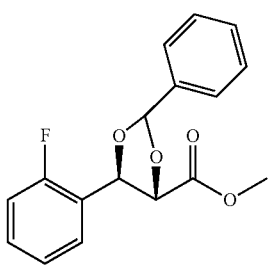

The substantially same method as described in Preparation Example 87 was conducted, except that benzaldehyde was used instead of 3-pentanone, to obtain the title compound (1.6 g, 50~70%).
¹H NMR (400 MHz, DMSO-d₆) δ 1.61~1.69 (m, 10H), 3.79 (s, 3H), 4.33 (d, J=8.0 Hz, 1H), 5.85 (d, J=8.0 Hz, 1H), 7.33~7.64 (m, 4H).

Preparation Example 100: ((4R,5R)-5-(2-fluorophenyl)-2-phenyl-1,3-dioxolane-4-yl)methanol

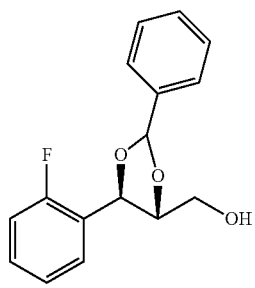

The substantially same method as described in Preparation example 65 was conducted, except that (2S, 3R)-methyl-3-(2-fluorophenyl)-2-phenyl-1,3-dioxolane-4-carboxylate (Preparation example 99) was used instead of (4S,5R)-methyl-5-(2-chlorophenyl)-2,2-diethyl-1,3-dioxolane-4-carboxylate (Preparation example 64), to obtain the title compound (1.3 g, 70~95%).
¹H NMR (400 MHz, DMSO-d₆) δ 1.63~1.75 (m, 10H), 3.52~3.81 (m, 2H), 3.95 (t, 1=8.0 Hz, 1H), 5.43 (d, J=7.6 Hz, 1H), 7.43~7.85 (m, 4H).

Preparation Example 101: (4R,5S)-methyl-5-(2-fluorophenyl)-2-phenyl-1,3-dioxolane-4-carboxylate

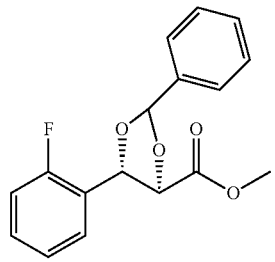

The substantially same method as described in Preparation example 89 was conducted, except that benzaldehyde was used instead of 3-pentanone, to obtain the title compound (1.7 g, 50~70%).
¹H NMR (400 MHz, DMSO-d₆) δ 1.61~1.69 (m, 10H), 3.79 (s, 3H), 4.33 (d, J=8.0 Hz, 1H), 5.85 (d, J=8.0 Hz, 1H), 7.33~7.64 (m, 4H).

Preparation Example 102: ((4S,5S)-5-(2-fluorophenyl)-2-phenyl-1,3-dioxolane-4-yl)methanol

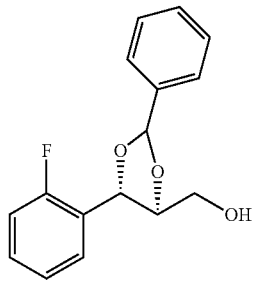

The substantially same method as described in Preparation example 65 was conducted, except that (2R,3S)-methyl-3-(2-fluorophenyl)-2-phenyl-1,3-dioxolane-4-carboxylate (Preparation example 101) was used instead of (4S,5R)-methyl-5-(2-chlorophenyl)-2,2-diethyl-1.3-dioxolane-4-carboxylate (Preparation example 64), to obtain the title compound (1.1 g, 70~95%).

$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.43~7.85 (m, 4H).

Preparation Example 103: (E)-Methyl-3-(2-iodophenyl)acrylate

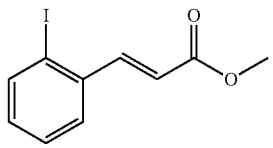

The substantially same method as described in Preparation example 24 was conducted, except that (E)-3(2-iodophenyl)-acrylic acid (Preparation example 17) was used instead of 2-chlorocinnamic acid, to obtain the title compound (3.2 g, 70~90%).

$^1$H NMR (400 MHz, CDCl$_3$) δ 3.84 (s, 3H), 6.45 (d, J=16.0 Hz, 1H), 7.01~7.35 (m, 4H), 8.09 (d, J=16.0 Hz, 1H).

Preparation Example 104: (2S,3R)-methyl-3-(2-iodophenyl)-2,3-dihydroxypropanoate

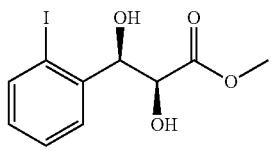

The substantially same method as described in Preparation Example 3 was conducted, except that (E)-Methyl-3-(2-iodophenyl)acrylate (Preparation example 103) was used instead of (E)-1-chloro-2-(3-(methoxymethoxy)prop-1-enyl)benzene (Preparation example 2), to obtain the title compound (3.2 g, 75~90%).

$^1$H NMR (400 MHz, CDCl$_3$) δ 4.31 (s, 3H), 5.44 (m, 4H), 5.89 (s, 1H), 7.30~7.71 (m, 4H).

Preparation Example 105: (2R,3S)-methyl-3-(2-iodophenyl)-2,3-dihydroxypropanoate

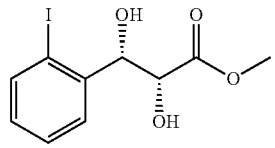

The substantially same method as described in Preparation example 25 was conducted, except that (E)-methyl-3-(2-iodophenyl)acrylate (Preparation example 103) was used instead of (E)-Methyl-3-(2-chlorophenyl)acrylate (Preparation example 24), to obtain the title compound (3.1 g, 60~80%).

$^1$H NMR (400 MHz, CDCl$_3$) δ 4.31 (s, 3H), 5.44 (m, 4H), 5.89 (s, 1H), 7.31~7.72 (m, 4H).

Preparation Example 106: ((4S,5R)-methyl-5-(2-iodophenyl)-2-methyl-1.3-dioxolane-4-carboxylate

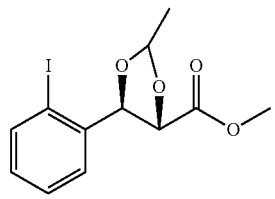

The substantially same method as described in Preparation example 60 was conducted, except that (2S,3R)-methyl-3-(2-iodophenyl)-2,3-dihydroxypropanoate (Preparation example 104) was used instead of (2S,3R)-methyl-3-(2-chlorophenyl)-2,3-dihydroxypropanoate (Preparation example 433), to obtain the title compound (2.7 g, 70~95%).

$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.29~7.70 (m, 4H).

Preparation Example 107: ((4R,5R)-5-(2-iodophenyl)-2-methyl-1.3-dioxolane-4-yl)methanol

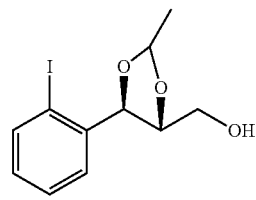

The substantially same method as described in Preparation example 27 was conducted, except that (4S,5R)-methyl-5-(2-iodophenyl)-2-methyl-1.3-dioxolane-4-carboxylate (Preparation example 106) was used instead of (4R,5S)-methyl-5-(2-chlorophenyl)-2,2-dimethyl-1.3-dioxolane-4-carboxylate (Preparation example 26), to obtain the title compound (2.3 g, 70~95%).

¹H NMR (400 MHz, CDCl₃) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.17~7.41 (m, 4H).

Preparation Example 108: ((4R,5S)-methyl-5-(2-iodophenyl)-2-methyl-1.3-dioxolane-4-carboxylate

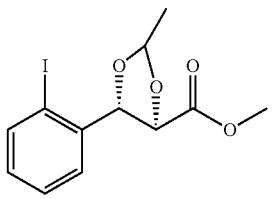

The substantially same method as described in Preparation example 60 was conducted, except that (2R,3S)-methyl-3-(2-iodophenyl)-2.3-dihydroxypropanoate (Preparation example 104) was used instead of (2S,3R)-methyl-3-(2-chlorophenyl)-2.3-dihydroxypropanoate (Preparation example 433), to obtain the title compound (2.4 g, 70~95%).

¹H NMR (400 MHz, CDCl₃) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.29~7.70 (m, 4H).

Preparation Example 109: ((4S,5S)-5-(2-iodophenyl)-2-methyl-1.3-dioxolane-4-yl)methanol

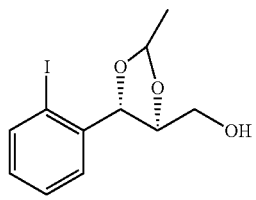

The substantially same method as described in Preparation example 107 was conducted, except that (4R,5S)-methyl-5-(2-iodophenyl)-2-methyl-1.3-dioxolane-4-carboxylate (Preparation example 108) was used instead of (4S,5R)-methyl-5-(2-iodophenyl)-2-methyl-1.3-dioxolane-4-carboxylate (Preparation example 106), to obtain the title compound (1.9 g, 70~95%).

¹H NMR (400 MHz, CDCl₃) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.17~7.41 (m, 4H).

Preparation Example 110: (4S,5R)-methyl-5-(2-Iodophenyl)-2,2-diethyl-1.3-dioxolane-4-carboxylate

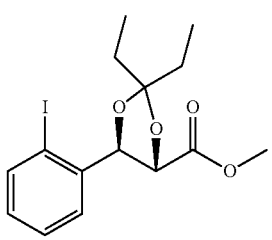

The substantially same method as described in Preparation example 64 was conducted, except that (2R,3S)-methyl-3-(2-iodophenyl)-2,3-dihydroxypropanoate (Preparation example 104) was used instead of (2S,3R)-methyl-3-(2-chlorophenyl)-2,3-dihydroxypropanoate (Preparation example 433), to obtain the title compound (2.6 g, 60~85%).

¹H NMR (400 MHz, CDCl₃) δ 0.96 (m, 6H), 1.59 (m, 4H), 3.67 (s, 3H), 5.11 (d, J=7.6 Hz, 1H), 5.81 (d, J=7.6 Hz, 1H), 7.23~7.65 (m, 4H).

Preparation Example 111: ((4R,5R)-5-(2-iodophenyl)-2,2-diethyl-1.3-dioxolane-4-yl)methanol

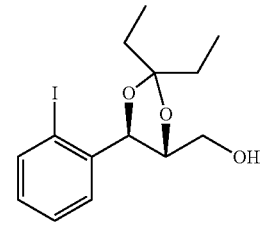

The substantially same method as described in Preparation example 107 was conducted, except that (4S,5R)-methyl-5-(2-iodophenyl)-2,2-diethyl-1.3-dioxolane-4-carboxylate (Preparation example 110) was used instead of (4S,5R)-methyl-5-(2-iodophenyl)-2-methyl-1.3-dioxolane-4-carboxylate (Preparation example 106), to obtain the title compound (2.1 g, 70~95%).

¹H NMR (400 MHz, CDCl₃) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.17~7.41 (m, 4H).

Preparation Example 112: (4R,5S)-methyl-5-(2-iodophenyl)-2,2-diethyl-1.3-dioxolane-4-carboxylate

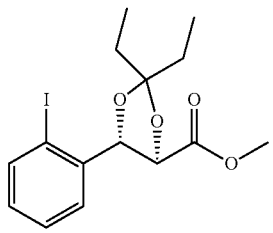

The substantially same method as described in Preparation example 110 was conducted, except that (2R,3S)-methyl-3-(2-iodophenyl)-2,3-dihydroxypropanoate (Preparation example 105) was used instead of (2S,3R)-methyl-3-(2-iodophenyl)-2,3-dihydroxypropanoate (Preparation example 104), to obtain the title compound (2.3 g, 60~85%).

¹H NMR (400 MHz, CDCl₃) δ 0.96 (m, 6H), 1.59 (m, 4H), 3.67 (s, 3H), 5.11 (d, J=7.6 Hz, 1H), 5.81 (d, J=7.6 Hz, 1H), 7.20~7.61 (m, 4H).

Preparation Example 113: ((4S,5S)-5-(2-iodophenyl)-2,2-diethyl-1.3-dioxolane-4-yl)methanol

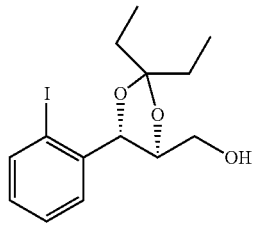

The substantially same method as described in Preparation example 107 was conducted, except that (4R,5S)-methyl-5-(2-iodophenyl)-2,2-diethyl-1.3-dioxolane-4-carboxylate (Preparation example 112) was used instead of (4S,5R)-methyl-5-(2-iodophenyl)-2-methyl-1.3-dioxolane-4-carboxylate (Preparation example 106), to obtain the title compound (1.8 g, 70~95%).
$^1$H NMR (400 MHz, CDCl$_3$) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.17~7.41 (m, 4H).

Preparation Example 114: (2S,3R)-methyl-3-(2-Iodophenyl)-1,4-dioxaspiro[4,4]nonane-2-carboxylate

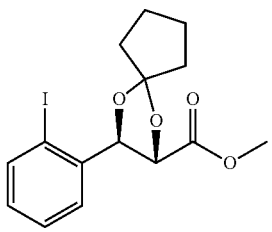

The substantially same method as described in Preparation example 110 was conducted, except that cyclopentanone was used instead of 3-pentanone, to obtain the title compound (2.7 g, 70~95%).
$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.19~7.44 (m, 4H).

Preparation Example 115: ((2R,2R)-3-(2-iodophenyl)-1,4-dioxaspiro[4,4]nonane-2-yl)methanol

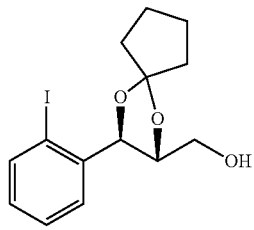

The substantially same method as described in Preparation example 107 was conducted, except that (2S,3R)-methyl-3-(2-iodophenyl)-1,4-dioxaspiro[4,4]nonane-2-carboxylate (Preparation example 114) was used instead of (4S,5R)-methyl-5-(2-iodophenyl)-2-methyl-1.3-dioxolane-4-carboxylate (Preparation example 106), to obtain the title compound (2.1 g, 70~95%).
$^1$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.20~7.45 (m, 4H).

Preparation Example 116: (2R,3S)-methyl-3-(2-iodophenyl)-1,4-dioxaspiro[4,4]nonane-2-carboxylate

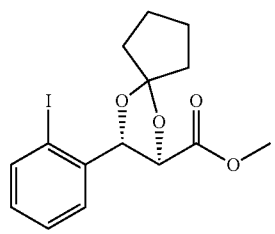

The substantially same method as described in Preparation example 112 was conducted, except that cyclopentanone was used instead of 3-pentanone, to obtain the title compound (2.9 g, 70~95%).
$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.19~7.44 (m, 4H).

Preparation Example 117: ((2S,2S)-3-(2-iodophenyl)-1,4-dioxaspiro[4,4]nonane-2-yl)methanol

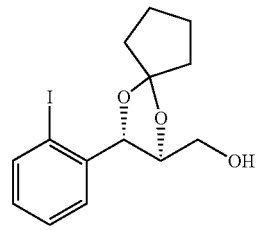

The substantially same method as described in Preparation example 107 was conducted, except that (2R,3S)-methyl-3-(2-iodophenyl)-1,4-dioxaspiro[4,4]nonane-2-carboxylate (Preparation example 116) was used instead of (4S,5R)-methyl-5-(2-iodophenyl)-2-methyl-1.3-dioxolane-4-carboxylate (Preparation example 106), to obtain the title compound (1.5 g, 70~95%).
$^1$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.20~7.45 (m, 4H).

Preparation Example 118: (2S,3R)-methyl-3-(2-iodophenyl)-1,4-dioxaspiro[4,5]decane-2-carboxylate

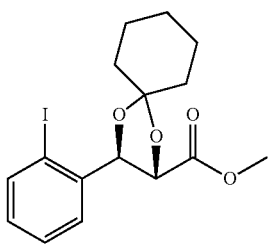

The substantially same method as described in Preparation example 114 was conducted, except that cyclohexanone was used instead of cyclopentanone, to obtain the title compound (1.9 g, 70~95%).
$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.17~7.43 (m, 4H).

Preparation Example 119: (2R,3R)-3-(2-iodophenyl)-1,4-dioxaspiro[4,5]decane-2-yl)methanol

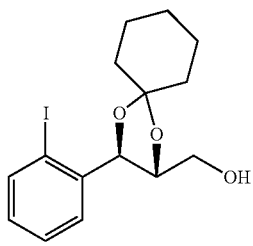

The substantially same method as described in Preparation example 107 was conducted, except that (2S,3R)-methyl-3-(2-iodophenyl)-1,4-dioxaspiro[4,5]decane-2-carboxylate (Preparation example 118) was used instead of (4S,5R)-methyl-5-(2-iodophenyl)-2-methyl-1,3-dioxolane-4-carboxylate (Preparation example 106), to obtain the title compound (1.3 g, 70~95%).
$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.19~7.49 (m, 4H).

Preparation Example 120: (2R,3S)-methyl-3-(2-iodophenyl)-1,4-dioxaspiro[4,5]decane-2-carboxylate

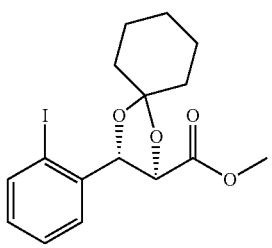

The substantially same method as described in Preparation example 116 was conducted, except that cyclohexanone was used instead of cyclopentanone, to obtain the title compound (2.3 g, 70~95%).
$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.17~7.43 (m, 4H).

Preparation Example 121: ((2S,3S)-3-(2-iodophenyl)-1,4-dioxaspiro[4,5]decane-2-yl)methanol

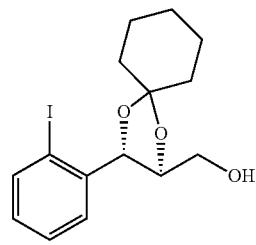

The substantially same method as described in Preparation example 107 was conducted, except that (2R,3S)-methyl-3-(2-iodophenyl)-1,4-dioxaspiro[4,5]decane-2-carboxylate (Preparation example 120) was used instead of (4S,5R)-methyl-5-(2-iodophenyl)-2-methyl-1,3-dioxolane-4-carboxylate (Preparation example 106), to obtain the title compound (1.7 g, 70~95%).
$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.19~7.49 (m, 4H).

Preparation Example 122: (4S,5R)-methyl-5-(2-iodophenyl)-2-phenyl-1,3-dioxolane-4-carboxylate

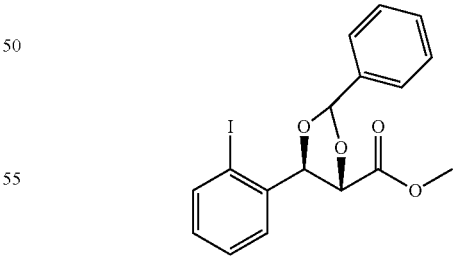

The substantially same method as described in Preparation example 118 was conducted, except that benzaldehyde was used instead of cyclohexanone, to obtain the title compound (1.9 g, 50~70%).
$^1$H NMR (400 MHz, DMSO-d$_6$) δ 3.67 (s, 3H), 5.11 (d, J=8.0 Hz, 1H), 5.81 (d, J=8.0 Hz, 1H), 6.18 (s, 1H), 6.96~7.57 (m, 9H).

Preparation Example 123: ((4R,5R)-5-(2-iodophenyl)-2-phenyl-1,3-dioxolane-4-yl)methanol

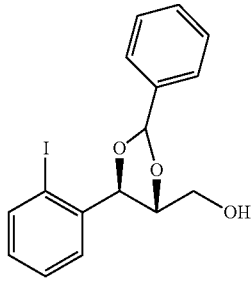

The substantially same method as described in Preparation example 107 was conducted, except that (4S,5R)-methyl-5-(2-iodophenyl)-2-phenyl-1,3-dioxolane-4-carboxylate (Preparation example 122) was used instead of (4S,5R)-methyl-5-(2-iodophenyl)-2-methyl-1.3-dioxolane-4-carboxylate (Preparation example 106), to obtain the title compound (1.4 g, 70~95%).
$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 6.94~7.59 (m, 9H).

Preparation Example 124: (4R,5S)-methyl-5-(2-iodophenyl)-2-phenyl-1,3-dioxolane-4-carboxylate

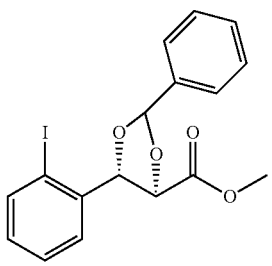

The substantially same method as described in Preparation example 120 was conducted, except benzaldehyde that was used instead of cyclohexanone, to obtain the title compound (2.1 g, 50~70%).
$^1$H NMR (400 MHz, DMSO-$d_6$) δ 3.67 (s, 3H), 5.11 (d, J=8.0 Hz, 1H), 5.81 (d, J=8.0 Hz, 1H), 6.18 (s, 1H), 6.96~7.57 (m, 9H).

Preparation Example 125: ((4S,5S)-5-(2-iodophenyl)-2-phenyl-1,3-dioxolane-4-yl)methanol

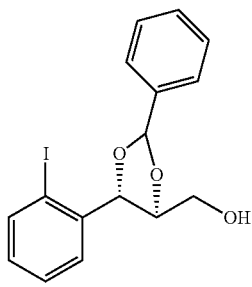

The substantially same method as described in Preparation example 107 was conducted, except that (4R,5S)-methyl-5-(2-iodophenyl)-2-phenyl-1,3-dioxolane-4-carboxylate (Preparation example 124) was used instead of (4S,5R)-methyl-5-(2-iodophenyl)-2-methyl-1.3-dioxolane-4-carboxylate (Preparation example 106), to obtain the title compound (1.3 g, 70~95%).
$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 6.94~7.59 (m, 9H).

Preparation Example 126: ((4S,5R)-methyl-5-(2,4-dichlorophenyl)-2-methyl-1.3-dioxolane-4-carboxylate

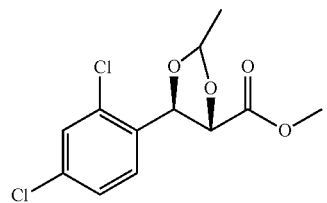

The substantially same method as described in Preparation example 60 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate (Preparation example 433), to obtain the title compound (0.9 g, 70~95%).
$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.07~7.21 (m, 3H).

Preparation Example 127: ((4R,5R)-5-(2,4-dichlorophenyl)-2-methyl-1.3-dioxolane-4-yl)methanol

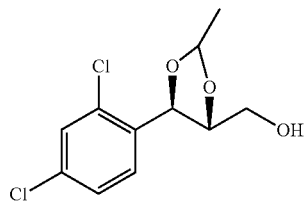

The substantially same method as described in Preparation example 27 was conducted, except that ((4S,5R)-methyl-5-(2,4-dichlorophenyl)-2-methyl-1.3-dioxolane-4-carboxylate (Preparation example 126) was used instead of (4R,5S)-methyl-5-(2-chlorophenyl)-2,2-dimethyl-1.3-dioxolane-4-carboxylate (Preparation example 26), to obtain the title compound (0.7 g, 70~95%).
$^1$H NMR (400 MHz, CDCl$_3$) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.08~7.39 (m, 3H).

Preparation Example 128: ((4R,5S)-methyl-5-(2,4-dichlorophenyl)-2-methyl-1.3-dioxolane-4-carboxylate

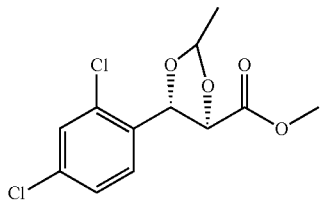

The substantially same method as described in Preparation example 126 was conducted, except that (2R,3S)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (1.9 g, 70~95%).
$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.07~7.21 (m, 3H).

Preparation Example 129: ((4S,5S)-5-(2,4-dichlorophenyl)-2-methyl-1.3-dioxolane-4-yl)methanol

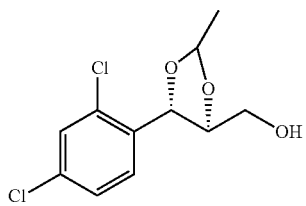

The substantially same method as described in Preparation example 27 was conducted, except that (4R,5S)-5-(2,4-dichlorophenyl)-2-methyl-1.3-dioxolane-4-carboxylate (Preparation example 128) was used instead of (4R,5S)-methyl-5-(2-chlorophenyl)-2,2-dimethyl-1.3-dioxolane-4-carboxylate (Preparation example 26), to obtain the title compound (1.5 g, 70~95%).
$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.08~7.39 (m, 3H).

Preparation Example 130: (4S,5R)-methyl-S-(2,4-dichlorophenyl)-2,2-diethyl-1.3-dioxolane-4-carboxylate

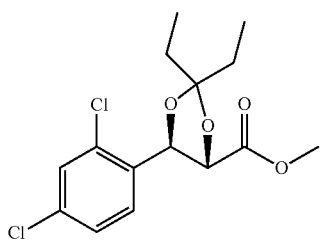 [SMILES: CCC1(CC)O[C@H](C(=O)OC)[C@@H](c2ccc(Cl)cc2Cl)O1]

The substantially same method as described in Preparation example 64 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate (Preparation example 433), to obtain the title compound (2.2 g, 60~85%).
$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.12~7.37 (m, 3H).

Preparation Example 131: ((4R,5R)-5-(2,4-dichlorophenyl)-2,2-diethyl-1.3-dioxolane-4-yl)methanol

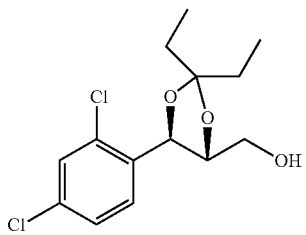 [SMILES: CCC1(CC)O[C@H](c2ccc(Cl)cc2Cl)[C@@H](CO)O1]

The substantially same method as described in Preparation example 27 was conducted, except that (4S,5R)-methyl-5-(2,4-dichlorophenyl)-2,2-diethyl-1.3-dioxolane-4-carboxylate (Preparation example 130) was used instead of (4R,5S)-methyl-5-(2-chlorophenyl)-2,2-dimethyl-1.3-dioxolane-4-carboxylate (Preparation example 26), to obtain the title compound (1.4 g, 70~95%).
$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.08~7.39 (m, 3H).

Preparation Example 132: (4R,5S)-methyl-5-(2,4-chlorophenyl)-2,2-diethyl-1.3-dioxolane-4-carboxylate

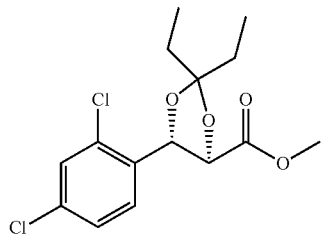 [SMILES: CCC1(CC)O[C@@H](C(=O)OC)[C@H](c2ccc(Cl)cc2Cl)O1]

The substantially same method as described in Preparation example 130 was conducted, except that (2R,3R)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (2.1 g, 70~95%).
$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.12~7.37 (m, 3H).

Preparation Example 133: ((4S,5S)-5-(2,4-chlorophenyl)-2,2-diethyl-1.3-dioxolane-4-yl)methanol

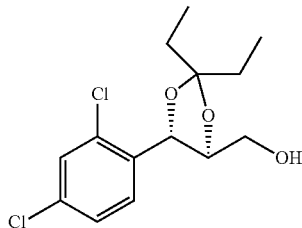 [SMILES: CCC1(CC)O[C@@H](CO)[C@H](c2ccc(Cl)cc2Cl)O1]

The substantially same method as described in Preparation example 131 was conducted, except that (4R,5S)-methyl-5-(2,4-dichlorophenyl)-2,2-diethyl-1.3-dioxolane-4-carboxylate (Preparation example 132) was used instead of ((4S,5R)-methyl-5-(2,4-dichlorophenyl)-2,2-diethyl-1.3-dioxolane-4-carboxylate (Preparation example 130), to obtain the title compound (1.2 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.08~7.39 (m, 3H).

Preparation Example 134: (2S,3R)-methyl-3-(2,4-chlorophenyl)-1,4-dioxaspiro[4,4]nonane-2-carboxylate

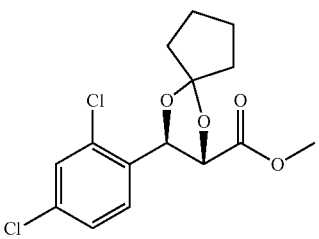 [SMILES: COC(=O)[C@H]1OC2(CCCC2)O[C@@H]1c1ccc(Cl)cc1Cl]

The substantially same method as described in Preparation example 131 was conducted, except that cyclopentanone was used instead of 3-pentanone, to obtain the title compound (2.5 g, 70~95%).

$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.03~7.36 (m, 3H).

Preparation Example 135: ((2R,3R)-3-(2,4-chlorophenyl)-1,4-dioxaspiro[4,4]nonane-2-yl)methanol

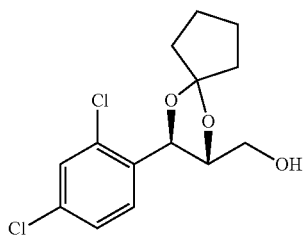 [SMILES: OC[C@H]1OC2(CCCC2)O[C@@H]1c1ccc(Cl)cc1Cl]

The substantially same method as described in Preparation example 65 was conducted, except that (2S,3R)-methyl-3-(2,4-dichlorophenyl)-1,4-dioxaspiro[4,4]nonane-2-carboxylate (Preparation example 134) was used instead of (4S,5R)-methyl-5-(2-chlorophenyl)-2,2-diethyl-1.3-dioxolane-4-carboxylate (Preparation example 64), to obtain the title compound (1.8 g, 70~95%).

$^1$H NMR (400 MHz, DMSO-d$_6$) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.02~7.37 (m, 3H).

Preparation Example 136: (2R,3S)-methyl-3-(2,4-chlorophenyl)-1,4-dioxaspiro[4,4]nonane-2-carboxylate

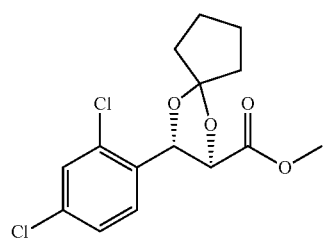 [SMILES: COC(=O)[C@@H]1OC2(CCCC2)O[C@H]1c1ccc(Cl)cc1Cl]

The substantially same method as described in Preparation example 132 was conducted, except that cyclopentanone was used instead of 3-pentanone, to obtain the title compound (2.2 g, 70~95%).

$^1$H NMR (400 MHz, DMSO-d$_6$) δ 1.69~1.71 (m, 4H), 1.82~1.86 (m, 1H), 1.91~2.00 (m, 3H), 3.68 (s, 3H), 4.40 (d, J=7.2 Hz, 1H), 5.39 (d, J=7.2 Hz, 1H), 7.03~7.36 (m, 3H).

Preparation Example 137: ((2S,3S)-3-(2,4-chlorophenyl)-1,4-dioxaspiro[4,4]nonane-2-yl)methanol

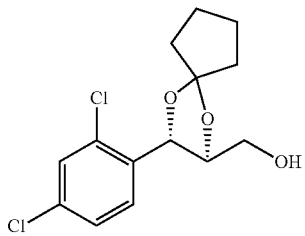 [SMILES: OC[C@@H]1OC2(CCCC2)O[C@H]1c1ccc(Cl)cc1Cl]

The substantially same method as described in Preparation example 135 was conducted, except that (2R,3S)-methyl-3-(2,4-dichlorophenyl)-1,4-dioxaspiro[4,4]nonane-2-carboxylate (Preparation example 136) was used instead of (2S,3R)-methyl-3-(2,4-dichlorophenyl)-1,4-dioxaspiro[4,4]nonane-2-carboxylate (Preparation example 134), to obtain the title compound (1.2 g, 70~95%).

$^1$H NMR (400 MHz, DMSO-ds) δ 1.60~1.72 (m, 4H), 1.83~1.94 (m, 1H), 3.52~3.65 (m, 2H), 3.82~3.86 (m, 1H), 4.90 (t, J=5.2 Hz, 1H), 5.12 (d, J=7.6 Hz, 1H), 7.02~7.37 (m, 3H).

Preparation Example 138: (2S,3R)-methyl-3-(2,4-chlorophenyl)-1,4-dioxaspiro[4,5]decane-2-carboxylate

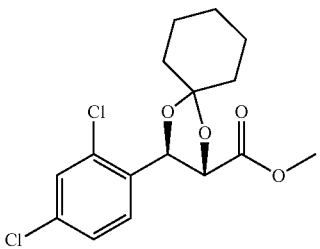 [SMILES: COC(=O)[C@H]1OC2(CCCCC2)O[C@@H]1c1ccc(Cl)cc1Cl]

The substantially same method as described in Preparation example 134 was conducted, except that cyclohexanone was used instead of cyclopentanone, to obtain the title compound (1.8 g, 70~95%).
$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.07~7.41 (m, 3H).

Preparation Example 139: ((2R,3R)-3-(2,4-chlorophenyl)-1,4-dioxaspiro[4,5]decane-2-yl)methanol

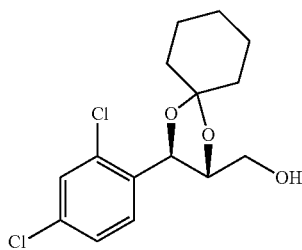 [SMILES: OC[C@H]1OC2(CCCCC2)O[C@@H]1c1ccc(Cl)cc1Cl]

The substantially same method as described in Preparation example 73 was conducted, except that (2S,3R)-methyl-3-(2,4-dichlorophenyl)-1,4-dioxaspiro[4,5]decane-2-carboxylate (Preparation example 138) was used instead of (2S,3R)-methyl-3-(2-chlorophenyl)-1,4-dioxaspiro[4,5]decane-2-carboxylate (Preparation example 72), to obtain the title compound (1.3 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.04~7.40 (m, 3H).

Preparation Example 140: (2R,3S)-methyl-3-(2,4-chlorophenyl)-1,4-dioxaspiro[4,5]decane-2-carboxylate

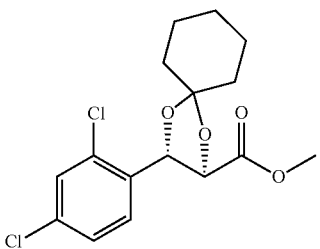 [SMILES: COC(=O)[C@@H]1OC2(CCCCC2)O[C@H]1c1ccc(Cl)cc1Cl]

The substantially same method as described in Preparation example 136 was conducted, except that cyclohexanone was used instead of cyclopentanone, to obtain the title compound (1.6 g, 70~95%).
$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.07~7.41 (m, 3H).

Preparation Example 141: ((2S,3S)-3-(2,4-chlorophenyl)-1,4-dioxaspiro[4,5]decane-2-yl)methanol

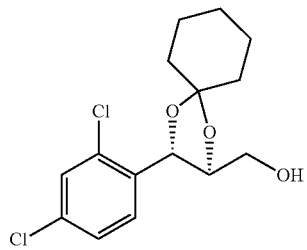 [SMILES: OC[C@@H]1OC2(CCCCC2)O[C@H]1c1ccc(Cl)cc1Cl]

The substantially same method as described in Preparation example 139 was conducted, except that (2R,3S)-methyl-3-(2,4-dichlorophenyl)-1,4-dioxaspiro[4,5]decane-2-carboxylate (Preparation example 140) was used instead of (2S,3R)-methyl-3-(2,4-dichlorophenyl)-1,4-dioxaspiro[4,5]decane-2-carboxylate (Preparation example 138), to obtain the title compound (1.2 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.04~7.40 (m, 3H).

Preparation Example 142: (4S,5R)-methyl-5-(2,4-chlorophenyl)-2-phenyl-1,3-dioxolane-4-carboxylate

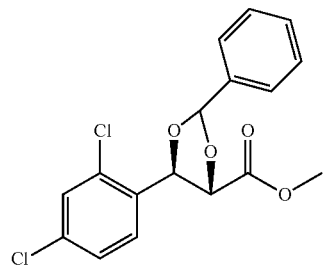

The substantially same method as described in Preparation example 138 was conducted, except that benzaldehyde was used instead of cyclohexanone, to obtain the title compound (1.9 g, 50~70%).
$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.03~7.41 (m, 3H).

Preparation Example 143: ((4R,5R)-5-(2,4-chlorophenyl)-2-phenyl-1,3-dioxolane-4-yl)methanol

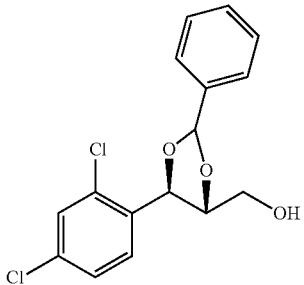

The substantially same method as described in Preparation example 65 was conducted, except that (4S,5R)-methyl-5-(2,4-chlorophenyl)-2-phenyl-1,3-dioxolane-4-carboxylate (Preparation example 142) was used instead of (4S,5R)-methyl-5-(2-chlorophenyl)-2,2-diethyl-1.3-dioxolane-4-carboxylate (Preparation example 64), to obtain the title compound (1.5 g, 70~95%).

$^1$H NMR (400 MHz, DMSO-d$_6$) δ 1.63~1.75 (m, 10H), 3.52~3.81 (m, 2H), 3.95 (t, 1=8.0 Hz, 1H), 5.43 (d, J=7.6 Hz, 1H), 7.04~7.42 (m, 3H).

Preparation Example 144: (4R,5S)-methyl-5-(2,4-chlorophenyl)-2-phenyl-1,3-dioxolane-4-carboxylate

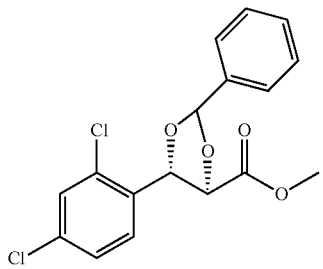

The substantially same method as described in Preparation example 140 was conducted, except that benzaldehyde was used instead of cyclohexanone, to obtain the title compound (1.6 g, 50~70%).

$^1$H NMR (400 MHz, DMSO-d$_6$) δ 1.61~1.69 (m, 10H), 3.79 (s, 3H), 4.33 (d, J=8.0 Hz, 1H), 5.85 (d, J=8.0 Hz, 1H), 7.03~7.41 (m, 3H).

Preparation Example 145: ((4S,5S)-5-(2,4-chlorophenyl)-2-phenyl-1,3-dioxolane-4-yl)methanol

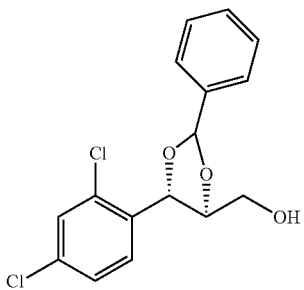

The substantially same method as described in Preparation example 143 was conducted, except that (4R,5S)-methyl-5-(2,4-chlorophenyl)-2-phenyl-1,3-dioxolane-4-carboxylate (Preparation example 144) was used instead of (2S,3R)-methyl-3-(2,4-chlorophenyl)-2-phenyl-1,3-dioxolane-4-carboxylate (Preparation example 142), to obtain the title compound (1.2 g, 70~95%).

$^1$H NMR (400 MHz, DMSO-d$_6$) δ 1.63~1.75 (m, 10H), 3.52~3.81 (m, 2H), 3.95 (t, J=8.0 Hz, 1H), 5.43 (d, J=7.6 Hz, 1H), 7.04~7.42 (m, 3H).

Preparation Example 146: ((4S,5R)-ethyl-5-(2,6-dichlorophenyl)-2-methyl-1.3-dioxolane-4-carboxylate

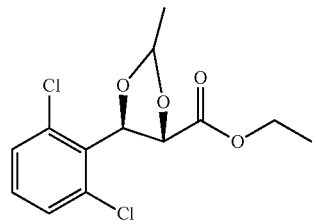

The substantially same method as described in Preparation example 60 was conducted, except that (2S,3R)-ethyl-3-(2,6-dichlorophenyl)-2,3-dihydroxypropanoate (Preparation example 39) was used instead of (2S,3R)-methyl-3-(2-chlorophenyl)-2,3-dihydroxypropanoate (Preparation example 433), to obtain the title compound (1.7 g, 70~95%).

$^1$H NMR (400 MHz, CDCl$_3$) δ 1.36 (d, J=6.4 Hz, 3H), 3.78 (s, 3H), 4.15 (m, 2H), 4.30 (d, J=7.6 Hz, 1H), 5.07 (m, 1H), 5.62 (d, J=7.6 Hz, 1H), 7.17~7.36 (m, 3H).

Preparation Example 147: ((4R,5R)-5-(2,6-dichlorophenyl)-2-methyl-1.3-dioxolane-4-yl)methanol

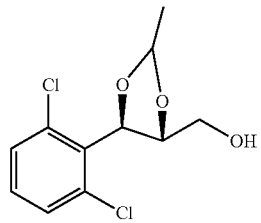

The substantially same method as described in Preparation example 27 was conducted, except that ((4S,5R)-ethyl-5-(2,6-dichlorophenyl)-2-methyl-1.3-dioxolane-4-carboxylate (Preparation example 146) was used instead of (4R,5S)-methyl-5-(2-chlorophenyl)-2,2-dimethyl-1.3-dioxolane-4-carboxylate (Preparation example 26), to obtain the title compound (1.2 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.18~7.39 (m, 3H).

Preparation Example 148: ((4R,5S)-ethyl-5-(2,6-dichlorophenyl)-2-methyl-1.3-dioxolane-4-carboxylate

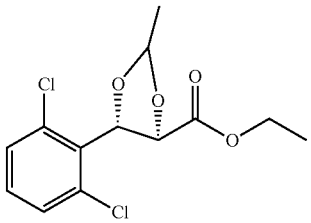

The substantially same method as described in Preparation example 146 was conducted, except that (2R,3S)-ethyl-3-(2,6-dichlorophenyl)-2,3-dihydroxypropanoate (Preparation example 33) was used instead of (2S,3R)-methyl-3-(2,4-dichlorophenyl)-2,3-dihydroxypropanoate (Preparation example 39), to obtain the title compound (1.8 g, 70~95%).

$^1$H NMR (400 MHz, CDCl$_3$) δ 1.36 (d, J=6.4 Hz, 3H), 3.78 (s, 3H), 4.15 (m, 2H), 4.30 (d, J=7.6 Hz, 1H), 5.07 (m, 1H), 5.62 (d, J=7.6 Hz, 1H), 7.17~7.36 (m, 3H).

Preparation Example 149: ((4S,5S)-5-(2,6-dichlorophenyl)-2-methyl-1.3-dioxolane-4-yl)methanol

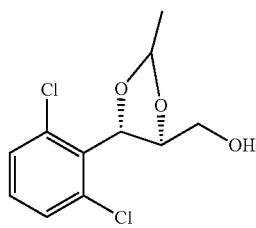

The substantially same method as described in Preparation example 147 was conducted, except that ((4R,5S)-ethyl-5-(2,6-dichlorophenyl)-2-methyl-1.3-dioxolane-4-carboxylate (Preparation example 148) was used instead of ((4S,5R)-ethyl-5-(2,6-dichlorophenyl)-2-methyl-1.3-dioxolane-4-carboxylate (Preparation example 146), to obtain the title compound (1.3 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.18~7.39 (m, 3H).

Preparation Example 150: (4S,5R)-ethyl-5-(2,6-dichlorophenyl)-2,2-diethyl-1.3-dioxolane-4-carboxylate

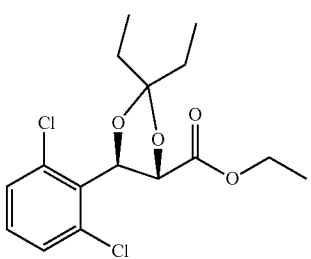 [SMILES: CCOC(=O)[C@H]1OC(CC)(CC)O[C@@H]1c1c(Cl)cccc1Cl]

The substantially same method as described in Preparation example 130 was conducted, except that (2S,3R)-ethyl-3-(2,6-dichlorophenyl)-2,3-dihydroxypropanoate (Preparation example 39) was used instead of (2S,3R)-methyl-3-(2,6-dichlorophenyl)-2,3-dihydroxypropanoate (Preparation example 36), to obtain the title compound (1.8 g, 60~85%).

$^1$H NMR (400 MHz, CDCl$_3$) δ 0.96 (m, 6H), 1.30 (t, J=8.0 Hz, 3H), 1.59 (m, 4H), 4.12 (m, 2H), 5.11 (d, J=7.6 Hz, 1H), 5.81 (d, J=7.6 Hz, 1H), 7.08~7.26 (m, 3H).

Preparation Example 151: ((4R,5R)-5-(2,6-dichlorophenyl)-2,2-diethyl-1.3-dioxolane-4-yl)methanol

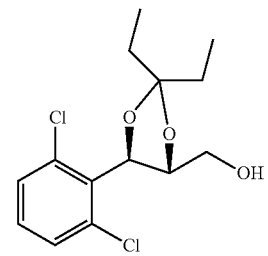 [SMILES: CCC1(CC)O[C@H](c2c(Cl)cccc2Cl)[C@@H](CO)O1]

The substantially same method as described in Preparation example 147 was conducted, except that (4S,5R)-ethyl-5-(2,6-dichlorophenyl)-2,2-diethyl-1.3-dioxolane-4-carboxylate (Preparation example 150) was used instead of ((4S,5R)-ethyl-5-(2,6-dichlorophenyl)-2-methyl-1.3-dioxolane-4-carboxylate (Preparation example 146), to obtain the title compound (1.2 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.07~7.29 (m, 3H).

Preparation Example 152: (4R,5S)-ethyl-5-(2,6-chlorophenyl)-2,2-diethyl-1.3-dioxolane-4-carboxylate

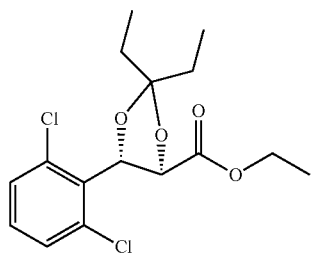 [SMILES: CCOC(=O)[C@@H]1OC(CC)(CC)O[C@H]1c1c(Cl)cccc1Cl]

The substantially same method as described in Preparation example 150 was conducted, except that (2R,3S)-ethyl-3-(2,6-dichlorophenyl)-2,3-dihydroxypropanoate (Preparation example 33) was used instead of (2S,3R)-ethyl-3-(2,6-dichlorophenyl)-2,3-dihydroxypropanoate (Preparation example 39), to obtain the title compound (2.5 g, 70~95%).

$^1$H NMR (400 MHz, CDCl$_3$) δ 0.96 (m, 6H), 1.30 (t, J=8.0 Hz, 3H), 1.59 (m, 4H), 4.12 (m, 2H), 5.11 (d, J=7.6 Hz, 1H), 5.81 (d, J=7.6 Hz, 1H), 7.08~7.26 (m, 3H).

Preparation Example 153: ((4S,5S)-5-(2,6-chlorophenyl)-2,2-diethyl-1.3-dioxolane-4-yl)methanol

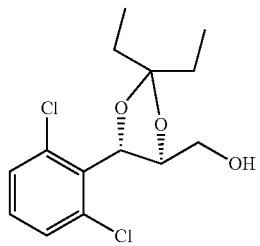 [SMILES: CCC1(CC)O[C@@H](CO)[C@H](c2c(Cl)cccc2Cl)O1]

The substantially same method as described in Preparation example 151 was conducted, except that (4R,5S)-ethyl-5-(2,6-dichlorophenyl)-2,2-diethyl-1.3-dioxolane-4-carboxylate (Preparation example 152) was used instead of (4S,5R)-ethyl-5-(2,6-dichlorophenyl)-2,2-diethyl-1.3-dioxolane-4-carboxylate (Preparation example 150), to obtain the title compound (2.1 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.07~7.29 (m, 3H).

Preparation Example 154: (2S,3R)-ethyl-3-(2,6-chlorophenyl)-1,4-dioxaspiro[4,4]nonane-2-carboxylate

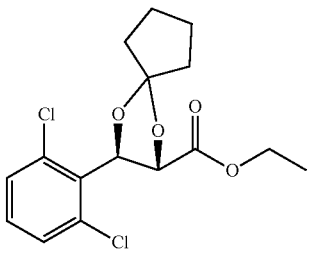 [SMILES: CCOC(=O)[C@H]1OC2(CCCC2)O[C@@H]1c1c(Cl)cccc1Cl]

The substantially same method as described in Preparation example 150 was conducted, except that cyclopentanone was used instead of 3-pentanone, to obtain the title compound (2.1 g, 70~95%).

$^1$H NMR (400 MHz, DMSO-d$_6$) δ 1.30 (t, J=7.8 Hz, 3H), 1.69~1.71 (m, 4H), 1.73~1.86 (m, 4H), 4.07~4.14 (m, 2H), 5.11 (d, J=7.2 Hz, 1H), 5.81 (d, J=7.2 Hz, 1H), 7.07~7.31 (m, 3H).

Preparation Example 155: ((2R,3R)-3-(2,6-chlorophenyl)-1,4-dioxaspiro[4,4]nonane-2-yl)methanol

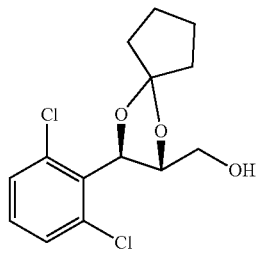 [SMILES: OC[C@H]1OC2(CCCC2)O[C@@H]1c1c(Cl)cccc1Cl]

The substantially same method as described in Preparation example 151 was conducted, except that (2S,3R)-ethyl-3-(2,6-dichlorophenyl)-1,4-dioxaspiro[4,4]nonane-2-carboxylate (Preparation example 154) was used instead of (4S,5R)-ethyl-5-(2,6-dichlorophenyl)-2,2-diethyl-1.3-dioxolane-4-carboxylate (Preparation example 150), to obtain the title compound (1.7 g, 70~95%).

$^1$H NMR (400 MHz, DMSO-d$_6$) δ 1.60~1.72 (m, 4H), 1.83~1.94 (m, 4H), 3.52~3.65 (m, 2H), 4.90 (t, J=5.2 Hz, 1H), 5.12 (d, J=7.6 Hz, 1H), 7.08~7.32 (m, 3H).

Preparation Example 156: (21R,3S)-ethyl-3-(2,6-chlorophenyl)-1,4-dioxaspiro[4,4]nonane-2-carboxylate

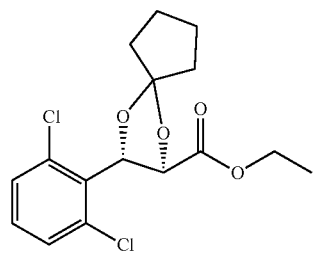 [SMILES: CCOC(=O)[C@@H]1OC2(CCCC2)O[C@H]1c1c(Cl)cccc1Cl]

The substantially same method as described in Preparation example 152 was conducted, except that cyclopentanone was used instead of 3-pentanone, to obtain the title compound (2.5 g, 70~95%).

$^1$H NMR (400 MHz, DMSO-d$_6$) δ 1.30 (t, J=7.8 Hz, 3H), 1.69~1.71 (m, 4H), 1.73~1.86 (m, 4H), 4.07~4.14 (m, 2H), 5.11 (d, J=7.2 Hz, 1H), 5.81 (d, J=7.2 Hz, 1H), 7.07~7.31 (m, 3H).

Preparation Example 157: ((2S,3S)-3-(2,6-chlorophenyl)-1,4-dioxaspiro[4,4]nonane-2-yl)methanol

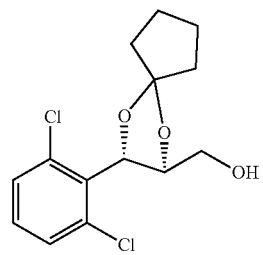 [SMILES: OC[C@@H]1OC2(CCCC2)O[C@H]1c1c(Cl)cccc1Cl]

The substantially same method as described in Preparation example 155 was conducted, except that (2R,3S)-ethyl-3-(2,6-dichlorophenyl)-1,4-dioxaspiro[4,4]nonane-2-carboxylate (Preparation example 156) was used instead of (2S,3R)-ethyl-3-(2,6-dichlorophenyl)-1,4-dioxaspiro[4,4]nonane-2-carboxylate (Preparation example 154), to obtain the title compound (2.0 g, 70~95%).

$^1$H NMR (400 MHz, DMSO-d$_6$) δ 1.60~1.72 (m, 4H), 1.83~1.94 (m, 4H), 3.52~3.65 (m, 2H), 4.90 (t, J=5.2 Hz, 1H), 5.12 (d, J=7.6 Hz, 1H), 7.08~7.32 (m, 3H).

Preparation Example 158: (2S,3R)-ethyl-3-(2,6-chlorophenyl)-1,4-dioxaspiro[4,5]decane-2-carboxylate

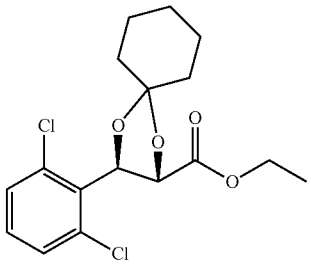 [SMILES: CCOC(=O)[C@H]1OC2(CCCCC2)O[C@@H]1c1c(Cl)cccc1Cl]

The substantially same method as described in Preparation example 154 was conducted, except that cyclohexanone was used instead of cyclopentanone, to obtain the title compound (2.2 g, 70~95%).
$^1$H NMR (400 MHz, DMSO-$d_6$) δ 1.30 (t, J=7.6 Hz, 3H), 1.61~1.69 (m, 10H), 4.08~4.18 (d, 2H), 4.33 (d, J=8.0 Hz, 1H), 5.85 (d, J=8.0 Hz, 1H), 7.07~7.31 (m, 3H).

Preparation Example 159: ((2R,3R)-3-(2,6-chlorophenyl)-1,4-dioxaspiro[4,5]decane-2-yl)methanol

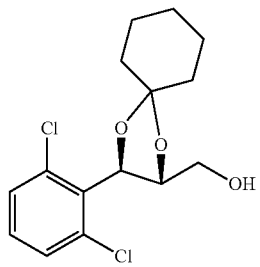 [SMILES: OC[C@H]1OC2(CCCCC2)O[C@@H]1c1c(Cl)cccc1Cl]

The substantially same method as described in Preparation example 155 was conducted, except that (2S,3R)-ethyl-3-(2,6-dichlorophenyl)-1,4-dioxaspiro[4,5]decane-2-carboxylate (Preparation example 158) was used instead of (2S,3R)-ethyl-3-(2,6-dichlorophenyl)-1,4-dioxaspiro[4,4]nonane-2-carboxylate (Preparation example 154), to obtain the title compound (1.7 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.05~7.30 (m, 3H).

Preparation Example 160: (2R,3S)-ethyl-3-(2,6-chlorophenyl)-1,4-dioxaspiro[4,5]decane-2-carboxylate

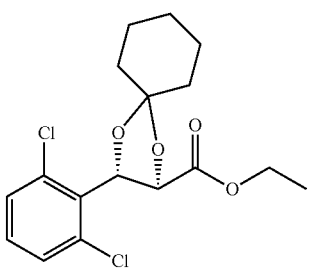 [SMILES: CCOC(=O)[C@@H]1OC2(CCCCC2)O[C@H]1c1c(Cl)cccc1Cl]

The substantially same method as described in Preparation example 156 was conducted, except that cyclohexanone was used instead of cyclopentanone, to obtain the title compound (1.9 g, 70~95%).
$^1$H NMR (400 MHz, DMSO-$d_6$) δ 1.30 (t, J=7.6 Hz, 3H), 1.61~1.69 (m, 10H), 4.08~4.18 (d, 2H), 4.33 (d, J=8.0 Hz, 1H), 5.85 (d, J=8.0 Hz, 1H), 7.07~7.31 (m, 3H).

Preparation Example 161: ((2S,3S)-3-(2,6-chlorophenyl)-1,4-dioxaspiro[4,5]decane-2-yl)methanol

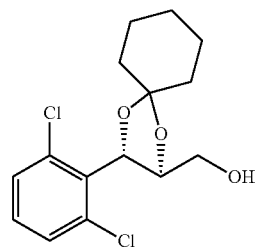 [SMILES: OC[C@@H]1OC2(CCCCC2)O[C@H]1c1c(Cl)cccc1Cl]

The substantially same method as described in Preparation example 159 was conducted, except that (2R,3S)-ethyl-3-(2,6-dichlorophenyl)-1,4-dioxaspiro[4,5]decane-2-carboxylate (Preparation example 160) was used instead of (2S,3R)-ethyl-3-(2,6-dichlorophenyl)-1,4-dioxaspiro[4,5]decane-2-carboxylate (Preparation example 158), to obtain the title compound (1.5 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.05~7.30 (m, 3H).

Preparation Example 162: (4S,5R)-ethyl-5-(2,6-chlorophenyl)-2-phenyl-1,3-dioxolane-4-carboxylate

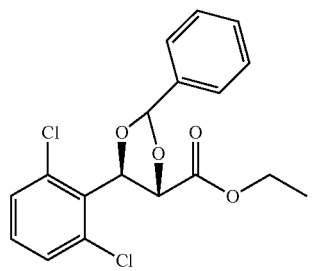

The substantially same method as described in Preparation example 158 was conducted, except that benzaldehyde was used instead of cyclohexanone, to obtain the title compound (2.0 g, 50~70%).
$^1$H NMR (400 MHz, DMSO-$d_6$) δ 1.30 (t, J=7.6 Hz, 3H), 4.08~4.18 (d, 2H), 5.13 (d, J=8.0 Hz, 1H), 5.85 (d, J=8.0 Hz, 1H), 6.18 (s, 1H), 7.03~7.22 (m, 8H).

Preparation Example 163: ((4R,5R)-5-(2,6-chlorophenyl)-2-phenyl-1,3-dioxolane-4-yl)methanol

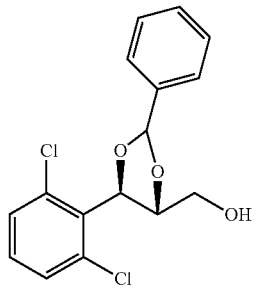

The substantially same method as described in Preparation example 159 was conducted, except that (4S,5R)-ethyl-5-(2,6-chlorophenyl)-2-phenyl-1,3-dioxolane-4-carboxylate (Preparation example 162) was used instead of (2S,RS)-ethyl-3-(2,6-dichlorophenyl)-1,4-dioxaspiro[4,5]decane-2-carboxylate (Preparation example 158), to obtain the title compound (1.6 g, 70~95%).
$^1$H NMR (400 MHz, DMSO-d$_6$) δ 3.50~3.79 (m, 2H), 5.13 (d, J=8.0 Hz, 1H), 5.85 (d, J=8.0 Hz, 1H), 6.18 (s, 1H), 7.03~7.22 (m, 8H).

Preparation Example 164: (4R,5S)-ethyl-5-(2,6-chlorophenyl)-2-phenyl-1,3-dioxolane-4-carboxylate

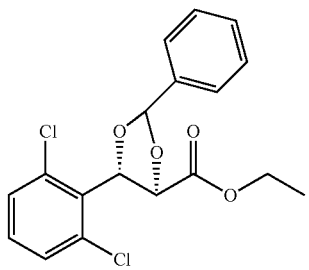

The substantially same method as described in Preparation example 160 was conducted, except that benzaldehyde was used instead of cyclohexanone, to obtain the title compound (1.8 g, 50~70%).
$^1$H NMR (400 MHz, DMSO-d$_6$) δ 1.30 (t, J=7.6 Hz, 3H), 4.08~4.18 (d, 2H), 5.13 (d, J=8.0 Hz, 1H), 5.85 (d, J=8.0 Hz, 1H), 6.18 (s, 1H), 7.03~7.22 (m, 8H).

Preparation Example 165: ((4S,5S)-5-(2,6-chlorophenyl)-2-phenyl-1,3-dioxolane-4-yl)methanol

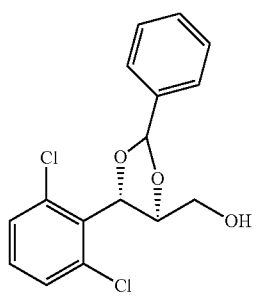

The substantially same method as described in Preparation example 163 was conducted, except that (4R,5S)-ethyl-5-(2,6-chlorophenyl)-2-phenyl-1,3-dioxolane-4-carboxylate (Preparation example 164) was used instead of (2S,3R)-ethyl-3-(2,6-chlorophenyl)-2-phenyl-1,3-dioxolane-4-carboxylate (Preparation example 162), to obtain the title compound (1.4 g, 70~95%).
$^1$H NMR (400 MHz, DMSO-d$_6$) δ 3.50~3.79 (m, 2H), 5.13 (d, J=8.0 Hz, 1H), 5.85 (d, J=8.0 Hz, 1H), 6.18 (s, 1H), 7.03~7.22 (m, 8H).

Preparation Example 166: ((4S,5R)-methyl-5-(2-nitrophenyl)-2-methyl-1,3-dioxolane-4-carboxylate

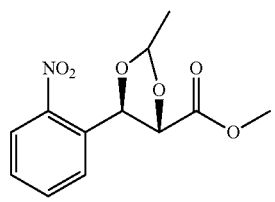

The substantially same method as described in Preparation example 60 was conducted, except that (2S,3R)-methyl-3-(2-nitrophenyl)-2,3-dihydroxypropanoate (Preparation example 44) was used instead of (2S,3R)-methyl-3-(2-chlorophenyl)-2,3-dihydroxypropanoate (Preparation example 433), to obtain the title compound (2.3 g, 70~95%).
$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.45~8.12 (m, 4H).

Preparation Example 167: ((4R,5R)-5-(2-nitrophenyl)-2-methyl-1.3-dioxolane-4-yl)methanol

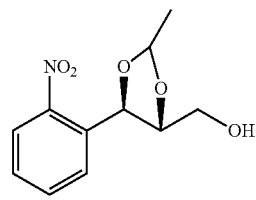

The substantially same method as described in Preparation example 27 was conducted, except that (4S,5R)-methyl-5-(2-nitrophenyl)-2-methyl-1,3-dioxolane-4-carboxylate (Preparation example 166) was used instead of (4R,5S)-methyl-5-(2-chlorophenyl)-2,2-dimethyl-1.3-dioxolane-4-carboxylate (Preparation example 26), to obtain the title compound (1.9 g, 70~95%).
$^1$H NMR (400 MHz, CDCl$_3$) δ 1.37 (d, J=6.0 Hz, 3H), 3.62~3.70 (m, 2H), 4.36 (dd. J=7.0, 7.0 Hz, 1H), 5.06 (m, 1H), 5.17 (d, J=7.0 Hz, 1H), 7.47~8.11 (m, 4H).

Preparation Example 168: ((4R,5S)-methyl-5-(2-nitrophenyl)-2-methyl-1,3-dioxolane-4-carboxylate

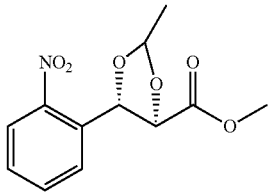

The substantially same method as described in Preparation example 160 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.0 g, 70~95%).

$^1$H NMR (400 MHz, CDCl$_3$) δ 1.36 (d, J=6.4 Hz, 3H), 3.78 (s, 3H), 4.30 (d, J=7.6 Hz, 1H), 5.07 (m, 1H), 5.62 (d, J=7.6 Hz, 1H), 7.45~8.12 (m, 4H).

Preparation Example 169: ((4S,5S)-5-(2-nitrophenyl)-2-methyl-1,3-dioxolane-4-yl)methanol

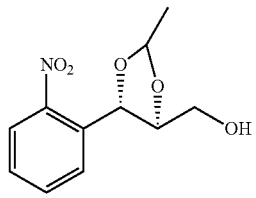

The substantially same method as described in Preparation example 167 was conducted, except that (4R,5S)-methyl-5-(2-nitrophenyl)-2-methyl-1,3-dioxolane-4-carboxylate (Preparation example 168) was used instead of (4S,5R)-methyl-5-(2-nitrophenyl)-2-methyl-1,3-dioxolane-4-carboxylate (Preparation example 166), to obtain the title compound (1.6 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.47~8.11 (m, 4H).

Preparation Example 170: (4S,5R)-methyl-5-(2-nitrophenyl)-2,2-diethyl-1,3-dioxolane-4-carboxylate

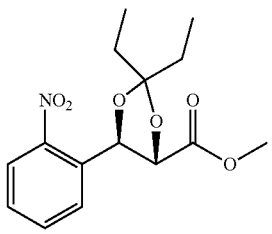 [SMILES: CCC1(CC)O[C@H](C(=O)OC)[C@@H](c2ccccc2[N+](=O)[O-])O1]

The substantially same method as described in Preparation example 150 was conducted, except that (2S,3R)-methyl-3-(2-nitrophenyl)-2,3-dihydroxypropanoate (Preparation example 44) was used instead of (2S,3R)-ethyl-3-(2,6-dichlorophenyl)-2,3-dihydroxypropanoate (Preparation example 39), to obtain the title compound (2.4 g, 60~85%).

$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.43~8.10 (m, 4H).

Preparation Example 171: ((4R,5R)-5-(2-nitrophenyl)-2,2-diethyl-1,3-dioxolane-4-yl)methanol

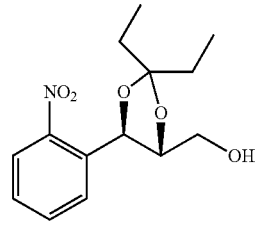 [SMILES: CCC1(CC)O[C@H](c2ccccc2[N+](=O)[O-])[C@@H](CO)O1]

The substantially same method as described in Preparation example 167 was conducted, except that (4S,5R)-methyl-5-(2-nitrophenyl)-2,2-diethyl-1,3-dioxolane-4-carboxylate (Preparation example 170) was used instead of (4S,5R)-methyl-5-(2-nitrophenyl)-2-methyl-1,3-dioxolane-4-carboxylate (Preparation example 166), to obtain the title compound (1.9 g, 70~95%).

$^1$H NMR (400 MHz, CDCl$_3$) δ 0.96 (m, 6H), 1.59 (m, 4H), 3.62~3.70 (m, 2H), 4.36 (dd, J=7.0, 7.0 Hz, 1H), 5.17 (d, J=7.0 Hz, 1H), 7.37~8.09 (m, 4H).

Preparation Example 172: (4R,5S)-methyl-5-(2-nitrophenyl)-2,2-diethyl-1,3-dioxolane-4-carboxylate

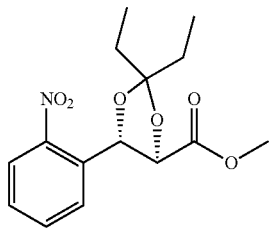 [SMILES: CCC1(CC)O[C@@H](C(=O)OC)[C@H](c2ccccc2[N+](=O)[O-])O1]

The substantially same method as described in Preparation example 170 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.5 g, 60~85%).

$^1$H NMR (400 MHz, CDCl$_3$) δ 0.96 (m, 6H), 1.59 (m, 4H), 3.67 (s, 3H), 5.11 (d, J=7.6 Hz, 1H), 5.81 (d, J=7.6 Hz, 1H), 7.43~8.10 (m, 4H).

Preparation Example 173: ((4S,5S)-5-(2-nitrophenyl)-2,2-diethyl-1.3-dioxolane-4-yl)methanol

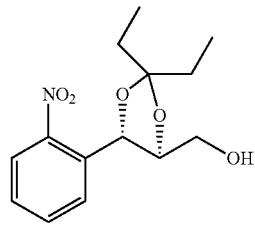 [SMILES: CCC1(CC)O[C@@H](CO)[C@H](c2ccccc2[N+](=O)[O-])O1]

The substantially same method as described in Preparation example 171 was conducted, except that (4R,5S)-methyl-5-(2-nitrophenyl)-2,2-diethyl-1.3-dioxolane-4-carboxylate (Preparation example 172) was used instead of (4S,5R)-methyl-5-(2-nitrophenyl)-2,2-diethyl-1.3-dioxolane-4-carboxylate (Preparation example 170), to obtain the title compound (2.0 g, 70~95%).

$^1$H NMR (400 MHz, CDCl$_3$) δ 0.96 (m, 6H), 1.59 (m, 4H), 3.62~3.70 (m, 2H), 4.36 (dd, J=7.0, 7.0 Hz, 1H), 5.17 (d, J=7.0 Hz, 1H), 7.37~8.09 (m, 4H).

Preparation Example 174: (2S, 3R)-methyl-3-(2-nitrophenyl)-1,4-dioxaspiro[4,4]nonane-2-carboxylate

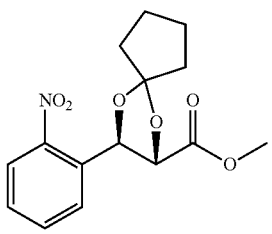

The substantially same method as described in Preparation example 170 was conducted, except that cyclopentanone was used instead of 3-pentanone, to obtain the title compound (2.5 g, 70~95%).

$^1$H NMR (400 MHz, DMSO-d$_t$) δ 1.69~1.71 (m, 4H), 1.82~1.86 (m, 4H), 3.68 (s, 3H), 4.40 (d, J=7.2 Hz, 1H), 5.39 (d, J=7.2 Hz, 1H), 7.44~8.06 (m, 4H).

Preparation Example 175: ((2R,3R)-3-(2-nitrophenyl)-1,4-dioxaspiro[4,4]nonane-2-yl)methanol

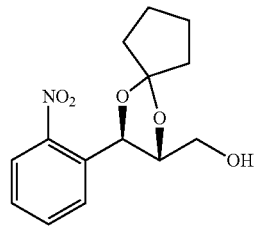 [SMILES: O=[N+]([O-])c1ccccc1[C@H]1OC2(CCCC2)O[C@@H]1CO]

The substantially same method as described in Preparation example 171 was conducted, except that (2S,3R)-methyl-3-(2-nitrophenyl)-1,4-dioxaspiro[4,4]nonane-2-carboxylate (Preparation example 174) was used instead of (4S,5R)-methyl-5-(2-nitrophenyl)-2,2-diethyl-1.3-dioxolane-4-carboxylate (Preparation example 170), to obtain the title compound (2.1 g, 70~95%).

$^1$H NMR (400 MHz, DMSO-d$_6$) δ 1.60~1.72 (m, 4H), 1.83~1.94 (m, 4H), 3.52~3.65 (m, 2H), 4.90 (t, J=5.2 Hz, 1H), 5.12 (d, J=7.6 Hz, 1H), 7.46~8.09 (m, 4H).

Preparation Example 176: (2R,3S)-methyl-3-(2-nitrophenyl)-1,4-dioxaspiro[4,4]nonane-2-carboxylate

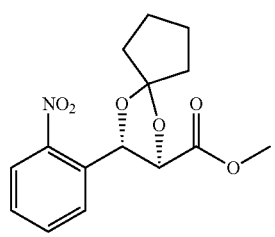 [SMILES: COC(=O)[C@@H]1OC2(CCCC2)O[C@H]1c1ccccc1[N+](=O)[O-]]

The substantially same method as described in Preparation example 172 was conducted, except that cyclopentanone was used instead of 3-pentanone, to obtain the title compound (2.9 g, 70~95%).

$^1$H NMR (400 MHz, DMSO-d$_b$) δ 1.69~1.71 (m, 4H), 1.82~1.86 (m, 4H), 3.68 (s, 3H), 4.40 (d, J=7.2 Hz, 1H), 5.39 (d, J=7.2 Hz, 1H), 7.44~8.06 (m, 4H).

Preparation Example 177: ((2S,3S)-3-(2-nitrophenyl)-1,4-dioxaspiro[4,4]nonane-2-yl)methanol

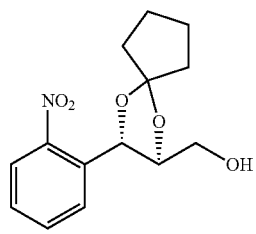 [SMILES: O=[N+]([O-])c1ccccc1[C@@H]1OC2(CCCC2)O[C@H]1CO]

The substantially same method as described in Preparation example 175 was conducted, except that (2R,3S)-methyl-3-(2-nitrophenyl)-1,4-dioxaspiro[4,4]nonane-2-carboxylate (Preparation example 176) was used instead of (2S,3R)-methyl-3-(2-nitrophenyl)-1,4-dioxaspiro[4,4]nonane-2-carboxylate (Preparation example 174), to obtain the title compound (2.0 g, 70~95%).

$^1$H NMR (400 MHz, DMSO-d$_6$) δ 1.60~1.72 (m, 4H), 1.83~1.94 (m, 4H), 3.52~3.65 (m, 2H), 4.90 (t, J=5.2 Hz, 1H), 5.12 (d, J=7.6 Hz, 1H), 7.46~8.09 (m, 4H).

Preparation Example 178: (2S,3R)-methyl-3-(2-nitrophenyl)-1,4-dioxaspiro[4,5]decane-2-carboxylate

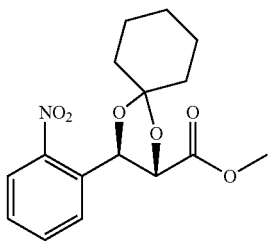 [SMILES: COC(=O)[C@H]1OC2(CCCCC2)O[C@@H]1c1ccccc1[N+](=O)[O-]]

The substantially same method as described in Preparation example 174 was conducted, except that cyclohexanone was used instead of cyclopentanone, to obtain the title compound (1.7 g, 70~95%).
$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.45~8.12 (m, 4H).

Preparation Example 179: ((2R,3R)-3-(2-nitrophenyl)-1,4-dioxaspiro[4,5]decane-2-yl)methanol

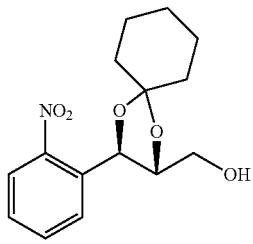 [SMILES: O=[N+]([O-])c1ccccc1[C@H]1OC2(CCCCC2)O[C@@H]1CO]

The substantially same method as described in Preparation example 175 was conducted, except that (2S,3R)-methyl-3-(2-nitrophenyl)-1,4-dioxaspiro[4,5]decane-2-carboxylate (Preparation example 178) was used instead of (2S,3R)-methyl-3-(2-nitrophenyl)-1,4-dioxaspiro[4,4]nonane-2-carboxylate (Preparation example 174), to obtain the title compound (1.4 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.46~8.09 (m, 4H).

Preparation Example 180: (21R,3S)-methyl-3-(2-nitrophenyl)-1,4-dioxaspiro[4,5]decane-2-carboxylate

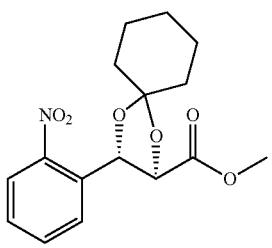 [SMILES: COC(=O)[C@@H]1OC2(CCCCC2)O[C@H]1c1ccccc1[N+](=O)[O-]]

The substantially same method as described in Preparation example 176 was conducted, except that cyclohexanone was used instead of cyclopentanone, to obtain the title compound (2.2 g, 70~95%).
$^1$H NMR (400 MHz, DMSO-$d_6$) δ 1.61~1.69 (m, 10H), 3.79 (s, 3H), 4.33 (d, J=8.0 Hz, 1H), 5.85 (d, J=8.0 Hz, 1H), 7.45~8.12 (m, 4H).

Preparation Example 181: ((2S,3S)-3-(2-nitrophenyl)-1,4-dioxaspiro[4,5]decane-2-yl)methanol

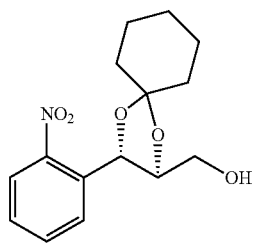 [SMILES: O=[N+]([O-])c1ccccc1[C@@H]1OC2(CCCCC2)O[C@H]1CO]

The substantially same method as described in Preparation example 179 was conducted, except that (2R,3S)-methyl-3-(2-nitrophenyl)-1,4-dioxaspiro[4,5]decane-2-carboxylate (Preparation example 180) was used instead of (2S,3R)-methyl-3-(2-nitrophenyl)-1,4-dioxaspiro[4,5]decane-2-carboxylate (Preparation example 178), to obtain the title compound (1.5 g, 70~95%).
$^1$H NMR (400 MHz, DMSO-$d_6$) δ 1.63~1.75 (m, 10H), 3.52~3.81 (m, 2H), 3.95 (t, J=8.0 Hz, 1H), 5.43 (d, J=7.6 Hz, 1H), 7.19~7.49 (m, 4H).

Preparation Example 182: (4S,5R)-methyl-5-(2-nitrophenyl)-2-phenyl-1,3-dioxolane-4-carboxylate

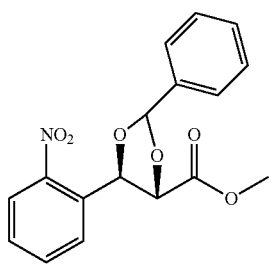

The substantially same method as described in Preparation example 178 was conducted, except that benzaldehyde was used instead of cyclohexanone, to obtain the title compound (1.9 g, 50~70%).
$^1$H NMR (400 MHz, DMSO-ds) δ 3.67 (s, 3H), 5.11 (d, J=8.0 Hz, 1H), 5.81 (d, J=8.0 Hz, 1H), 6.18 (s, 1H), 6.96~8.12 (m, 9H).

Preparation Example 183: ((4R,5R)-5-(2-nitrophenyl)-2-phenyl-1,3-dioxolan-4-yl)methanol

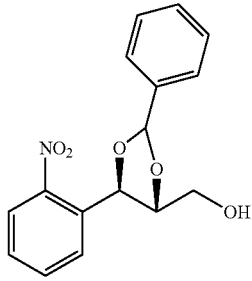

The substantially same method as described in Preparation example 179 was conducted, except that (4S,5R)-methyl-5-(2-nitrophenyl)-2-phenyl-1,3-dioxolane-4-carboxylate (Preparation example 182) was used instead of (2S,3R)-methyl-3-(2-nitrophenyl)-1,4-dioxaspiro[4,4]nonane-2-carboxylate (Preparation example 174), to obtain the title compound (1.5 g, 70~95%).

$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 7.06~8.14 (m, 9H).

Preparation Example 184: (4R,5S)-methyl-5-(2-nitrophenyl)-2-phenyl-1,3-dioxolane-4-carboxylate

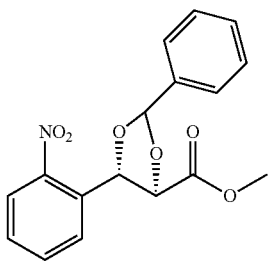

The substantially same method as described in Preparation example 180 was conducted, except benzaldehyde that was used instead of cyclohexanone, to obtain the title compound (1.8 g, 50~70%).

$^1$H NMR (400 MHz, DMSO-$d_6$) δ 3.67 (s, 3H), 5.11 (d, J=8.0 Hz, 1H), 5.81 (d, J=8.0 Hz, 1H), 6.18 (s, 1H), 6.96~8.12 (m, 9H).

Preparation Example 185: ((4S,5S)-5-(2-nitrophenyl)-2-phenyl-1,3-dioxolan-4-yl)methanol

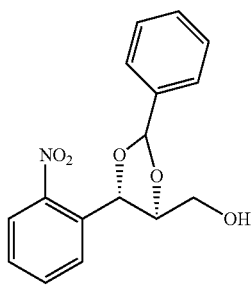

The substantially same method as described in Preparation example 183 was conducted, except that (4R,5S)-methyl-5-(2-nitrophenyl)-2-phenyl-1,3-dioxolane-4-carboxylate (Preparation example 184) was used instead of (2S,3R)-methyl-3-(2-nitrophenyl)-2-phenyl-1,3-dioxolane-4-carboxylate (Preparation example 182), to obtain the title compound (1.3 g, 70~95%).

$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 7.06~8.14 (m, 9H).

Preparation Example 186: (4S,5R)-methyl-5-(2-methylphenyl)-2-methyl-1.3-dioxolane-4-carboxylate

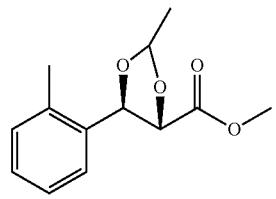

The substantially same method as described in Preparation example 60 was conducted, except that (2S,3R)-methyl-3-(2-methylphenyl)-2,3-dihydroxypropanoate (Preparation example 54) was used instead of (2S,3R)-methyl-3-(2-chlorophenyl)-2,3-dihydroxypropanoate (Preparation example 433), to obtain the title compound (2.1 g, 70~95%).

$^1$H NMR (400 MHz, CDCl$_3$) δ 1.36 (d, J=6.4 Hz, 3H), 2.35 (s, 3H), 3.68 (s, 3H), 5.07 (m, 1H), 5.11 (d, J=7.6 Hz, 1H), 5.82 (d, J=7.6 Hz, 1H), 7.19~7.39 (m, 4H).

Preparation Example 187: ((4R,5R)-5-(2-methylphenyl)-2-methyl-1,3-dioxolan-4-yl)methanol

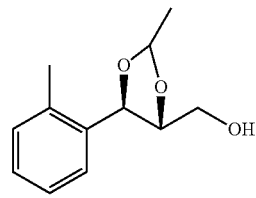

The substantially same method as described in Preparation example 185 was conducted, except that (4S,5R)-methyl-5-(2-methylphenyl)-2-methyl-1.3-dioxolane-4-carboxylate (Preparation example 186) was used instead of (2R,3S)-methyl-3-(2-nitrophenyl)-2-phenyl-1,3-dioxolane-4-carboxylate (Preparation example 184), to obtain the title compound (1.7 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.17~7.41 (m, 4H).

Preparation Example 188: (4R,5S)-methyl-5-(2-methylphenyl)-2-methyl-1.3-dioxolane-4-carboxylate

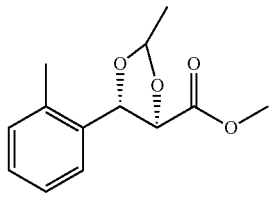

The substantially same method as described in Preparation example 186 was conducted, except that (2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (1.8 g, 70~95%).

$^1$H NMR (400 MHz, CDCl$_3$) δ 1.36 (d, J=6.4 Hz, 3H), 2.35 (s, 3H), 3.68 (s, 3H), 5.07 (m, 1H), 5.11 (d, J=7.6 Hz, 1H), 5.82 (d, J=7.6 Hz, 1H), 7.19~7.39 (m, 4H).

Preparation Example 189: ((4S,5S)-5-(2-methylphenyl)-2-methyl-1.3-dioxolane-4-yl)methanol

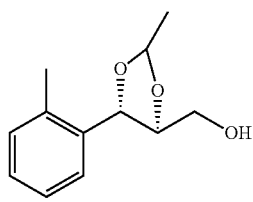

The substantially same method as described in Preparation example 187 was conducted, except that (4R,5S)-methyl-5-(2-methylphenyl)-2-methyl-1.3-dioxolane-4-carboxylate (Preparation example 188) was used instead of (4S,5R)-methyl-5-(2-methylphenyl)-2-methyl-1.3-dioxolane-4-carboxylate (Preparation example 186), to obtain the title compound (1.6 g, 70~95%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.17~7.41 (m, 4H).

Preparation Example 190: (4S,5R)-methyl-5-(2-methylphenyl)-2,2-diethyl-1.3-dioxolane-4-carboxylate

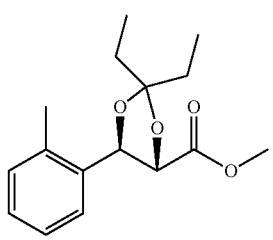 [SMILES: CCC1(CC)O[C@H](C(=O)OC)[C@@H](c2ccccc2C)O1]

The substantially same method as described in Preparation example 170 was conducted, except that (2S,3R)-methyl-3-(2-methylphenyl)-2,3-dihydroxypropanoate (Preparation example 54) was used instead of (2S,3R)-methyl-3-(2-nitrophenyl)-2,3-dihydroxypropanoate (Preparation example 44), to obtain the title compound (2.1 g, 60~85%).

$^1$H NMR (400 MHz, CDCl$_3$) δ 0.96 (m, 6H), 1.59 (m, 4H), 2.33 (s, 1H), 3.67 (s, 3H), 5.11 (d, J=7.6 Hz, 1H), 5.81 (d, J=7.6 Hz, 1H), 7.00~7.17 (m, 4H).

Preparation Example 191: ((4R,5R-5-(2-methylphenyl)-2,2-diethyl-1.3-dioxolane-4-yl)methanol

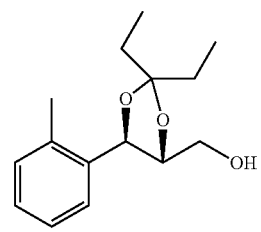 [SMILES: CCC1(CC)O[C@H](c2ccccc2C)[C@@H](CO)O1]

The substantially same method as described in Preparation example 187 was conducted, except that (4S,5R)-methyl-5-(2-methylphenyl)-2,2-diethyl-1,3-dioxolane-4-carboxylate (Preparation example 190) was used instead of (4S,5R)-methyl-5-(2-methylphenyl)-2-methyl-1.3-dioxolane-4-carboxylate (Preparation example 186), to obtain the title compound (1.7 g, 70~95%).

$^1$H NMR (400 MHz, CDCl$_3$) δ 0.96 (m, 6H), 1.59 (m, 4H), 2.37 (s, 3H), 3.62~3.70 (m, 2H), 4.36 (dd, J=7.0, 7.0 Hz, 1H), 5.17 (d, J=7.0 Hz, 1H), 7.15~7.39 (m, 4H).

Preparation Example 192: (4R,5S)-methyl-5-(2-methylphenyl)-2,2-diethyl-1.3-dioxolane-4-carboxylate

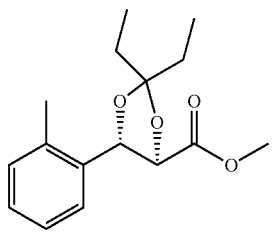 [SMILES: CCC1(CC)O[C@@H](C(=O)OC)[C@H](c2ccccc2C)O1]

The substantially same method as described in Preparation example 190 was conducted, except that (2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (2.2 g, 60~85%).

$^1$H NMR (400 MHz, CDCl$_3$) δ 0.96 (m, 6H), 1.59 (m, 4H), 2.33 (s, 1H), 3.67 (s, 3H), 5.11 (d, J=7.6 Hz, 1H), 5.81 (d, J=7.6 Hz, 1H), 7.00~7.17 (m, 4H).

Preparation Example 193: ((4S,5S)-5-(2-methylphenyl)-2,2-diethyl-1,3-dioxolane-4-yl)methanol

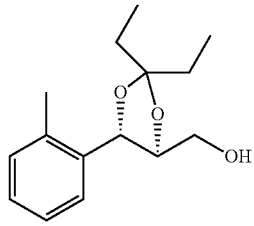

The substantially same method as described in Preparation example 191 was conducted, except that (4R,5S)-methyl-5-(2-methylphenyl)-2,2-diethyl-1,3-dioxolane-4-carboxylate (Preparation example 192) was used instead of (4S,5R)-methyl-5-(2-methylphenyl)-2,2-diethyl-1,3-dioxolane-4-carboxylate (Preparation example 190), to obtain the title compound (1.8 g, 70~95%).

$^1$H NMR (400 MHz, CDCl$_3$) δ 0.96 (m, 6H), 1.59 (m, 4H), 2.37 (s, 3H), 3.62~3.70 (m, 2H), 4.36 (dd, J=7.0, 7.0 Hz, 1H), 5.17 (d, J=7.0 Hz, 1H), 7.15~7.39 (m, 4H).

Preparation Example 194: (2S,3R)-methyl-3-(2-methylphenyl)-1,4-dioxaspiro[4,4]nonane-2-carboxylate

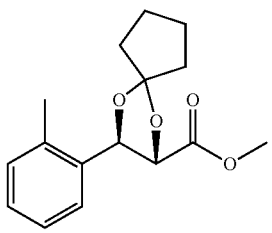 [SMILES: COC(=O)[C@H]1OC2(CCCC2)O[C@@H]1c1ccccc1C]

The substantially same method as described in Preparation example 190 was conducted, except that cyclopentanone was used instead of 3-pentanone, to obtain the title compound (2.1 g, 70~95%).

$^1$H NMR (400 MHz, DMSO-d$_6$) δ 1.49~1.57 (m, 4H), 1.72~1.81 (m, 4H), 2.35 (s, 3H), 3.68 (s, 3H), 5.14 (d, J=7.2 Hz, 1H), 5.89 (d, J=7.2 Hz, 1H), 7.02~7.25 (m, 4H).

Preparation Example 195: ((2R,3R)-3-(2-methylphenyl)-1,4-dioxaspiro[4,4]nonane-2-yl)methanol

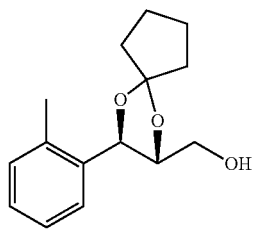

The substantially same method as described in Preparation example 191 was conducted, except that (2S,3R)-methyl-3-(2-methylphenyl)-1,4-dioxaspiro[4,4]nonane-2-carboxylate (Preparation example 194) was used instead of (4S,5R)-methyl-5-(2-methylphenyl)-2,2-diethyl-1,3-dioxolane-4-carboxylate (Preparation example 190), to obtain the title compound (1.6 g, 70~95%).

$^1$H NMR (400 MHz, DMSO-d$_6$) δ 1.49~1.57 (m, 4H), 1.72~1.81 (m, 4H), 2.35 (s, 3H), 3.52~3.65 (m, 2H), 4.90 (t, J=5.2 Hz, 1H), 5.12 (d, J=7.6 Hz, 1H), 7.02~7.25 (m, 4H).

Preparation Example 196: (2R,3S)-methyl-3-(2-methylphenyl)-1,4-dioxaspiro[4,4]nonane-2-carboxylate

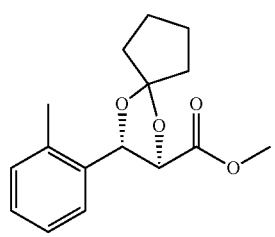 [SMILES: COC(=O)[C@@H]1OC2(CCCC2)O[C@H]1c1ccccc1C]

The substantially same method as described in Preparation example 192 was conducted, except that cyclopentanone was used instead of 3-pentanone, to obtain the title compound (2.5 g, 70~95%).

$^1$H NMR (400 MHz, DMSO-d$_6$) δ 1.49~1.57 (m, 4H), 1.72~1.81 (m, 4H), 2.35 (s, 3H), 3.68 (s, 3H), 5.14 (d, J=7.2 Hz, 1H), 5.89 (d, J=7.2 Hz, 1H), 7.02~7.25 (m, 4H).

Preparation Example 197: ((2S,3S)-3-(2-methylphenyl)-1,4-dioxaspiro[4,4]nonane-2-yl)methanol

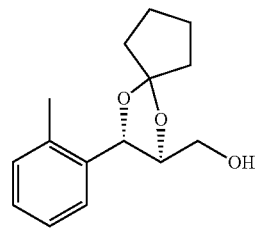 [SMILES: Cc1ccccc1[C@@H]1OC2(CCCC2)O[C@H]1CO]

The substantially same method as described in Preparation example 195 was conducted, except that (2R,3S)-methyl-3-(2-methylphenyl)-1,4-dioxaspiro[4,4]nonane-2-carboxylate (Preparation example 196) was used instead of (2S,3R)-methyl-3-(2-methylphenyl)-1,4-dioxaspiro[4,4]nonane-2-carboxylate (Preparation example 194), to obtain the title compound (2.0 g, 70~95%).

$^1$H NMR (400 MHz, DMSO-d$_6$) δ 1.49~1.57 (m, 4H), 1.72~1.81 (m, 4H), 2.35 (s, 3H), 3.52~3.65 (m, 2H), 4.90 (t, J=5.2 Hz, 1H), 5.12 (d, J=7.6 Hz, 1H), 7.02~7.25 (m, 4H).

Preparation Example 198: (2S,3R)-methyl-3-(2-methylphenyl)-1,4-dioxaspiro[4,5]decane-2-carboxylate

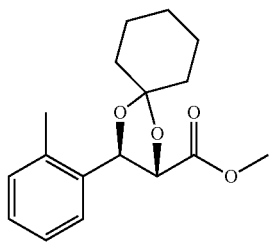 [SMILES: COC(=O)[C@H]1OC2(CCCCC2)O[C@@H]1c1ccccc1C]

The substantially same method as described in Preparation example 194 was conducted, except that cyclohexanone was used instead of cyclopentanone, to obtain the tide compound (1.8 g, 70~95%).
$^1$H NMR (400 MHz, DMSO-$d_6$) δ 1.61~1.69 (m, 10H), 2.34 (s, 3H), 3.79 (s, 3H), 4.33 (d, J=8.0 Hz, 1H), 5.85 (d, J=8.0 Hz, 1H), 7.01~7.30 (m, 4H).

Preparation Example 199: ((2R,3R)-3-(2-methylphenyl)-1,4-dioxaspiro[4,5]decane-2-yl)methanol

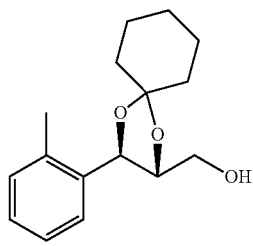 [SMILES: Cc1ccccc1[C@H]1OC2(CCCCC2)O[C@@H]1CO]

The substantially same method as described in Preparation example 195 was conducted, except that (2S,3R)-methyl-3-(2-methylphenyl)-1,4-dioxaspiro[4,5]decane-2-carboxylate (Preparation example 198) was used instead of (2S,3R)-methyl-3-(2-methylphenyl)-1,4-dioxaspiro[4,4]nonane-2-carboxylate (Preparation example 194), to obtain the title compound (1.5 g, 70~95%).
$^1$H NMR (400 MHz, DMSO-$d_6$) δ 1.63~1.75 (m, 10H), 2.33 (s, 3H), 3.52~3.81 (m, 2H), 3.95 (t, J=8.0 Hz, 1H), 5.43 (d, J=7.6 Hz, 1H), 7.02~7.28 (m, 4H).

Preparation Example 200: (2R,3S)-methyl-3-(2-methylphenyl)-1,4-dioxaspiro[4,5]decane-2-carboxylate

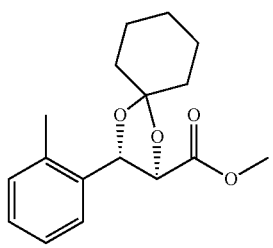 [SMILES: COC(=O)[C@@H]1OC2(CCCCC2)O[C@H]1c1ccccc1C]

The substantially same method as described in Preparation example 196 was conducted, except that cyclohexanone was used instead of cyclopentanone, to obtain the tide compound (2.2 g, 70~95%).
$^1$H NMR (400 MHz, DMSO-$d_6$) δ 1.61~1.69 (m, 10H), 2.34 (s, 3H), 3.79 (s, 3H), 4.33 (d, J=8.0 Hz, 1H), 5.85 (d, J=8.0 Hz, 1H), 7.01~7.30 (m, 4H).

Preparation Example 201: ((2S,3S)-3-(2-methylphenyl)-1,4-dioxaspiro[4,5]decane-2-yl)methanol

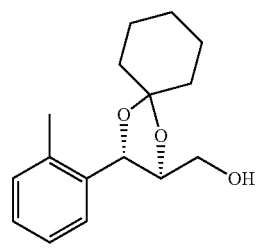 [SMILES: Cc1ccccc1[C@@H]1OC2(CCCCC2)O[C@H]1CO]

The substantially same method as described in Preparation example 199 was conducted, except that (2R,3S)-methyl-3-(2-methylphenyl)-1,4-dioxaspiro[4,5]decane-2-carboxylate (Preparation example 200) was used instead of (2S,3R)-methyl-3-(2-methylphenyl)-1,4-dioxaspiro[4.5]decane-2-carboxylate (Preparation example 198), to obtain the title compound (1.5 g, 70~95%).
$^1$H NMR (400 MHz, DMSO-$d_6$) δ 1.63~1.75 (m, 10H), 2.33 (s, 3H), 3.52~3.81 (m, 2H), 3.95 (t, J=8.0 Hz, 1H), 5.43 (d, J=7.6 Hz, 1H), 7.02~7.28 (m, 4H).

Preparation Example 202: (4S,5R)-methyl-5-(2-methylphenyl)-2-phenyl-1,3-dioxolane-4-carboxylate

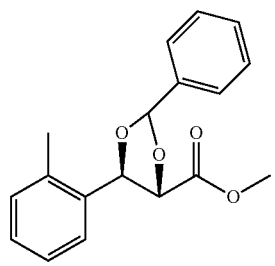

The substantially same method as described in Preparation example 198 was conducted, except that benzaldehyde was used instead of cyclohexanone, to obtain the title compound (2.2 g, 50~70%).
$^1$H NMR (400 MHz, DMSO-$d_6$) δ 2.33 (s, 3H), 3.67 (s, 3H), 5.11 (d, J=8.0 Hz, 1H), 5.81 (d, J=8.0 Hz, 1H), 6.18 (s, 1H), 6.96~7.32 (m, 9H).

Preparation Example 203: ((4R,5R)-5-(2-methylphenyl)-2-phenyl-1,3-dioxolane-4-yl)methanol

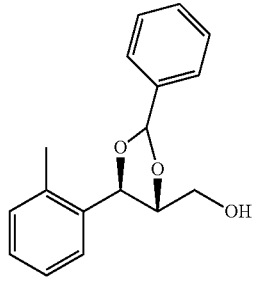

The substantially same method as described in Preparation example 199 was conducted, except that (4S,5R)-methyl-5-(2-methylphenyl)-2-phenyl-1,3-dioxolane-4-carboxylate (Preparation example 202) was used instead of (2S,3R)-methyl-3-(2-methylphenyl)-1,4-dioxaspiro[4,5]decane-2-carboxylate (Preparation example 198), to obtain the title compound (1.6 g, 70~95%).

$^1$H NMR (400 MHz, DMSO-d$_6$) δ 2.32 (s, 3H), 3.66 (d, J=7.6 Hz, 2H), 4.36 (m, 1H), 5.17 (d, J=8.0 Hz, 1H), 6.18 (s, 1H), 6.99~7.33 (m, 9H).

Preparation Example 204: (4R,5S)-methyl-5-(2-methylphenyl)-2-phenyl-1,3-dioxolane-4-carboxylate

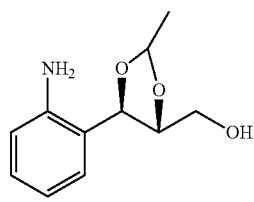

The substantially same method as described in Preparation example 200 was conducted, except benzaldehyde that was used instead of cyclohexanone, to obtain the title compound (1.9 g, 50~70%).

$^1$H NMR (400 MHz, DMSO-d$_6$) δ 2.33 (s, 3H), 3.67 (s, 3H), 5.11 (d, J=8.0 Hz, 1H), 5.81 (d, J=8.0 Hz, 1H), 6.18 (s, 1H), 6.96~7.32 (m, 9H).

Preparation Example 205: ((4S,5S)-5-(2-methylphenyl)-2-phenyl-1,3-dioxolane-4-yl)methanol

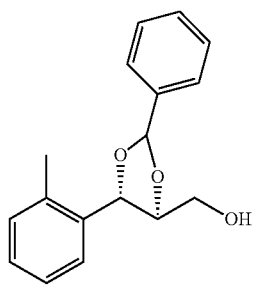

The substantially same method as described in Preparation example 203 was conducted, except that (4R,5S)-methyl-5-(2-methylphenyl)-2-phenyl-1,3-dioxolane-4-carboxylate (Preparation example 204) was used instead of (4S,5R)-methyl-5-(2-methylphenyl)-2-phenyl-1,3-dioxolane-4-carboxylate (Preparation example 202), to obtain the title compound (1.3 g, 70~95%).

$^1$H NMR (400 MHz, DMSO-d$_6$) δ 2.32 (s, 3H), 3.66 (d, J=7.6 Hz, 2H), 4.36 (m, 1H), 5.17 (d, J=8.0 Hz, 1H), 6.18 (s, 1H), 6.99~7.33 (m, 9H).

Preparation Example 206: ((4R,5R)-5-(2-aminophenyl)-2-methyl-1.3-dioxolane-4-yl)methanol

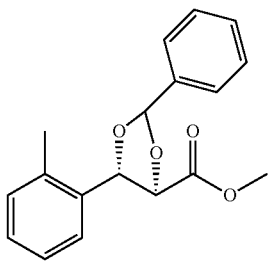

The substantially same method as described in Preparation example 47 was conducted, except that ((4R,5R)-5-(2-nitrophenyl)-2-methyl-1.3-dioxolane-4-yl)methanol (Preparation example 167) was used instead of ((4R,5R)-5-(2-nitrophenyl)-2,2-dimethyl-1.3-dioxolane-4-yl)methanol (Preparation example 46), to obtain the title compound (1.5 g, 65~85%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.57~8.08 (m, 4H).

Preparation Example 207: ((4S,5S)-5-(2-aminophenyl)-2-methyl-1.3-dioxolane-4-yl)methanol

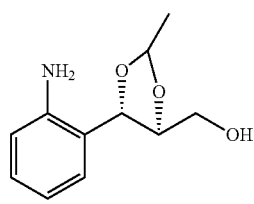

The substantially same method as described in Preparation example 47 was conducted, except that ((4S,5S)-5-(2-nitrophenyl)-2-methyl-1.3-dioxolane-4-yl)methanol (Preparation example 169) was used instead of ((4R,5R)-5-(2-nitrophenyl)-2,2-dimethyl-1.3-dioxolane-4-yl)methanol (Preparation example 46), to obtain the title compound (1.1 g, 65~85%).

$^1$H NMR (400 MHz, CDCl$_3$) δ 1.37 (d, J=6.0 Hz, 3H), 3.62~3.70 (m, 2H), 4.36 (dd, J=7.0, 7.0 Hz, 1H), 5.06 (m, 1H), 5.17 (d, J=7.0 Hz, 1H), 7.57~8.08 (m, 4H).

Preparation Example 208: ((4R,5R)-5-(2-aminophenyl)-2,2-diethyl-1,3-dioxolane-4-yl)methanol

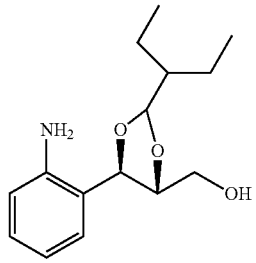

The substantially same method as described in Preparation example 47 was conducted, except that ((4R,5R)-5-(2-nitrophenyl)-2,2-diethyl-1,3-dioxolane-4-yl)methanol (Preparation example 171) was used instead of ((4R,5R)-5-(2-nitrophenyl)-2,2-dimethyl-1,3-dioxolane-4-yl)methanol (Preparation example 46), to obtain the title compound (1.5 g, 65~85%).

$^1$H NMR (400 MHz, CDCl$_3$) δ 0.96 (m, 6H), 1.59 (m, 4H), 3.62~3.70 (m, 2H), 4.36 (dd, J=7.0, 7.0 Hz, 1H), 5.17 (d, J=7.0 Hz, 1H), 7.55~8.09 (m, 4H).

Preparation Example 209: ((4S,5S)-5-(2-aminophenyl)-2,2-diethyl-1,3-dioxolane-4-yl)methanol

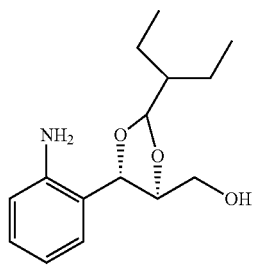

The substantially same method as described in Preparation example 47 was conducted, except that ((4S,5S)-5-(2-nitrophenyl)-2,2-diethyl-1,3-dioxolane-4-yl)methanol (Preparation example 173) was used instead of ((4R,5R)-5-(2-nitrophenyl)-2,2-dimethyl-1,3-dioxolane-4-yl)methanol (Preparation example 46), to obtain the title compound (1.4 g, 65~85%).

$^1$H NMR (400 MHz, CDCl$_3$) δ 0.96 (m, 6H), 1.59 (m, 4H), 3.62~3.70 (m, 2H), 4.36 (dd, J=7.0, 7.0 Hz, 1H), 5.17 (d, J=7.0 Hz, 1H), 7.55~8.09 (m, 4H).

Preparation Example 210: ((2R,3R)-3-(2-aminophenyl)-1,4-dioxaspiro[4,4]nonane-2-yl)methanol

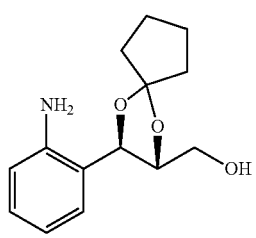

The substantially same method as described in Preparation example 47 was conducted, except that ((4R,5R)-5-(2-nitrophenyl)-1,4-dioxaspiro[4,4]nonane-2-yl)methanol (Preparation example 175) was used instead of ((4R,5R)-5-(2-nitrophenyl)-2,2-dimethyl-1,3-dioxolane-4-yl)methanol (Preparation example 46), to obtain the title compound (1.7 g, 65~85%).

$^1$H NMR (400 MHz, DMSO-d$_6$) δ 1.62~1.73 (m, 4H), 1.82~1.95 (m, 4H), 3.52~3.65 (m, 2H), 4.90 (t, J=5.2 Hz, 1H), 5.12 (d, J=7.6 Hz, 1H), 7.56~8.11 (m, 4H).

Preparation Example 211: ((2S,3S)-3-(2-aminophenyl)-1,4-dioxaspiro[4,4]nonane-2-yl)methanol

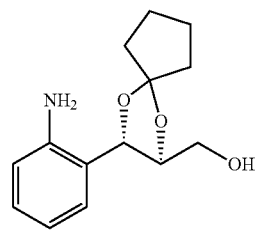

The substantially same method as described in Preparation example 47 was conducted, except that ((4S,5S)-5-(2-nitrophenyl)-1,4-dioxaspiro[4,4]nonane-2-yl)methanol (Preparation example 177) was used instead of ((4R,5R)-5-(2-nitrophenyl)-2,2-dimethyl-1,3-dioxolane-4-yl)methanol (Preparation example 46), to obtain the title compound (1.6 g, 65~85%).

$^1$H NMR (400 MHz, DMSO-d$_6$) δ 1.62~1.73 (m, 4H), 1.82~1.95 (m, 4H), 3.52~3.65 (m, 2H), 4.90 (t, J=5.2 Hz, 1H), 5.12 (d, J=7.6 Hz, 1H), 7.56~8.11 (m, 4H).

Preparation Example 212: ((2R,3R)-3-(2-aminophenyl)-1,4-dioxaspiro[4,5]decane-2-yl)methanol

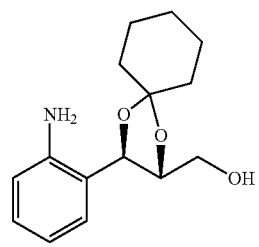 [SMILES: Nc1ccccc1[C@H]1OC2(CCCCC2)O[C@@H]1CO]

The substantially same method as described in Preparation example 47 was conducted, except that ((4R,5R)-5-(2-nitrophenyl)-1,4-dioxaspiro[4,5]decane-2-yl)methanol (Preparation example 179) was used instead of ((4R,5R)-5-(2-nitrophenyl)-2,2-dimethyl-1,3-dioxolane-4-yl)methanol (Preparation example 46), to obtain the title compound (1.1 g, 65~85%).

$^1$H NMR (400 MHz, DMSO-d$_6$) δ 1.61~1.75 (m, 10H), 3.52~3.81 (m, 2H), 3.95 (t, J=8.0 Hz, 1H), 5.43 (d, J=7.6 Hz, 1H), 7.49~8.12 (m, 4H).

Preparation Example 213: ((2S,3S)-3-(2-aminophenyl)-1,4-dioxaspiro[4,5]decane-2-yl)methanol

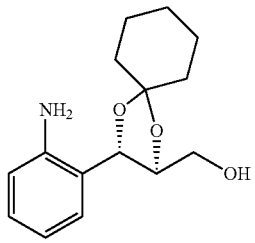

The substantially same method as described in Preparation example 47 was conducted, except that ((4S,5S)-5-(2-nitrophenyl)-1,4-dioxaspiro[4,5]decane-2-yl)methanol (Preparation example 181) was used instead of ((4R,5R)-5-(2-nitrophenyl)-2,2-dimethyl-1.3-dioxolane-4-yl)methanol (Preparation example 46), to obtain the title compound (1.0 g, 65~85%).
$^1$H NMR (400 MHz, DMSO-$d_6$) δ 1.61~1.75 (m, 10H), 3.52~3.81 (m, 2H), 3.95 (t, J=8.0 Hz, 1H), 5.43 (d, J=7.6 Hz, 1H), 7.49~8.12 (m, 4H).

Preparation Example 214: ((4R,5R)-5-(2-aminophenyl)-2-phenyl-1,3-dioxolane-4-yl)methanol

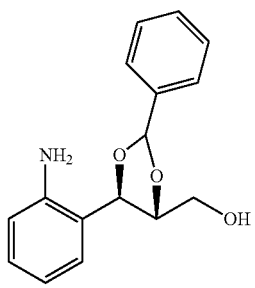

The substantially same method as described in Preparation example 47 was conducted, except that ((4R,5R)-5-(2-nitrophenyl)-2-phenyl-1,3-dioxolane-4-yl)methanol (Preparation example 183) was used instead of ((4R,5R)-5-(2-nitrophenyl)-2,2-dimethyl-1.3-dioxolane-4-yl)methanol (Preparation example 46), to obtain the title compound (1.2 g, 65~85%).
$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 7.06~8.14 (m, 9H).

Preparation Example 215: ((4S,5S)-5-(2-aminophenyl)-2-phenyl-1,3-dioxolane-4-yl)methanol

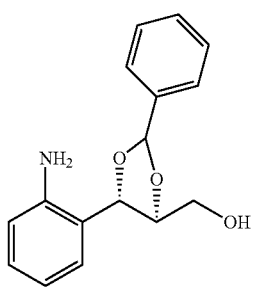

The substantially same method as described in Preparation example 47 was conducted, except that ((4S,5S)-5-(2-nitrophenyl)-2-phenyl-1,3-dioxolane-4-yl)methanol (Preparation example 185) was used instead of ((4R,5R)-5-(2-nitrophenyl)-2,2-dimethyl-1.3-dioxolane-4-yl)methanol (Preparation example 46), to obtain the title compound (0.9 g, 65~85%).
$^1$H NMR (400 MHz, DMSO-$d_6$) δ 3.66 (d, J=7.6 Hz, 2H), 4.36 (m, 1H), 5.17 (d, J=8.0 Hz, 1H), 6.18 (s, 1H), 7.06~8.14 (m, 9H).

Preparation Example 216: (E)-Methyl cinnamate

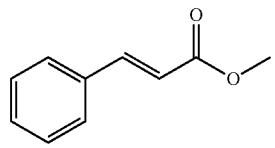

To a round-bottomed flask, trans-cinnamic acid (7.0 g, 47.25 mmol) and MeOH (70 mL) were added. POCl$_3$ (0.43 mL, 4.73 mmol) was added dropwise. The reaction mixture was stirred under reflux for 3 h. The reaction mixture was cooled to room temperature, quenched with 1 N NaOH solution. The mixture was extracted by EtOAc and washed with H$_2$O. The aqueous layer was further extracted with EtOAc. The combined organic layer was dried over anhydrous magnesium sulfate (MgSO$_4$), filtered and concentrated under vacuum (7.1 g, 80~95%).
$^1$H NMR (400 MHz, CDCl$_3$) δ 3.81 (s, 3H), 6.42 (d, J=15.9 Hz, 1H), 7.37~7.39 (m, 3H), 7.50~7.53 (m, 2H), 7.67 (d, J=15.9 Hz, 1H).

Preparation Example 217: (2S,3R)-methyl-3-phenyl-2,3-dihydroxypropanoate

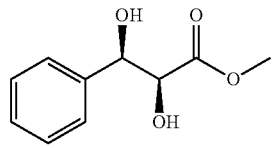

The substantially same method as described in Preparation example 36 was conducted, except that (E)-Methyl cinnamate (Preparation example 216) was used instead of (E)-methyl-3-(2,4-dichlorophenyl)acrylate (Preparation example 28), to obtain the title compound (6.2 g, 70~95%).
$^1$H NMR (400 MHz, CDCl$_3$) δ 2.70 (bs, 1H), 3.08 (bs, 1H), 3.82 (s, 3H), 4.38 (d, J=2.9 Hz, 1H), 5.03 (d, J=2.9 Hz, 1H), 7.30~7.42 (m, 5H).

Preparation Example 218: (4S,5R)-methyl-2,2-dimethyl-5-phenyl-1,3-dioxolane-4-carboxylate

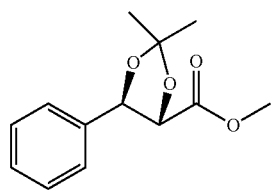 [SMILES: COC(=O)[C@H]1OC(C)(C)O[C@@H]1c1ccccc1]

The substantially same method as described in Preparation example 45 was conducted, except that (2S,3R)-methyl-3-phenyl-2,3-dihydroxypropanoate (Preparation example 217) was used instead of (2S,3R)-methyl-3-(2-nitrophenyl)-2,3-dihydroxypropanoate (Preparation example 44), to obtain the title compound (5.6 g, 70~95%).

$^1$H NMR (400 MHz, CDCl$_3$) δ 1.56 (s, 3H), 1.61 (s, 3H), 3.79 (s, 3H), 4.36 (d, J=7.8 Hz, 1H), 5.17 (d, J=7.8 Hz, 1H), 7.31~7.40 (m, 5H).

Preparation Example 219: ((4R,5R)-5-phenyl-2,2-dimethyl-1,3-dioxolane-4-yl)methanol

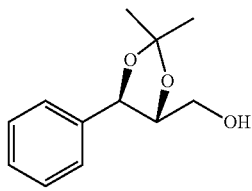

The substantially same method as described in Preparation example 46 was conducted, except that (4S,5R)-methyl-2,2-dimethyl-5-phenyl-1,3-dioxolane-4-carboxylate (Preparation example 218) was used instead of (4S,5R)-methyl-5-(2-nitrophenyl)-1,3-dioxolane-4-carboxylate (Preparation example 45), to obtain the title compound (4.4 g, 70~95%).

$^1$H NMR (400 MHz, CDCl$_3$) δ 1.41 (s, 3H), 1.46 (s, 3H), 2.79 (bs, 1H), 3.48~3.52 (m, 1H), 3.68~3.76 (m, 2H), 4.76 (d, J=8.8 Hz, 1H), 7.18~7.28 (m, 5H).

Preparation Example 220: (2R,3S)-methyl-3-phenyl-2,3-dihydroxypropanoate

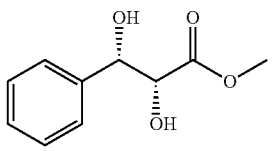

The substantially same method as described in Preparation example 30 was conducted, except that (E)-Methyl cinnamate (Preparation example 216) was used instead of (E)-methyl-3-(2,4-dichlorophenyl)acrylate (Preparation example 28), to obtain the title compound (8.6 g, 70~95%).

$^1$H NMR (400 MHz, CDCl$_3$) δ 2.70 (bs, 1H), 3.08 (bs, 1H), 3.82 (s, 3H), 4.38 (d, J=2.9 Hz, 1H), 5.03 (d, J=2.9 Hz, 1H), 7.30~7.42 (m, 5H).

Preparation Example 221: (4R,5S)-methyl-2,2-dimethyl-5-phenyl-1,3-dioxolane-4-carboxylate

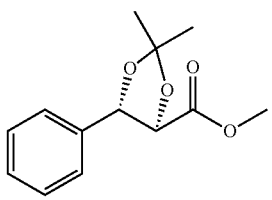 [SMILES: COC(=O)[C@@H]1OC(C)(C)O[C@H]1c1ccccc1]

The substantially same method as described in Preparation example 45 was conducted, except that (2S,3R)-methyl-3-phenyl-2,3-dihydroxypropanoate (Preparation example 217) was used instead of (2S,3R)-methyl-3-(2-nitrophenyl)-2,3-dihydroxypropanoate (Preparation example 44), to obtain the title compound (5.6 g, 70~95%).

$^1$H NMR (400 MHz, CDCl$_3$) δ 1.56 (s, 3H), 1.61 (s, 3H), 3.79 (s, 3H), 4.36 (d, J=7.8 Hz, 1H), 5.17 (d, J=7.8 Hz, 1H), 7.31~7.40 (m, 5H).

Preparation Example 222: ((4S,5S)-5-phenyl-2,2-dimethyl-1,3-dioxolane-4-yl)methanol

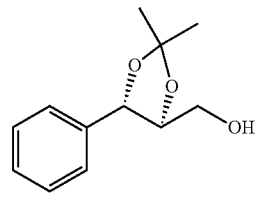

The substantially same method as described in Preparation example 46 was conducted, except that (4R,5S)-methyl-2,2-dimethyl-5-phenyl-1,3-dioxolane-4-carboxylate (Preparation example 221) was used instead of (4S,5R)-methyl-5-(2-nitrophenyl)-1,3-dioxolane-4-carboxylate (Preparation example 45), to obtain the title compound (6.5 g, 70~95%).

$^1$H NMR (400 MHz, CDCl$_3$) δ 1.41 (s, 3H), 1.46 (s, 3H), 2.79 (bs, 1H), 3.48~3.52 (m, 1H), 3.68~3.76 (m, 2H), 4.76 (d, J=8.8 Hz, 1H), 7.18~7.28 (m, 5H).

Preparation Example 223: (4S,5R)-methyl-2,2-diethyl-5-phenyl-1,3-dioxolane-4-carboxylate

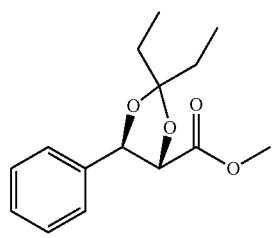 [SMILES: CCC1(CC)O[C@H](C(=O)OC)[C@@H](c2ccccc2)O1]

The substantially same method as described in Preparation example 190 was conducted, except that (2S,3R)-methyl-3-phenyl-2,3-dihydroxypropanoate (Preparation example 217) was used instead of (2S,3R)-methyl-3-(2-methylphenyl)-2,3-dihydroxypropanoate (Preparation example 54), to obtain the title compound (1.9 g, 70~95%).

$^1$H NMR (400 MHz, CDCl$_3$) δ 1.01 (t, J=7.4 Hz, 1H), 1.06 (t, J=7.6 Hz, 3H), 1.78~1.90 (m, 4H), 3.78 (s, 3H), 5.12 (d, J=8.4 Hz, 1H), 7.32~7.45 (m, 5H).

Preparation Example 224: ((4R,5R)-5-phenyl-2,2-diethyl-1,3-dioxolane-4-yl)methanol

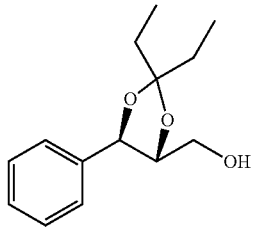 [SMILES: CCC1(CC)O[C@H](c2ccccc2)[C@@H](CO)O1]

The substantially same method as described in Preparation example 219 was conducted, except that (4S,5R)-methyl-2,2-diethyl-5-phenyl-1,3-dioxolane-4-carboxylate (Preparation example 223) was used instead of (4S,5R)-methyl-2,2-dimethyl-5-phenyl-1,3-dioxolane-4-carboxylate (Preparation example 218), to obtain the title compound (1.3 g, 70~95%).

$^1$H NMR (400 MHz, CDCl$_3$) δ 1.00 (t, J=7.6 Hz, 1H), 1.06 (t, J=7.4 Hz, 1H), 1.74~1.90 (m, 4H), 3.64 (ddd, J=3.4, 8.4, 12.1 Hz, 1H), 3.84~3.91 (m, 2H), 4.89 (d, J=8.8 Hz, 1H), 7.30~7.43 (m, 5H).

Preparation Example 225: (4R,5S)-methyl-2,2-diethyl-5-phenyl-1,3-dioxolane-4-carboxylate

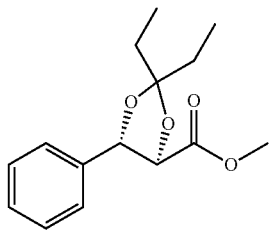 [SMILES: CCC1(CC)O[C@@H](C(=O)OC)[C@H](c2ccccc2)O1]

The substantially same method as described in Preparation example 223 was conducted, except that (2R,3S)-methyl-3-phenyl-2,3-dihydroxypropanoate (Preparation example 220) was used instead of (2S,3R)-methyl-3-phenyl-2,3-dihydroxypropanoate (Preparation example 217), to obtain the title compound (5.6 g, 70~95%).

$^1$H NMR (400 MHz, CDCl$_3$) δ 1.01 (t, J=7.4 Hz, 1H), 1.06 (t, J=7.6 Hz, 3H), 1.78~1.90 (m, 4H), 3.78 (s, 3H), 5.12 (d, J=8.4 Hz, 1H), 7.32~7.45 (m, 5H).

Preparation Example 226: ((4S,5S)-5-phenyl-2,2-dimethyl-1,3-dioxolane-4-yl)methanol

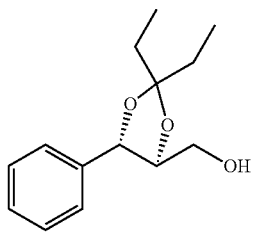 [SMILES: CCC1(CC)O[C@@H](CO)[C@H](c2ccccc2)O1]

The substantially same method as described in Preparation example 224 was conducted, except that (4R,5S)-methyl-2,2-dimethyl-5-phenyl-1,3-dioxolane-4-carboxylate (Preparation example 225) was used instead of (4S,5R)-methyl-2,2-dimethyl-5-phenyl-1,3-dioxolane-4-carboxylate (Preparation example 218), to obtain the title compound (6.5 g, 70~95%).

$^1$H NMR (400 MHz, CDCl$_3$) δ 1.00 (t, J=7.6 Hz, 1H), 1.06 (t, J=7.4 Hz, 1H), 1.74~1.90 (m, 4H), 3.64 (ddd, J=3.4, 8.4, 12.1 Hz, 1H), 3.84~3.91 (m, 2H), 4.89 (d, J=8.8 Hz, 1H), 7.30~7.43 (m, 5H).

Preparation Example 227: (2S,3R)-methyl-3-phenyl-1,4-dioxaspiro[4,4]nonane-2-carboxylate

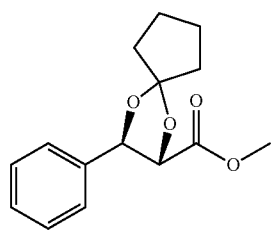 [SMILES: COC(=O)[C@H]1OC2(CCCC2)O[C@@H]1c1ccccc1]

The substantially same method as described in Preparation example 223 was conducted, except that cyclopentanone was used instead of 3-pentanone, to obtain the title compound (0.9 g, 50~75%).

$^1$H NMR (400 MHz, CDCl$_3$) δ 1.71~1.80 (m, 4H), 1.87~1.94 (m, 1H), 2.00~2.08 (m, 3H), 3.79 (s, 3H), 4.35 (d, J=7.2 Hz, 1H), 5.08 (d, J=7.2 Hz, 1H), 7.32~7.45 (m, 5H).

Preparation Example 228: ((2R,3R)-3-phenyl-1,4-dioxaspiro[4,4]nonan-2-yl)methanol

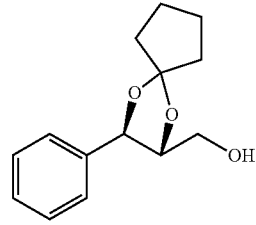 [SMILES: OC[C@H]1OC2(CCCC2)O[C@@H]1c1ccccc1]

The substantially same method as described in Preparation example 224 was conducted, except that (2S,3R)-methyl-3-phenyl-1,4-dioxaspiro[4,4]nonane-2-carboxylate (Preparation example 227) was used instead of (4S,5R)-methyl-2,2-diethyl-5-phenyl-1,3-dioxolane-4-carboxylate (Preparation example 223), to obtain the title compound (0.7 g, 70~95%).

$^1$H NMR (400 MHz, CDCl$_3$) δ 1.69~1.82 (m, 4H), 1.85~2.03 (m, 4H), 3.66 (ddd, J=3.7, 8.1, 12.1 Hz, 1H), 3.83~3.90 (m, 2H), 4.84 (d, J=8.4 Hz, 1H), 7.26~7.41 (m, 5H).

Preparation Example 229: (2R,3S)-methyl-3-phenyl-1,4-dioxaspiro[4,4]nonane-2-carboxylate

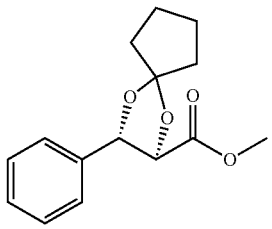 [SMILES: COC(=O)[C@@H]1OC2(CCCC2)O[C@H]1c1ccccc1]

The substantially same method as described in Preparation example 225 was conducted, except that cyclopentanone was used instead of 3-pentanone, to obtain the title compound (0.8 g, 50~75%).

$^1$H NMR (400 MHz, CDCl$_3$) δ 1.71~1.80 (m, 4H), 1.87~1.94 (m, 1H), 2.00~2.08 (m, 3H), 3.79 (s, 3H), 4.35 (d, J=7.2 Hz, 1H), 5.08 (d, J=7.2 Hz, 1H), 7.32~7.45 (m, 5H).

Preparation Example 230: ((2S,3S)-3-phenyl-1,4-dioxaspiro[4,4]nonan-2-yl)methanol

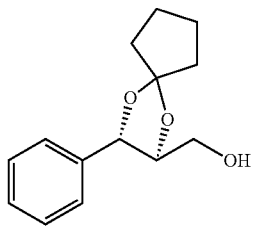 [SMILES: OC[C@@H]1OC2(CCCC2)O[C@H]1c1ccccc1]

The substantially same method as described in Preparation example 228 was conducted, except that (2R,3S)-methyl-3-phenyl-1,4-dioxaspiro[4,4]nonane-2-carboxylate (Preparation example 229) was used instead (2S,3R)-methyl-3-phenyl-1,4-dioxaspiro[4,4]nonane-2-carboxylate (Preparation example 227), to obtain the title compound (0.5 g, 70~95%).

$^1$H NMR (400 MHz, CDCl$_3$) δ 1.69~1.82 (m, 4H), 1.85~2.03 (m, 4H), 3.66 (ddd, J=3.7, 8.1, 12.1 Hz, 1H), 3.83~3.90 (m, 2H), 4.84 (d, J=8.4 Hz, 1H), 7.26~7.41 (m, 5H).

Preparation Example 231: (2S,3R)-methyl 3-phenyl-1,4-dioxaspiro[4,5]decane-2-carboxylate

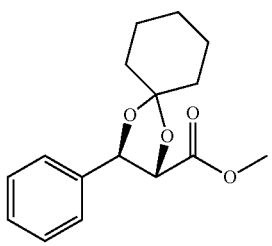 [SMILES: COC(=O)[C@H]1OC2(CCCCC2)O[C@@H]1c1ccccc1]

The substantially same method as described in Preparation example 227 was conducted, except that cyclohexanone was used instead of cyclopentanone, to obtain the title compound (1.4 g, 50~75%).

$^1$H NMR (400 MHz, CDCl$_3$) δ 1.41~1.49 (m, 2H), 1.58~1.76 (m, 4H), 1.79~1.90 (m, 4H), 3.78 (s, 3H), 4.36 (d, J=7.6 Hz, 1H), 5.16 (d, J=7.2 Hz, 1H), 7.31~7.44 (m, 5H).

Preparation Example 232: ((2R,3R)-3-phenyl-1,4-dioxaspiro[4,5]decan-2-yl)methanol

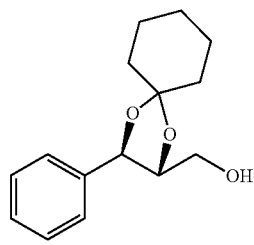 [SMILES: OC[C@H]1OC2(CCCCC2)O[C@@H]1c1ccccc1]

The substantially same method as described in Preparation example 224 was conducted, except that (2S,3R)-methyl 3-phenyl-1,4-dioxaspiro[4,5]decane-2-carboxylate (Preparation example 231) was used instead of (4S,5R)-methyl-2,2-diethyl-5-phenyl-1,3-dioxolane-4-carboxylate (Preparation example 223), to obtain the title compound (1.0 g, 70~95%).

$^1$H NMR (400 MHz, CDCl$_3$) δ 1.41~1.50 (m, 2H), 1.61~1.89 (m, 8H), 3.60~3.66 (m, 1H), 3.85~3.90 (m, 2H), 4.91 (d, J=8.4 Hz, 1H), 7.30~7.42 (m, 5H).

Preparation Example 233: (2R,3S)-methyl-3-phenyl-1,4-dioxaspiro[4,5]decane-2-carboxylate

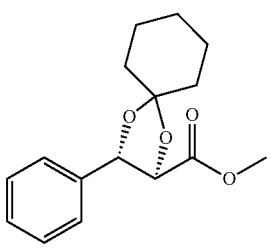 [SMILES: COC(=O)[C@@H]1OC2(CCCCC2)O[C@H]1c1ccccc1]

The substantially same method as described in Preparation example 229 was conducted, except that cyclohexanone was used instead of cyclopentanone, to obtain the title compound (1.2 g, 50~75%).

$^1$H NMR (400 MHz, CDCl$_3$) δ 1.41~1.49 (m, 2H), 1.58~1.76 (m, 4H), 1.79~1.90 (m, 4H), 3.78 (s, 3H), 4.36 (d, J=7.6 Hz, 1H), 5.16 (d, J=7.2 Hz, 1H), 7.31~7.44 (m, 5H).

Preparation Example 234: ((2S,3S)-3-phenyl-1,4-dioxaspiro[4,5]decane-2-yl)methanol

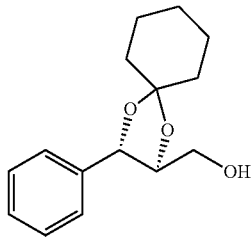 [SMILES: OC[C@@H]1OC2(CCCCC2)O[C@H]1c1ccccc1]

The substantially same method as described in Preparation example 232 was conducted, except that (2R,3S)-methyl-3-phenyl-1,4-dioxaspiro[4,5]decane-2-carboxylate (Preparation example 233) was used instead of (2S,3R)-methyl-3-phenyl-1,4-dioxaspiro[4,5]decane-2-carboxylate (Preparation example 231), to obtain the title compound (0.8 g, 70~95%).

$^1$H NMR (400 MHz, CDCl$_3$) δ 1.41~1.50 (m, 2H), 1.61~1.89 (m, 8H), 3.60~3.66 (m, 1H), 3.85~3.90 (m, 2H), 4.91 (d, J=8.4 Hz, 1H), 7.30~7.42 (m, 5H).

Preparation Example 235: (E)-5-phenylpent-3-enoic Acid

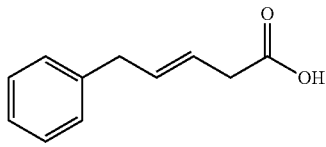 [SMILES: O=C(O)C/C=C/Cc1ccccc1]

A solution of malonic acid (17.06 g, 163.96 mmol) in DMSO (65 mL) was treated with a solution of AcOH (0.1 mL, 1.49 mmol) and piperidine (0.15 mL, 1.49 mmol) in DMSO (4 mL). The reaction solution was warmed to 65° C. and hydrocinnamaldehyde (10.0 g, 74.53 mmol) was added dropwise within 1.5 hr. After the addition ended, the reaction mixture was stirred for further 2 h at 65 T. The solution was cooled to room temperature, taken up in H$_2$O and extracted with Et$_2$O. The combined organic extracts were washed with 5% aqueous KHSO$_4$ and brine, dried over MgSO$_4$, and evaporated to dryness. The crude compound was purified by a silica gel column to produce the title compound (10.4 g, 75~90%).

$^1$H NMR (400 MHz, CDCl$_3$) δ 3.19 (d, J=6.9 Hz, 2H), 3.46 (d, J=6.9 Hz, 2H), 5.69~5.78 (m, 1H), 5.83~5.91 (m, 1H), 7.01~7.56 (m, 5H), 11.79 (s, 1H).

Preparation Example 236: (E)-5-phenylpent-3-en-1-ol

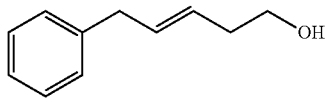 [SMILES: OCC/C=C/Cc1ccccc1]

To stirred solution of LAH (LiAlH$_4$. 3.3 g, 86.73 mmol) in THF (66 mL) was added dropwise a solution (E)-5-phenylpent-3-enoic acid (Preparation example 235, 11.0 g, 57.82 mmol) in THF (44 mL) at 0° C. then stirred at room temperature for 1 h. The reaction mixture was quenched with H$_2$O at 0° C., filtered through celite, washed with EtOAc, dried over anhydrous magnesium sulfate (MgSO$_4$), filtered and concentrated. The crude compound was purified by a silica gel column to produce the title compound (7.2 g, 70~90%).

$^1$H NMR (400 MHz, CDCl$_3$) δ 1.40 (bs, 1H), 2.31 (q, J=6.3 Hz, 2H), 3.37 (d, J=6.8 Hz, 2H), 3.66 (t, J=6.4 Hz, 2H), 5.49 (dt, J=4.9 Hz, 11.0, 1H), 5.73 (dt, J=4.8, 10.9 Hz, 1H), 7.17~7.31 (m, 5H).

Preparation Example 237: (E)-tert-butyldimethyl(5-phenylpent-3-enyloxy)silane

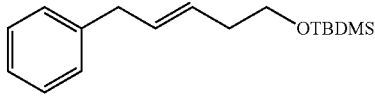 [SMILES: CC(C)(C)[Si](C)(C)OCC/C=C/Cc1ccccc1]

To a stirred solution of (E)-5-phenylpent-3-en-1-ol (Preparation example 236, 6.3 g, 38.83 mmol) in CH$_2$Cl$_2$ was added imidazole (3.4 g, 50.48 mmol) and TBDMS-Cl (7.6 g, 50.48 mmol) at 0° C. then stirred for 1 h at room temperature. The resulting mixture was diluted with EtOAc, washed with water, dried over MgSO$_4$, filtered, and concentrated under reduced pressure. The crude compound was purified by a silica gel column to produce the title compound (10.6 g, 80~98%).

$^1$H NMR (400 MHz, CDCl$_3$) δ 0.00 (s, 6H), 0.84 (s, 9H), 2.21 (ddd, J=0.8, 6.8, 13.6 Hz, 2H), 3.29 (d, J=6.8 Hz, 2H), 3.59 (t, J=6.8 Hz, 2H), 5.41~5.49 (m, 1H), 5.56~5.63 (m, 1H), 7.13~7.26 (m, 5H).

Preparation Example 238: (E)-5-phenylpent-3-enyl pivalate

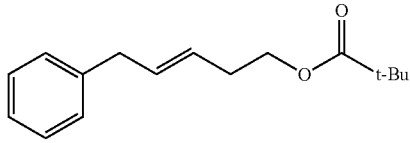 [SMILES: CC(C)(C)C(=O)OCC/C=C/Cc1ccccc1]

To a stirred solution of (E)-5-phenylpent-3-en-1-ol (Preparation example 236, 3.8 g, 23.42 mmol) in CH$_2$Cl$_2$ (40 mL) was added pyridine (2.3 mL, 28.1 mmol) and pivaloyl chloride (3.5 mL, 28.1 mmol) at 0° C. under N$_2$. The mixture was stirred for 14 h. The resulting mixture was diluted with CH$_2$Cl$_2$, washed with water, dried over MgSO$_4$, filtered, and concentrated under reduced pressure. The crude compound was purified by a silica gel column to produce the title compound (5.5 g, 80~95%).

$^1$H NMR (400 MHz, CDCl$_3$) δ 1.17 (s, 9H), 2.36 (q, J=6.7 Hz, 2H), 3.34 (d, J=6.8 Hz, 2H), 4.09 (t, J=6.8 Hz, 2H), 5.45~5.51 (m, 1H), 5.64~5.69 (m, 1H), 7.16~7.21 (m, 3H), 7.26~7.30 (m, 2H).

Preparation Example 239: (2S,3S)-5-(tert-butyldimethylsilyloxy)-1-phenylpentane-2,3-diol

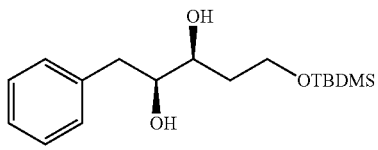 [SMILES: CC(C)(C)[Si](C)(C)OCC[C@H](O)[C@@H](O)Cc1ccccc1]

The substantially same method as described in Preparation example 217 was conducted, except that (E)-tert-butyldimethyl(5-phenylpent-3-enyloxy)silane (Preparation example 237) was used instead of (E)-Methyl cinnamate (Preparation example 216), to obtain the title compound (8.7 g, 70~95%).

$^1$H NMR (400 MHz, CDCl$_3$) δ 0.00 (s, 6H), 0.82 (s, 9H), 1.57~1.62 (m, 1H), 1.73~1.80 (m, 1H), 2.51 (d, J=6.0 Hz, 1H), 2.77 (dq, J=6.9, 14.9 Hz, 2H), 3.50 (d, J=3.6 Hz, 1H), 3.59~3.62 (m, 1H), 3.66 (dq, J=3.1, 5.4 Hz, 1H), 3.72~3.82 (m, 2H), 7.12~7.25 (m, 5H).

Preparation Example 240: (2-((4S,5S)-5-benzyl-2,2-dimethyl-1,3-dioxolane-4-yl)ethoxy)(tert-butyl)dimethylsilane

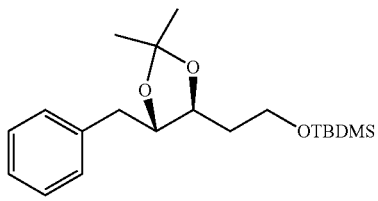 [SMILES: CC1(C)O[C@@H](CCO[Si](C)(C)C(C)(C)C)[C@H](Cc2ccccc2)O1]

The substantially same method as described in Preparation example 218 was conducted, except that (2S,3S)-5-(tert-butyldimethylsilyloxy)-1-phenylpentane-2,3-diol (Preparation example 239) was used instead of (2R,3S)-methyl-3-phenyl-2,3-dihydroxypropanoate (Preparation example 217), to obtain the title compound (9.5 g, 70~95%).

$^1$H NMR (400 MHz, CDCl$_3$) δ 0.00 (s, 6H), 0.85 (s, 9H), 1.29 (s, 3H), 1.34 (s, 3H), 1.52~1.58 (m, 2H), 2.87 (dq, J=5.5, 14.2 Hz, 2H), 3.64~3.69 (m, 2H), 3.80~3.88 (m, 2H), 7.18~7.27 (m, 5H).

Preparation Example 241: 2-((4S,5S)-5-benzyl-2,2-dimethyl-1,3-dioxolane-4-yl)ethanol

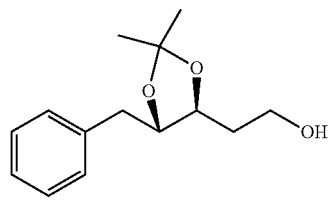 [SMILES: CC1(C)O[C@@H](CCO)[C@H](Cc2ccccc2)O1]

To a stirred solution of (2-((4S,5S)-5-benzyl-2,2-dimethyl-1,3-dioxolan-4-yl)ethoxy)(tert-butyl)dimethylsilane (Preparation example 240, 11.5 g, 32.80 mmol) in THF (115 mL) was slowly added tetrabutylammonium fluoride (TBAF, 1.0 M in THF, 48.8 mL, 48.8 mmol) at room temperature. The mixture was stirred for 5 h. The resulting mixture was diluted with EtOAc, washed with water, dried over anhydrous magnesium sulfate, filtered and concentrated. The crude compound was purified by a silica gel column to produce the title compound (7.3 g, 80~95%).

$^1$H NMR (400 MHz, CDCl$_3$) δ 1.38 (s, 3H), 1.40 (s, 3H), 1.50~1.63 (m, 2H), 2.29 (t, J=5.4 Hz, 1H), 2.82 (dd, J=5.8, 13.8 Hz, 1H), 3.01 (dd, J=6.4, 14.0 Hz, 1H), 3.72 (q, J=5.5 Hz, 2H), 3.86 (dt, J=3.2, 8.4 Hz, 1H), 3.92~3.97 (m, 1H), 7.22~7.32 (m, 5H).

Preparation Example 242: (2R,3R)-5-(tert-butyldimethylsilyloxy)-1-phenylpentane-2,3-diol

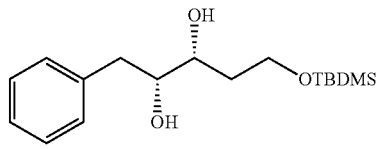 [SMILES: CC(C)(C)[Si](C)(C)OCC[C@@H](O)[C@H](O)Cc1ccccc1]

The substantially same method as described in Preparation example 220 was conducted, except that (E)-tert-butyldimethyl(5-phenylpent-3-enyloxy)silane (Preparation example 237) was used instead of (E)-Methyl cinnamate (Preparation example 216), to obtain the title compound (10.6 g, 70~95%).

$^1$H NMR (400 MHz, CDCl$_3$) δ 0.00 (s, 6H), 0.82 (s, 9H), 1.57~1.62 (m, 1H), 1.73~1.80 (m, 1H), 2.51 (d, J=6.0 Hz, 1H), 2.77 (dq, J=6.9, 14.9 Hz, 2H), 3.50 (d, J=3.6 Hz, 1H), 3.59~3.62 (m, 1H), 3.66 (dq, J=3.1, 5.4 Hz, 1H), 3.72~3.82 (m, 2H), 7.12~7.25 (m, 5H).

Preparation Example 243: (2-((4R,5R)-5-benzyl-2,2-dimethyl-1,3-dioxolane-4-yl)ethoxy)(tert-butyl)dimethylsilane

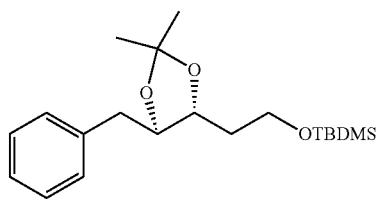 [SMILES: CC1(C)O[C@H](CCO[Si](C)(C)C(C)(C)C)[C@@H](Cc2ccccc2)O1]

The substantially same method as described in Preparation example 221 was conducted, except that (2R,3R)-5-(tert-butyldimethylsilyloxy)-1-phenylpentane-2,3-diol (Preparation example 242) was used instead of (2R,3S)-methyl-3-phenyl-2,3-dihydroxypropanoate (Preparation example 217), to obtain the title compound (11.5 g, 70~95%).

$^1$H NMR (400 MHz, CDCl$_3$) δ 0.00 (s, 6H), 0.85 (s, 9H), 1.29 (s, 3H), 1.34 (s, 3H), 1.52~1.58 (m, 2H), 2.87 (dq, J=5.5, 14.2 Hz, 2H), 3.64~3.69 (m, 2H), 3.80~3.88 (m, 2H), 7.18~7.27 (m, 5H).

Preparation Example 244: 2-((4R,5R)-5-benzyl-2,2-dimethyl-1,3-dioxolane-4-yl)ethanol

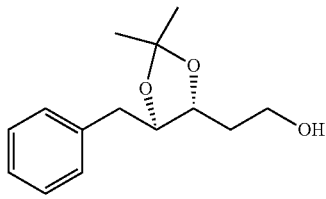 [SMILES: CC1(C)O[C@H](CCO)[C@@H](Cc2ccccc2)O1]

The substantially same method as described in Preparation example 241 was conducted, except that (2-((4R,5R)-5-benzyl-2,2-dimethyl-1.3-dioxolan-4-yl)ethoxy)(tert-butyl)dimethylsilane (Preparation example 243) was used instead of (2-((4S,5S)-5-benzyl-2,2-dimethyl-1,3-dioxolan-4-yl)ethoxy)(tert-butyl)dimethylsilane (Preparation example 240), to obtain the title compound (7.4 g, 80~95%).

$^1$H NMR (400 MHz, CDCl$_3$) δ 1.38 (s, 3H), 1.40 (s, 3H), 1.50~1.63 (m, 2H), 2.29 (t, J=5.4 Hz, 1H), 2.82 (dd, J=5.8, 13.8 Hz, 1H), 3.01 (dd, J=6.4, 14.0 Hz, 1H), 3.72 (q, J=5.5 Hz, 2H), 3.86 (dt, J=3.2, 8.4 Hz, 1H), 3.92~3.97 (m, 1H), 7.22~7.32 (m, 5H).

Preparation Example 245: (3S,4S)-3,4-dihydroxy-5-phenylpentyl pivalate

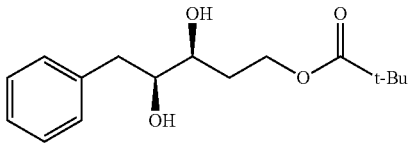 [SMILES: CC(C)(C)C(=O)OCC[C@H](O)[C@@H](O)Cc1ccccc1]

The substantially same method as described in Preparation example 239 was conducted, except that (E)-5-phenyl-pent-3-enyl pivalate (Preparation example 238) was used instead of (E)-tert-butyldimethyl(5-phenylpent-3-enyloxy)silane (Preparation example 237), to obtain the title compound (5.5 g, 70~95%).

$^1$H NMR (400 MHz, CDCl$_3$) δ 1.16 (s, 9H), 1.83~1.88 (m, 2H), 2.08 (d, J=4.8 Hz, 1H), 2.67 (d, J=5.2 Hz, 1H), 2.80 (dd, J=8.0, 13.6 Hz, 1H), 2.92 (dd, J=5.2, 13.6 Hz, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H).

Preparation Example 246: (2-((4S,5S)-5-benzyl-2,2-diethyl-1,3-dioxolane-4-yl)ethyl pivalate

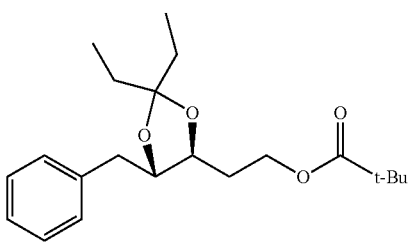 [SMILES: CCC1(CC)O[C@@H](CCOC(=O)C(C)(C)C)[C@H](Cc2ccccc2)O1]

The substantially same method as described in Preparation example 223 was conducted, except that (3S,4S)-3,4-dihydroxy-5-phenylpentyl pivalate (Preparation example 245) was used instead of (2R,3S)-methyl-3-phenyl-2,3-dihydroxypropanoate (Preparation example 217), to obtain the title compound (0.9 g, 70~95%).

$^1$H NMR (400 MHz, CDCl$_3$) δ 1.15 (s, 9H), 1.76 (q, J=7.6 Hz, 2H), 1.84~1.90 (m, 2H), 2.00~2.07 (m, 2H), 3.85 (dt, J=3.7, 8.5 Hz, 1H), 4.14~4.27 (m, 2H), 5.17 (d, J=8.4 Hz, 1H), 7.22~7.28 (m, 1H), 7.32~7.38 (m, 2H), 7.64 (dd, J=1.4, 7.8 Hz, 1H).

Preparation Example 247: 2-((4S,5S)-5-benzyl-2,2-diethyl-1,3-dioxolane-4-yl)ethanol

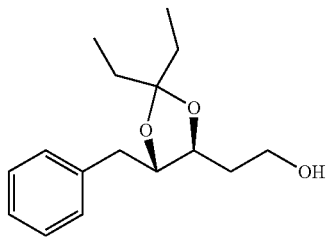 [SMILES: CCC1(CC)O[C@@H](CCO)[C@H](Cc2ccccc2)O1]

To a stirred solution of (2-((4S,5S)-5-benzyl-2,2-diethyl-1,3-dioxolan-4-yl)ethyl pivalate (Preparation example 246, 1.0 g, 2.87 mmol) in MeOH (10 mL) was added NaOMe (0.47 g, 8.61 mmol) and then warm to 45° C. The mixture was stirred for 14 h. The resulting mixture was diluted with EtOAc, washed with water, dried over MgSO4, filtered, and concentrated under reduced pressure. The crude compound was purified by a silica gel column to produce the title compound (0.7 g, 80~95%).

$^1$H NMR (400 MHz, CDCl$_1$) δ 0.89 (t, J=7.4 Hz, 6H), 1.44~1.50 (m, 1H), 1.54~1.66 (m, 5H), 2.37 (t, J=5.6 Hz, 1H), 2.80 (dd, J=5.6, 14.0 Hz, 1H), 3.03 (dd, J=6.4, 14.0 Hz, 1H), 3.72 (q, J=5.5 Hz, 2H), 3.80~3.85 (m, 1H), 3.89~3.94 (m, 1H), 7.21~7.24 (m, 3H), 7.28~7.31 (m, 2H).

Preparation Example 248: 3R,4R)-3,4-dihydroxy-5-phenylpentyl pivalate

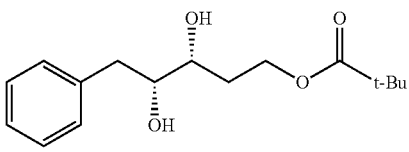 [SMILES: CC(C)(C)C(=O)OCC[C@@H](O)[C@H](O)Cc1ccccc1]

The substantially same method as described in Preparation example 242 was conducted, except that (E)-5-phenyl-pent-3-enyl pivalate (Preparation example 238) was used instead of (E)-tert-butyldimethyl (5-phenylpent-3-enyloxy)silane (Preparation example 237), to obtain the title compound (4.5 g, 70~95%).

$^1$H NMR (400 MHz, CDCl$_3$) δ 1.16 (s, 9H), 1.83~1.88 (m, 2H), 2.08 (d, J=4.8 Hz, 1H), 2.67 (d, J=5.2 Hz, 1H), 2.80 (dd, J=8.0, 13.6 Hz, 1H), 2.92 (dd, J=5.2, 13.6 Hz, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H).

Preparation Example 249: (2-((4R,5R)-5-benzyl-2,2-diethyl-1,3-dioxolane-4-yl)ethyl pivalate

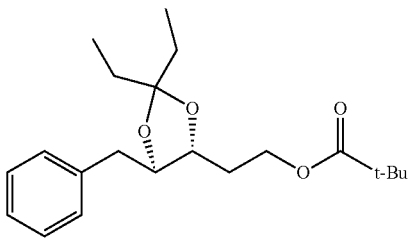 [SMILES: CCC1(CC)O[C@H](CCOC(=O)C(C)(C)C)[C@@H](Cc2ccccc2)O1]

The substantially same method as described in Preparation example 246 was conducted, except that (3R,4R)-3,4-dihydroxy-5-phenylpentyl pivalate (Preparation example 248) was used instead of (3S,4S)-3,4-dihydroxy-5-phenylpentyl pivalate (Preparation example 245), to obtain the title compound (1.1 g, 70~95%).

$^1$H NMR (400 MHz, CDCl$_3$) δ 1.15 (s, 9H), 1.76 (q, J=7.6 Hz, 2H), 1.84~1.90 (m, 2H), 2.00~2.07 (m, 2H), 3.85 (dt, J=3.7, 8.5 Hz, 1H), 4.14~4.27 (m, 2H), 5.17 (d, J=8.4 Hz, 1H), 7.22~7.28 (m, 1H), 7.32~7.38 (m, 2H), 7.64 (dd. J=1.4, 7.8 Hz, 1H).

Preparation Example 250: 2-((4R,5R)-5-benzyl-2,2-diethyl-1,3-dioxolane-4-yl)ethanol

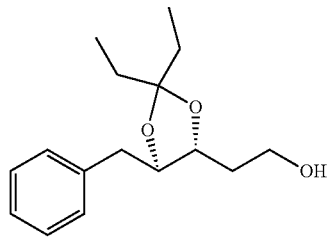 [SMILES: CCC1(CC)O[C@H](CCO)[C@@H](Cc2ccccc2)O1]

The substantially same method as described in Preparation example 247 was conducted, except that (2-((4R,5R)-5-benzyl-2,2-diethyl-1,3-dioxolan-4-yl)ethyl pivalate (Preparation example 249) was used instead of (2-((4S,5S)-5-benzyl-2,2-diethyl-1,3-dioxolan-4-yl)ethyl pivalate (Preparation example 246), to obtain the title compound (0.9 g, 80~95%).

$^1$H NMR (400 MHz, CDCl$_3$) δ 0.89 (t, J=7.4 Hz, 6H), 1.44~1.50 (m, 1H), 1.54~1.66 (m, 5H), 2.37 (t, J=5.6 Hz, 1H), 2.80 (dd, J=5.6, 14.0 Hz, 1H), 3.03 (dd, J=6.4, 14.0 Hz, 1H), 3.72 (q, J=5.5 Hz, 2H), 3.80~3.85 (m, 1H), 3.89~3.94 (m, 1H), 7.21~7.24 (m, 3H), 7.28~7.31 (m, 2H).

Preparation Example 251: 2-((2S,3S)-3-benzyl-1,4-dioxaspiro[4.4]nonane-2-yl)ethyl pivalate

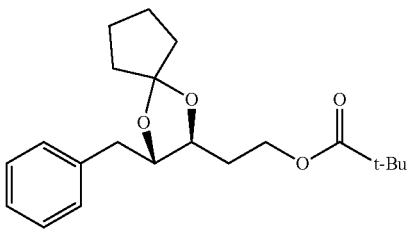 [SMILES: CC(C)(C)C(=O)OCC[C@@H]1OC2(CCCC2)O[C@H]1Cc1ccccc1]

The substantially same method as described in Preparation example 246 was conducted, except that cyclopentanone was used instead of 3-pentanone, to obtain the title compound (1.2 g, 60~85%).

$^1$H NMR (400 MHz, CDCl$_3$) δ 1.18 (s, 9H), 1.53~1.80 (m, 10H), 2.81 (dd, J=6.0, 13.6 Hz, 1H), 3.00 (dd, J=6.4, 14.0 Hz, 1H), 3.75~3.80 (m, 1H), 3.84~3.89 (m, 1H), 4.05~4.16 (m, 2H), 7.20~7.24 (m, 3H), 7.27~7.31 (m, 2H).

Preparation Example 252: 2-((2S,3S)-3-benzyl-1,4-dioxaspiro[4.4]nonane-2-yl)ethanol

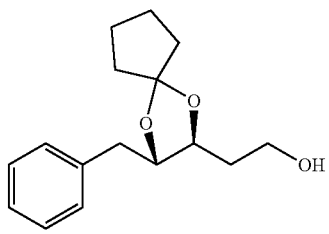 [SMILES: OCC[C@@H]1OC2(CCCC2)O[C@H]1Cc1ccccc1]

The substantially same method as described in Preparation example 247 was conducted, except that 2-((2S,3S)-3-benzyl-1,4-dioxaspiro[4.4]nonan-2-yl)ethyl pivalate (Preparation example 251) was used instead of (2-((4S,5S)-5-benzyl-2,2-diethyl-1,3-dioxolan-4-yl)ethyl pivalate (Preparation example 246), to obtain the title compound (0.7 g, 80~95%).

$^1$H NMR (400 MHz, CDCl$_3$) δ 1.44~1.51 (m, 1H), 1.56~1.60 (m, 1H), 1.63~1.70 (m, 4H), 1.72~1.81 (m, 4H), 2.26 (t, J=5.4 Hz, 1H), 2.80 (dd, J=6.0, 14.0 Hz, 1H), 3.03 (dd, J=6.4, 14.0 Hz, 1H), 3.71 (q, J=5.5 Hz, 2H), 3.81~3.92 (m, 2H), 7.22~7.24 (m, 3H), 7.28~7.32 (m, 2H).

Preparation Example 253: 2-((2R,3R)-3-benzyl-1,4-dioxaspiro[4.4]nonane-2-yl)ethyl pivalate

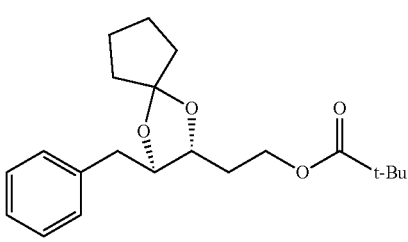 [SMILES: CC(C)(C)C(=O)OCC[C@H]1OC2(CCCC2)O[C@@H]1Cc1ccccc1]

The substantially same method as described in Preparation example 249 was conducted, except that cyclopentanone was used instead of 3-pentanone, to obtain the title compound (1.7 g, 60~85%).

¹H NMR (400 MHz, CDCl₃) δ 1.18 (s, 9H), 1.53~1.80 (m, 10H), 2.81 (dd. J=6.0, 13.6 Hz, 1H), 3.00 (dd, J=6.4, 14.0 Hz, 1H), 3.75~3.80 (m, 1H), 3.84~3.89 (m, 1H), 4.05~4.16 (m, 2H), 7.20~7.24 (m, 3H), 7.27~7.31 (m, 2H).

Preparation Example 254: 2-((2R,3R)-3-benzyl-1,4-dioxaspiro[4.4]nonane-2-yl)ethanol

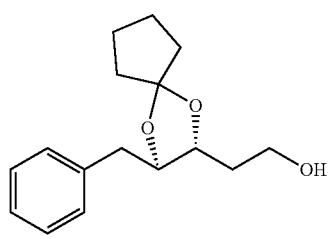 [SMILES: OCC[C@H]1OC2(CCCC2)O[C@@H]1Cc1ccccc1]

The substantially same method as described in Preparation example 252 was conducted, except that 2-((2R,3R)-3-benzyl-1,4-dioxaspiro[4.4]nonan-2-yl)ethyl pivalate (Preparation example 253) was used instead of 2-((2S,3S)-3-benzyl-1,4-dioxaspiro[4.4]nonan-2-yl)ethyl pivalate (Preparation example 251), to obtain the title compound (0.8 g, 80~95%).

¹H NMR (400 MHz, CDCl₃) δ 1.44~1.51 (m, 1H), 1.56~1.60 (m, 1H), 1.63~1.70 (m, 4H), 1.72~1.81 (m, 4H), 2.26 (t, J=5.4 Hz, 1H), 2.80 (dd, J=6.0, 14.0 Hz, 1H), 3.03 (dd, J=6.4, 14.0 Hz, 1H), 3.71 (q, J=5.5 Hz, 2H), 3.81~3.92 (m, 2H), 7.22~7.24 (m, 3H), 7.28~7.32 (m, 2H).

Preparation Example 255: 2-((2S,3S)-3-benzyl-1,4-dioxaspiro[4.5]decane-2-yl)ethyl pivalate

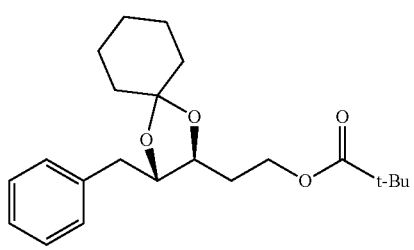 [SMILES: CC(C)(C)C(=O)OCC[C@@H]1OC2(CCCCC2)O[C@H]1Cc1ccccc1]

The substantially same method as described in Preparation example 251 was conducted, except that cyclohexanone was used instead of cyclopentanone, to obtain the title compound (1.4 g, 60~85%).

¹H NMR (400 MHz, CDCl₃) δ 1.18 (s, 9H), 1.53~1.60 (m, 10H), 1.61~1.66 (m, 2H), 2.83 (dd, J=5.6, 14.0 Hz, 1H), 2.98 (dd, J=6.0, 14.0 Hz, 1H), 3.78 (dt, J=3.5, 8.2 Hz, 1H), 3.86~3.91 (m, 1H), 4.11~4.15 (m, 2H), 7.20~7.31 (m, 5H).

Preparation Example 256: 2-((2S,3S)-3-benzyl-1,4-dioxaspiro[4.5]decane-2-yl)ethanol

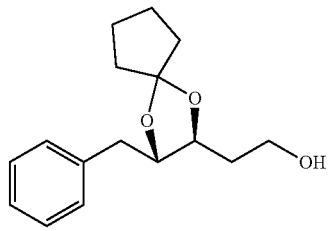 [SMILES: OCC[C@@H]1OC2(CCCC2)O[C@H]1Cc1ccccc1]

The substantially same method as described in Preparation example 254 was conducted, except that 2-((2S,3S)-3-benzyl-1,4-dioxaspiro[4.5]decan-2-yl)ethyl pivalate (Preparation example 255) was used instead of 2-((2R,3R)-3-benzyl-1,4-dioxaspiro[4.4]nonan-2-yl)ethyl pivalate (Preparation example 253), to obtain the title compound (1.0 g, 80~95%).

¹H NMR (400 MHz, CDCl₃) δ 1.34~1.43 (m, 2H), 1.48~1.61 (m, 10H), 2.42 (t, J=5.6 Hz, 1H), 2.81 (dd, J=5.6, 14.0 Hz, 1H), 3.02 (dd, J=6.2, 13.8 Hz, 1H), 3.72 (q, J=5.5 Hz, 2H), 3.82~3.87 (m, 1H), 3.91~3.96 (m, 1H), 7.21~7.31 (m, 5H).

Preparation Example 257: 2-((2R,3R)-3-benzyl-1,4-dioxaspiro[4,5]decane-2-yl)ethyl pivalate

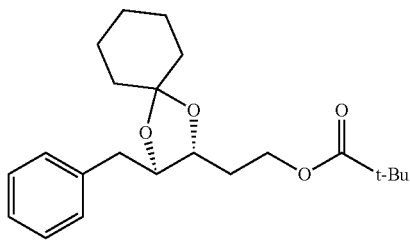 [SMILES: CC(C)(C)C(=O)OCC[C@H]1OC2(CCCCC2)O[C@@H]1Cc1ccccc1]

The substantially same method as described in Preparation example 253 was conducted, except that cyclohexanone was used instead of cyclopentanone, to obtain the title compound (1.6 g, 60~85%).

¹H NMR (400 MHz, CDCl₃) δ 1.18 (s, 9H), 1.53~1.60 (m, 10H), 1.61~1.66 (m, 2H), 2.83 (dd, J=5.6, 14.0 Hz, 1H), 2.98 (dd, J=6.0, 14.0 Hz, 1H), 3.78 (dt, J=3.5, 8.2 Hz, 1H), 3.86~3.91 (m, 1H), 4.11~4.15 (m, 2H), 7.20~7.31 (m, 5H).

Preparation Example 258: 2-((2R,3R)-3-benzyl-1,4-dioxaspiro[4.5]decane-2-yl)ethanol

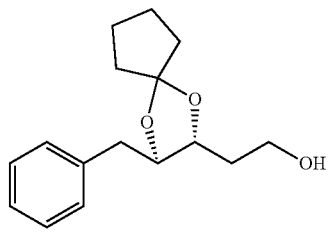 [SMILES: OCC[C@H]1OC2(CCCC2)O[C@@H]1Cc1ccccc1]

The substantially same method as described in Preparation example 256 was conducted, except that 2-((2R,3R)-3-benzyl-1,4-dioxaspiro[4.5]decan-2-yl)ethyl pivalate (Preparation example 257) was used instead of 2-((2S,3S)-3-benzyl-1,4-dioxaspiro[4.5]decan-2-yl)ethyl pivalate (Preparation example 255), to obtain the title compound (1.1 g, 80~95%).

$^1$H NMR (400 MHz, CDCl$_3$) δ 1.34~1.43 (m, 2H), 1.48~1.61 (m, 10H), 2.42 (t, J=5.6 Hz, 1H), 2.81 (dd, J=5.6, 14.0 Hz, 1H), 3.02 (dd, J=6.2, 13.8 Hz, 1H), 3.72 (q, J=5.5 Hz, 2H), 3.82~3.87 (m, 1H), 3.91~3.96 (m, 1H), 7.21~7.31 (m, 5H).

Preparation Example 259:
(E)-methyl-4-phenylbut-2-enoate

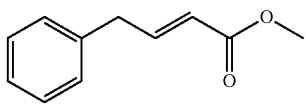

To a solution of phenyl acetaldehyde (5.0 g, 41.61 mmol) in toluene (500 mL) was added methyl (triphenylphosphoranylidene) acetate (13.9 g, 41.61 mmol). The reaction mixture was stirred at reflux for 3 h. The resulting mixture was diluted with EtOAc, washed with water, dried over MgSO$_4$, filtered, and concentrated under reduced pressure. The crude product was added ether/hexane (=1:1, v/v) at 0° C. then stirred for 30 min. The filtrate was concentrated then purified by a silica gel column to produce the title compound (5.9 g, 70~90%).

$^1$H NMR (400 MHz, CDCl$_3$) δ 3.47 (d, J=6.8 Hz, 2H), 3.67 (s, 3H), 5.79 (d, J=15.4 Hz, 1H), 7.06 (dt, J=6.8, 15.4 Hz, 1H), 7.28~7.12 (m, 5H).

Preparation Example 260: (2R,3S)-methyl 2,3-dihydroxy-4-phenylbutanoate

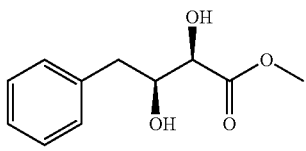

The substantially same method as described in Preparation example 245 was conducted, except that (E)-methyl-4-phenylbut-2-enoate (Preparation example 259) was used instead of (E)-5-phenylpent-3-enyl pivalate (Preparation example 238), to obtain the title compound (3.5 g, 70~95%).

$^1$H NMR (400 MHz, CDCl$_3$) δ 2.96 (ddd, J=7.3, 13.5, 17.1 Hz, 2H), 3.10 (d, J=5.2 Hz, 1H), 3.80 (s, 3H), 4.08 (dd, J=1.4, 5.4 Hz, 1H), 7.23~7.34 (m, 5H).

Preparation Example 261: (4R,5S)-methyl-5-benzyl-2,2-dimethyl-1,3-dioxolane-4-carboxylate

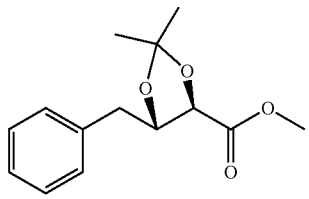 [SMILES: COC(=O)[C@@H]1OC(C)(C)O[C@H]1Cc1ccccc1]

The substantially same method as described in Preparation example 240 was conducted, except that (2R,3S)-methyl 2,3-dihydroxy-4-phenylbutanoate (Preparation example 260) was used instead of (2S,3S)-5-(tert-butyldimethylsilyloxy)-1-phenylpentane-2,3-diol (Preparation example 239), to obtain the title compound (3.1 g, 70~95%).

$^1$H NMR (400 MHz, CDCl$_3$) δ 1.42 (s, 3H), 1.43 (s, 3H), 3.01 (dd, J=6.8, 14.4 Hz, 1H), 3.12 (dd, J=4.4, 14.4 Hz, 1H), 3.72 (s, 3H), 4.19 (d, J=7.6 Hz, 1H), 4.40 (ddd, J=4.4, 7.0, 7.8 Hz, 1H), 7.22~7.33 (m, 5H).

Preparation Example 262: ((4S,5S)-5-benzyl-2,2-dimethyl-1,3-dioxolan-4-yl)methanol

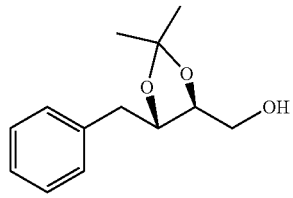 [SMILES: CC1(C)O[C@@H](CO)[C@H](Cc2ccccc2)O1]

The substantially same method as described in Preparation example 234 was conducted, except that (4R,5S)-methyl 5-benzyl-2,2-dimethyl-1,3-dioxolane-4-carboxylate (Preparation example 261) was used instead of (4S,5R)-methyl-3-phenyl-1,4-dioxaspiro[4,5]decane-2-carboxylate (Preparation example 233), to obtain the title compound (2.3 g, 70~95%).

$^1$H NMR (400 MHz, CDCl$_3$) δ 1.41 (s, 6H), 1.79 (q, J=4.3 Hz, 1H), 2.83 (dd, J=6.2, 13.8 Hz, 1H), 3.07 (dd, J=6.4, 14.0 Hz, 1H), 3.29 (ddd, J=4.7, 7.5, 12.1 Hz, 1H), 3.54 (ddd, J=2.8, 5.2, 12.0 Hz, 1H), 3.83 (ddd, J=3.9, 3.9, 7.1 Hz, 1H), 4.15 (q. J=7.1 Hz, 1H), 7.22~7.32 (m, 5H).

Preparation Example 263: (4R,5S)-methyl-5-benzyl-2,2-diethyl-1,3-dioxolane-4-carboxylate

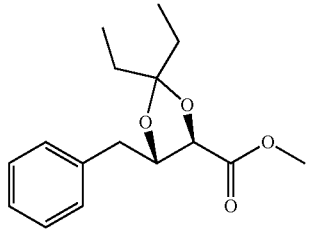 [SMILES: CCC1(CC)O[C@@H](Cc2ccccc2)[C@H](C(=O)OC)O1]

To a stirred solution of (2R,3S)-methyl 2,3-dihydroxy-4-phenylbutanoate (Preparation example 260, 2.0 g, 9.51 mmol) in 3-pentanone (5 mL, 47.55 mmol) was added a catalytic amount of $H_2SO_4$ (0.051 mL, 0.951 mmol) at room temperature. The mixture was stirred for 20 h. The resulting mixture was diluted with EtOAc, washed with water, dried over $MgSO_4$, filtered, and concentrated under reduced pressure. The crude compound was purified by a silica gel column to produce the title compound (1.2 g, 50~75%).

$^1$H NMR (400 MHz, $CDCl_3$) δ 0.85 (t, J=6.0 Hz, 3H), 0.92 (t, J=7.6 Hz, 3H), 1.66 (dq, J=7.6, 14.7 Hz, 4H), 3.01 (dd, J=6.6, 14.2 Hz, 1H), 3.10 (dd. J=4.4, 14.4 Hz, 1H), 3.71 (s, 3H), 4.17 (d, J=8.4 Hz, 1H), 4.32~4.37 (m, 1H), 7.23~7.32 (m, 5H).

Preparation Example 264: ((4S,5S)-5-benzyl-2,2-diethyl-1,3-dioxolan-4-yl)methanol

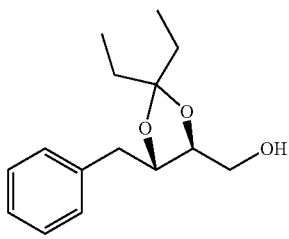 [SMILES: CCC1(CC)O[C@@H](CO)[C@H](Cc2ccccc2)O1]

The substantially same method as described in Preparation example 262 was conducted, except that (4R,5S)-methyl-5-benzyl-2,2-dimethyl-1,3-dioxolane-4-carboxylate (Preparation example 263) was used instead of (4R,5S)-methyl 5-benzyl-2,2-dimethyl-1,3-dioxolane-4-carboxylate (Preparation example 261), to obtain the title compound (0.8 g, 70~95%).

$^1$H NMR (400 MHz, $CDCl_3$) δ 0.91 (dt, J=1.9, 7.5 Hz, 6H), 1.61~1.68 (m, 4H), 1.77 (t, J=6.2 Hz, 1H), 2.81 (dd, J=6.4, 14.0 Hz, 1H), 3.09 (dd, J=6.2, 13.8 Hz, 1H), 3.24~3.30 (m, 1H), 3.49~3.54 (m, 1H), 3.78~3.82 (m, 1H), 4.08~4.13 (m, 1H), 7.21~7.32 (m, 5H).

Preparation Example 265: (21R,3S)-methyl 3-benzyl-1,4-dioxaspiro[4.4]nonane-2-carboxylate

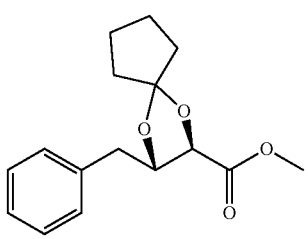 [SMILES: COC(=O)[C@@H]1OC2(CCCC2)O[C@H]1Cc1ccccc1]

The substantially same method as described in Preparation example 263 was conducted, except that cyclopentanone was used instead of 3-pentanone, to obtain the title compound (1.3 g, 60~85%).

$^1$H NMR (400 MHz, $CDCl_3$) δ 1.61~1.79 (m, 5H), 1.85~1.92 (m, 3H), 3.00~3.11 (m, 2H), 3.70 (s, 3H), 4.17 (d, J=7.2 Hz, 1H), 4.32 (dt, J=4.9, 7.0 Hz, 1H), 7.21~7.33 (m, 5H).

Preparation Example 266: ((2S,3S)-3-benzyl-1,4-dioxaspiro[4.4]nonane-2-yl)methanol

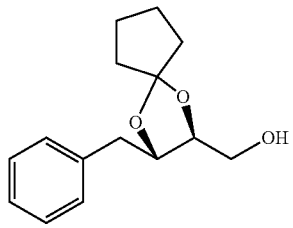 [SMILES: OC[C@@H]1OC2(CCCC2)O[C@H]1Cc1ccccc1]

The substantially same method as described in Preparation example 264 was conducted, except that (2R,3S)-methyl 3-benzyl-1,4-dioxaspiro[4.4]nonane-2-carboxylate (Preparation example 265) was used instead of (4R,5S)-methyl-5-benzyl-2,2-dimethyl-1,3-dioxolane-4-carboxylate (Preparation example 263), to obtain the title compound (0.8 g, 70~95%).

$^1$H NMR (400 MHz, $CDCl_3$) δ 1.57~1.88 (m, 8H), 2.82 (dd, J=6.6, 13.8 Hz, 1H), 3.08 (dd, J=6.4, 14.0 Hz, 1H), 3.27~3.33 (m, 1H), 3.47~3.52 (m, 1H), 3.79~3.83 (m, 1H), 4.07 (q, J=6.8 Hz, 1H), 7.21~7.32 (m, 5H).

Preparation Example 267: (2R,3S)-methyl-3-benzyl-1,4-dioxaspiro[4.5]decane-2-carboxylate

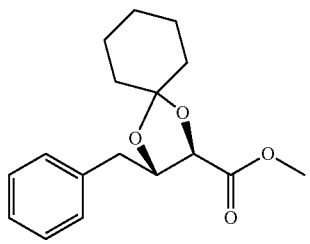 [SMILES: COC(=O)[C@@H]1OC2(CCCCC2)O[C@H]1Cc1ccccc1]

The substantially same method as described in Preparation example 265 was conducted, except that cyclohexanone was used instead of cyclopentanone, to obtain the title compound (1.5 g, 60~85%).

$^1$H NMR (400 MHz, $CDCl_3$) δ 1.54~1.74 (m, 10H), 2.99~3.12 (m, 2H), 3.70 (s, 3H), 4.18 (d, J=7.6 Hz, 1H), 4.36~4.41 (m, 1H), 7.21~7.32 (m, 5H).

Preparation Example 268: ((2S,3S)-3-benzyl-1,4-dioxaspiro[4.4]decan-2-yl)methanol

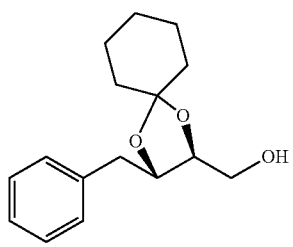 [SMILES: OC[C@@H]1OC2(CCCCC2)O[C@H]1Cc1ccccc1]

The substantially same method as described in Preparation example 266 was conducted, except that (2R,3S)-methyl-3-benzyl-1,4-dioxaspiro[4.5]decane-2-carboxylate (Preparation example 267) was used instead of (2R,3S)-methyl 3-benzyl-1,4-dioxaspiro[4.4]nonane-2-carboxylate (Preparation example 265), to obtain the title compound (0.8 g, 70~95%).

¹H NMR (400 MHz, CDCl₃) δ 1.53~1.65 (m, 10H), 2.82 (dd, J=6.2, 13.8 Hz, 1H), 3.07 (dd, J=6.4, 13.6 Hz, 1H), 3.24~3.30 (m, 1H), 3.52~3.56 (m, 1H), 3.80~3.84 (m, 1H), 4.10~4.15 (m, 1H), 7.21~7.31 (m, 5H).

Preparation Example 269: (2S,3R)-methyl-2,3-dihydroxy-4-phenylbutanoate

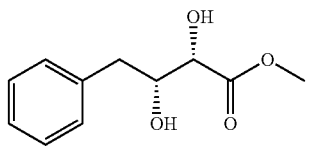

The substantially same method as described in Preparation example 242 was conducted, except that (E)-methyl-4-phenylbut-2-enoate (Preparation example 259) was used instead of (E)-tert-butyldimethyl(5-phenylpent-3-enyloxy)silane (Preparation example 237), to obtain the title compound (3.5 g, 70~95%).

¹H NMR (400 MHz, CDCl₃) δ 2.96 (ddd, J=7.3, 13.5, 17.1 Hz, 2H), 3.10 (d, J=5.2 Hz, 1H), 3.80 (s, 3H), 4.08 (dd, J=1.4, 5.4 Hz, 1H), 7.23~7.34 (m, 5H).

Preparation Example 270: (4S,5R)-methyl-5-benzyl-2,2-dimethyl-1,3-dioxolane-4-carboxylate

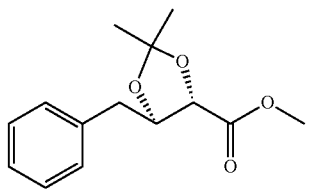 [SMILES: COC(=O)[C@H]1OC(C)(C)O[C@@H]1Cc1ccccc1]

The substantially same method as described in Preparation example 261 was conducted, except that (2S,3R)-methyl-2,3-dihydroxy-4-phenylbutanoate (Preparation example 269) was used instead of (2R,3S)-methyl 2,3-dihydroxy-4-phenylbutanoate (Preparation example 260), to obtain the title compound (3.4 g, 70~95%).

¹H NMR (400 MHz, CDCl₃) δ 1.41 (s, 6H), 1.79 (q, J=4.3 Hz, 1H), 2.83 (dd, J=6.2, 13.8 Hz, 1H), 3.07 (dd, J=6.4, 14.0 Hz, 1H), 3.29 (ddd, J=4.7, 7.5, 12.1 Hz, 1H), 3.54 (ddd, J=2.8, 5.2, 12.0 Hz, 1H), 3.83 (ddd, J=3.9, 3.9, 7.1 Hz, 1H), 4.15 (q, J=7.1 Hz, 1H), 7.22~7.32 (m, 5H).

Preparation Example 271: ((4R,5R)-5-benzyl-2,2-dimethyl-1,3-dioxolan-4-yl)methanol

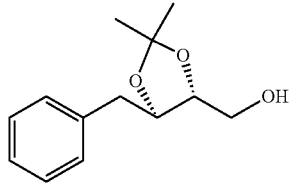 [SMILES: CC1(C)O[C@H](CO)[C@@H](Cc2ccccc2)O1]

The substantially same method as described in Preparation example 262 was conducted, except that (4S,5R)-methyl-5-benzyl-2,2-dimethyl-1,3-dioxolane-4-carboxylate (Preparation example 270) was used instead of (4R,5S)-methyl 5-benzyl-2,2-dimethyl-1,3-dioxolane-4-carboxylate (Preparation example 261), to obtain the title compound (2.7 g, 70~95%).

¹H NMR (400 MHz, CDCl₃) δ 1.41 (s, 6H), 1.79 (q, J=4.3 Hz, 1H), 2.83 (dd, J=6.2, 13.8 Hz, 1H), 3.07 (dd, J=6.4, 14.0 Hz, 1H), 3.29 (ddd, J=4.7, 7.5, 12.1 Hz, 1H), 3.54 (ddd, J=2.8, 5.2, 12.0 Hz, 1H), 3.83 (ddd, J=3.9, 3.9, 7.1 Hz, 1H), 4.15 (q, J=7.1 Hz, 1H), 7.22~7.32 (m, 5H).

Preparation Example 272: (4S,5R)-methyl-5-benzyl-2,2-diethyl-1,3-dioxolane-4-carboxylate

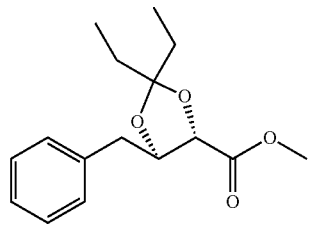 [SMILES: CCC1(CC)O[C@H](C(=O)OC)[C@@H](Cc2ccccc2)O1]

The substantially same method as described in Preparation example 263 was conducted, except that (2S,3R)-methyl-2,3-dihydroxy-4-phenylbutanoate (Preparation example 269) was used instead of (2,3-dihydroxy-4-phenylbutanoate (Preparation example 260), to obtain the title compound (1.5 g, 50~75%).

¹H NMR (400 MHz, CDCl₃) δ 0.85 (t, J=6.0 Hz, 3H), 0.92 (t, J=7.6 Hz, 3H), 1.66 (dq, J=7.6, 14.7 Hz, 4H), 3.01 (dd, J=6.6, 14.2 Hz, 1H), 3.10 (dd, J=4.4, 14.4 Hz, 1H), 3.71 (s, 3H), 4.17 (d, J=8.4 Hz, 1H), 4.32~4.37 (m, 1H), 7.23~7.32 (m, 5H).

Preparation Example 273: ((4R,5R)-5-benzyl-2,2-diethyl-1,3-dioxolan-4-yl)methanol

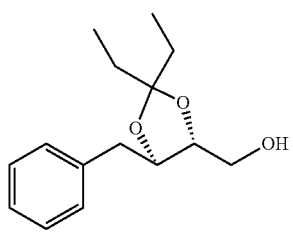 [SMILES: CCC1(CC)O[C@H](CO)[C@@H](Cc2ccccc2)O1]

The substantially same method as described in Preparation example 264 was conducted, except that (4S,5R)-methyl-5-benzyl-2,2-dimethyl-1,3-dioxolane-4-carboxylate (Preparation example 272) was used instead of (4R,5S)-methyl-5-benzyl-2,2-dimethyl-1,3-dioxolane-4-carboxylate (Preparation example 263), to obtain the title compound (1.2 g, 70~95%).

¹H NMR (400 MHz, CDCl₃) δ 0.91 (dt, J=1.9, 7.5 Hz, 6H), 1.61~1.68 (m, 4H), 1.77 (t, J=6.2 Hz, 1H), 2.81 (dd, J=6.4, 14.0 Hz, 1H), 3.09 (dd, J=6.2, 13.8 Hz, 1H), 3.24~3.30 (m, 1H), 3.49~3.54 (m, 1H), 3.78~3.82 (m, 1H), 4.08~4.13 (m, 1H), 7.21~7.32 (m, 5H).

Preparation Example 274: (2S,3R)-methyl-3-benzyl-1,4-dioxaspiro[4.4]nonane-2-carboxylate

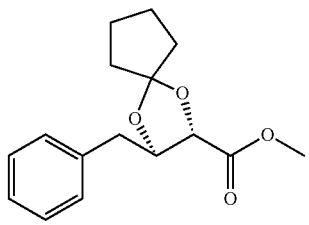 [SMILES: COC(=O)[C@H]1OC2(CCCC2)O[C@@H]1Cc1ccccc1]

The substantially same method as described in Preparation example 272 was conducted, except that cyclopentanone was used instead of 3-pentanone, to obtain the title compound (1.2 g, 60~85%).

¹H NMR (400 MHz, CDCl₃) δ 1.61~1.79 (m, 5H), 1.85~1.92 (m, 3H), 3.00~3.11 (m, 2H), 3.70 (s, 3H), 4.17 (d, J=7.2 Hz, 1H), 4.32 (dt, J=4.9, 7.0 Hz, 1H), 7.21~7.33 (m, 5H).

Preparation Example 275: ((2R,3R)-3-benzyl-1,4-dioxaspiro[4.4]nonane-2-yl)methanol

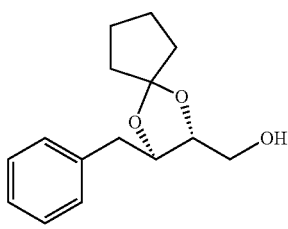 [SMILES: OC[C@H]1OC2(CCCC2)O[C@@H]1Cc1ccccc1]

The substantially same method as described in Preparation example 266 was conducted, except that (2S,3R)-methyl-3-benzyl-1,4-dioxaspiro[4.4]nonane-2-carboxylate (Preparation example 274) was used instead of (2R,3S)-methyl-3-benzyl-1,4-dioxaspiro[4.4]nonane-2-carboxylate (Preparation example 265), to obtain the title compound (1.1 g, 70~95%).

¹H NMR (400 MHz, CDCl₃) δ 1.57~1.88 (m, 8H), 2.82 (dd, J=6.6, 13.8 Hz, 1H), 3.08 (dd, J=6.4, 14.0 Hz, 1H), 3.27~3.33 (m, 1H), 3.47~3.52 (m, 1H), 3.79~3.83 (m, 1H), 4.07 (q, J=6.8 Hz, 1H), 7.21~7.32 (m, 5H).

Preparation Example 276: (2S,3R)-methyl-3-benzyl-1,4-dioxaspiro[4.5]decane-2-carboxylate

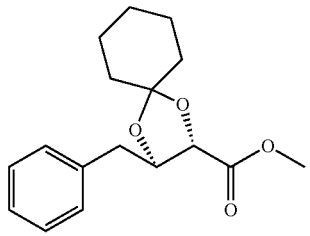 [SMILES: COC(=O)[C@H]1OC2(CCCCC2)O[C@@H]1Cc1ccccc1]

The substantially same method as described in Preparation example 274 was conducted, except that cyclohexanone was used instead of cyclopentanone, to obtain the title compound (1.4 g, 60~85%).

¹H NMR (400 MHz, CDCl₃) δ 1.54~1.74 (m, 10H), 2.99~3.12 (m, 2H), 3.70 (s, 3H), 4.18 (d, J=7.6 Hz, 1H), 4.36~4.41 (m, 1H), 7.21~7.32 (m, 5H).

Preparation Example 277: ((2R,3R)-3-benzyl-1,4-dioxaspiro[4.4]nonane-2-yl)methanol

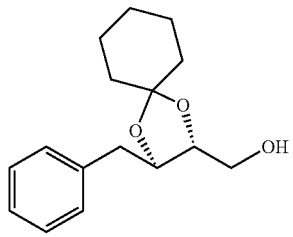 [SMILES: OC[C@H]1OC2(CCCCC2)O[C@@H]1Cc1ccccc1]

The substantially same method as described in Preparation example 268 was conducted, except that (2S,3R)-methyl-3-benzyl-1,4-dioxaspiro[4.5]decane-2-carboxylate (Preparation example 276) was used instead of (2R,3S)-methyl-3-benzyl-1,4-dioxaspiro[4.5]decane-2-carboxylate (Preparation example 267), to obtain the title compound (1.4 g, 70~95%).

¹H NMR (400 MHz, CDCl₃) δ 1.53~1.65 (m, 10H), 2.82 (dd, J=6.2, 13.8 Hz, 1H), 3.07 (dd, J=6.4, 13.6 Hz, 1H), 3.24~3.30 (m, 1H), 3.52~3.56 (m, 1H), 3.80~3.84 (m, 1H), 4.10~4.15 (m, 1H), 7.21~7.31 (m, 5H).

Preparation Example 278: (E)-4-phenylbut-3-enoic Acid

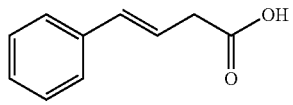 [SMILES: O=C(O)C/C=C/c1ccccc1]

To a stirred solution of 2-phenylacetaldehyde (5.0 g, 32.3 mmol) and malonic acid (4.0 g, 38.8 mmol) in pyridine (25.0 mL) was added a catalytic amount of piperidine (0.64 mL, 6.46 mmol) then heated to reflux. After 3 h, the resulting mixture was cooled to room temperature and concentrated under reduced pressure. The crude product was slowly added 2 N HCl. The white precipitate was filtered off and dried under vacuum to produce the title compound (3.5 g, 55~80%).

¹H NMR (400 MHz, CDCl₃) δ 3.39 (d, J=8.8 Hz, 2H), 6.31 (td, J=7.9, 14.8 Hz, 1H), 6.94 (d, J=16.0 Hz, 1H), 7.17~7.45 (m, 3H), 7.56~7.59 (m, 1H).

Preparation Example 279:
(E)-4-phenylbut-3-en-1-ol

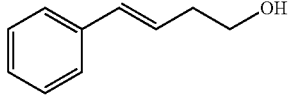 [SMILES: OCC/C=C/c1ccccc1]

To stirred solution of Zn(BH₄)₂ (40.0 mL, 20.0 mmol) in THF (40 mL) was added dropwise a solution (E)-4-phenyl-but-3-enoic acid (Preparation example 278, 2.0 g, 10.0 mmol) in THF (5 mL) at 0° C. then heated to reflux for 0.5 h. The reaction mixture was quenched with H₂O at 0° C. filtered through celite, washed with EtOAc, dried over anhydrous magnesium sulfate (MgSO₄), filtered and concentrated. The crude compound was purified by a silica gel column to produce the title compound (1.0 g, 50~75%).

¹H NMR (400 MHz, CDCl₃) δ 2.55 (ddd, J=4.1, 11.9, 21.5 Hz, 2H), 3.82 (t, J=5.8 Hz, 2H), 6.24 (td, J=7.2, 15.7 Hz, 1H), 6.87 (d, J=14.8 Hz, 1H), 7.12~7.25 (m, 3H), 7.36 (dd, J=1.2, 8.0 Hz, 1H), 7.52 (dd, J=1.6, 9.2 Hz, 1H).

Preparation Example 280: (E)-tert-butyldimethyl(4-phenylbut-3-enyloxy)silane

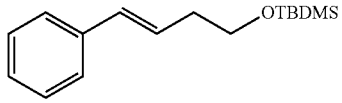 [SMILES: CC(C)(C)[Si](C)(C)OCC/C=C/c1ccccc1]

The substantially same method as described in Preparation example 237 was conducted, except that (E)-4-phenyl-but-3-en-1-ol (Preparation example 279) was used instead of (E)-5-phenylpent-3-en-1-ol (Preparation example 236), to obtain the title compound (1.7 g, 80~98%).

¹H NMR (400 MHz, CDCl₃) 00.07 (s, 3H), 0.10 (s, 3H), 0.92 (d, J=6.4 Hz, 9H), 2.51 (q, J=4.5 Hz, 2H), 3.78 (t, J=6.6 Hz, 2H), 6.26 (td, J=7.2, 15.7 Hz, 1H), 6.84 (d, J=15.6 Hz, 1H), 7.13~7.24 (m, 3H), 7.36 (dd, J=5.6, 12.4 Hz, 1H), 7.53 (dd, J=1.4, 7.8 Hz, 1H).

Preparation Example 281: (E)-4-phenylbut-3-enyl pivalate

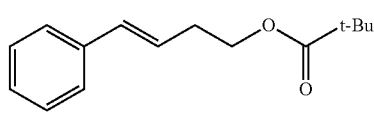 [SMILES: CC(C)(C)C(=O)OCC/C=C/c1ccccc1]

The substantially same method as described in Preparation example 238 was conducted, except that (E)-4-phenyl-but-3-en-1-ol (Preparation example 279) was used instead of (E)-5-phenylpent-3-en-1-ol (Preparation example 236), to obtain the title compound (10.8 g, 75~95%).

¹H NMR (400 MHz, CDCl₃) δ 1.22 (s, 9H), 2.57 (ddd, J=1.3, 6.7, 13.5 Hz, 2H), 4.22 (t, J=6.6 Hz, 2H), 6.19 (td, J=7.0, 16.0 Hz, 1H), 6.49 (d, J=16.0 Hz, 1H), 7.23~7.26 (m, 1H), 7.31~7.41 (m, 4H).

Preparation Example 282: (1R,2R)-4-(tert-butyldimethylsilyloxy)-1-phenylbutane-1,2-diol

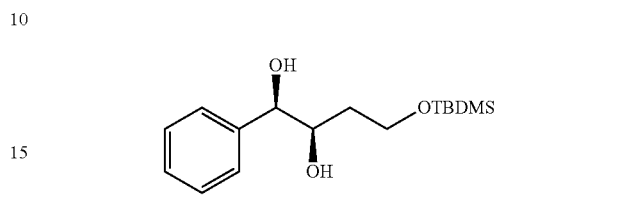

The substantially same method as described in Preparation example 239 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.8 g, 70~95%).

¹H NMR (400 MHz, CDCl₃) δ 0.10 (s, 3H), 0.11 (s, 3H), 0.92 (s, 9H), 1.69~1.70 (m, 1H), 1.93~2.07 (m, 1H), 3.51 (d, J=4.8 Hz, 1H), 3.86 (d, J=3.2 Hz, 1H), 3.87 (dd, J=3.2, 9.2 Hz, 1H), 3.91~3.96 (m, 1H), 4.01~4.06 (m, 1H), 5.05 (t, J=4.6 Hz, 1H), 7.22~7.26 (m, 1H), 7.31~7.37 (m, 2H), 7.59 (dd, J=1.2, 7.6 Hz, 1H).

Preparation Example 283:
(3R,4R)-3,4-dihydroxy-4-phenylbutyl pivalate

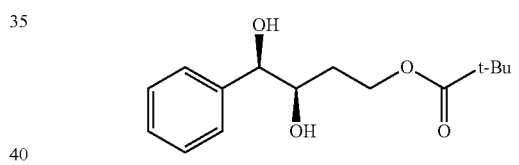

The substantially same method as described in Preparation example 282 was conducted, except that (E)-4-phenyl-but-3-enyl pivalate (Preparation example 281) was used instead of (E)-tert-butyldimethyl(4-phenylbut-3-enyloxy)silane (Preparation example 280), to obtain the title compound (8.7 g, 70~95%).

¹H NMR (400 MHz, CDCl₃) δ 1.18 (s, 9H), 1.65~1.74 (m, 2H), 2.83 (d, J=2.4 Hz, 1H), 2.96 (d, J=3.2 Hz, 1H), 3.74~3.79 (m, 1H), 4.10~4.17 (m, 1H), 4.33 (ddd, J=4.0, 7.2, 12.6 Hz, 1H), 4.49 (d, J=5.6 Hz, 1H), 7.31~7.41 (m, 5H).

Preparation Example 284: tert-butyl(2-((4R,5R)-5-phenyl-2,2-dimethyl-1,3-dioxolan-4-yl)ethoxy)dimethylsilane

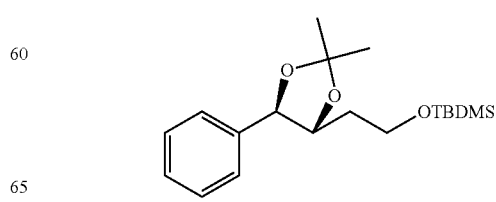

The substantially same method as described in Preparation example 218 was conducted, except that (1R,2R)-4-(tert-butyldimethylsilyloxy)-1-phenylbutane-1,2-diol (Preparation example 282) was used instead of (2R,3S)-methyl-3-phenyl-2,3-dihydroxypropanoate (Preparation example 217), to obtain the title compound (1.6 g, 70~95%).

¹H NMR (400 MHz, CDCl₃) δ 0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7 Hz, 1H), 5.16 (d, J=8.4 Hz, 1H), 7.21~7.27 (m, 1H), 7.31~7.38 (m, 2H), 7.60 (dd, J=1.6, 7.6 Hz, 1H).

Preparation Example 285: 2-((4R,5R)-5-phenyl-2,2-dimethyl-1,3-dioxolan-4-yl)ethanol

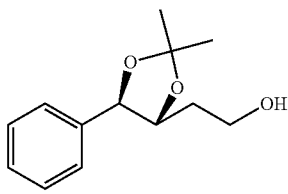 [SMILES: CC1(C)O[C@H](c2ccccc2)[C@@H](CCO)O1]

The substantially same method as described in Preparation example 244 was conducted, except that tertbutyl(2-((4R,5R)-5-phenyl-2,2-dimethyl-1,3-dioxolan-4-yl)ethoxy)dimethylsilane (Preparation example 284) was used instead of (2-((4R,5R)-5-benzyl-2,2-dimethyl-1,3-dioxolan-4-yl)ethoxy)(tert-butyl)dimethylsilane (Preparation example 243), to obtain the title compound (1.4 g, 80~95%).

¹H NMR (400 MHz, CDCl₃) δ 1.56 (s, 3H), 1.62 (s, 3H), 1.92~2.04 (m, 2H), 2.26 (q, J=3.7 Hz, 1H), 3.75~3.90 (m, 2H), 3.94 (td, J=3.9, 8.5 Hz, 1H), 5.23 (d, J=15.6 Hz, 1H), 7.22~7.27 (m, 1H), 7.33~7.39 (m, 2H), 7.62 (dd, J=1.6, 7.6 Hz, 1H).

Preparation Example 286: (1S,2S)-4-(tert-butyldimethylsilyloxy)-1-phenylbutane-1,2-diol

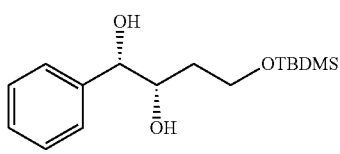 [SMILES: CC(C)(C)[Si](C)(C)OCC[C@H](O)[C@@H](O)c1ccccc1]

The substantially same method as described in Preparation example 242 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.7 g, 70~95%).

¹H NMR (400 MHz, CDCl₃) δ 0.10 (s, 3H), 0.11 (s, 3H), 0.92 (s, 9H), 1.69~1.70 (m, 1H), 1.93~2.07 (m, 1H), 3.51 (d, J=4.8 Hz, 1H), 3.86 (d, J=3.2 Hz, 1H), 3.87 (dd, J=3.2, 9.2 Hz, 1H), 3.91~3.96 (m, 1H), 4.01~4.06 (m, 1H), 5.05 (t, J=4.6 Hz, 1H), 7.22~7.26 (m, 1H), 7.31~7.37 (m, 2H), 7.59 (dd, J=1.2, 7.6 Hz, 1H).

Preparation Example 287: (3S,4S)-3,4-dihydroxy-4-phenylbutyl pivalate

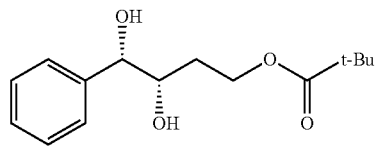 [SMILES: CC(C)(C)C(=O)OCC[C@H](O)[C@@H](O)c1ccccc1]

The substantially same method as described in Preparation example 286 was conducted, except that (E)-4-phenyl-but-3-enyl pivalate (Preparation example 281) was used instead of (E)-tert-butyldimethyl(4-phenylbut-3-enyloxy)silane (Preparation example 280), to obtain the title compound (10.4 g, 70~95%).

¹H NMR (400 MHz, CDCl₃) δ 1.18 (s, 9H), 1.65~1.74 (m, 2H), 2.83 (d, J=2.4 Hz, 1H), 2.96 (d, J=3.2 Hz, 1H), 3.74~3.79 (m, 1H), 4.10~4.17 (m, 1H), 4.33 (ddd, J=4.0, 7.2, 12.6 Hz, 1H), 4.49 (d, J=5.6 Hz, 1H), 7.31~7.41 (m, 5H).

Preparation Example 288: tert-butyl(2-((4S,5S)-5-phenyl-2,2-dimethyl-1,3-dioxolan-4-yl)ethoxy)dimethylsilane

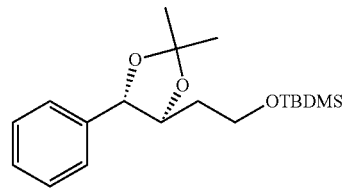 [SMILES: CC1(C)O[C@@H](CCO[Si](C)(C)C(C)(C)C)[C@H](c2ccccc2)O1]

The substantially same method as described in Preparation example 284 was conducted, except that (1S,2S)-4-(tert-butyldimethylsilyloxy)-1-phenylbutane-1,2-diol (Preparation example 286) was used instead of (1R,2R)-4-(tert-butyldimethylsilyloxy)-1-phenylbutane-1,2-diol (Preparation example 282), to obtain the title compound (0.7 g, 70~95%).

¹H NMR (400 MHz, CDCl₃) δ 0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7 Hz, 1H), 5.16 (d, J=8.4 Hz, 1H), 7.21~7.27 (m, 1H), 7.31~7.38 (m, 2H), 7.60 (dd, J=1.6, 7.6 Hz, 1H).

Preparation Example 289: 2-((4S,5S)-5-phenyl-2,2-dimethyl-1,3-dioxolan-4-yl)ethanol

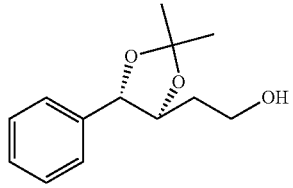 [SMILES: CC1(C)O[C@@H](CCO)[C@H](c2ccccc2)O1]

The substantially same method as described in Preparation example 285 was conducted, except that tertbutyl(2-

((4S,5S)-5-phenyl-2,2-dimethyl-1,3-dioxolan-4-yl)ethoxy)dimethylsilane (Preparation example 288) was used instead of that tertbutyl(2-((4R,5R)-5-phenyl-2,2-dimethyl-1,3-dioxolan-4-yl)ethoxy)dimethylsilane (Preparation example 284), to obtain the title compound (0.4 g, 80~95%).

¹H NMR (400 MHz, CDCl₃) δ 1.56 (s, 3H), 1.62 (s, 3H), 1.92~2.04 (m, 2H), 2.26 (q, J=3.7 Hz, 1H), 3.75~3.90 (m, 2H), 3.94 (td, J=3.9, 8.5 Hz, 1H), 5.23 (d, J=15.6 Hz, 1H), 7.22~7.27 (m, 1H), 7.33~7.39 (m, 2H), 7.62 (dd, J=1.6, 7.6 Hz, 1H).

Preparation Example 290: 2-((4R,5R)-2,2-diethyl-5-phenyl-1,3-dioxolan-4-yl)ethyl pivalate

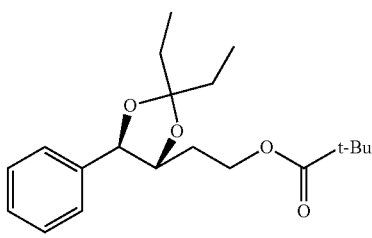 [SMILES: CCC1(CC)O[C@H](c2ccccc2)[C@@H](CCOC(=O)C(C)(C)C)O1]

The substantially same method as described in Preparation example 264 was conducted, except that (3R,4R)-3,4-dihydroxy-4-phenylbutyl pivalate (Preparation example 283) was used instead of (4R,5S)-methyl-5-benzyl-2,2-dimethyl-1,3-dioxolane-4-carboxylate (Preparation example 263), to obtain the title compound (1.8 g, 70~95%).

¹H NMR (400 MHz, CDCl₃) δ 1.00 (t, J=7.4 Hz, 3H), 1.08 (t, J=7.6 Hz, 3H), 1.14 (s, 9H), 1.76 (q, J=7.5 Hz, 2H), 1.81~1.89 (m, 2H), 1.91~1.98 (m, 2H), 3.87 (td, J=5.8, 8.8 Hz, 1H), 4.13~4.18 (m, 1H), 4.22~4.28 (m, 1H), 4.58 (d, J=8.8 Hz, 1H), 7.31~7.43 (m, 5H).

Preparation Example 291: 2-((4R,5R)-2,2-diethyl-5-phenyl-1,3-dioxolan-4-yl)ethyl pivalate

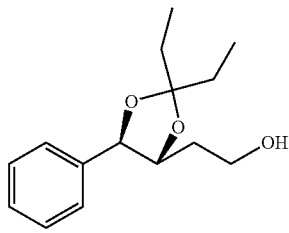 [SMILES: CCC1(CC)O[C@H](c2ccccc2)[C@@H](CCO)O1]

The substantially same method as described in Preparation example 258 was conducted, except that 2-((4R,5R)-2,2-diethyl-5-phenyl-1,3-dioxolan-4-yl)ethyl pivalate (Preparation example 290) was used instead of 2-((2R,3R)-3-benzyl-1,4-dioxaspiro[4.5]decan-2-yl)ethyl pivalate (Preparation example 257), to obtain the title compound (0.9 g, 80~95%).

¹H NMR (400 MHz, CDCl₃) δ 1.01 (t, J=7.4 Hz, 3H), 1.07 (t, J=7.6 Hz, 3H), 1.79 (q, J=7.5 Hz, 2H), 1.83~1.90 (m, 4H), 2.38 (q, J=3.7 Hz, 1H), 3.75~3.87 (m, 2H), 3.90~3.95 (m, 1H), 4.63 (d, J=8.8 Hz, 1H), 7.32~7.43 (m, 5H).

Preparation Example 292: 2-((2R,3R)-3-phenyl-1,4-dioxaspiro[4.4]nonan-2-yl)ethyl pivalate

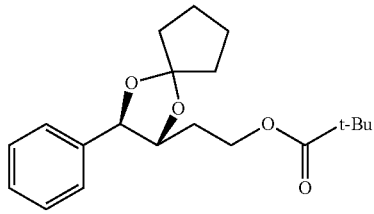 [SMILES: CC(C)(C)C(=O)OCC[C@H]1OC2(CCCC2)O[C@@H]1c1ccccc1]

The substantially same method as described in Preparation example 290 was conducted, except that cyclopentanone was used instead of 3-pentanone, to obtain the title compound (1.8 g, 60~85%).

¹H NMR (400 MHz, CDCl₃) δ 1.14 (s, 9H), 1.67~1.83 (m, 4H), 1.88~2.07 (m, 6H), 3.84 (td, J=6.0, 8.4 Hz, 1H), 4.13 (td, J=7.0, 11.1 Hz, 1H), 4.24 (td, J=6.4, 11.2 Hz, 1H), 4.55 (d, J=8.4 Hz, 1H), 7.31~7.39 (m, 5H).

Preparation Example 293: 2-((2R,3R)-3-phenyl-1,4-dioxaspiro[4.4]nonan-2-yl)ethanol

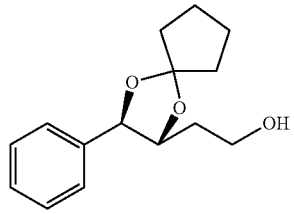 [SMILES: OCC[C@H]1OC2(CCCC2)O[C@@H]1c1ccccc1]

The substantially same method as described in Preparation example 291 was conducted, except that 2-((2R,3R)-3-phenyl-1,4-dioxaspiro[4.4]nonan-2-yl)ethyl pivalate (Preparation example 292) was used instead of that 2-((4S,5S)-2,2-diethyl-5-phenyl-1,3-dioxolan-4-yl)ethyl pivalate (Preparation example 290), to obtain the title compound (0.9 g, 80~95%).

¹H NMR (400 MHz, CDCl₃) δ 1.71~1.81 (m, 4H), 1.87~2.07 (m, 6H), 2.27 (q, J=3.7 Hz, 1H), 3.79~3.85 (m, 2H), 3.89~3.92 (m, 1H), 4.59 (d, J=8.4 Hz, 1H), 7.32~7.41 (m, 5H).

Preparation Example 294: 2-((2R,3R)-3-phenyl-1,4-dioxaspiro[4.5]decan-2-yl)ethyl pivalate

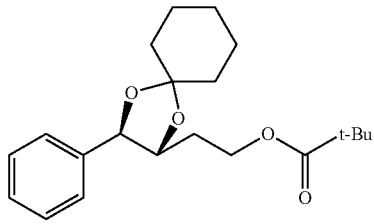 [SMILES: CC(C)(C)C(=O)OCC[C@H]1OC2(CCCCC2)O[C@@H]1c1ccccc1]

The substantially same method as described in Preparation example 292 was conducted, except that cyclohexanone was used instead of cyclopentanone, to obtain the title compound (2.0 g, 60~85%).

¹H NMR (400 MHz, CDCl₃) δ 1.14 (s, 9H), 1.67~1.83 (m, 4H), 1.88~2.07 (m, 6H), 3.84 (td, J=6.0, 8.4 Hz, 1H), 4.10~4.17 (m, 1H), 4.21~4.27 (m, 1H), 4.55 (d, J=8.4 Hz, 1H), 7.31~7.39 (m, 5H).

Preparation Example 295: 2-((2R,3R)-3-phenyl-1,4-dioxaspiro[4.5]decan-2-yl)ethanol

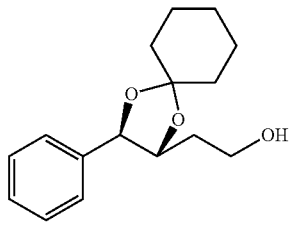 [SMILES: OCC[C@H]1OC2(CCCCC2)O[C@@H]1c1ccccc1]

The substantially same method as described in Preparation example 293 was conducted, except that 2-((2R,3R)-3-phenyl-1,4-dioxaspiro[4.5]decan-2-yl)ethyl pivalate (Preparation example 294) was used instead of that 2-((2R,3R)-3-phenyl-1,4-dioxaspiro[4.4]nonan-2-yl)ethyl pivalate (Preparation example 292), to obtain the title compound (1.2 g, 80~95%).

¹H NMR (400 MHz, CDCl₃) δ 1.71~1.83 (m, 4H), 1.87~2.05 (m, 6H), 2.27 (q, J=3.7 Hz, 1H), 3.79~3.85 (m, 2H), 3.86~3.91 (m, 1H), 4.59 (d, J=8.4 Hz, 1H), 7.32~7.41 (m, 5H).

Preparation Example 296: 2-((4S,5S)-2,2-diethyl-5-phenyl-1,3-dioxolan-4-yl)ethyl pivalate

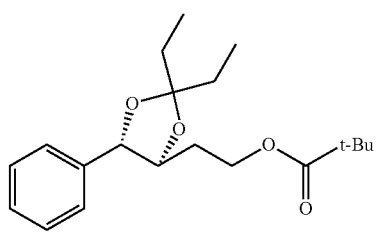 [SMILES: CCC1(CC)O[C@@H](CCOC(=O)C(C)(C)C)[C@H](c2ccccc2)O1]

The substantially same method as described in Preparation example 290 was conducted, except that (3S,4S)-3,4-dihydroxy-4-phenylbutyl pivalate (Preparation example 287) was used instead of (3R,4R)-3,4-dihydroxy-4-phenylbutyl pivalate (Preparation example 283), to obtain the title compound (2.2 g, 70~95%).

¹H NMR (400 MHz, CDCl₃) δ 1.00 (t, J=7.4 Hz, 3H), 1.08 (t, J=7.6 Hz, 3H), 1.14 (s, 9H), 1.76 (q, J=7.5 Hz, 2H), 1.81~1.89 (m, 2H), 1.91~1.98 (m, 2H), 3.87 (td, J=5.8, 8.8 Hz, 1H), 4.13~4.18 (m, 1H), 4.22~4.28 (m, 1H), 4.58 (d, J=8.8 Hz, 1H), 7.31~7.43 (m, 5H).

Preparation Example 297: 2-((4S,5S)-2,2-diethyl-5-phenyl-1,3-dioxolan-4-yl)ethyl pivalate

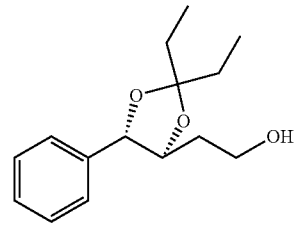 [SMILES: CCC1(CC)O[C@@H](CCO)[C@H](c2ccccc2)O1]

The substantially same method as described in Preparation example 295 was conducted, except 2-((4S,5S)-2,2-diethyl-5-phenyl-1,3-dioxolan-4-yl)ethyl pivalate (Preparation example 296) was used instead of 2-((2R,3R)-3-phenyl-1,4-dioxaspiro[4.5]decan-2-yl) ethyl pivalate (Preparation example 294), to obtain the title compound (0.7 g, 80~95%).

¹H NMR (400 MHz, CDCl₃) δ 1.01 (t, J=7.4 Hz, 3H), 1.07 (t, J=7.6 Hz, 3H), 1.79 (q, J=7.5 Hz, 2H), 1.83~1.90 (m, 4H), 2.38 (q, J=3.7 Hz, 1H), 3.75~3.87 (m, 2H), 3.90~3.95 (m, 1H), 4.63 (d, J=8.8 Hz, 1H), 7.32~7.43 (m, 5H).

Preparation Example 298: 2-((2S,3S)-3-phenyl-1,4-dioxaspiro[4.4]nonan-2-yl)ethyl pivalate

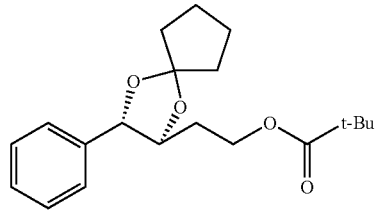 [SMILES: CC(C)(C)C(=O)OCC[C@@H]1OC2(CCCC2)O[C@H]1c1ccccc1]

The substantially same method as described in Preparation example 296 was conducted, except that cyclopentanone was used instead of 3-pentanone, to obtain the title compound (2.4 g, 60~85%).

¹H NMR (400 MHz, CDCl₃) δ 1.14 (s, 9H), 1.67~1.83 (m, 4H), 1.88~2.07 (m, 6H), 3.84 (td, J=6.0, 8.4 Hz, 1H), 4.13 (td, J=7.0, 11.1 Hz, 1H), 4.24 (td, J=6.4, 11.2 Hz, 1H), 4.55 (d, J=8.4 Hz, 1H), 7.31~7.39 (m, 5H).

Preparation Example 299: 2-((2S,3S)-3-phenyl-1,4-dioxaspiro[4.4]nonan-2-yl)ethanol

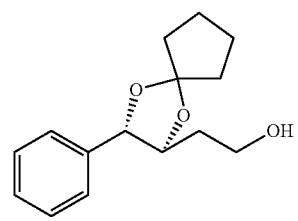 [SMILES: OCC[C@@H]1OC2(CCCC2)O[C@H]1c1ccccc1]

The substantially same method as described in Preparation example 297 was conducted, except that 2-((2S,3S)-3-phenyl-1,4-dioxaspiro[4.4]nonan-2-yl)ethyl pivalate (Preparation example 298) was used instead of that 2-((4S,5S)-2,2-diethyl-5-phenyl-1,3-dioxolan-4-yl)ethyl pivalate (Preparation example 296), to obtain the title compound (0.7 g, 80~95%).

¹H NMR (400 MHz, CDCl₃) δ 1.71~1.81 (m, 4H), 1.87~2.07 (m, 6H), 2.27 (q, J=3.7 Hz, 1H), 3.79~3.85 (m, 2H), 3.89~3.92 (m, 1H), 4.59 (d, J=8.4 Hz, 1H), 7.32~7.41 (m, 5H).

Preparation Example 300: 2-((2S,3S)-3-phenyl-1,4-dioxaspiro[4.5]decan-2-yl)ethyl pivalate

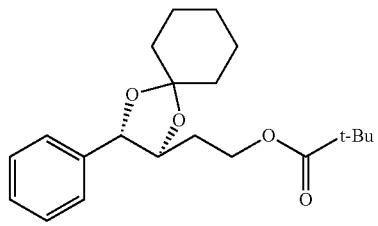 [SMILES: CC(C)(C)C(=O)OCC[C@@H]1OC2(CCCCC2)O[C@H]1c1ccccc1]

The substantially same method as described in Preparation example 298 was conducted, except that cyclohexanone was used instead of cyclopentanone, to obtain the title compound (2.4 g, 60~85%).

¹H NMR (400 MHz, CDCl₃) δ 1.14 (s, 9H), 1.67~1.83 (m, 4H), 1.88~2.07 (m, 6H), 3.84 (td, J=6.0, 8.4 Hz, 1H), 4.10~4.17 (m, 1H), 4.21~4.27 (m, 1H), 4.55 (d, J=8.4 Hz, 1H), 7.31~7.39 (m, 5H).

Preparation Example 301: 2-((2S,3S)-3-phenyl-1,4-dioxaspiro[4.5]decan-2-yl)ethanol

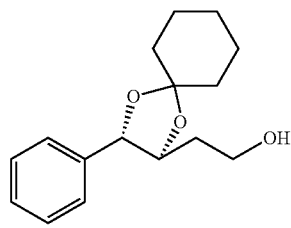 [SMILES: OCC[C@@H]1OC2(CCCCC2)O[C@H]1c1ccccc1]

The substantially same method as described in Preparation example 299 was conducted, except that 2-((2S,3S)-3-phenyl-1,4-dioxaspiro[4.5]decan-2-yl)ethyl pivalate (Preparation example 300) was used instead of that 2-((2S,3S)-3-phenyl-1,4-dioxaspiro[4.4]nonan-2-yl)ethyl pivalate (Preparation example 298), to obtain the title compound (1.2 g, 80~95%).

¹H NMR (400 MHz, CDCl₃) δ 1.71~1.83 (m, 4H), 1.87~2.05 (m, 6H), 2.27 (q, J=3.7 Hz, 1H), 3.79~3.85 (m, 2H), 3.86~3.91 (m, 1H), 4.59 (d, J=8.4 Hz, 1H), 7.32~7.41 (m, 5H).

Preparation Example 302: (E)-5-(2-chlorophenyl)pent-3-enoic acid

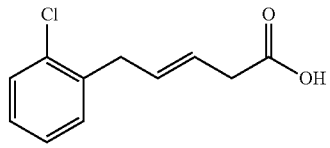 [SMILES: O=C(O)C/C=C/Cc1ccccc1Cl]

The substantially same method as described in Preparation example 235 was conducted, except that 3-(2-chlorophenyl)propanal was used instead of that hydrocinnamaldehyde (6.1 g, 70~90%).

¹H NMR (400 MHz, CDCl₃) δ 3.15 (dd, J=0.8, 6.8 Hz, 2H), 3.53 (d, J=6.4 Hz, 2H), 5.61~5.69 (m, 1H), 5.75~5.82 (m, 1H), 7.16~7.28 (m, 3H), 7.36~7.38 (m, 1H).

Preparation Example 303: (E)-5-(2-chlorophenyl)pent-3-en-1-ol

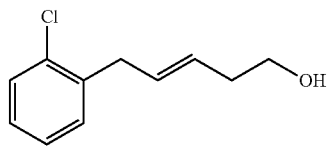 [SMILES: OCC/C=C/Cc1ccccc1Cl]

The substantially same method as described in Preparation example 236 was conducted, except that (E)-5-(2-chlorophenyl)pent-3-enoic acid (Preparation example 302) was used instead of that (E)-5-phenylpent-3-enoic acid (Preparation example 235), to obtain the title compound (4.6 g, 70~90%).

¹H NMR (400 MHz, CDCl₃) δ 2.33 (dq, J=1.0, 6.5 Hz, 2H), 3.50 (dd, J=1.8, 5.0 Hz, 2H), 3.67 (q, J=6.0 Hz, 2H), 5.45~5.53 (m, 1H), 5.70~5.77 (m, 1H), 7.15~7.37 (m, 4H).

Preparation Example 304: (E)-tert-butyl(5-(2-chlorophenyl)pent-3-enyloxy)dimethylsilane

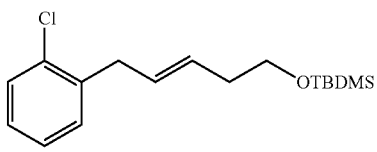 [SMILES: CC(C)(C)[Si](C)(C)OCC/C=C/Cc1ccccc1Cl]

The substantially same method as described in Preparation example 237 was conducted, except that (E)-5-(2-chlorophenyl)pent-3-en-1-ol (Preparation example 303) was used instead of that (E)-5-phenylpent-3-en-1-ol (Preparation example 236), to obtain the title compound (4.9 g, 75~95%).

¹H NMR (400 MHz, CDCl₃) δ 0.60 (s, 6H), 0.90 (s, 9H), 2.28 (dq, J=1.0, 6.7 Hz, 2H), 3.47 (d, J=6.4 Hz, 2H), 3.65 (t, J=6.8 Hz, 2H), 5.49~5.56 (m, 1H), 5.62~5.70 (m, 1H), 7.14~7.36 (m, 4H).

Preparation Example 305: (E)-5-(2-chlorophenyl)pent-3-enyl pivalate

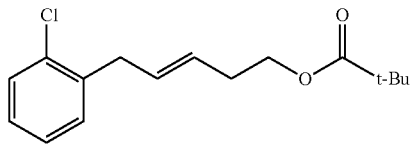 [SMILES: CC(C)(C)C(=O)OCC/C=C/Cc1ccccc1Cl]

The substantially same method as described in Preparation example 238 was conducted, except that (E)-5-(2-chlorophenyl)pent-3-en-1-ol (Preparation example 303) was used instead of that (E)-5-phenylpent-3-en-1-ol (Preparation example 236), to obtain the title compound (7.2 g, 75~95%).

$^1$H NMR (400 MHz, CDCl$_3$) δ 1.18 (s, 9H), 2.36 (q, J=6.7 Hz, 2H), 3.45 (d, J=6.4 Hz, 2H), 4.08 (t, J=6.6 Hz, 2H), 5.43~5.50 (m, 1H), 5.63~5.70 (m, 1H), 7.12~7.35 (m, 4H).

Preparation Example 306: (2S,3S)-5-(tert-butyldimethylsilyloxy)-1-(2-chlorophenyl)pentane-2,3-diol

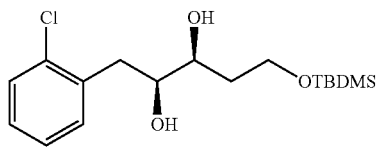 [SMILES: CC(C)(C)[Si](C)(C)OCC[C@H](O)[C@@H](O)Cc1ccccc1Cl]

The substantially same method as described in Preparation example 239 was conducted, except that (E)-tert-butyl (5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (2.8 g, 90%).

$^1$H NMR (400 MHz, CDCl$_3$) δ 0.11 (s, 6H), 0.92 (s, 9H), 1.68~1.77 (m, 1H), 1.87~1.96 (m, 1H), 2.64 (d, J=6.0 Hz, 1H), 2.93 (dd, J=8.2, 13.4 Hz, 1H), 3.07 (dd, J=4.8, 13.6 Hz, 1H), 3.68 (d, J=3.2 Hz, 1H), 3.76~3.96 (m, 4H), 7.17~7.25 (m, 2H), 7.35~7.39 (m, 2H).

Preparation Example 307: (2-(4S,5S)-5-(2chlorobenzyl)-2,2-dimethyl-1,3-dioxolan-4-yl)ethoxy)(tert-butyl)dimethylsilane

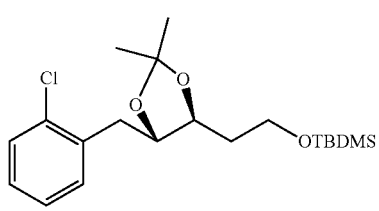 [SMILES: CC1(C)O[C@@H](CCO[Si](C)(C)C(C)(C)C)[C@H](Cc2ccccc2Cl)O1]

The substantially same method as described in Preparation example 240 was conducted, except that (2S,3S)-5-(tert-butyldimethylsilyloxy)-1-(2-chlorophenyl)pentane-2,3-diol (Preparation example 306) was used instead of that (2S,3S)-5-(tert-butyldimethylsilyloxy)-1-phenylpentane-2,3-diol (Preparation example 239), to obtain the title compound (3.6 g, 75~90%).

$^1$H NMR (400 MHz, CDCl$_3$) δ 0.06 (s, 6H), 0.91 (s, 9H), 1.39 (s, 3H), 1.40 (s, 3H), 1.69 (q, J=6.5 Hz, 2H), 3.05 (dq, J=5.8, 15.1 Hz, 2H), 3.70~3.80 (m, 2H), 3.86~3.93 (m, 1H), 3.97~4.02 (m, 1H), 7.17~7.25 (m, 2H), 7.36~7.38 (m, 2H).

Preparation Example 308: 2-((4S,5S)-5-(2-chlorobenzyl)-2,2-dimethyl-1,3-dioxolan-4-yl)ethanol

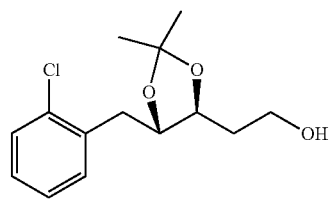 [SMILES: CC1(C)O[C@@H](CCO)[C@H](Cc2ccccc2Cl)O1]

The substantially same method as described in Preparation example 241 was conducted, except that (2-(4S,5S)-5-(2chlorobenzyl)-2,2-dimethyl-1,3-dioxolan-4-yl)ethoxy)(tert-butyl)dimethylsilane (Preparation example 307) was used instead of that (2-(4S,5S)-5-benzyl-2,2-dimethyl-1,3-dioxolan-4-yl)ethoxy)(tert-butyl) dimethylsilane (Preparation example 240), to obtain the title compound (3.2 g, 80~95%).

$^1$H NMR (400 MHz, CDCl$_3$) δ 1.38 (s, 3H), 1.40 (s, 3H), 1.50~1.63 (m, 2H), 2.29 (t, J=5.4 Hz, 1H), 2.82 (dd, J=5.8, 13.8 Hz, 1H), 3.01 (dd, J=6.4, 14.0 Hz, 1H), 3.72 (q, J=5.5 Hz, 2H), 3.86 (dt, J=3.2, 8.4 Hz, 1H), 3.92~3.97 (m, 1H), 7.17~7.25 (m, 2H), 7.36~7.38 (m, 2H).

Preparation Example 309: (2R,3R)-5-(tert-butyldimethylsilyloxy)-1-(2-chlorophenyl)pentane-2,3-diol

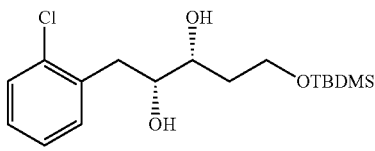 [SMILES: CC(C)(C)[Si](C)(C)OCC[C@@H](O)[C@H](O)Cc1ccccc1Cl]

The substantially same method as described in Preparation example 242 was conducted, except that (E)-tert-butyl (5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (4.4 g, 90%).

$^1$H NMR (400 MHz, CDCl$_3$) δ 0.11 (s, 6H), 0.92 (s, 9H), 1.68~1.77 (m, 1H), 1.87~1.96 (m, 1H), 2.64 (d, J=6.0 Hz, 1H), 2.93 (dd, J=8.2, 13.4 Hz, 1H), 3.07 (dd, J=4.8, 13.6 Hz, 1H), 3.68 (d, J=3.2 Hz, 1H), 3.76~3.96 (m, 4H), 7.17~7.25 (m, 2H), 7.35~7.39 (m, 2H).

Preparation Example 310: (2-(4R,5R)-5-(2chlorobenzyl)-2,2-dimethyl-1,3-dioxolan-4-yl)ethoxy)(tert-butyl)dimethyl silane

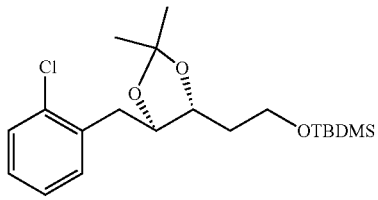 [SMILES: CC1(C)O[C@H](CCO[Si](C)(C)C(C)(C)C)[C@@H](Cc2ccccc2Cl)O1]

The substantially same method as described in Preparation example 307 was conducted, except that (2R,3R)-5-(tert-butyldimethylsilyloxy)-1-(2-chlorophenyl)pentane-2,3-diol (Preparation example 309) was used instead of (2S,3S)-5-(tert-butyldimethylsilyloxy)-1-(2-chlorophenyl)pentane-2,3-diol (Preparation example 306), to obtain the title compound (4.6 g, 70~95%).

$^1$H NMR (400 MHz, CDCl$_3$) δ 0.06 (s, 6H), 0.91 (s, 9H), 1.39 (s, 3H), 1.40 (s, 3H), 1.69 (q, J=6.5 Hz, 2H), 3.05 (dq, J=5.8, 15.1 Hz, 2H), 3.70~3.80 (m, 2H), 3.86~3.93 (m, 1H), 3.97~4.02 (m, 1H), 7.17~7.25 (m, 2H), 7.36~7.38 (m, 2H).

Preparation Example 311: 2-((4R,5R)-5-(2-chlorobenzyl)-2,2-dimethyl-1,3-dioxolan-4-yl)ethanol

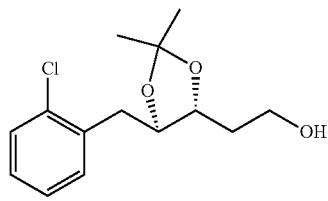 [SMILES: CC1(C)O[C@H](CCO)[C@@H](Cc2ccccc2Cl)O1]

The substantially same method as described in Preparation example 241 was conducted, except that (2-(4S,5S)-5-(2chlorobenzyl)-2,2-dimethyl-1,3-dioxolan-4-yl)ethoxy)(tert-butyl)dimethylsilane (Preparation example 307) was used instead of that (2-(4S,5S)-5-benzyl-2,2-dimethyl-1,3-dioxolan-4-yl)ethoxy)(tert-butyl)dimethylsilane (Preparation example 240), to obtain the title compound (3.0 g, 80~95%).

$^1$H NMR (400 MHz, CDCl$_3$) δ 1.38 (s, 3H), 1.40 (s, 3H), 1.50~1.63 (m, 2H), 2.29 (t, J=5.4 Hz, 1H), 2.82 (dd, J=5.8, 13.8 Hz, 1H), 3.01 (dd, J=6.4, 14.0 Hz, 1H), 3.72 (q, J=5.5 Hz, 2H), 3.86 (dt, J=3.2, 8.4 Hz, 1H), 3.92~3.97 (m, 1H), 7.17~7.25 (m, 2H), 7.36~7.38 (m, 2H).

Preparation Example 312: (3S,4S)-3,4-dihydroxy-5-(2chlorophenyl)pentyl pivalate

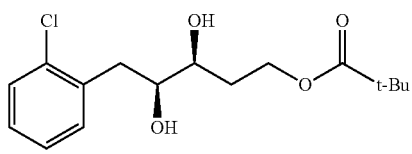 [SMILES: CC(C)(C)C(=O)OCC[C@H](O)[C@@H](O)Cc1ccccc1Cl]

The substantially same method as described in Preparation example 306 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (6.0 g, 70~95%).

$^1$H NMR (400 MHz, CDCl$_3$) δ 1.16 (s, 9H), 1.85~1.91 (m, 2H), 2.17 (d, J=6.0 Hz, 1H), 2.73 (d, J=5.2 Hz, 1H), 2.91 (dd, J=8.4, 13.6 Hz, 1H), 3.08 (dd, J=5.6, 13.6 Hz, 1H), 3.52~3.55 (m, 1H), 3.77~3.80 (m, 1H), 4.11~4.19 (m, 1H), 4.37~4.41 (m, 1H), 7.18~7.23 (m, 2H), 7.31 (dd. J=2.2, 7.0 Hz, 1H), 7.36 (dd, J=1.8, 7.4 Hz, 1H).

Preparation Example 313: 2-((4S,5S)-5-(2-chlorobenzyl)-2,2-diethyl-1,3-dioxolan-4-yl)ethyl pivalate

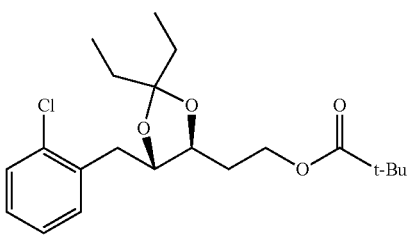 [SMILES: CCC1(CC)O[C@@H](CCOC(=O)C(C)(C)C)[C@H](Cc2ccccc2Cl)O1]

The substantially same method as described in Preparation example 246 was conducted, except that (3S,4S)-3,4-dihydroxy-5-(2chlorophenyl)pentyl pivalate (Preparation example 312) was used instead of (3S,4S)-3,4-dihydroxy-5-phenylpentyl pivalate (Preparation example 245), to obtain the title compound (1.7 g, 70~95%).

$^1$H NMR (400 MHz, CDCl$_3$) δ 0.90 (t, J=7.4 Hz, 6H), 1.21 (s, 9H), 1.58~1.66 (m, 4H), 1.70~1.77 (m, 2H), 3.06 (d, J=5.6 Hz, 2H), 3.81~3.86 (m, 1H), 3.94~3.99 (m, 1H), 4.15~4.25 (m, 2H), 7.18~7.24 (m, 2H), 7.36~7.38 (m, 2H).

Preparation Example 314: 2-((4S,5S)-5-(2-chlorobenzyl)-2,2-dimethyl-1,3-dioxolan-4-yl)ethanol

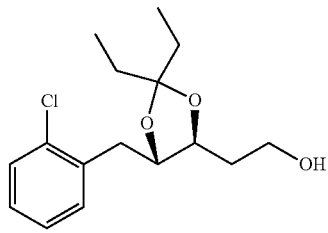 [SMILES: CCC1(CC)O[C@@H](CCO)[C@H](Cc2ccccc2Cl)O1]

The substantially same method as described in Preparation example 247 was conducted, except that 2-((4S,5S)-5-(2-chlorobenzyl)-2,2-diethyl-1,3-dioxolan-4-yl)ethyl pivalate (Preparation example 313) was used instead of 2-((4S,5S)-5-benzyl-2,2-diethyl-1,3-dioxolan-4-yl)ethyl pivalate (Preparation example 246), to obtain the title compound (0.9 g, 80~95%).

$^1$H NMR (400 MHz, CDCl$_3$) δ 0.91 (dt, J=2.5, 7.5 Hz, 6H), 1.46~1.79 (m, 6H), 2.42 (t, J=5.6 Hz, 1H), 3.01~3.12 (m, 2H), 3.79 (q, J=5.6 Hz, 2H), 3.88~3.93 (m, 1H), 3.98~4.06 (m, 1H), 7.18~7.25 (m, 2H), 7.35~7.39 (m, 2H).

Preparation Example 315: (3R,4R)-3,4-dihydroxy-5-(2-chlorophenyl)pentyl pivalate

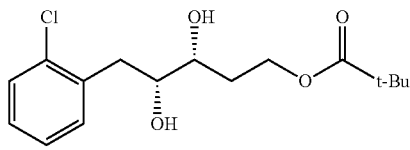 [SMILES: CC(C)(C)C(=O)OCC[C@@H](O)[C@H](O)Cc1ccccc1Cl]

The substantially same method as described in Preparation example 309 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (4.4 g, 70~95%).

$^1$H NMR (400 MHz, CDCl$_3$) δ 0.11 (s, 6H), 0.92 (s, 9H), 1.68~1.77 (m, 1H), 1.87~1.96 (m, 1H), 2.64 (d, J=6.0 Hz, 1H), 2.93 (dd, J=8.2, 13.4 Hz, 1H), 3.07 (dd, J=4.8, 13.6 Hz, 1H), 3.68 (d, J=3.2 Hz, 1H), 3.76~3.96 (m, 4H), 7.17~7.25 (m, 2H), 7.35~7.39 (m, 2H).

Preparation Example 316: 2-((4R, 5R)-5-(2-chlorobenzyl)-2,2-diethyl-1,3-dioxolan-4-yl)ethyl pivalate

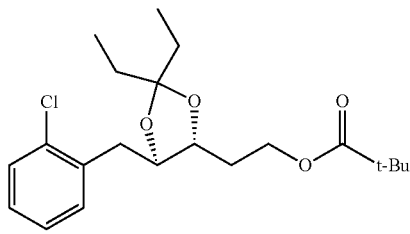 [SMILES: CCC1(CC)O[C@H](CCOC(=O)C(C)(C)C)[C@@H](Cc2ccccc2Cl)O1]

The substantially same method as described in Preparation example 313 was conducted, except that (3R,4R)-3,4-dihydroxy-5-(2chlorophenyl)pentyl pivalate (Preparation example 315) was used instead of (3S,4S)-3,4-dihydroxy-5-(2chlorophenyl)pentyl pivalate (Preparation example 312), to obtain the title compound (1.7 g, 70~95%).

$^1$H NMR (400 MHz, CDCl$_3$) δ 0.90 (t, J=7.4 Hz, 6H), 1.21 (s, 9H), 1.58~1.66 (m, 4H), 1.70~1.77 (m, 2H), 3.06 (d, J=5.6 Hz, 2H), 3.81~3.86 (m, 1H), 3.94~3.99 (m, 1H), 4.15~4.25 (m, 2H), 7.18~7.24 (m, 2H), 7.36~7.38 (m, 2H).

Preparation Example 317: 2-((4R,5R)-5-(2-chlorobenzyl)-2,2-dimethyl-1,3-dioxolan-4-yl)ethanol

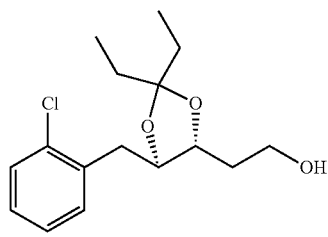 [SMILES: CCC1(CC)O[C@H](CCO)[C@@H](Cc2ccccc2Cl)O1]

The substantially same method as described in Preparation example 314 was conducted, except that 2-((4R,5R)-5-(2-chlorobenzyl)-2,2-diethyl-1,3-dioxolan-4-yl)ethyl pivalate (Preparation example 316) was used instead of 2-((4S, 5S)-5-(2-chlorobenzyl)-2,2-diethyl-1,3-dioxolan-4-yl)ethyl pivalate (Preparation example 313), to obtain the title compound (0.9 g, 80~95%).

$^1$H NMR (400 MHz, CDCl$_3$) δ 0.91 (dt, J=2.5, 7.5 Hz, 6H), 1.46~1.79 (m, 6H), 2.42 (t. J=5.6 Hz, 1H), 3.01~3.12 (m, 2H), 3.79 (q, J=5.6 Hz, 2H), 3.88~3.93 (m, 1H), 3.98~4.06 (m, 1H), 7.18~7.25 (m, 2H), 7.35~7.39 (m, 2H).

Preparation Example 318: 2-((2S,3S)-3-(2-chlorobenzyl)-1,4-dioxaspiro[4.4]nonan-2-yl)ethyl pivalate

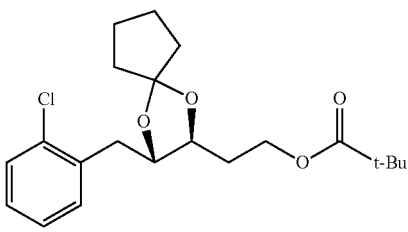 [SMILES: CC(C)(C)C(=O)OCC[C@@H]1OC2(CCCC2)O[C@H]1Cc1ccccc1Cl]

The substantially same method as described in Preparation example 313 was conducted, except that cyclopentanone was used instead of 3-pentanone, to obtain the title compound (1.2 g, 60~85%).

$^1$H NMR (400 MHz, CDCl$_3$) δ 1.21 (s, 9H), 1.64~1.74 (m, 5H), 1.75~1.88 (m, 5H), 3.03~3.11 (m, 2H), 3.81~3.86 (m, 1H), 3.97 (q, J=6.5 Hz, 1H), 4.12~4.22 (m, 2H), 7.18~7.25 (m, 2H), 7.34~7.39 (m, 2H).

Preparation Example 319: 2-((2S,3S)-3-(2-chlorobenzyl)-1,4-dioxaspiro[4.4]nonan-2-yl)ethanol

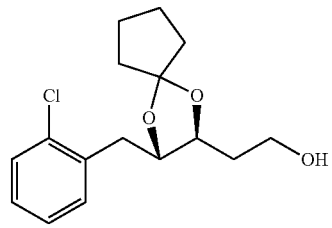 [SMILES: OCC[C@@H]1OC2(CCCC2)O[C@H]1Cc1ccccc1Cl]

The substantially same method as described in Preparation example 317 was conducted, except that 2-((2S,3S)-3-(2-chlorobenzyl)-1,4-dioxaspiro[4.4]nonan-2-yl)ethyl pivalate (Preparation example 318) was used instead of 2-((4R, 5R)-5-(2-chlorobenzyl)-2,2-diethyl-1,3-dioxolan-4-yl)ethyl pivalate (Preparation example 316), to obtain the title compound (0.7 g, 80~95%).

$^1$H NMR (400 MHz, CDCl$_3$) δ 1.62~1.74 (m, 6H), 1.75~1.88 (m, 4H), 2.28 (t, J=5.6 Hz, 1H), 3.03~3.12 (m, 2H), 3.78 (q, J=5.6 Hz, 1H), 3.88~3.95 (m, 1H), 3.97~4.06 (m, 1H), 7.18~7.26 (m, 2H), 7.34~7.39 (m, 2H).

Preparation Example 320: 2-((2R,3R)-3-(2-chlorobenzyl)-1,4-dioxaspiro[4.4]nonan-2-yl)ethyl pivalate

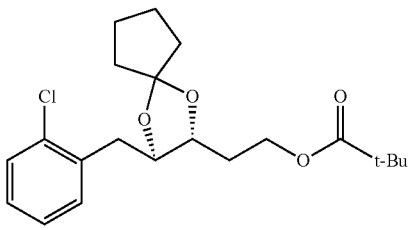 [SMILES: CC(C)(C)C(=O)OCC[C@H]1OC2(CCCC2)O[C@@H]1Cc1ccccc1Cl]

The substantially same method as described in Preparation example 316 was conducted, except that cyclopentanone was used instead of 3-pentanone, to obtain the title compound (1.4 g, 60~85%).

$^1$H NMR (400 MHz, CDCl$_3$) δ 1.21 (s, 9H), 1.64~1.74 (m, 5H), 1.75~1.88 (m, 5H), 3.03~3.11 (m, 2H), 3.81~3.86 (m, 1H), 3.97 (q, J=6.5 Hz, 1H), 4.12~4.22 (m, 2H), 7.18~7.25 (m, 2H), 7.34~7.39 (m, 2H).

Preparation Example 321: 2-((2R,3R)-3-(2-chlorobenzyl)-1,4-dioxaspiro[4.4]nonan-2-yl)ethanol

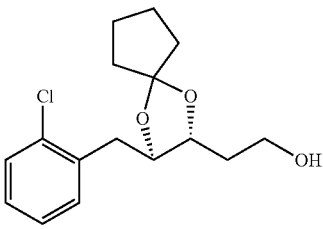 [SMILES: OCC[C@H]1OC2(CCCC2)O[C@@H]1Cc1ccccc1Cl]

The substantially same method as described in Preparation example 319 was conducted, except that 2-((2R,3R)-3-(2-chlorobenzyl)-1,4-dioxaspiro[4.4]nonan-2-yl)ethyl pivalate (Preparation example 320) was used instead of 2-((2S,3S)-3-(2-chlorobenzyl)-1,4-dioxaspiro[4.4]nonan-2-yl) ethyl pivalate (Preparation example 318), to obtain the title compound (0.8 g, 80~95%).

$^1$H NMR (400 MHz, CDCl$_3$) δ 1.62~1.74 (m, 6H), 1.75~1.88 (m, 4H), 2.28 (t, J=5.6 Hz, 1H), 3.03~3.12 (m, 2H), 3.78 (q, J=5.6 Hz, 1H), 3.88~3.95 (m, 1H), 3.97~4.06 (m, 1H), 7.18~7.26 (m, 2H), 7.34~7.39 (m, 2H).

Preparation Example 322: 2-((2S,3S)-3-(2-chlorobenzyl)-1,4-dioxaspiro[4.5]decan-2-yl)ethyl pivalate

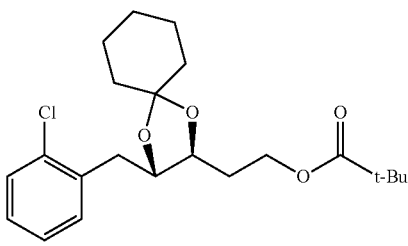 [SMILES: CC(C)(C)C(=O)OCC[C@@H]1OC2(CCCCC2)O[C@H]1Cc1ccccc1Cl]

The substantially same method as described in Preparation example 318 was conducted, except that cyclohexanone was used instead of cyclopentanone, to obtain the title compound (1.1 g, 60~85%).

$^1$H NMR (400 MHz, CDCl$_3$) δ 1.21 (s, 9H), 1.58~1.61 (m, 8H), 1.77 (q, J=6.8 Hz, 2H), 3.07 (d, J=6.0 Hz, 2H), 3.81~3.88 (m, 1H), 3.96~4.01 (m, 1H), 4.16~4.22 (m, 2H), 7.17~7.25 (m, 2H), 7.36~7.39 (m, 2H).

Preparation Example 323: 2-((2S,3S)-3-(2-chlorobenzyl)-1,4-dioxaspiro[4.5]decan-2-yl)ethanol

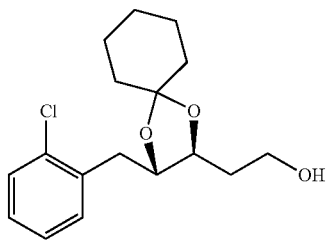 [SMILES: OCC[C@@H]1OC2(CCCCC2)O[C@H]1Cc1ccccc1Cl]

The substantially same method as described in Preparation example 321 was conducted, except that 2-((2S,3S)-3-(2-chlorobenzyl)-1,4-dioxaspiro[4.5]decan-2-yl)ethyl pivalate (Preparation example 322) was used instead of 2-((2R,3R)-3-(2-chlorobenzyl)-1,4-dioxaspiro[4.4]nonan-2-yl) ethyl pivalate (Preparation example 320), to obtain the title compound (0.7 g, 80~95%).

$^1$H NMR (400 MHz, CDCl$_3$) δ 1.51~1.64 (m, 8H), 1.65~1.74 (m, 2H), 2.59~2.63 (m, 1H), 3.06 (d, J=6.0 Hz, 2H), 3.76~3.78 (m, 2H), 3.89~3.94 (m, 1H), 3.99~4.04 (m, 1H), 7.16~7.24 (m, 2H), 7.35~7.38 (m, 2H).

Preparation Example 324: 2-((2R,3R)-3-(2-chlorobenzyl)-1,4-dioxaspiro[4.5]decan-2-yl)ethyl pivalate

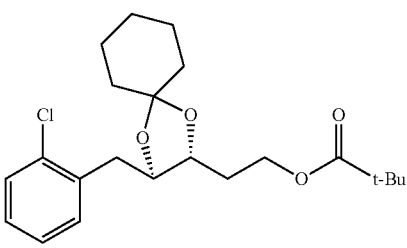 [SMILES: CC(C)(C)C(=O)OCC[C@H]1OC2(CCCCC2)O[C@@H]1Cc1ccccc1Cl]

The substantially same method as described in Preparation example 320 was conducted, except that cyclohexanone was used instead of cyclopentanone, to obtain the title compound (1.5 g, 60~85%).

$^1$H NMR (400 MHz, CDCl$_3$) δ 1.21 (s, 9H), 1.58~1.61 (m, 8H), 1.77 (q, J=6.8 Hz, 2H), 3.07 (d, J=6.0 Hz, 2H), 3.81~3.88 (m, 1H), 3.96~4.01 (m, 1H), 4.16~4.22 (m, 2H), 7.17~7.25 (m, 2H), 7.36~7.39 (m, 2H).

Preparation Example 325: 2-((2R,3R)-3-(2-chlorobenzyl)-1,4-dioxaspiro[4.5]decan-2-yl)ethanol

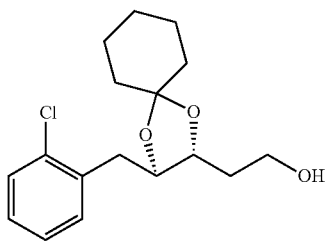 [SMILES: OCC[C@H]1OC2(CCCCC2)O[C@@H]1Cc1ccccc1Cl]

The substantially same method as described in Preparation example 323 was conducted, except that 2-((2R,3R)-3-(2-chlorobenzyl)-1,4-dioxaspiro[4.5]decan-2-yl)ethyl pivalate (Preparation example 324) was used instead of 2-((2S,3S)-3-(2-chlorobenzyl)-1,4-dioxaspiro[4.5]decan-2-yl)ethyl pivalate (Preparation example 322), to obtain the title compound (0.9 g, 80~95%).

$^1$H NMR (400 MHz, CDCl$_3$) δ 1.51~1.64 (m, 8H), 1.65~1.74 (m, 2H), 2.59~2.63 (m, 1H), 3.06 (d, J=6.0 Hz, 2H), 3.76~3.78 (m, 2H), 3.89~3.94 (m, 1H), 3.99~4.04 (m, 1H), 7.16~7.24 (m, 2H), 7.35~7.38 (m, 2H).

Preparation Example 326: (E)-methyl-4-(2-chlorophenyl)but-2-enoate

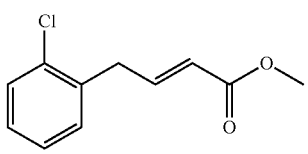

The substantially same method as described in Preparation example 259 was conducted, except that 2-chlorophenyl acetaldehyde was used instead of phenyl acetaldehyde, to obtain the title compound (5.0 g, 65~85%).

$^1$H NMR (400 MHz, CDCl$_3$) δ 3.47 (d, J=6.8 Hz, 2H), 3.67 (s, 3H), 5.79 (d, J=15.4 Hz, 1H), 7.06 (dt, J=6.8, 15.4 Hz, 1H), 7.12~7.28 (m, 4H).

Preparation Example 327: (2R,3S)-methyl-4-(2chlorophenyl)-2,3-dihydroxybutanoate

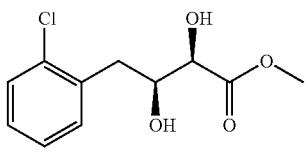 [SMILES: COC(=O)[C@H](O)[C@@H](O)Cc1ccccc1Cl]

The substantially same method as described in Preparation example 260 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.0 g, 70~95%).

$^1$H NMR (400 MHz, CDCl$_3$) δ 3.08~3.17 (m, 2H), 3.84 (s, 3H), 4.12 (dd. J=1.6, 5.2 Hz, 1H), 4.28~4.34 (m, 1H), 7.20~7.27 (m, 2H), 7.33~7.36 (m, 1H), 7.39~7.41 (m, 1H).

Preparation Example 328: (4R,5S)-methyl-5-(2-chlorobenzyl)-2,2-dimethyl-1,3-dioxolane-4-carboxylate

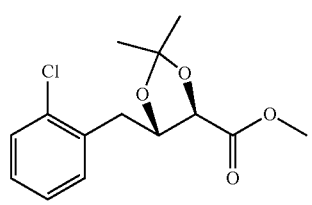 [SMILES: COC(=O)[C@@H]1OC(C)(C)O[C@H]1Cc1ccccc1Cl]

The substantially same method as described in Preparation example 261 was conducted, except that (2R,3S)-methyl-4-(2chlorophenyl)-2,3-dihydroxybutanoate (Preparation example 327) was used instead of (2R,3S)-methyl 2,3-dihydroxy-4-phenylbutanoate (Preparation example 260), to obtain the title compound (0.6 g, 70~95%).

$^1$H NMR (400 MHz, CDCl$_3$) δ 1.45 (s, 3H), 1.49 (s, 3H), 3.11 (dd, J=7.6, 14.4 Hz, 1H), 3.35 (dd, J=4.4, 14.4 Hz, 1H), 3.74 (s, 3H), 4.30 (d, J=7.6 Hz, 1H), 4.50 (dt, J=4.0, 7.6 Hz, 1H), 7.19~7.26 (m, 2H), 7.36~7.40 (m, 2H).

Preparation Example 329: ((4S,5S)-5-(2-chlorobenzyl)-2,2-dimethyl-1,3-dioxolan-4-yl)methanol

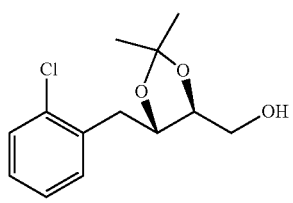 [SMILES: CC1(C)O[C@@H](CO)[C@H](Cc2ccccc2Cl)O1]

The substantially same method as described in Preparation example 262 was conducted, except that (4R,5S)-methyl-5-(2-chlorobenzyl)-2,2-dimethyl-1,3-dioxolane-4-carboxylate (Preparation example 328) was used instead of (4R,5S)-methyl 5-benzyl-2,2-dimethyl-1,3-dioxolane-4-carboxylate (Preparation example 261), to obtain the title compound (0.5 g, 70~95%).

$^1$H NMR (400 MHz, CDCl$_3$) δ 1.43 (s, 6H), 1.83 (q, J=4.3 Hz, 1H), 3.06~3.17 (m, 2H), 3.45 (ddd, J=4.6, 7.4, 12.0 Hz, 1H), 3.68 (ddd, J=3.2, 5.2, 12.0 Hz, 1H), 3.91 (ddd, J=3.3, 4.7, 8.0 Hz, 1H), 4.22~4.27 (m, 1H), 7.20~7.26 (m, 2H), 7.35~7.40 (m, 2H).

Preparation Example 330: (4R,5S)-methyl-5-(2-chlorobenzyl)-2,2-diethyl-1,3-dioxolane-4-carboxylate

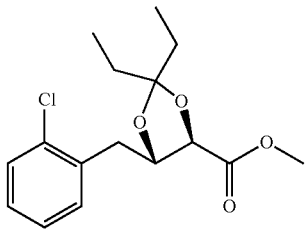 [SMILES: CCC1(CC)O[C@@H](Cc2ccccc2Cl)[C@H](C(=O)OC)O1]

The substantially same method as described in Preparation example 263 was conducted, except that (2R,3S)-methyl-4-(2chlorophenyl)-2,3-dihydroxybutanoate (Preparation example 327) was used instead of (2R,3S)-methyl 2,3-dihydroxy-4-phenylbutanoate (Preparation example 260), to obtain the title compound (0.8 g, 50~75%).
$^1$H NMR (400 MHz, CDCl$_3$) δ 0.93 (t, J=7.4 Hz, 6H), 1.67~1.74 (m, 4H), 3.10 (dd. J=8.0, 14.4 Hz, 1H), 3.35 (dd, J=4.0, 14.4 Hz, 1H), 3.73 (s, 3H), 4.27 (d, J=8.4 Hz, 1H), 4.42~4.47 (m, 1H), 7.18~7.26 (m, 2H), 7.37~7.40 (m, 2H).

Preparation Example 331: ((4S,5S)-5-(2-chlorobenzyl)-2,2-diethyl-1,3-dioxolan-4-yl)methanol

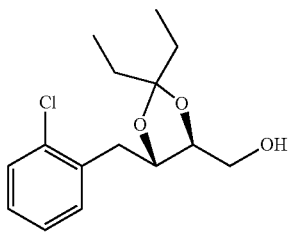 [SMILES: CCC1(CC)O[C@@H](CO)[C@H](Cc2ccccc2Cl)O1]

The substantially same method as described in Preparation example 329 was conducted, except that (4R,5S)-methyl-5-(2-chlorobenzyl)-2,2-dimethyl-1,3-dioxolane-4-carboxylate (Preparation example 330) was used instead of (4R,5S)-methyl-5-(2-chlorobenzyl)-2,2-dimethyl-1,3-dioxolane-4-carboxylate (Preparation example 328), to obtain the title compound (0.6 g, 70~95%).
$^1$H NMR (400 MHz, CDCl$_3$) δ 0.93 (dt, J=2.1, 7.5 Hz, 6H), 1.62~1.70 (m, 4H), 1.83 (q, J=4.3 Hz, 1H), 3.11 (ddd, J=6.0, 14.2, 28.0 Hz, 2H), 3.44 (ddd, J=4.8, 7.2, 12.0 Hz, 1H), 3.64~3.69 (m, 1H), 3.88 (ddd, J=3.3, 4.9, 8.3 Hz, 1H), 4.18~4.24 (m, 1H), 7.19~7.26 (m, 2H), 7.36~7.39 (m, 2H).

Preparation Example 332: (2R,3S)-methyl-3-(2-chlorobenzyl)-1,4-dioxaspiro[4.4]nonane-2-carboxylate

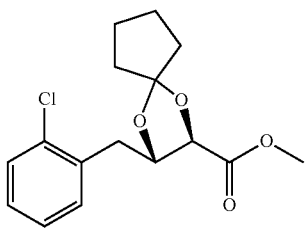 [SMILES: COC(=O)[C@@H]1OC2(CCCC2)O[C@H]1Cc1ccccc1Cl]

The substantially same method as described in Preparation example 330 was conducted, except that cyclopentanone was used instead of 3-pentanone, to obtain the title compound (0.8 g, 60~85%).
$^1$H NMR (400 MHz, CDCl$_3$) δ 1.65~1.80 (m, 5H), 1.89~2.00 (m, 3H), 3.13 (dd, J=7.8, 14.2 Hz, 1H), 3.32 (dd, J=4.6, 14.2 Hz, 1H), 3.72 (s, 3H), 4.28 (d, J=7.2 Hz, 1H), 4.41~4.46 (m, 1H), 7.19~7.26 (m, 2H), 7.35~7.40 (m, 2H).

Preparation Example 333: ((2S,3S)-3-(-2chlorobenzyl)-1,4-dioxaspiro[4.4]nonan-2-yl)methanol

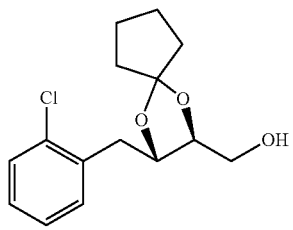 [SMILES: OC[C@@H]1OC2(CCCC2)O[C@H]1Cc1ccccc1Cl]

The substantially same method as described in Preparation example 331 was conducted, except that (2R,3S)-methyl-3-(2-chlorobenzyl)-1,4-dioxaspiro[4.4]nonane-2-carboxylate (Preparation example 332) was used instead of (4R,5S)-methyl-5-(2-chlorobenzyl)-2,2-dimethyl-1,3-dioxolane-4-carboxylate (Preparation example 330), to obtain the title compound (0.6 g, 70~95%).
$^1$H NMR (400 MHz, CDCl$_3$) δ 1.69~1.74 (m, 3H), 1.77~1.85 (m, 5H), 3.11 (ddd, J=6.3, 14.1, 31.3 Hz, 2H), 3.42~3.48 (m, 1H), 3.61~3.66 (m, 1H), 3.87~3.91 (m, 1H), 4.19 (q, J=6.8 Hz, 1H), 7.19~7.26 (m, 2H), 7.34~7.40 (m, 2H).

Preparation Example 334: (2R,3S)-methyl-3-(2-chlorobenzyl)-1,4-dioxaspiro[4.5]decane-2-carboxylate

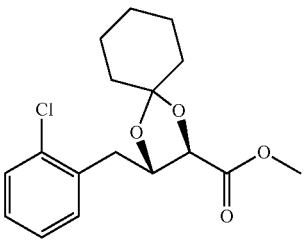 [SMILES: COC(=O)[C@@H]1OC2(CCCCC2)O[C@H]1Cc1ccccc1Cl]

The substantially same method as described in Preparation example 332 was conducted, except that cyclohexanone was used instead of cyclopentanone, to obtain the title compound (0.5 g, 60~85%).
$^1$H NMR (400 MHz, CDCl$_3$) δ 1.54~1.77 (m, 10H), 3.12 (dd. J=7.6, 14.4 Hz, 1H), 3.32 (dd, J=4.4, 14.4 Hz, 1H), 3.72 (s, 3H), 4.30 (d, J=7.6 Hz, 1H), 4.46~4.51 (m, 1H), 7.18~7.26 (m, 2H), 7.37~7.39 (m, 2H).

Preparation Example 335: ((2S,3S)-3-(-2chlorobenzyl)-1,4-dioxaspiro[4.5]decan-2-yl)methanol

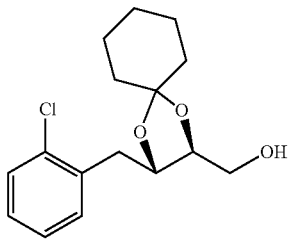 [SMILES: OC[C@@H]1OC2(CCCCC2)O[C@H]1Cc1ccccc1Cl]

The substantially same method as described in Preparation example 333 was conducted, except that (2R,3S)-methyl-3-(2-chlorobenzyl)-1,4-dioxaspiro[4.5]decane-2-carboxylate (Preparation example 334) was used instead of (2R,3S)-methyl-3-(2-chlorobenzyl)-1,4-dioxaspiro[4.4]nonane-2-carboxylate (Preparation example 332), to obtain the title compound (0.5 g, 70~95%).

$^1$H NMR (400 MHz, CDCl$_3$) δ 1.38~1.45 (m, 2H), 1.58~1.63 (m, 8H), 1.84 (q, J=4.3 Hz, 1H), 3.11 (ddd, J=7.9, 15.9, 22.1 Hz, 2H), 3.43 (ddd, J=4.6, 7.6, 12.1 Hz, 1H), 3.66~3.71 (m, 1H), 3.88~3.92 (m, 1H), 4.21~4.26 (m, 1H), 7.18~7.26 (m, 2H), 7.37~7.39 (m, 2H).

Preparation Example 336: (2S,3R)-methyl-4-(2chlorophenyl)-2,3-dihydroxybutanoate

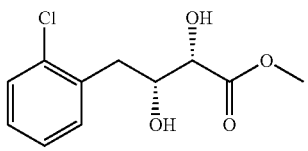 [SMILES: COC(=O)[C@@H](O)[C@H](O)Cc1ccccc1Cl]

The substantially same method as described in Preparation example 269 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.5 g, 70~95%).

$^1$H NMR (400 MHz, CDCl$_3$) δ 3.08~3.17 (m, 2H), 3.84 (s, 3H), 4.12 (dd, J=1.6, 5.2 Hz, 1H), 4.28~4.34 (m, 1H), 7.20~7.27 (m, 2H), 7.33~7.36 (m, 1H), 7.39~7.41 (m, 1H).

Preparation Example 337: (4S,5R)-methyl-5-(2-chlorobenzyl)-2,2-dimethyl-1,3-dioxolane-4-carboxylate

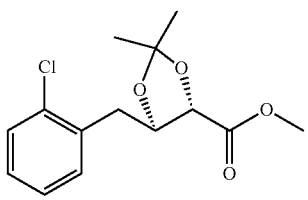 [SMILES: COC(=O)[C@H]1OC(C)(C)O[C@@H]1Cc1ccccc1Cl]

The substantially same method as described in Preparation example 328 was conducted, except that (2S,3R)-methyl-4-(2chlorophenyl)-2,3-dihydroxybutanoate (Preparation example 336) was used instead of (2R,3S)-methyl-4-(2chlorophenyl)-2,3-dihydroxybutanoate (Preparation example 327), to obtain the title compound (3.4 g, 70~95%).

$^1$H NMR (400 MHz, CDCl$_3$) δ 1.41 (s, 6H), 1.79 (q, J=4.3 Hz, 1H), 2.83 (dd, J=6.2, 13.8 Hz, 1H), 3.07 (dd, J=6.4, 14.0 Hz, 1H), 3.29 (ddd, J=4.7, 7.5, 12.1 Hz, 1H), 3.54 (ddd, J=2.8, 5.2, 12.0 Hz, 1H), 3.83 (ddd, J=3.9, 3.9, 7.1 Hz, 1H), 4.15 (q. J=7.1 Hz, 1H), 7.22~7.32 (m, 5H).

Preparation Example 338: ((4R,5R)-5-(-2chlorobenzyl)-2,2-dimethyl-1,3-dioxolan-4-yl)methanol

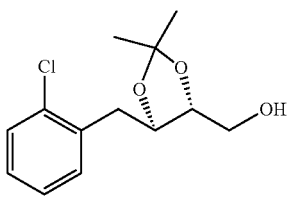 [SMILES: CC1(C)O[C@H](CO)[C@@H](Cc2ccccc2Cl)O1]

The substantially same method as described in Preparation example 335 was conducted, except that (4S,5R)-methyl-5-(2-chlorbenzyl)-2,2-dimethyl-1,3-dioxolane-4-carboxylate (Preparation example 337) was used instead of (2R,3S)-methyl-3-(2-chlorobenzyl)-1,4-dioxaspiro[4.5]decane-2-carboxylate (Preparation example 334), to obtain the title compound (2.7 g, 70~95%).

$^1$H NMR (400 MHz, CDCl$_3$) δ 1.41 (s, 6H), 1.79 (q, J=4.3 Hz, 1H), 2.83 (dd, J=6.2, 13.8 Hz, 1H), 3.07 (dd, J=6.4, 14.0 Hz, 1H), 3.29 (ddd, J=4.7, 7.5, 12.1 Hz, 1H), 3.54 (ddd, J=2.8, 5.2, 12.0 Hz, 1H), 3.83 (ddd, J=3.9, 3.9, 7.1 Hz, 1H), 4.15 (q, J=7.1 Hz, 1H), 7.22~7.32 (m, 5H).

Preparation Example 339: (4S,5R)-methyl-(5~2-chloro)benzyl-2,2-diethyl-1,3-dioxolane-4-carboxylate

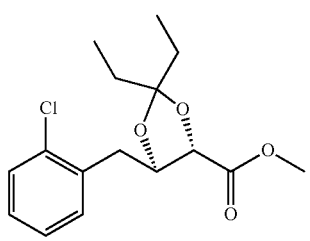 [SMILES: CCC1(CC)O[C@H](C(=O)OC)[C@@H](Cc2ccccc2Cl)O1]

The substantially same method as described in Preparation example 330 was conducted, except that (2S,3R)-methyl-2,3-dihydroxy-4-phenylbutanoate (Preparation example 336) was used instead of that (2R,3S)-methyl-4-(2chlorophenyl)-2,3-dihydroxybutanoate (Preparation example 327), to obtain the title compound (0.6 g, 50~75%).

$^1$H NMR (400 MHz, CDCl$_3$) δ 0.93 (t, J=7.4 Hz, 6H), 1.67~1.74 (m, 4H), 3.10 (dd, J=8.0, 14.4 Hz, 1H), 3.35 (dd, J=4.0, 14.4 Hz, 1H), 3.73 (s, 3H), 4.27 (d, J=8.4 Hz, 1H), 4.42~4.47 (m, 1H), 7.18~7.26 (m, 2H), 7.37~7.40 (m, 2H).

Preparation Example 340: ((4R,5R)-5-(2-chlorobenzyl)-2,2-diethyl-1,3-dioxolan-4-yl)methanol

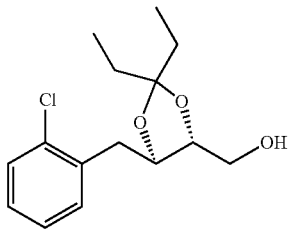 [SMILES: CCC1(CC)O[C@H](CO)[C@@H](Cc2ccccc2Cl)O1]

The substantially same method as described in Preparation example 338 was conducted, except that (4S,5R)-methyl-(5~2-chloro)benzyl-2,2-diethyl-1,3-dioxolane-4-carboxylate (Preparation example 339) was used instead of (4S,5R)-methyl-5-(2-chlorobenzyl)-2,2-dimethyl-1,3-dioxolane-4-carboxylate (Preparation example 337), to obtain the title compound (0.5 g, 70~95%).

$^1$H NMR (400 MHz, CDCl$_3$) δ 0.93 (dt, J=2.1, 7.5 Hz, 6H), 1.62~1.70 (m, 4H), 1.83 (q, J=4.3 Hz, 1H), 3.11 (ddd, J=6.0, 14.2, 28.0 Hz, 2H), 3.44 (ddd, J=4.8, 7.2, 12.0 Hz, 1H), 3.64~3.69 (m, 1H), 3.88 (ddd, J=3.3, 4.9, 8.3 Hz, 1H), 4.18~4.24 (m, 1H), 7.19~7.26 (m, 2H), 7.36~7.39 (m, 2H).

Preparation Example 341: (2S,3R)-methyl-3-(2-chlorobenzyl)-1,4-dioxaspiro[4.4]nonane-2-carboxylate

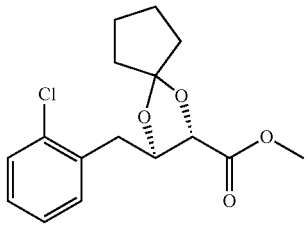 [SMILES: COC(=O)[C@H]1OC2(CCCC2)O[C@@H]1Cc1ccccc1Cl]

The substantially same method as described in Preparation example 339 was conducted, except that cyclopentanone was used instead of 3-pentanone, to obtain the title compound (0.5 g, 60~85%).

$^1$H NMR (400 MHz, CDCl$_3$) δ 1.65~1.80 (m, 5H), 1.89~2.00 (m, 3H), 3.13 (dd, J=7.8, 14.2 Hz, 1H), 3.32 (dd, J=4.6, 14.2 Hz, 1H), 3.72 (s, 3H), 4.28 (d, J=7.2 Hz, 1H), 4.41~4.46 (m, 1H), 7.19~7.26 (m, 2H), 7.35~7.40 (m, 2H).

Preparation Example 342: ((2R,3R)-3-(2-chlorobenzyl)-1,4-dioxaspiro[4.4]nonan-2-yl)methanol

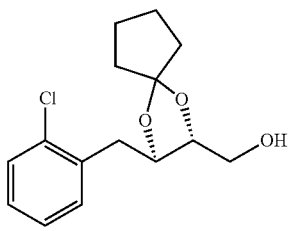 [SMILES: OC[C@H]1OC2(CCCC2)O[C@@H]1Cc1ccccc1Cl]

The substantially same method as described in Preparation example 340 was conducted, except that (2S,3R)-methyl-3-(2-chlorobenzyl)-1,4-dioxaspiro[4.4]nonane-2-carboxylate (Preparation example 341) was used instead of that (4S,5R)-methyl-(5~2-chloro)benzyl-2,2-diethyl-1,3-dioxolane-4-carboxylate (Preparation example 339), to obtain the title compound (0.4 g, 70~95%).

$^1$H NMR (400 MHz, CDCl$_3$) δ 1.69~1.74 (m, 3H), 1.77~1.85 (m, 5H), 3.11 (ddd, J=6.3, 14.1, 31.3 Hz, 2H), 3.42~3.48 (m, 1H), 3.61~3.66 (m, 1H), 3.87~3.91 (m, 1H), 4.19 (q, J=6.8 Hz, 1H), 7.19~7.26 (m, 2H), 7.34~7.40 (m, 2H).

Preparation Example 343: (2S,3R)-methyl-3-(2-chlorobenzyl)-1,4-dioxaspiro[4.5]decane-2-carboxylate

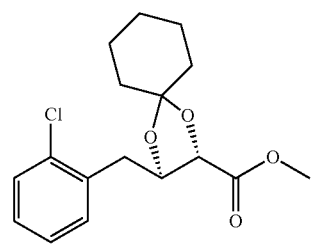 [SMILES: COC(=O)[C@H]1OC2(CCCCC2)O[C@@H]1Cc1ccccc1Cl]

The substantially same method as described in Preparation example 341 was conducted, except that cyclohexanone was used instead of cyclopentanone, to obtain the title compound (0.9 g, 60~85%).

$^1$H NMR (400 MHz, CDCl$_3$) δ 1.54~1.77 (m, 10H), 3.12 (dd. J=7.6, 14.4 Hz, 1H), 3.32 (dd, J=4.4, 14.4 Hz, 1H), 3.72 (s, 3H), 4.30 (d, J=7.6 Hz, 1H), 4.46~4.51 (m, 1H), 7.18~7.26 (m, 2H), 7.37~7.39 (m, 2H).

Preparation Example 344: ((2R,3R)-3-(2-chlorobenzyl)-1,4-dioxaspiro[4.5]decan-2-yl)methanol

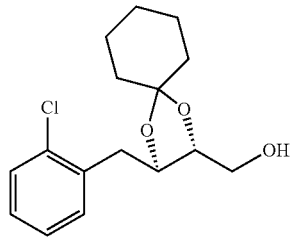 [SMILES: OC[C@H]1OC2(CCCCC2)O[C@@H]1Cc1ccccc1Cl]

The substantially same method as described in Preparation example 342 was conducted, except that (2S,3R)-methyl-3-(2-chlorobenzyl)-1,4-dioxaspiro[4.5]decane-2-carboxylate (Preparation example 343) was used instead of (2S,3R)-methyl-3-(2-chlorobenzyl)-1,4-dioxaspiro[4.4]nonane-2-carboxylate (Preparation example 341), to obtain the title compound (0.7 g, 70~95%).

$^1$H NMR (400 MHz, CDCl$_3$) δ 1.38~1.45 (m, 2H), 1.58~1.63 (m, 8H), 1.84 (q, J=4.3 Hz, 1H), 3.11 (ddd, J=7.9, 15.9, 22.1 Hz, 2H), 3.43 (ddd, J=4.6, 7.6, 12.1 Hz, 1H), 3.66~3.71 (m, 1H), 3.88~3.92 (m, 1H), 4.21~4.26 (m, 1H), 7.18~7.26 (m, 2H), 7.37~7.39 (m, 2H).

Preparation Example 345: (E)-4-(2chlorophenyl)but-3-enoic Acid

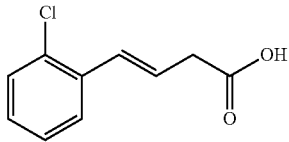 [SMILES: O=C(O)C/C=C/c1ccccc1Cl]

The substantially same method as described in Preparation example 278 was conducted, except that 2-(2-chlorophenyl)acetaldehyde was used instead of phenylacetaldehyde, to obtain the title compound (4.0 g, 55~80%).

$^1$H NMR (400 MHz, CDCl$_3$) δ 3.39 (d, J=8.8 Hz, 2H), 6.31 (td, J=7.9, 14.8 Hz, 1H), 6.94 (d, J=16.0 Hz, 1H), 7.17~7.45 (m, 3H), 7.56~7.59 (m, 1H).

Preparation Example 346: (E)-4-(2-chlorophenyl)but-3-en-1-ol

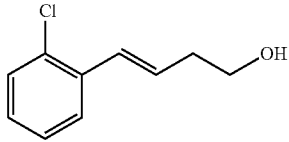 [SMILES: OCC/C=C/c1ccccc1Cl]

The substantially same method as described in Preparation example 279 was conducted, except that (E)-4-(2chlorophenyl)but-3-enoic acid (Preparation example 345) was used instead of (E)-4-phenylbut-3-enoic acid (Preparation example 278), to obtain the title compound (1.2 g, 55~80%).

$^1$H NMR (400 MHz, CDCl$_3$) δ 2.55 (ddd, J=4.1, 11.9, 21.5 Hz, 2H), 3.82 (t, J=5.8 Hz, 2H), 6.24 (td, J=7.2, 15.7 Hz, 1H), 6.87 (d, J=14.8 Hz, 1H), 7.12~7.25 (m, 3H), 7.36 (dd, J=1.2, 8.0 Hz, 1H), 7.52 (dd, J=1.6, 9.2 Hz, 1H).

Preparation Example 347: (E)-tert-butyldimethyl(4-(2-chlorophenyl)but-3-enyloxy)silane

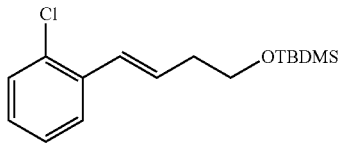 [SMILES: CC(C)(C)[Si](C)(C)OCC/C=C/c1ccccc1Cl]

The substantially same method as described in Preparation example 280 was conducted, except that (E)-4-(2-chlorophenyl)but-3-en-1-ol (Preparation example 346) was used instead of (E)-4-phenylbut-3-en-1-ol (Preparation example 279), to obtain the title compound (1.1 g, 80~98%).

$^1$H NMR (400 MHz, CDCl$_3$) δ 0.07 (s, 3H), 0.10 (s, 3H), 0.92 (d, J=6.4 Hz, 9H), 2.51 (q, J=4.5 Hz, 2H), 3.78 (t, J=6.6 Hz, 2H), 6.26 (td, J=7.2, 15.7 Hz, 1H), 6.84 (d, J=15.6 Hz, 1H), 7.13~7.24 (m, 3H), 7.36 (dd, J=5.6, 12.4 Hz, 1H), 7.53 (dd, J=1.4, 7.8 Hz, 1H).

Preparation Example 348: (E)-4-(2-chlorophenyl)but-3-enyl pivalate

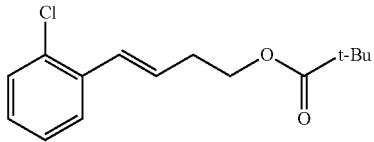 [SMILES: CC(C)(C)C(=O)OCC/C=C/c1ccccc1Cl]

The substantially same method as described in Preparation example 281 was conducted, except that (E)-4-(2-chlorophenyl)but-3-en-1-ol (Preparation example 346) was used instead of (E)-4-phenylbut-3-en-1-ol (Preparation example 279), to obtain the title compound (3.5 g, 75~95%).

$^1$H NMR (400 MHz, CDCl$_3$) δ 1.21 (s, 9H), 2.55~2.64 (m, 2H), 4.24 (t, J=6.4 Hz, 2H), 6.18 (td, J=7.9, 14.8 Hz, 1H), 6.86 (d, J=16.0 Hz, 1H), 7.22~7.26 (m, 2H), 7.38 (dd, J=3.6, 10.8 Hz, 1H), 7.51 (dd, J=1.6, 7.6 Hz, 1H).

Preparation Example 349: (1R,2R)-4-(tert-butyldimethylsilyloxy)-1-(2-chlorophenyl)butane-1,2-diol

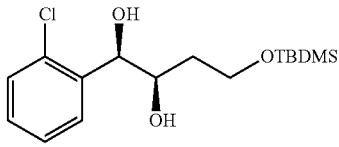 [SMILES: CC(C)(C)[Si](C)(C)OCC[C@@H](O)[C@H](O)c1ccccc1Cl]

The substantially same method as described in Preparation example 282 was conducted, except that (E)-tert-butyldimethyl(4~2-chlorophenyl)but-3-enyloxy)silane (Preparation example 347) was used instead of (E)-tert-butyldimethyl (5-phenylpent-3-enyloxy)silane (Preparation example 237), to obtain the title compound (0.7 g, 70~95%).

$^1$H NMR (400 MHz, CDCl$_3$) δ 0.10 (s, 3H), 0.11 (s, 3H), 0.92 (s, 9H), 1.69~1.70 (m, 1H), 1.93~2.07 (m, 1H), 3.51 (d, J=4.8 Hz, 1H), 3.86 (d, J=3.2 Hz, 1H), 3.87 (dd. J=3.2, 9.2 Hz, 1H), 3.91~3.96 (m, 1H), 4.01~4.06 (m, 1H), 5.05 (t, J=4.6 Hz, 1H), 7.22~7.26 (m, 1H), 7.31~7.37 (m, 2H), 7.59 (dd, J=1.2, 7.6 Hz, 1H).

Preparation Example 350: (3R,4R)-3,4-dihydroxy-4-(2-chlorophenyl)butyl pivalate

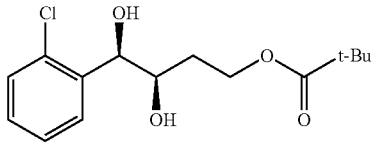 [SMILES: CC(C)(C)C(=O)OCC[C@@H](O)[C@H](O)c1ccccc1Cl]

The substantially same method as described in Preparation example 349 was conducted, except that (E)-4-(2-chlorophenyl)but-3-enyl pivalate (Preparation example 348) was used instead of (E)-tert-butyldimethyl(4~2-chlorophenyl)but-3-enyloxy)silane (Preparation example 347), to obtain the title compound (3.2 g, 70~95%).

$^1$H NMR (400 MHz, CDCl$_3$) δ 1.19 (s, 9H), 1.76~1.84 (m, 1H), 1.90~1.98 (m, 1H), 2.70 (d, J=4.4 Hz, 1H), 2.86 (d,

Preparation Example 351: tert-butyl(2-((4R,5R)-5-(2-chlorophenyl)-2,2-dimethyl-1,3-dioxolan-4-yl)ethoxy)dimethylsilane

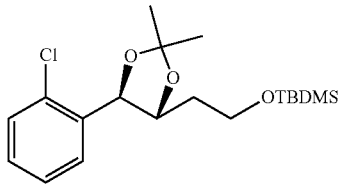 [SMILES: CC1(C)O[C@H](c2ccccc2Cl)[C@@H](CCO[Si](C)(C)C(C)(C)C)O1]

The substantially same method as described in Preparation example 284 was conducted, except that (1R,2R)-4-(tert-butyldimethylsilyloxy)-1-(2-chlorophenyl)butane-1,2-diol (Preparation example 349) was used instead of (1R,2R)-4-(tert-butyldimethylsilyloxy)-1-phenylbutane-1,2-diol (Preparation example 282), to obtain the title compound (0.8 g, 70~95%).

$^1$H NMR (400 MHz, CDCl$_3$) δ 0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7 Hz, 1H), 5.16 (d, J=8.4 Hz, 1H), 7.21~7.27 (m, 1H), 7.31~7.38 (m, 2H), 7.60 (dd, J=1.6, 7.6 Hz, 1H).

Preparation Example 352: 2-((4R,5R)-5-(2-chlorophenyl)-2,2-dimethyl-1,3-dioxolan-4-yl)ethanol

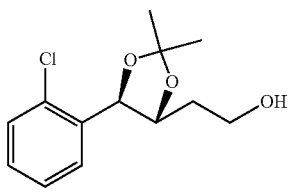 [SMILES: CC1(C)O[C@H](c2ccccc2Cl)[C@@H](CCO)O1]

The substantially same method as described in Preparation example 285 was conducted, except tert-butyl(2-((4R,5R)-5-(2-chlorophenyl)-2,2-dimethyl-1,3-dioxolan-4-yl)ethoxy)dimethylsilane (Preparation example 351) was used instead of tertbutyl(2-((4R,5R)-5-phenyl-2,2-dimethyl-1,3-dioxolan-4-yl)ethoxy)dimethylsilane (Preparation example 284), to obtain the title compound (0.7 g, 80~95%).

$^1$H NMR (400 MHz, CDCl$_3$) δ 1.56 (s, 3H), 1.62 (s, 3H), 1.92~2.04 (m, 2H), 2.26 (q, J=3.7 Hz, 1H), 3.75~3.90 (m, 2H), 3.94 (td, J=3.9, 8.5 Hz, 1H), 5.23 (d, J=15.6 Hz, 1H), 7.22~7.27 (m, 1H), 7.33~7.39 (m, 2H), 7.62 (dd, J=1.6, 7.6 Hz, 1H).

Preparation Example 353: (1S,2S)-4-(tert-butyldimethylsilyloxy)-1-(2-chlorophenyl)butane-1,2-diol

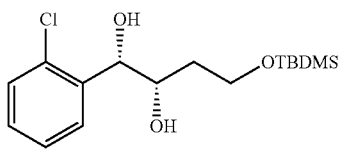 [SMILES: CC(C)(C)[Si](C)(C)OCC[C@H](O)[C@@H](O)c1ccccc1Cl]

The substantially same method as described in Preparation example 286 was conducted, except that (E)-tert-butyldimethyl(4-(2-chlorophenyl)but-3-enyloxy)silane (Preparation example 347) was used instead of (E)-tert-butyldimethyl(4-phenylbut-3-enyloxy)silane (Preparation example 280), to obtain the title compound (0.7 g, 70~95%).

$^1$H NMR (400 MHz, CDCl$_3$) δ 1.19 (s, 9H), 1.76~1.84 (m, 1H), 1.90~1.98 (m, 1H), 2.70 (d, J=4.4 Hz, 1H), 2.86 (d, J=5.2 Hz, 1H), 3.84~3.90 (m, 1H), 4.14~4.21 (m, 1H), 4.35~4.41 (m, 1H), 5.05 (t, J=5.0 Hz, 1H), 7.23~7.39 (m, 3H), 7.54 (dd, J=1.6, 7.6 Hz, 1H).

Preparation Example 354: (3S,4S)-3,4-dihydroxy-4-(2-chlorophenyl)butyl pivalate

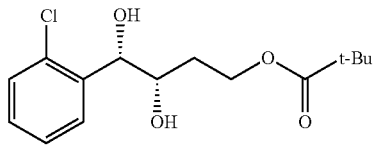 [SMILES: CC(C)(C)C(=O)OCC[C@H](O)[C@@H](O)c1ccccc1Cl]

The substantially same method as described in Preparation example 353 was conducted, except that (E)-4-(2-chlorophenyl)but-3-enyl pivalate (Preparation example 348) was used instead of ((E)-tert-butyldimethyl(4-(2-chlorophenyl)but-3-enyloxy)silane (Preparation example 347), to obtain the title compound (3.0 g, 70~95%).

$^1$H NMR (400 MHz, CDCl$_3$) δ 1.19 (s, 9H), 1.76~1.84 (m, 1H), 1.90~1.98 (m, 1H), 2.70 (d, J=4.4 Hz, 1H), 2.86 (d, J=5.2 Hz, 1H), 3.84~3.90 (m, 1H), 4.14~4.21 (m, 1H), 4.35~4.41 (m, 1H), 5.05 (t, J=5.0 Hz, 1H), 7.23~7.39 (m, 3H), 7.54 (dd, J=1.6, 7.6 Hz, 1H).

Preparation Example 355: tert-butyl(2-((4S,5S)-5-(2-chlorophenyl)-2,2-dimethyl-1,3-dioxolan-4-yl)ethoxy)dimethylsilane

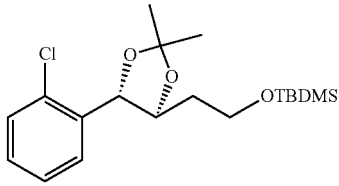 [SMILES: CC1(C)O[C@@H](CCO[Si](C)(C)C(C)(C)C)[C@H](c2ccccc2Cl)O1]

The substantially same method as described in Preparation example 351 was conducted, except that (1S,2S)-4-(tert-butyldimethylsilyloxy)-1-(2-chlorophenyl)butane-1,2-diol (Preparation example 353) was used instead of 1R,2R)-4-(tert-butyldimethylsilyloxy)-1-(2-chlorophenyl)butane-1,2-diol (Preparation example 349), to obtain the title compound (0.7 g, 70~95%).

$^1$H NMR (400 MHz, CDCl$_3$) δ 0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7 Hz, 1H), 5.16 (d, J=8.4 Hz, 1H), 7.21~7.27 (m, 1H), 7.31~7.38 (m, 2H), 7.60 (dd, J=1.6, 7.6 Hz, 1H).

Preparation Example 356: 2-((4S,5S)-5-(2-chlorophenyl)-2,2-dimethyl-1,3-dioxolan-4-yl)ethanol

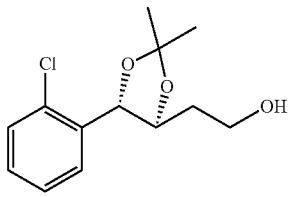 [SMILES: CC1(C)O[C@@H](CCO)[C@H](c2ccccc2Cl)O1]

The substantially same method as described in Preparation example 352 was conducted, except that tert-butyl(2-((4S,5S)-5-(2-chlorophenyl)-2,2-dimethyl-1,3-dioxolan-4-yl)ethoxy)dimethylsilane (Preparation example 355) was used instead of that tertbutyl(2-((4R,5R)-5-(2-chlorophenyl)-2,2-dimethyl-1,3-dioxolan-4-yl)ethoxy)dimethyl silane (Preparation example 351), to obtain the title compound (0.3 g, 80~95%).

$^1$H NMR (400 MHz, CDCl$_3$) δ 1.56 (s, 3H), 1.62 (s, 3H), 1.92~2.04 (m, 2H), 2.26 (q, J=3.7 Hz, 1H), 3.75~3.90 (m, 2H), 3.94 (td, J=3.9, 8.5 Hz, 1H), 5.23 (d, J=15.6 Hz, 1H), 7.22~7.27 (m, 1H), 7.33~7.39 (m, 2H), 7.62 (dd, J=1.6, 7.6 Hz, 1H).

Preparation Example 357: 2-((4R,5R)-2,2-diethyl-5-(2-chlorophenyl)-1,3-dioxolan-4-yl)ethyl pivalate

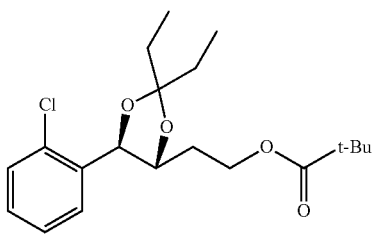 [SMILES: CCC1(CC)O[C@H](c2ccccc2Cl)[C@@H](CCOC(=O)C(C)(C)C)O1]

The substantially same method as described in Preparation example 290 was conducted, except that (3R,4R)-3,4-dihydroxy-4-(2-chlorophenyl)butyl pivalate (Preparation example 350) was used instead of (3R,4R)-3,4-dihydroxy-4-phenylbutyl pivalate (Preparation example 283), to obtain the title compound (0.8 g, 70~95%).

$^1$H NMR (400 MHz, CDCl$_3$) δ 1.15 (s, 9H), 1.76 (q, J=7.6 Hz, 2H), 1.84~1.90 (m, 2H), 2.00~2.07 (m, 2H), 3.85 (dt, J=3.7, 8.5 Hz, 1H), 4.14~4.27 (m, 2H), 5.17 (d, J=8.4 Hz, 1H), 7.22~7.28 (m, 1H), 7.32~7.38 (m, 2H), 7.64 (dd, J=1.4, 7.8 Hz, 1H).

Preparation Example 358: 2-((4R,5R)-2,2-diethyl-5-(2-chlorophenyl)-1,3-dioxolan-4-yl)ethyl pivalate

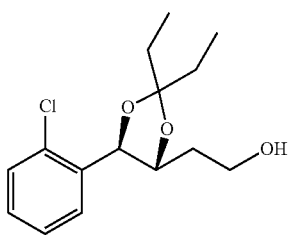 [SMILES: CCC1(CC)O[C@H](c2ccccc2Cl)[C@@H](CCO)O1]

The substantially same method as described in Preparation example 291 was conducted, except that 2-((4R,5R)-2,2-diethyl-5-(2-chlorophenyl)-1,3-dioxolan-4-yl)ethyl pivalate (Preparation example 357) was used instead of 2-((4R,5R)-2,2-diethyl-5-phenyl-1,3-dioxolan-4-yl)ethyl pivalate (Preparation example 290), to obtain the title compound (0.6 g, 80~95%).

$^1$H NMR (400 MHz, CDCl$_3$) δ 1.02 (t, J=7.4 Hz, 3H), 1.08 (t, J=7.4 Hz, 3H), 1.80 (q, J=7.5 Hz, 2H), 1.86~1.91 (m, 2H), 1.96~2.00 (m, 2H), 2.37 (q, J=3.7 Hz, 1H), 3.76~3.95 (m, 3H), 5.23 (d, J=8.4 Hz, 1H), 7.25~7.27 (m, 1H), 7.32~7.39 (m, 2H), 7.65 (dd, J=1.8, 7.8 Hz, 1H).

Preparation Example 359: 2-((2R,3R)-3-(2-chlorophenyl)-1,4-dioxaspiro[4.4]nonan-2-yl)ethyl pivalate

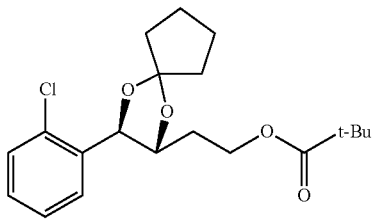 [SMILES: CC(C)(C)C(=O)OCC[C@H]1OC2(CCCC2)O[C@@H]1c1ccccc1Cl]

The substantially same method as described in Preparation example 357 was conducted, except that cyclopentanone was used instead of 3-pentanone, to obtain the title compound (0.8 g, 60~85%).

$^1$H NMR (400 MHz, CDCl$_3$) δ 1.17 (s, 9H), 1.58~2.02 (m, 10H), 3.86 (ddd, J=3.8, 8.2, 8.2 Hz, 1H), 4.11~4.28 (m, 2H), 5.13 (d, J=8.0 Hz, 1H), 7.20~7.39 (m, 3H), 7.58 (dd, J=1.6, 8.0 Hz, 1H).

Preparation Example 360: 2-((2R,3R)-3-(2-chlorophenyl)-1,4-dioxaspiro[4.4]nonan-2-yl)ethanol

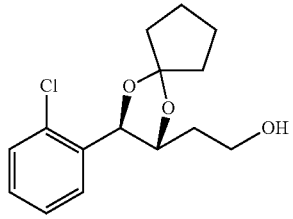 [SMILES: OCC[C@H]1OC2(CCCC2)O[C@@H]1c1ccccc1Cl]

The substantially same method as described in Preparation example 358 was conducted, except that 2-((2R,3R)-3-(2-chlorophenyl)-1,4-dioxaspiro[4.4]nonan-2-yl)ethyl pivalate (Preparation example 359) was used instead of that 2-((4R,5R)-2,2-diethyl-5-(2-chlorophenyl)-1,3-dioxolan-4-yl)ethyl pivalate (Preparation example 357), to obtain the title compound (0.5 g, 80~95%).

$^1$H NMR (400 MHz, CDCl$_3$) δ 1.72~1.90 (m, 4H), 1.93~1.98 (m, 6H), 2.28 (q, J=3.7 Hz, 1H), 3.76~3.93 (m, 3H), 5.18 (d, J=8.0 Hz, 1H), 7.24~7.29 (m, 1H), 7.32~7.38 (m, 2H), 7.60 (dd, J=1.8, 7.8 Hz, 1H).

Preparation Example 361: 2-((2R,3R)-3-(2-chlorophenyl)-1,4-dioxaspiro[4.5]decan-2-yl)ethyl pivalate

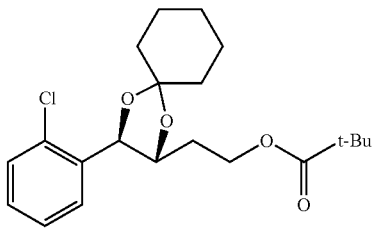 [SMILES: CC(C)(C)C(=O)OCC[C@H]1OC2(CCCCC2)O[C@@H]1c1ccccc1Cl]

The substantially same method as described in Preparation example 359 was conducted, except that cyclohexanone was used instead of cyclopentanone, to obtain the title compound (1.0 g, 60~85%).

$^1$H NMR (400 MHz, CDCl$_3$) δ 1.15 (s, 9H), 1.70~1.94 (m, 10H), 2.06~2.09 (m, 2H), 3.86 (dt, J=3.5, 8.5 Hz, 1H), 4.16~4.26 (m, 2H), 5.18 (d, J=8.4 Hz, 1H), 7.22~7.28 (m, 1H), 7.32~7.38 (m, 2H), 7.61 (dd, J=1.4, 7.8 Hz, 1H).

Preparation Example 362: 2-((2R, 3R)-3-(2-chlorophenyl)-1,4-dioxaspiro[4.5]decan-2-yl)ethanol

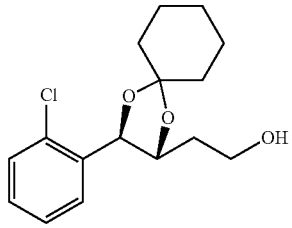 [SMILES: OCC[C@H]1OC2(CCCCC2)O[C@@H]1c1ccccc1Cl]

The substantially same method as described in Preparation example 360 was conducted, except that 2-((2R,3R)-3-(2-chlorophenyl)-1,4-dioxaspiro[4.5]decan-2-yl)ethyl pivalate (Preparation example 361) was used instead of that 2-((2R,3R)-3-(2-chlorophenyl)-1,4-dioxaspiro[4.4]nonan-2-yl)ethyl pivalate (Preparation example 359), to obtain the title compound (0.6 g, 80~95%).

$^1$H NMR (400 MHz, CDCl$_3$) δ 1.42~1.50 (m, 2H), 1.63~1.77 (m, 5H), 1.82~1.89 (m, 5H), 2.41 (q, J=3.9 Hz, 1H), 3.78~3.96 (m, 3H), 5.25 (d, J=8.4 Hz, 1H), 7.21~7.28 (m, 1H), 7.32~7.38 (m, 2H), 7.63 (dd, J=1.4, 7.8 Hz, 1H).

Preparation Example 363: 2-((4S,5S)-2,2-diethyl-5-(2-chlorophenyl)-1,3-dioxolan-4-yl)ethyl pivalate

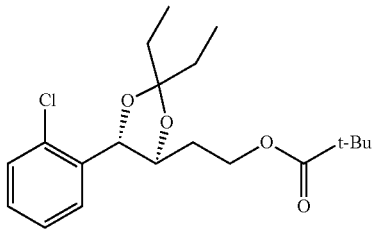 [SMILES: CCC1(CC)O[C@@H](CCOC(=O)C(C)(C)C)[C@H](c2ccccc2Cl)O1]

The substantially same method as described in Preparation example 357 was conducted, except that (3S,4S)-3,4-dihydroxy-4-(2-chlorophenyl)butyl pivalate (Preparation example 354) was used instead of (3R,4R)-3,4-dihydroxy-4-(2-chlorophenyl)butyl pivalate (Preparation example 350), to obtain the title compound (0.7 g, 70~95%).

$^1$H NMR (400 MHz, CDCl$_3$) δ 1.15 (s, 9H), 1.76 (q, J=7.6 Hz, 2H), 1.84~1.90 (m, 2H), 2.00~2.07 (m, 2H), 3.85 (dt, J=3.7, 8.5 Hz, 1H), 4.14~4.27 (m, 2H), 5.17 (d, J=8.4 Hz, 1H), 7.22~7.28 (m, 1H), 7.32~7.38 (m, 2H), 7.64 (dd, J=1.4, 7.8 Hz, 1H).

Preparation Example 364: 2-((4S,5S)-2,2-diethyl-5-(2-chlorophenyl)-1,3-dioxolan-4-yl)ethanol

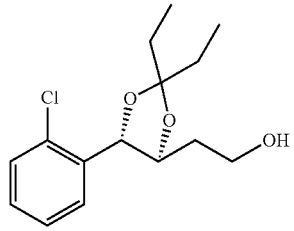 [SMILES: CCC1(CC)O[C@@H](CCO)[C@H](c2ccccc2Cl)O1]

The substantially same method as described in Preparation example 358 was conducted, except that 2-((4S,5S)-2,2-diethyl-5-(2-chlorophenyl)-1,3-dioxolan-4-yl)ethyl pivalate (Preparation example 363) was used instead of 2-((4R,5R)-2,2-diethyl-5-(2-chlorophenyl)-1,3-dioxolan-4-yl)ethyl pivalate (Preparation example 357), to obtain the title compound (0.5 g, 80~95%).

$^1$H NMR (400 MHz, CDCl$_3$) δ 1.02 (t, J=7.4 Hz, 3H), 1.08 (t, J=7.4 Hz, 3H), 1.80 (q, J=7.5 Hz, 2H), 1.86~1.91 (m, 2H), 1.96~2.00 (m, 2H), 2.37 (q, J=3.7 Hz, 1H), 3.76~3.95 (m, 3H), 5.23 (d, J=8.4 Hz, 1H), 7.25~7.27 (m, 1H), 7.32~7.39 (m, 2H), 7.65 (dd, J=1.8, 7.8 Hz, 1H).

Preparation Example 365: 2-((2S,3S)-3-(2-chlorophenyl)-1,4-dioxaspiro[4.4]nonan-2-yl)ethyl pivalate

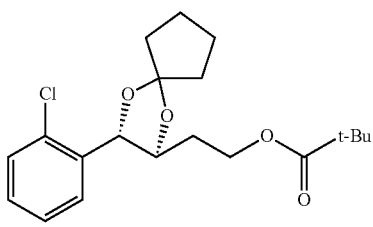 [SMILES: CC(C)(C)C(=O)OCC[C@@H]1OC2(CCCC2)O[C@H]1c1ccccc1Cl]

The substantially same method as described in Preparation example 363 was conducted, except that cyclopentanone was used instead of 3-pentanone, to obtain the title compound (0.6 g, 60~85%).

$^1$H NMR (400 MHz, CDCl$_3$) δ 1.17 (s, 9H), 1.58~2.02 (m, 10H), 3.86 (ddd, J=3.8, 8.2, 8.2 Hz, 1H), 4.11~4.28 (m, 2H), 5.13 (d, J=8.0 Hz, 1H), 7.20~7.39 (m, 3H), 7.58 (dd, J=1.6, 8.0 Hz, 1H).

Preparation Example 366:2-((2S,3S)-3-(2-chlorophenyl)-1,4-dioxaspiro[4.4]nonan-2-yl)ethanol

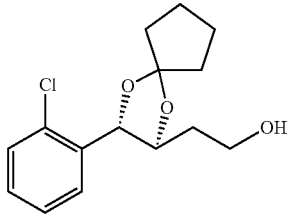 [SMILES: OCC[C@@H]1OC2(CCCC2)O[C@H]1c1ccccc1Cl]

The substantially same method as described in Preparation example 364 was conducted, except that 2-((2S,3S)-3-(2-chlorophenyl)-1,4-dioxaspiro[4.4]nonan-2-yl)ethyl pivalate (Preparation example 365) was used instead of that 2-((4S,5S)-2,2-diethyl-5-(2-chlorophenyl)-1,3-dioxolan-4-yl)ethyl pivalate (Preparation example 363), to obtain the title compound (0.4 g, 80~95%).

$^1$H NMR (400 MHz, CDCl$_3$) δ 1.72~1.90 (m, 4H), 1.93~1.98 (m, 6H), 2.28 (q, J=3.7 Hz, 1H), 3.76~3.93 (m, 3H), 5.18 (d, J=8.0 Hz, 1H), 7.24~7.29 (m, 1H), 7.32~7.38 (m, 2H), 7.60 (dd, J=1.8, 7.8 Hz, 1H).

Preparation Example 367: 2-((2S,3S)-3-(2-chlorophenyl)-1,4-dioxaspiro[4.5]decan-2-yl)ethyl pivalate

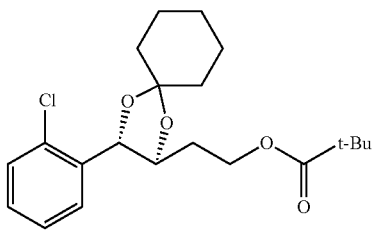 [SMILES: CC(C)(C)C(=O)OCC[C@@H]1OC2(CCCCC2)O[C@H]1c1ccccc1Cl]

The substantially same method as described in Preparation example 366 was conducted, except that cyclohexanone was used instead of cyclopentanone, to obtain the title compound (0.7 g, 60~85%).

$^1$H NMR (400 MHz, CDCl$_3$) δ 1.15 (s, 9H), 1.70~1.94 (m, 10H), 2.06~2.09 (m, 2H), 3.86 (dt, J=3.5, 8.5 Hz, 1H), 4.16~4.26 (m, 2H), 5.18 (d, J=8.4 Hz, 1H), 7.22~7.28 (m, 1H), 7.32~7.38 (m, 2H), 7.61 (dd, J=1.4, 7.8 Hz, 1H).

Preparation Example 368: 2-((2R,3R)-3-(2-chlorophenyl)-1,4-dioxaspiro[4.5]decan-2-yl)ethanol

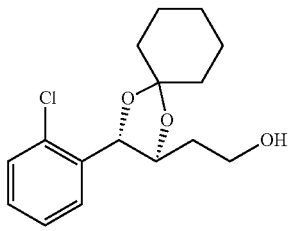 [SMILES: OCC[C@@H]1OC2(CCCCC2)O[C@H]1c1ccccc1Cl]

The substantially same method as described in Preparation example 366 was conducted, except that 2-((2S,3S)-3-(2-chlorophenyl)-1,4-dioxaspiro[4.5]decan-2-yl)ethyl pivalate (Preparation example 367) was used instead of that 2-((2S,3S)-3-(2-chlorophenyl)-1,4-dioxaspiro[4.4]nonan-2-yl)ethyl pivalate (Preparation example 365), to obtain the title compound (0.4 g, 80~95%).

$^1$H NMR (400 MHz, CDCl$_3$) δ 1.42~1.50 (m, 2H), 1.63~1.77 (m, 5H), 1.82~1.89 (m, 5H), 2.41 (q, J=3.9 Hz, 1H), 3.78~3.96 (m, 3H), 5.25 (d, J=8.4 Hz, 1H), 7.21~7.28 (m, 1H), 7.32~7.38 (m, 2H), 7.63 (dd, J=1.4, 7.8 Hz, 1H).

Preparation Example 369: (E)-1-(3(benzyloxy)prop-1enyl)$_2$-chlorobenzene

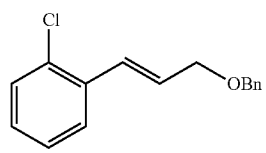 [SMILES: Clc1ccccc1/C=C/COCc1ccccc1]

To a solution of (E)-3-(2-chlorophenyl) prop-2-en-1-ol (Preparation example 1, 5.3 g, 31.6 mmol) in THF was added NaH (60% in mineral oil, 0.91 g, 37.7 mmol) and Benzyl bromide (4.12 mL, 34.8 mmol), sequently at 0° C. The reaction mixture was stirred at room temperature for 18 hr. The TLC showed complete consumption of SM. The reaction mixture was quenched with H$_2$O at 0° C. then extracted with EtOAc. The aqueous layer was extracted with EtOAc and separated. The combined organic layer was washed with H$_2$O, then dried over MgSO$_4$ and evaporated under reduced pressure. The crude compound was purified by silica gel column to produce the title compound (4.94 g, 70~90%).

$^1$H NMR (400 MHz, CDCl$_3$) δ 7.57 (dd, J=2.0, 7.76 Hz, 1H), 7.42~7.13 (m, 3H), 7.05 (d, J=16.0 Hz, 1H), 6.37~6.30 (m, 1H), 4.62 (s, 2H), 4.26 (dd, J=1.6, 6.0 Hz, 2H).

Preparation Example 370: (±)-2-(benzyloxymethyl)-3-(2-chlorophenyl)oxirane

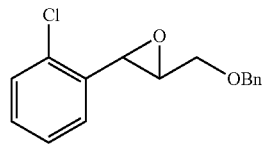 [SMILES: Clc1ccccc1C1OC1COCc1ccccc1]

To a solution of (E)-1-(3-(benzyloxy)prop-1-enyl)-2-chlorobenzene (Preparation example 369, 4.94 g, 22 mmol) in CH$_2$Cl$_2$ (110 mL) was added 3-chloroperoxybenzoic acid (70~75%, 8.0 g, 33 mmol) portionwise at 0° C. The mixture was stirred for 18 hr at room temperature. The TLC showed complete consumption of SM. The reaction mixture was quenched with H$_2$O at 0° C. then extracted with EtOAc. The aqueous layer was extracted with EtOAc and separated. The combined organic layer was washed with sat' NaHCO$_3$, H$_2$O, then dried over MgSO$_4$ and evaporated under reduced pressure. The crude compound was purified by silica gel column to produce the title compound (4.3 g, 60~80%).

$^1$H NMR (400 MHz, CDCl$_3$) δ 7.42~7.24 (m, 9H), 4.68 (d, J=14.8 Hz, 2H), 4.18 (d, J=2.0 Hz, 1H), 3.96 (dd, J=11.6, 2.8 Hz, 1H), 3.69~3.64 (m, 1H), 3.14 (qt, J=2.4 Hz, 1H).

Preparation Example 371: (±)-3-(benzyloxy)-1-(2-chlorophenyl)-2-hydroxypropyl acetate & (±)-3-(benzyloxy)-1-(2-chlorophenyl)-1-hydroxypropan-2-yl acetate

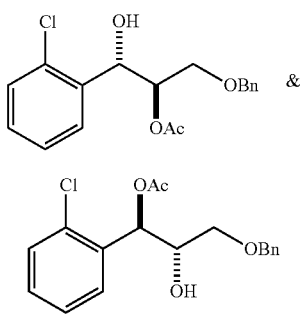

To a solution of (±)-2-(benzyloxymethyl)-3-(2-chlorophenyl)oxirane (Preparation example 370, 4.3 g, 15.6 mmol) in Acetic acid (78 mL) was added Cerium Ammonium Nitrate (1.71 g, 3.1 mmol) at room temperature. The mixture was stirred for 18 hr at room temperature. The TLC showed complete consumption of SM. The reaction mixture was quenched with sat' NaHCO₃ to pH 7 at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (1) (1.2 g, 23%), (2) (1.8 g, 34%).

(1) ¹H NMR (400 MHz, CDCl₃) δ 7.55~7.22 (m, 9H), 5.41 (t, J=5.0 Hz, 1H), 5.33~5.29 (m, 1H), 4.61~4.47 (m, 2H), 3.70~3.63 (m, 2H, —OH), 2.09 (s, 3H).

(2) ¹H NMR (400 MHz, CDCl₃) δ 7.46~7.24 (m, 9H), 6.31 (d, J=5.6 Hz, 1H), 4.55 (d, J=9.6 Hz, 2H), 4.24~4.22 (m, 1H), 3.67~3.55 (m, 2H), 2.52 (d, J=5.2 Hz, —OH), 2.10 (s, 3H).

Preparation Example 372: (±)-3-(benzyloxy)-1-(2-chlorophenyl)propane-1,2-diol (Anti Mixture)

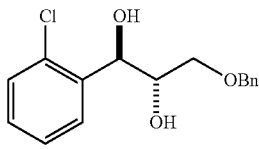 [SMILES: O[C@H](c1ccccc1Cl)[C@@H](O)COCc1ccccc1]

To a solution of (±)-3-(benzyloxy)-1-(2-chlorophenyl)-2-hydroxypropyl acetate and (±)-3-(benzyloxy)-1-(2-chlorophenyl)-1-hydroxypropan-2-yl acetate (Preparation example 371, 3.0 g, 8.9 mmol) in MeOH (36 mL) and H₂O (4 mL) was added K₂CO₃ (3.69 g, 26.7 mmol) at 0° C. The mixture was stirred for 1.5 hr at 0° C. The TLC showed complete consumption of SM. The reaction mixture was quenched with H₂O at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (2.4 g, 80.5%).

¹H NMR (400 MHz, CDCl₃) δ 7.50 (dd, J=1.2, 7.6 Hz, 1H), 7.35~7.19 (m, 8H), 5.28 (t, J=4.8 Hz, 1H), 4.46 (d, J=6 Hz, 2H), 4.18~4.13 (m, 1H), 3.55~3.42 (m, 3H, —OH), 3.02 (d, J=5.2 Hz, —OH).

Preparation Example 373: (±)-4-(benzyloxymethyl)-5-(2-chlorophenyl)-2,2-dimethyl-1,3-dioxolane

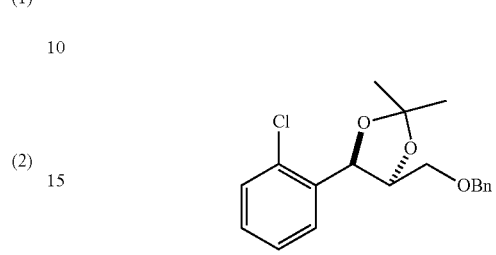

To a solution of (±)-3-(benzyloxy)-1-(2-chlorophenyl)propane-1,2-diol (Preparation example 372, 2.4 g, 8.2 mmol) in CH₂Cl₂ (40 mL) was added p-toluenesulfonyl chloride (15.2 g, 0.08 mmol), and 2,2-dimethoxypropan (8.4 mL, 9.84 mmol) at 0° C. sequently. The mixture was stirred for 1.5 hr at room temperature. The TLC showed complete consumption of SM. The reaction mixture was quenched with H₂O then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (2.2 g, 75~90%).

¹H NMR (400 MHz, CDCl₃) δ 7.61 (dd, J=1.6, 7.4 Hz, 1H), 7.35~7.16 (m, 8H), 5.63 (d, J=6.8 Hz, 1H), 4.83~4.78 (m, 1H), 4.26 (d, J=12.0 Hz, 2H), 3.14~3.06 (m, 2H), 1.66 (s, 3H), 1.53 (s, 3H).

Preparation Example 374: 5-(2-chlorophenyl)-2,2-dimethyl-1,3-dioxolan-4-yl)methanol (SR & RS Mixture)

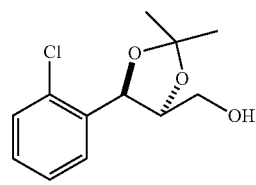 [SMILES: CC1(C)O[C@@H](CO)[C@@H](c2ccccc2Cl)O1]

To a solution of (±)-4-(benzyloxymethyl)-5-(2-chlorophenyl)-2,2-dimethyl-1.3-dioxolane (Preparation example 375, 2.2 g, 6.6 mmol) in EtOAc (33 mL) was added 10% Pd/C on carbon (0.11 g) at room temperature. The mixture was stirred for 1 hr at room temperature under H₂ (g). The TLC showed complete consumption of SM. The reaction mixture was filtered through celite pad then evaporated under reduced pressure. The crude compound was purified by silica gel column to produce the title compound (1.5 g, 80~95%).

¹H NMR (400 MHz, CDCl₃) δ 7.61 (dd, J=1.6, 7.4 Hz, 1H), 7.35~7.16 (m, 8H), 5.63 (d, J=6.8 Hz, 1H), 4.83~4.78 (m, 1H), 4.26 (d, J=12.0 Hz, 2H), 3.14~3.06 (m, 2H), 1.66 (s, 3H), 1.53 (s, 3H).

Preparation Example 375: (2R,3R)-2-(benzyloxymethyl)-3-(2-chlorophenyl)oxirane

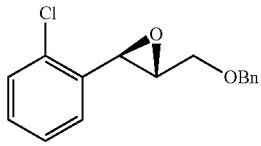 [SMILES: Clc1ccccc1[C@H]1O[C@@H]1COCc1ccccc1]

To a solution of (E)-1-(3-(benzyloxy)prop-1-enyl)-2-chlorobenzene (Preparation example 369, 4.16 g, 18.6 mmol) and 1,2;4,5-di-O-isopropylidene-β-D-erythro-2,3-hexodiulo-2,6-pyranose (5.76 g, 22.3 mmol) in ACN-DMM (3:1, v/v) (185 mL) was added buffer (0.2 M $K_2CO_3$—AcOH in $4×10^{-4}$ M aq. EDTA, buffer pH=8.0) (185 mL) and $Bu_4NHSO_4$ (0.26 g, 0.75 mmol). After the mixture was cooled to 0° C., a solution of Oxone (15.76 g, 25.64 mmol) in $4×10^{-4}$ M aq. EDTA (100 mL) and a solution of $K_2CO_3$ (13.6 g, 98.47 mmol) in $H_2O$ (100 mL) were added dropwise separately over a period of 3.5 hr via a syringe pump at 0° C. The reaction mixture was stirred for 14 hr at 0° C. The reaction mixture was quenched with $H_2O$ then extracted with EtOAc. The aqueous layer was extracted with EtOAc and separated. The combined organic layer was washed with $H_2O$ then dried over $MgSO_4$ and evaporated under reduced pressure. The crude compound was purified by silica gel column to produce the title compound (2.9 g, 50~65%).

$^1$H NMR (400 MHz, CDCl$_3$) δ 3.14 (qt, J=2.4 Hz, 1H), 3.69~3.64 (m, 1H), 3.96 (dd. J=2.8, 11.6 Hz, 1H), 4.18 (d, J=2.0 Hz, 1H), 4.68 (d, J=14.8, 2H), 7.42~7.24 (m, 9H).

Preparation Example 376: (1S,2R)-3-(benzyloxy)-1-(2-chlorophenyl)-2-hydroxypropyl acetate

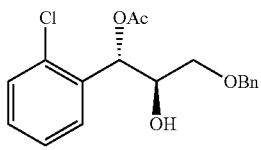 [SMILES: CC(=O)O[C@@H](c1ccccc1Cl)[C@H](O)COCc1ccccc1]

To a solution of (2R,3R)-2-(benzyloxymethyl)-3-(2-chlorophenyl)oxirane (Preparation example 375, 2.9 g, 10.55 mmol) in Acetic acid (55 mL) was added Cerium Ammonium Nitrate (1.15 g, 2.11 mmol) at room temperature. The mixture was stirred for 18 hr at room temperature. The TLC showed complete consumption of SM. The reaction mixture was quenched with sat' NaHCO$_3$ to pH 7 at 0° C. then extracted with EtOAc. The aqueous layer was extracted with EtOAc and separated. The combined organic layer was washed with $H_2O$, then dried over $MgSO_4$ and evaporated under reduced pressure. The crude compound was purified by silica gel column to produce the title compound (1.2 g, 30~50%).

$^1$H NMR (400 MHz, CDCl$_3$) δ 2.10 (s, 3H), 2.52 (d, J=5.2 Hz, —OH), 3.67~3.55 (m, 2H), 4.24~4.22 (m, 1H), 4.55 (d, J=9.6 Hz, 2H), 6.31 (d, J=5.6 Hz, 1H), 7.46~7.24 (m, 9H).

Preparation Example 377: (1S,2R)-3-(benzyloxy)-1-(2-chlorophenyl)propane-1,2-diol

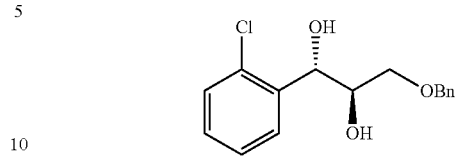

To a solution of (1S,2R)-3-(benzyloxy)-1-(2-chlorophenyl)-2-hydroxypropyl acetate (Preparation example 376, 1.2 g, 3.58 mmol) in MeOH (16.2 mL) and $H_2O$ (1.8 mL) was added $K_2CO_3$ (1.48 g, 10.74 mmol) at 0°. The mixture was stirred for 1.5 hr at 0° C. The TLC showed complete consumption of SM. The reaction mixture was quenched with $H_2O$ at 0° C. then extracted with EtOAc. The aqueous layer was extracted with EtOAc and separated. The combined organic layer was washed with H, O, then dried over $MgSO_4$ and evaporated under reduced pressure. The crude compound was purified by silica gel column to produce the title compound (1.0 g, 80~100%).

$^1$H NMR (400 MHz, CDCl$_3$) δ 3.02 (d, J=5.2 Hz, 1H), 3.55~3.42 (m, 3H, 10H), 4.18~4.13 (m, 1H), 4.46 (d, J=6.0 Hz, 2H), 5.28 (t, J=4.8 Hz, 1H), 7.35~7.19 (m, 8H), 7.50 (dd, J=1.2, 7.6 Hz, 1H).

Preparation Example 378: (4R,5S)-4-(benzyloxymethyl)-5-(2-chlorophenyl)-2,2-dimethyl-1,3-dioxolane

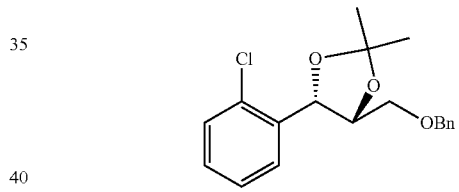

The substantially same method as described in Preparation example 373 was conducted, except that (1S,2R)-3-(benzyloxy)-1-(2-chlorophenyl)propane-1,2-diol (Preparation example 377) was used instead of that (±)-3-(benzyloxy)-1-(2-chlorophenyl)propane-1,2-diol (Preparation example 372), to obtain the title compound (0.77 g, 80~100%).

$^1$H NMR (400 MHz, CDCl$_3$) δ 1.53 (s, 3H), 1.66 (s, 3H), 3.14~3.06 (m, 2H), 4.26 (d, J=12.0 Hz, 2H), 4.83~4.78 (m, 1H), 5.63 (d, J=6.8 Hz, 1H), 7.35~7.16 (m, 8H), 7.61 (dd, J=1.6, 7.4 Hz, 1H).

Preparation Example 379: ((4R,5S)-5-(2-chlorophenyl)-2,2-dimethyl-1,3-dioxolan-4-yl)methanol

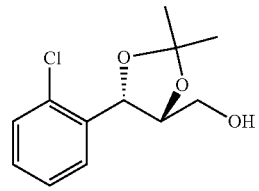 [SMILES: CC1(C)O[C@H](CO)[C@H](c2ccccc2Cl)O1]

The substantially same method as described in Preparation example 374 was conducted, except that ((4R,5S)-4-(benzyloxymethyl)-5-(2-chlorophenyl)-2,2-dimethyl-1,3-dioxolane (Preparation example 378) was used instead of that (±)-4-(benzyloxymethyl)-5-(2-chlorophenyl)-2,2-dimethyl-1,3-dioxolane (Preparation example 373), to obtain the title compound (0.58 g, 80~100%).

$^1$H NMR (400 MHz, CDCl$_3$) δ 1.66 (s, 3H), 1.53 (s, 3H), 3.14~3.06 (m, 2H), 4.26 (d, J=12.0 Hz, 2H), 4.83~4.78 (m, 1H), 5.63 (d, J=6.8 Hz, 1H), 7.35~7.16 (m, 8H), 7.61 (dd, J=1.6, 7.4 Hz, 1H).

Preparation Example 380: (E)-ethyl 3-(2,4-dichlorothiazol-5-yl)acrylate

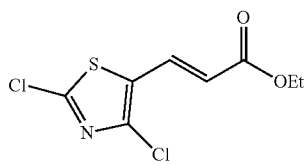 [SMILES: CCOC(=O)/C=C/c1sc(Cl)nc1Cl]

To a stirred solution of 2,4-dichlorothiazole-5-carbaldehyde (5.0 g, 27.5 mmol) in THF (200 mL) was added triethylphosphonoacetate (6.6 mL, 32.9 mmol) and Lithiumhydroxide (0.79 mL, 32.9 mmol), 4 A molecular sieve 5.0 g at room temperature under N$_2$. The mixture was stirred for 3 h. The resulting mixture was diluted with EtOAc, washed with water, dried over anhydrous magnesium sulfate (MgSO$_4$), filtered, and concentrated under reduced pressure. The crude compound was purified by a silica gel column to produce the title compound (6.1 g, 80~95%).

$^1$H NMR (400 MHz, DMSO-d$_6$) δ 1.22 (q, J=12.5 Hz, 3H), 4.23 (q, J=7.0 Hz, 2H), 6.54 (d, J=16.0 Hz, 1H), 7.54 (d, J=16.0 Hz, 1H).

Preparation Example 381: (2S,3S)-ethyl 3-(2,4-dichlorothiazol-5-yl)-2,3-dihydroxypropanoate

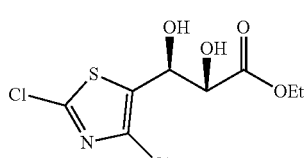

The substantially same method as described in Preparation Example 3 was conducted, except that (E)-ethyl 3-(2,4-dichlorothiazol-5-yl)acrylate (Preparation example 380) was used instead of (E)-1-chloro-2-(3-(methoxymethoxy)prop-1-enyl)benzene (Preparation example 2), to obtain the title compound (3.94 g, 50~70%).

$^1$H NMR (400 MHz, DMSO-d$_6$) δ 1.22 (q, J=12.5 Hz, 3H), 4.18 (q, J=7.0 Hz, 2H), 4.20 (dd, J=2.4, 7.6 Hz, 1H), 5.19 (dd, J=2.6, 5.8 Hz, 1H), 6.03 (d, J=7.6 Hz, 1H), 6.37 (d, J=5.6 Hz, 1H).

Preparation Example 382: (4S,5S)-ethyl 5-(2,4-dichlorothiazol-5-yl)-2,2-dimethyl-1,3-dioxolane-4-carboxylate

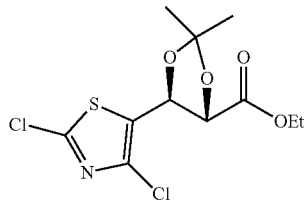 [SMILES: CCOC(=O)[C@H]1OC(C)(C)O[C@@H]1c1sc(Cl)nc1Cl]

The substantially same method as described in Preparation example 26 was conducted, except that (2S,3S)-ethyl 3-(2,4-dichlorothiazol-5-yl)-2,3-dihydroxypropanoate (Preparation example 381) was used instead of (2S,3R)-methyl-3-(2-chlorophenyl)-2,3-dihydroxypropanoate (Preparation example 25), to obtain the title compound (0.13 g, 65~80%).

$^1$H NMR (400 MHz, DMSO-d$_6$) δ 1.20 (t, J=7.2 Hz, 3H), 1.42 (s, 3H), 1.49 (s, 3H), 4.18 (m, 2H), 4.66 (d, J=6.8 Hz, 1H), 5.44 (d, J=6.8 Hz, 1H).

Preparation Example 383: ((4R,5S)-5-(2,4-dichlorothiazol-5-yl)-2,2-dimethyl-1,3-dioxolan-4-yl)methanol

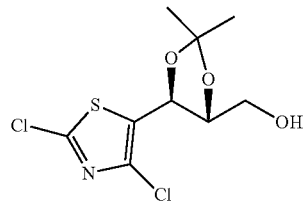 [SMILES: CC1(C)O[C@H](c2sc(Cl)nc2Cl)[C@@H](CO)O1]

The substantially same method as described in Preparation example 27 was conducted, except that (4S,5S)-ethyl 5-(2,4-dichlorothiazol-5-yl)-2,2-dimethyl-1,3-dioxolane-4-carboxylate (Preparation example 382) was used instead of (4S,5R)-methyl-5-(2-chlorophenyl)-2,2-dimethyl-1.3-dioxolane-4-carboxylate (Preparation example 26), to obtain the title compound (0.05 g, 50~70%).

$^1$H NMR (400 MHz, DMSO-d$_6$) δ 1.42 (d, J=6.0 Hz, 6H), 3.59 (m, 1H), 3.67 (m, 1H), 3.97 (m, 1H), 5.04 (t, J=5.4 Hz, 1H), 5.10 (d, J=8.4 Hz, 1H).

Preparation Example 384: (2R,3R)-ethyl 3-(2,4-dichlorothiazol-5-yl)-2,3-dihydroxypropanoate

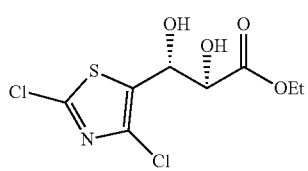 [SMILES: CCOC(=O)[C@H](O)[C@@H](O)c1sc(Cl)nc1Cl]

The substantially same method as described in Preparation Example 381 was conducted, except that (DHQ)$_2$-

PHAL was used instead of (DHQD)$_2$-PHAL, to obtain the tide compound (3.9 g, 50~70%).

$^1$H NMR (400 MHz, DMSO-d$_6$) δ 1.22 (q, J=12.5 Hz, 3H), 4.18 (q, J=7.0 Hz, 2H), 4.20 (dd, J=2.4, 7.6 Hz, 1H), 5.19 (dd, J=2.6, 5.8 Hz, 1H), 6.03 (d, J=7.6 Hz, 1H), 6.37 (d, J=5.6 Hz, 1H).

Preparation Example 385: (4R,5R)-ethyl 5-(2,4-dichlorothiazol-5-yl)-2,2-dimethyl-1,3-dioxolane-4-carboxylate

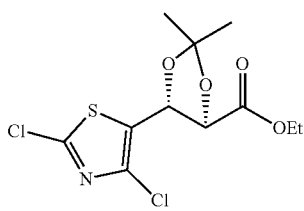 [SMILES: CCOC(=O)[C@@H]1OC(C)(C)O[C@H]1c1sc(Cl)nc1Cl]

The substantially same method as described in Preparation Example 382 was conducted, except that (2R,3R)-ethyl 3-(2,4-dichlorothiazol-5-yl)-2,3-dihydroxypropanoate (Preparation example 384) was used instead of (2S,3S)-ethyl 3-(2,4-dichlorothiazol-5-yl)-2,3-dihydroxypropanoate (Preparation example 381), to obtain the title compound (0.13 g, 65~80%).

$^1$H NMR (400 MHz, DMSO-d$_6$) δ 1.20 (t, J=7.2 Hz, 3H), 1.42 (s, 3H), 1.49 (s, 3H), 4.18 (m, 2H), 4.66 (d, J=6.8 Hz, 1H), 5.44 (d, J=6.8 Hz, 1H).

Preparation Example 386: ((4S,5R)-5-(2,4-dichlorothiazol-5-yl)-2,2-dimethyl-1,3-dioxolan-4-yl)methanol

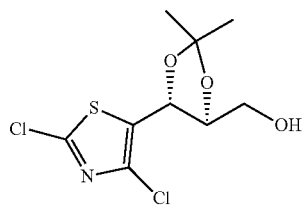 [SMILES: CC1(C)O[C@@H](CO)[C@H](c2sc(Cl)nc2Cl)O1]

The substantially same method as described in Preparation Example 383 was conducted, except that (4R,5R)-ethyl 5-(2,4-dichlorothiazol-5-yl)-2,2-dimethyl-1,3-dioxolane-4-carboxylate (Preparation example 385) was used instead of (4S,5S)-ethyl 5-(2,4-dichlorothiazol-5-yl)-2,2-dimethyl-1,3-dioxolane-4-carboxylate (Preparation example 382), to obtain the title compound (0.05 g, 50~70%).

$^1$H NMR (400 MHz, DMSO-d$_6$) δ 1.42 (d, J=6.0 Hz, 6H), 3.59 (m, 1H), 3.67 (m, 1H), 3.97 (m, 1H), 5.04 (t, J=5.4 Hz, 1H), 5.10 (d, J=8.4 Hz, 1H).

Preparation Example 387: (E)-ethyl 3-(2-chlorothiazol-5-yl)acrylate

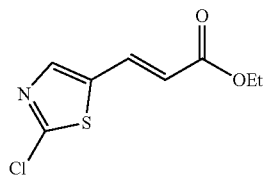 [SMILES: CCOC(=O)/C=C/c1cnc(Cl)s1]

The substantially same method as described in Preparation Example 380 was conducted, except that 2-chlorothiazole-5-carbaldehyde was used instead of 2,4-dichlorothiazole-5-carbaldehyde, to obtain the title compound (4.7 g, 80~95%).

$^1$H NMR (400 MHz, DMSO-d$_6$) δ 1.25 (t, J=7.0 Hz, 3H), 4.19 (q, J=7.2 Hz, 2H), 6.40 (d, J=16.0 Hz, 1H), 7.81 (d, J=16.0 Hz, 1H), 8.11 (s, 1H).

Preparation Example 388: (2S,3S)-ethyl-3-(2-chlorothiazol-5-yl)-2,3-dihydroxypropanoate

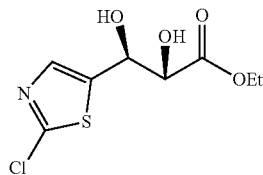 [SMILES: CCOC(=O)[C@@H](O)[C@H](O)c1cnc(Cl)s1]

The substantially same method as described in Preparation Example 381 was conducted, except that (E)-ethyl 3-(2-chlorothiazol-5-yl)acrylate (Preparation example 387) was used instead of (E)-ethyl 3-(2,4-dichlorothiazol-5-yl)acrylate (Preparation example 380), to obtain the title compound (4.1 g, 50~70%).

$^1$H NMR (400 MHz, DMSO-d$_t$) δ 1.20 (t, J=7.0 Hz, 3H), 4.12 (q, J=7.2 Hz, 2H), 5.18 (d, J=1.6 Hz, 1H), 5.87 (s, 1H), 6.12 (s, 1H), 7.63 (s, 1H).

Preparation Example 389: (4S,5S)-ethyl-5-(2-chlorothiazol-5-yl)-2,2-dimethyl-1,3-dioxolane-4-carboxylate

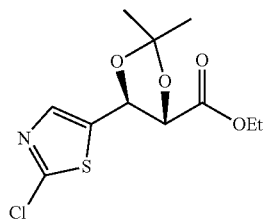 [SMILES: CCOC(=O)[C@H]1OC(C)(C)O[C@@H]1c1cnc(Cl)s1]

The substantially same method as described in Preparation Example 382 was conducted, except that (2S,3S)-ethyl 3-(2-chlorothiazol-5-yl)-2,3-dihydroxypropanoate (Preparation example 388) was used instead of (2S,3S)-ethyl 3-(2,4-dichlorothiazol-5-yl)-2,3-dihydroxypropanoate (Preparation example 381), to obtain the title compound (1.0 g, 65~80%).

¹H NMR (400 MHz, DMSO-ds) δ 1.44 (d, J=16.8 Hz, 3H), 4.18 (m, 2H), 4.62 (d, J=7.6 Hz, 1H), 5.50 (d, J=7.2 Hz, 1H), 7.74 (s, 1H).

Preparation Example 390: (4R,5S)-5-(2-chlorothiazol-5-yl)2,2-dimethyl-1,3-dioxolan-4-yl)methanol

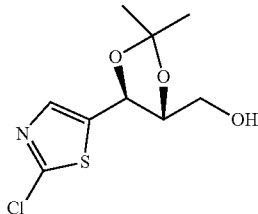

The substantially same method as described in Preparation Example 386 was conducted, except that (4S,5S)-ethyl 5-(2-chlorothiazol-5-yl)-2,2-dimethyl-1,3-dioxolane-4-carboxylate (Preparation example 389) was used instead of (4R,5R)-ethyl 5-(2,4-dichlorothiazol-5-yl)-2,2-dimethyl-1,3-dioxolane-4-carboxylate (Preparation example 385), to obtain the title compound (0.84 g, 70~90%).
¹H NMR (400 MHz, DMSO-d₆) δ 1.40 (d, J=2.0 Hz, 6H), 3.59 (q, J=4.7 Hz, 2H), 3.94 (m, 1H), 5.06 (t, J=6.6 Hz, 1H), 5.09 (d, J=0.8 Hz, 1H), 7.69 (s, 1H).

Preparation Example 391: (2R,3R)-ethyl 3-(2-chlorothiazol-5-yl)-2,3-dihydroxypropanoate

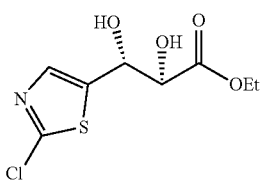 [SMILES: CCOC(=O)[C@H](O)[C@@H](O)c1cnc(Cl)s1]

The substantially same method as described in Preparation Example 384 was conducted, except that (E)-ethyl-3-(2-chlorothiazol-5-yl)acrylate (Preparation example 387) was used instead of (E)-ethyl 3-(2,4-dichlorothiazol-5-yl) acrylate (Preparation example 380), to obtain the title compound (3.9 g, 50~70%).
¹H NMR (400 MHz, DMSO-d₇) δ 1.20 (t, J=7.0 Hz, 3H), 4.12 (q, J=7.2 Hz, 2H), 5.18 (d, J=1.6 Hz, 1H), 5.87 (s, 1H), 6.12 (s, 1H), 7.63 (s, 1H).

Preparation Example 392: (4R,5R)-ethyl-5-(2-chlorothiazol-5-yl)-2,2-dimethyl-1,3-dioxolane-4-carboxylate

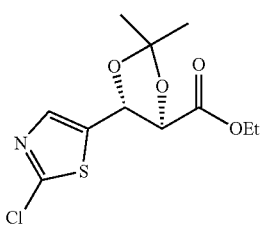 [SMILES: CCOC(=O)[C@@H]1OC(C)(C)O[C@H]1c1cnc(Cl)s1]

The substantially same method as described in Preparation Example 382 was conducted, except that (2R. 3R)-ethyl-3-(2-chlorothiazol-5-yl)-2,3-dihydroxypropanoate (Preparation example 391) was used instead of (2S,3S)-ethyl 3-(2,4-dichlorothiazol-5-yl)-2,3-dihydroxypropanoate (Preparation example 381), to obtain the title compound (0.73 g, 65~80%).
¹H NMR (400 MHz, DMSO-d₆) δ 1.44 (d, J=16.8 Hz, 3H), 4.18 (m, 2H), 4.62 (d, J=7.6 Hz, 1H), 5.50 (d, J=7.2 Hz, 1H), 7.74 (s, 1H).

Preparation Example 393: (4S,5R)-5-(2-chlorothiazol-5-yl)2,2-dimethyl-1,3-dioxolan-4-yl)methanol

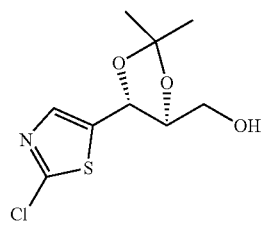

The substantially same method as described in Preparation Example 386 was conducted, except that (4R,5R)-ethyl-5-(2-chlorothiazol-5-yl)-2,2-dimethyl-1,3-dioxolane-4-carboxylate (Preparation example 392) was used instead of (4R,5R)-ethyl 5-(2,4-dichlorothiazol-5-yl)-2,2-dimethyl-1,3-dioxolane-4-carboxylate (Preparation example 385), to obtain the title compound (0.60 g, 70~90%).
¹H NMR (400 MHz, DMSO-d₆) δ 1.40 (d, J=2.0 Hz, 6H), 3.59 (q, J=4.7 Hz, 2H), 3.94 (m, 1H), 5.06 (t, J=6.6 Hz, 1H), 5.09 (d, J=0.8 Hz, 1H), 7.69 (s, 1H).

Preparation Example 394: (E)-ethyl-3-(4-methylthiazol-5-yl)acrylate

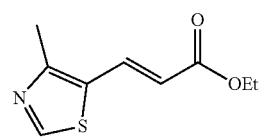

The substantially same method as described in Preparation Example 380 was conducted, except that 4-methythiazole-5-carbaldehyde was used instead of 2,4-dichlorothiazole-5-carbaldehyde, to obtain the title compound (15.0 g, 80~95%).
¹H NMR (400 MHz, DMSO-d₆) δ 1.25 (t, J=7.0 Hz, 3H), 1.45 (s 3H), 4.19 (q, J=7.0 Hz, 2H), 6.12 (d, J=16.0 Hz, 1H), 7.77 (d, J=16.0 Hz, 1H), 9.09 (s, 1H).

Preparation Example 395: (2S,3S)-ethyl-3-(4-methylthiazol-5-yl)-2,3-dihydroxypropanoate

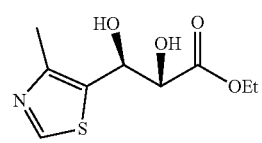

The substantially same method as described in Preparation Example 2 was conducted, except that (E)-ethyl-3-(4-methylthiazol-5-yl)acrylate (Preparation example 394) was used instead of (E)-ethyl-3-(2,4-dichlorothiazol-5-yl)acrylate (Preparation example 381), to obtain the title compound (4.0 g, 50~70%).

$^1$H NMR (400 MHz, DMSO-d$_6$) δ 1.11 (t, J=7.0 Hz, 3H), 1.43 (s, 3H), 4.04 (m, 2H), 5.11 (t, J=3.8 Hz, 1H), 5.70 (d, J=20.7 Hz, 1H), 5.92 (d, J=4.0 Hz, 1H), 6.81 (s, 1H), 8.86 (s, 1H).

Preparation Example 396: (4S,5S)-ethyl-5-(4-methylthiazol-5-yl)-2,2-dimethyl-1,3-dioxolane-4-carboxylate

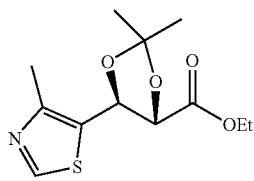 [SMILES: CCOC(=O)[C@H]1OC(C)(C)O[C@@H]1c1scnc1C]

The substantially same method as described in Preparation Example 382 was conducted, except that (2S,3S)-ethyl-3-(4-methylthiazol-5-yl)-2,3-dihydroxypropanoate (Preparation example 395) was used instead of (2S,3S)-ethyl 3-(2,4-dichlorothiazol-5-yl)-2,3-dihydroxypropanoate (Preparation example 381), to obtain the title compound (2.6 g, 55~70%).

$^1$H NMR (400 MHz, DMSO-d$_6$) δ 1.17 (t, J=3.6 Hz, 3H), 1.43 (S, 3H), 1.49 (s, 3H), 2.34 (s, 3H), 4.17 (q, J=7.0 Hz, 2H), 4.40 (d, J=14.0 Hz, 1H), 5.53 (d, J=7.2 Hz, 1H), 9.01 (s, 1H).

Preparation Example 397: (4R,5S)-5-(4-methylthiazol-5-yl)2,2-dimethyl-1,3-dioxolan-4-yl)methanol

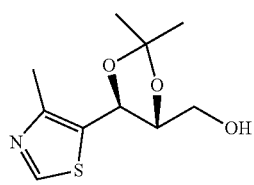

The substantially same method as described in Preparation Example 386 was conducted, except that (4S,5S)-ethyl-5-(4-methylthiazol-5-yl)-2,2-dimethyl-1,3-dioxolane-4-carboxylate (Preparation example 396) was used instead of (4R,5R)-ethyl 5-(2,4-dichlorothiazol-5-yl)-2,2-dimethyl-1,3-dioxolane-4-carboxylate (Preparation example 385), to obtain the title compound (1.7 g, 70~90%).

$^1$H NMR (400 MHz, DMSO-d$_6$) δ 1.42 (d, J=7.6 Hz, 6H), 2.36 (s, 3H), 3.58 (m, 2H), 3.80 (d, J=3.2 Hz, 1H), 5.02 (t, J=5.4 Hz, 1H), 5.17 (d, J=8.4 Hz, 1H), 8.98 (s, 1H).

Preparation Example 398: (21R, 3R)-ethyl-3-(4-methylthiazol-5-yl)-2,3-dihydroxypropanoate

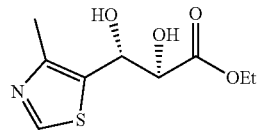

The substantially same method as described in Preparation Example 384 was conducted, except that (E)-ethyl-3-(4-methylthiazol-5-yl)acrylate (Preparation example 394) was used instead of (E)-ethyl13-(2,4-dichlorothiazol-5-yl)acrylate (Preparation example 380), to obtain the title compound (6.0 g, 50~70%).

$^1$H NMR (400 MHz, DMSO-d$_6$) δ 1.11 (t, J=7.0 Hz, 3H), 1.43 (s, 3H), 4.04 (m, 2H), 5.11 (t, J=3.8 Hz, 1H), 5.70 (d, J=20.7 Hz, 1H), 5.92 (d, J=4.0 Hz, 1H), 6.81 (s, 1H), 8.86 (s, 1H).

Preparation Example 399: (4R,5R)-ethyl-5-(4-methylthiazol-5-yl)-2,2-dimethyl-1,3-dioxolane-4-carboxylate

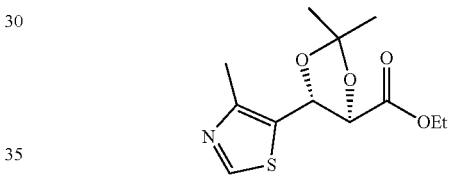

The substantially same method as described in Preparation Example 382 was conducted, except that (2R,3R)-ethyl-3-(4-methylthiazol-5-yl)-2,3-dihydroxypropanoate (Preparation example 398) was used instead of (2S,3S)-ethyl 3-(2,4-dichlorothiazol-5-yl)-2,3-dihydroxypropanoate (Preparation example 381), to obtain the title compound (5.0 g, 65~80%).

$^1$H NMR (400 MHz, DMSO-d$_6$) δ 1.17 (t, J=3.6 Hz, 3H), 1.43 (S, 3H), 1.49 (s, 3H), 2.34 (s, 3H), 4.17 (q, J=7.0 Hz, 2H), 4.40 (d, J=14.0 Hz, 1H), 5.53 (d, J=7.2 Hz, 1H), 9.01 (s, 1H).

Preparation Example 400: (4S,5R)-5-(4-methylthiazol-5-yl)2,2-dimethyl-1,3-dioxolan-4-yl)methanol

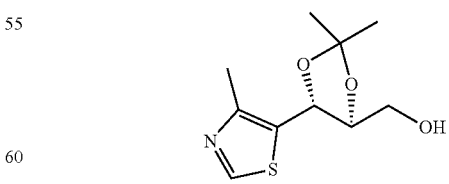

The substantially same method as described in Preparation Example 386 was conducted, except that (4R,5R)-ethyl-5-(4-methylthiazol-5-yl)-2,2-dimethyl-1,3-dioxolane-4-carboxylate (Preparation example 399) was used instead of (4R,5R)-ethyl-5-(2,4-dichlorothiazol-5-yl)-2,2-dimethyl-1, 3-dioxolane-4-carboxylate (Preparation example 385), to obtain the title compound (4.1 g, 70~90%).

¹H NMR (400 MHz, DMSO-d₆) δ 1.42 (d, J=7.6 Hz, 6H), 2.36 (s, 3H), 3.58 (m, 2H), 3.80 (d, J=3.2 Hz, 1H), 5.02 (t, J=5.4 Hz, 1H), 5.17 (d, J=8.4 Hz, 1H), 8.98 (s, 1H).

Preparation Example 401: (4R,5S)-ethyl-5-(2-chloro-4-methylthiazol-5-yl)-2,2-dimethyl-1,3-dioxolane-4-carboxylate

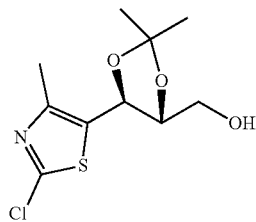 [SMILES: Cc1nc(Cl)sc1[C@H]1OC(C)(C)O[C@@H]1CO]

To a stirred solution of (4R,5S)-5-(4-methylthiazol-5-yl)2,2-dimethyl-1,3-dioxolan-4-yl)methanol (Preparation example 397, 3.1 g, 14.3 mmol) in THF (20 mL) was added n-Butyllithium (14.3 mL, 35.7 mmol) and CCl₄ (4.1 mL, 42.8 mmol) at −78° C. The mixture was stirred for 0.5 h. The resulting mixture was diluted with EtOAc, washed with water, dried over MgSO₄, filtered, and concentrated under reduced pressure. The crude compound was purified by a silica gel column to produce the title compound (2.8 g, 70~90%).

¹H NMR (400 MHz, DMSO-d₆) δ 1.40 (d, J=5.6 Hz, 6H), 2.28 (s, 3H), 3.58 (m, 2H), 3.80 (m, 1H), 5.06 (m, 1H), 5.13 (d, J=8.4 Hz, 1H).

Preparation Example 402: (4S,5R)-ethyl-5-(2-chloro-4-methylthiazol-5-yl)-2,2-dimethyl-1,3-dioxolane-4-carboxylate

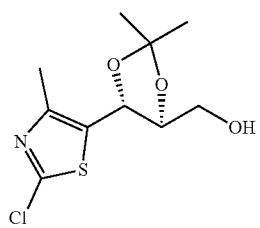 [SMILES: Cc1nc(Cl)sc1[C@@H]1OC(C)(C)O[C@H]1CO]

The substantially same method as described in Preparation Example 401 was conducted, except that (4S,5R)-5-(4-methylthiazol-5-yl)2,2-dimethyl-1,3-dioxolan-4-yl)methanol (Preparation example 400) was used instead of (4R,5S)-5-(4-methylthiazol-5-yl)2,2-dimethyl-1,3-dioxolan-4-yl)methanol (Preparation example 397), to obtain the title compound (1.5 g, 70~90%).

¹H NMR (400 MHz, DMSO) δ 1.40 (d, J=5.6 Hz, 6H), 2.28 (s, 3H), 3.58 (m, 2H), 3.80 (m, 1H), 5.06 (m, 1H), 5.13 (d, J=8.4 Hz, 1H).

Preparation Example 403: (E)-ethyl 3-(thiophen-3-yl)acrylate

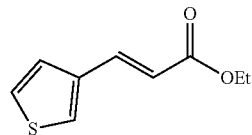 [SMILES: CCOC(=O)/C=C/c1ccsc1]

To a stirred solution of triethylphosphonoacetate (5.36 mL, 26.7 mmol) in THF (40 mL) was added to t-BuOK (3.0 g, 26.7 mmol) dropwise at rt and stirred at this temperature for 30 min. Then thiophene-3-carbaldehyde (3.0 g, 26.7 mmol) was added and stirred at 90° C. and stirred at this temperature for 30 min. The product was quenched with 1 M HCl solution. The resulting mixture was extracted with ethyl acetate form water. The combined organic layer was dried (Na₂SO₄), filtered and concentrated. The residue was purified by silica gel column to produce the title compound (3.9 g, 70~90%).

¹H NMR (400 MHz, CDCl₃) δ 1.34 (t, J=7.2 Hz, 3H), 4.26 (q, J=7.2 Hz, 2H), 6.31 (d, J=15.6 Hz, 1H), 6.89 (d, J=4.0 Hz, 1H), 7.69 (s, 1H), 7.73 (d, J=4.0 Hz, 1H), 7.80 (d, J=15.6 Hz, 1H).

Preparation Example 404: (2R,3S)-ethyl 2,3-dihydroxy-3-(thiophen-3-yl)propanoate

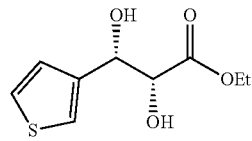 [SMILES: CCOC(=O)[C@H](O)[C@@H](O)c1ccsc1]

The substantially same method as described in Preparation Example 384 was conducted, except that (E)-ethyl 3-(thiophen-3-yl)acrylate (Preparation example 403) was used instead of (E)-ethyl3-(2,4-dichlorothiazol-5-yl)acrylate (Preparation example 380), to obtain the title compound (6.0 g, 60~80%).

¹H NMR (400 MHz, CDCl₃) δ 1.34 (t, J=7.2 Hz, 3H), 4.26 (q, J=7.2 Hz, 2H), 4.65 (d, J=5.5 Hz, 1H), 5.13 (d, J=5.5 Hz, 1H), 6.93 (dd, J=1.32, 6.09 Hz, 1H), 7.47 (dd, J=1.73, 6.09 Hz, 1H), 7.88 (dd, J=1.32, 1.73 Hz, 1H).

Preparation Example 405: (4R,5S)-ethyl 2,2-dimethyl-5-(thiophen-3-yl)-1,3-dioxolane-4-carboxylate

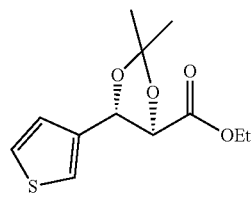 [SMILES: CCOC(=O)[C@@H]1OC(C)(C)O[C@H]1c1ccsc1]

The substantially same method as described in Preparation Example 382 was conducted, except that (2R,3S)-ethyl 2,3-dihydroxy-3-(thiophen-3-yl)propanoate (Preparation example 404) was used instead of (2S,3S)-ethyl 3-(2,4-dichlorothiazol-5-yl)-2,3-dihydroxypropanoate (Preparation example 381), to obtain the title compound (3.0 g, 65~80%).

¹H NMR (400 MHz, CDCl₃) δ 1.18 (t, J=7.1 Hz, 3H), 1.41 (S, 3H), 1.43 (S, 3H), 4.16 (q, J=7.1 Hz, 2H), 4.21 (d, J=7.0 Hz, 1H), 4.94 (d, J=7.0 Hz, 1H), 6.95 (dd, J=1.3, 6.0 Hz, 1H), 7.48 (dd. J=1.7, 6.0 Hz, 1H), 7.90 (dd, J=1.3, 1.7 Hz, 1H).

Preparation Example 406: ((4S,5S)-2,2-dimethyl-5-(thiophen-3-yl)-1,3-dioxolan-4-yl)methanol

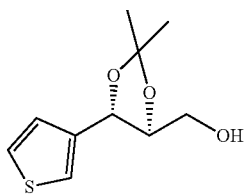

The substantially same method as described in Preparation Example 386 was conducted, except that (4R,5R)-ethyl 2,2-dimethyl-5-(thiophen-3-yl)-1,3-dioxolane-4-carboxylate (Preparation example 405) was used instead of (4R,5R)-ethyl-5-(2,4-dichlorothiazol-5-yl)-2,2-dimethyl-1,3-dioxolane-4-carboxylate (Preparation example 385), to obtain the title compound (2.2 g, 70~90%).

¹H NMR (400 MHz, CDCl₃) δ 1.39 (S, 3H), 1.42 (S, 3H), 3.47~3.6 (m, 2H), 3.84~3.88 (m, 1H) 4.82 (d, J=7.0 Hz, 1H), 6.93 (dd, J=1.3, 6.1 Hz, 1H), 7.47 (dd. J=1.7, 6.1 Hz, 1H), 7.89 (dd, J=1.3, 1.7 Hz, 1H).

Preparation Example 407: (E)-ethyl 3-(5-chlorothiophen-2-yl)acrylate

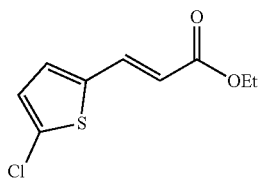 [SMILES: CCOC(=O)/C=C/c1ccc(Cl)s1]

The substantially same method as described in Preparation Example 403 was conducted, except that 5-chlorothiophene-2-carbaldehyde was used instead of thiophene-3-carbaldehyde, to obtain the title compound (4.0 g, 70~90%).

¹H NMR (400 MHz, CDCl₃) δ 1.36 (t, J=7.2 Hz, 3H), 4.20 (q, J=7.2 Hz, 2H), 6.13 (d, J=15.6 Hz, 1H), 6.89 (d, J=4.0 Hz, 1H), 7.65 (d, J=15.6 Hz, 1H), 7.83 (d, J=4.2 Hz, 1H).

Preparation Example 408: (2R,3S)-ethyl 2,3-dihydroxy-3-(5-chlorothiophen-2-yl)propanoate

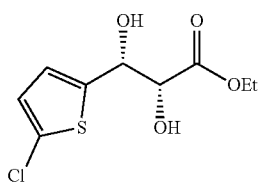 [SMILES: CCOC(=O)[C@H](O)[C@@H](O)c1ccc(Cl)s1]

The substantially same method as described in Preparation Example 404 was conducted, except that (E)-ethyl 3-(5-chlorothiophen-2-yl)acrylate (Preparation example 407) was used instead of (E)-ethyl 3-(thiophen-3-yl)acrylate (Preparation example 403), to obtain the title compound (2.8 g, 60~80%).

¹H NMR (400 MHz, CDCl₃) δ 1.34 (t, J=7.2 Hz, 3H), 2.76 (d, J=8.4 Hz, 1H), 3.32 (d, J=5.6 Hz, 1H), 4.33 (q, J=7.2 Hz, 2H), 4.4 (dd, J=2.4, 5.2 Hz, 1H), 5.16 (dd, J=2.0, 8.0 Hz, 1H), 6.82 (d, J=4.0 Hz, 1H), 6.88 (dd, J=0.8, 3.6 Hz, 1H).

Preparation Example 409: (4R,5S)-ethyl 2,2-dimethyl-5-(5-chlorothiophen-2-yl)-1,3-dioxolane-4-carboxylate

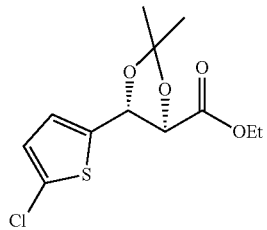 [SMILES: CCOC(=O)[C@@H]1OC(C)(C)O[C@H]1c1ccc(Cl)s1]

The substantially same method as described in Preparation Example 405 was conducted, except that (2R,3S)-ethyl 2,3-dihydroxy-3-(5-chlorothiophen-2-yl)propanoate (Preparation example 408) was used instead of (2R,3S)-ethyl 2,3-dihydroxy-3-(thiophen-3-yl)propanoate (Preparation example 404), to obtain the title compound (0.85 g, 65~80%).

¹H NMR (400 MHz, CDCl₃) δ 1.31 (t, J=7.2 Hz, 3H), 1.54 (s, 3H), 1.58 (s, 3H), 4.29~4.36 (m, 2H), 4.42 (d, J=7.2 Hz, 1H), 5.29 (d, J=7.2 Hz, 1H), 6.81 (q, J=4.0 Hz, 1H), 6.88 (d, J=3.2 Hz, 1H).

Preparation Example 410: ((4S,5S)-2,2-dimethyl-5-(5-chlorothiophen-2-yl)-1,3-dioxolan-4-yl)methanol

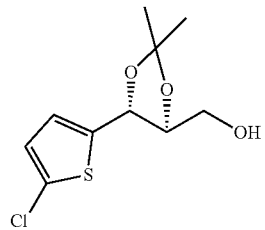

The substantially same method as described in Preparation Example 406 was conducted, except that (4R,5R)-ethyl 2,2-dimethyl-5-(5-chlorothiophen-2-yl)-1,3-dioxolane-4-carboxylate (Preparation example 409) was used instead of (4R,5R)-ethyl 2,2-dimethyl-5-(thiophen-3-yl)-1,3-dioxolane-4-carboxylate (Preparation example 405), to obtain the title compound (0.8 g, 70~90%).

¹H NMR (400 MHz, CDCl₃) δ 1.39 (S, 3H), 1.42 (S, 3H), 3.54~3.79 (m, 2H), 4.28~4.42 (m, 1H), 5.17 (d, J=7.2 Hz, 1H), 6.47 (d, J=6.1 Hz, 1H), 6.51 (d, J=6.1 Hz, 1H).

Preparation Example 411: 3-chloroisonicotinaldehyde

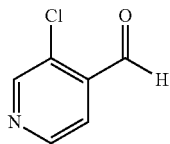

To a 250 mL round-bottomed flask, LDA (11 mL, 22.02 mmol) was added to 3-chloropyridine (1.0 g, 8.80 mmol) in THF (20 mL) dropwise at −78° C. and stirred at same temperature for 1~2 hr. Then DMF (822 μL, 10.56 mmol) was added and stirred at room temperature for 1 hr. EA (Ethyl acetate) and water were added to the reaction mixture, and after the separation of the layers, the aqueous phase was further extracted with the organic solvent. The combined organic extracts were dried over anhydrous Sodium sulfate ($Na_2SO_4$), filtered and concentrated under vacuum. The crude compound was purified by a silica gel column to produce the title compound (0.33 g, 30~65%).

$^1$H NMR (400 MHz, $CDCl_3$) δ 7.73 (d, J=8.0 Hz, 1H), 8.71 (d, J=4.0 Hz, 1H), 8.81 (s, 1H), 10.52 (s, 1H).

Preparation Example 412: (E)-ethyl 3-(3-chloropyridin-4-yl)acrylate

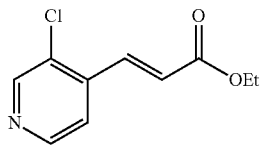 [SMILES: CCOC(=O)/C=C/c1ccncc1Cl]

3-chloroisonicotinaldehyde (Preparation example 411, 0.54 g, 3.79 mmol) was dissolved in benzene. At the room temperature, triethyl phosphoacetate (753 μL, 3.79 mmol) and potassium tert-butoxide (468 mg, 4.17 mmol) were added and stirred. When the reaction was completed, the obtained product was washed with water and ethylacetate (EA). Then, the organic layer was dehydrated with anhydrous magnesium sulfate ($MgSO_4$), filtrated, and concentrated under reduced pressure. The crude compound was purified by a silica gel column to produce the title compound (0.57 g, 70~90%).

$^1$H NMR (400 MHz, $CDCl_3$) δ 1.40 (t, J=12.0 Hz, 3H), 4.13 (q, J=6.6 Hz, 2H), 6.61 (d, J=16.0 Hz, 1H), 7.46 (d, J=16.0 Hz, 1H), 7.97 (d, J=8.0 Hz, 1H), 8.51 (d, J=4.0 Hz, 1H), 8.66 (s, 1H).

Preparation Example 413: Ethyl 3-(3-chloropyridin-4-yl)-2,3-dihydroxypropanoate

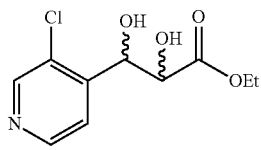 [SMILES: CCOC(=O)C(O)C(O)c1ccncc1Cl]

(E)-ethyl 3-(3-chloropyridin-4-yl)acrylate (Preparation example 412, 0.57 g, 2.69 mmol) was dissolved in the mixture of acetone (11.4 mL)/water (2.3 mL)/t-BuOH (2.3 mL). NMO (0.47 g, 4.03 mmol). Osmium tetroxide (13.6 mg, 0.05 mmol) were added thereto and stirred at 40° C. When the reaction was completed, the obtained product was washed with water and ethylacetate (EA). Then, the organic layer was dehydrated with anhydrous magnesium sulfate ($MgSO_4$), filtrated, and concentrated under reduced pressure. The crude compound was purified by a silica gel column to produce the title compound (0.44 g, 60~80%).

$^1$H NMR (400 MHz, $CDCl_3$) δ 1.28 (t, J=12.0 Hz, 3H), 4.15 (q, J=6.6 Hz, 2H), 4.26 (d, J=4.0 Hz, 1H), 5.24 (d, J=4.0 Hz, 1H), 5.44 (br, s, 1H), 5.98 (br, s, 1H), 7.59 (d, J=8.0 Hz, 1H), 8.52 (d, J=4.0 Hz, 1H), 8.56 (s, 1H).

Preparation Example 414: Ethyl 5-(3-chloropyridin-4-yl)-2,2-dimethyl-1,3-dioxolane-4-carboxylate

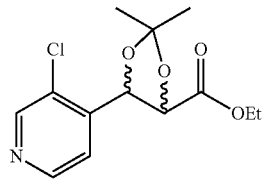 [SMILES: CCOC(=O)C1OC(C)(C)OC1c1ccncc1Cl]

The substantially same method as described in Preparation Example 405 was conducted, except that Ethyl 3-(3-chloropyridin-4-yl)-2,3-dihydroxypropanoate (Preparation example 413) was used instead of (2R,3S)-ethyl 2,3-dihydroxy-3-(thiophen-3-yl)propanoate (Preparation example 404), to obtain the title compound (5.26 g, 70~90%).

$^1$H NMR (400 MHz, $CDCl_3$) δ 1.28 (t, J=12.0 Hz, 3H), 1.61 (s, 3H), 1.65 (s, 3H), 4.23 (q, J=6.0 Hz, 2H) 4.38 (d, J=7.2 Hz, 1H), 5.67 (d, J=8.0 Hz, 1H), 7.55 (d, J=8.0 Hz, 1H), 8.56 (d, J=4.0 Hz, 1H), 8.57 (s, 1H).

Preparation Example 415: (5-(3-chloropyridin-4-yl)-2,2-dimethyl-1,3-dioxolan-4-yl)methanol

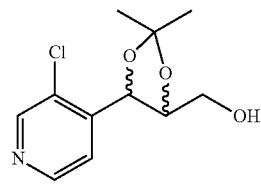 [SMILES: CC1(C)OC(CO)C(c2ccncc2Cl)O1]

The substantially same method as described in Preparation Example 406 was conducted, except that Ethyl 5-(3-chloropyridin-4-yl)-2,2-dimethyl-1,3-dioxolane-4-carboxylate (Preparation example 414) was used instead of (4R,5R)-ethyl 2,2-dimethyl-5-(thiophen-3-yl)-1,3-dioxolane-4-carboxylate (Preparation example 405), to obtain the title compound (0.18 g, 70~90%).

$^1$H NMR (400 MHz, $CDCl_3$) δ 1.56 (s, 3H), 1.59 (s, 3H), 3.79~3.67 (m, 1H), 3.85 (dd, J=6.0, 8.0 Hz, 1H), 4.06~3.90 (m, 1H), 4.14 (dd, J=6.0, 8.0 Hz, 1H), 5.37 (d, J=8.0 Hz, 1H), 7.57 (d, J=6.0 Hz, 1H), 8.57 (d, J=12.0 Hz, 2H).

Preparation Example 416: 4-chloroisonicotinaldehyde

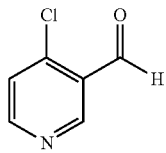

The substantially same method as described in Preparation Example 411 was conducted, except that Ethyl 4-chloropyridine was used instead of 3-chloropyridine, to obtain the title compound (3.0 g, 60~80%).

$^1$H NMR (400 MHz, CDCl$_3$) δ 7.45 (d, J=5.2 Hz, 1H), 8.70 (d, J=5.2 Hz, 1H), 9.06 (s, 1H), 10.52 (s, 1H).

Preparation Example 417: (E)-ethyl 3-(4-chloropyridin-3-yl)acrylate

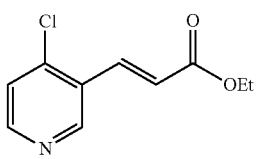 [SMILES: CCOC(=O)/C=C/c1cnccc1Cl]

The substantially same method as described in Preparation Example 412 was conducted, except that Ethyl 4-chloronicotinaldehyde (Preparation example 416) was used instead of 3-chloroisonicotinaldehyde (Preparation example 411), to obtain the title compound (4.0 g, 70~90%).

$^1$H NMR (400 MHz, CDCl$_3$) δ 1.37 (t, J=7.0 Hz, 3H), 4.33 (q, J=6.6 Hz, 2H), 6.57 (d, J=16.4 Hz, 1H), 7.39 (d, J=5.2 Hz, 1H), 7.98 (d, J=16.0 Hz, 1H), 8.49 (d, J=5.2 Hz, 1H), 8.82 (s, 1H).

Preparation Example 418: Ethyl 3-(4-chloropyridin-3-yl)-2,3-dihydroxypropanoate

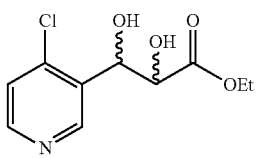 [SMILES: CCOC(=O)C(O)C(O)c1cnccc1Cl]

The substantially same method as described in Preparation Example 413 was conducted, except that (E)-ethyl 3-(4-chloropyridin-3-yl)acrylate (Preparation example 417) was used instead of (E)-ethyl 3-(3-chloropyridin-4-yl)acrylate (Preparation example 412), to obtain the title compound (2.4 g, 60~80%).

$^1$H NMR (400 MHz, CDCl$_3$) δ 1.34 (t, J=7.2 Hz, 3H), 4.35 (q, J=7.0 Hz, 2H), 4.45 (d, J=2.4 Hz, 1H), 5.49 (d, J=2.0 Hz, 1H), 7.32 (d, J=5.2 Hz, 1H), 8.46 (d, J=4.4 Hz, 1H), 8.79 (s, 1H).

Preparation Example 419: Ethyl 5-(4-chloropyridin-3-yl)-2,2-dimethyl-1,3-dioxolane-4-carboxylate

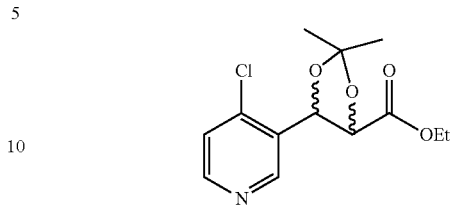

The substantially same method as described in Preparation Example 414 was conducted, except that Ethyl 3-(4-chloropyridin-3-yl)-2,3-dihydroxypropanoate (Preparation example 418) was used instead of Ethyl 3-(3-chloropyridin-4-yl)-2,3-dihydroxypropanoate (Preparation example 413), to obtain the title compound (1.3 g, 70~90%).

$^1$H NMR (400 MHz, CDCl$_3$) δ 1.25 (t, J=7.2 Hz, 3H), 1.59 (s, 3H), 1.64 (s, 3H), 4.22 (q, J=8.27 Hz, 2H), 4.37 (d, J=7.6 Hz, 1H), 5.56 (d, J=7.6 Hz, 1H), 7.31 (d, J=5.2 Hz, 1H), 8.48 (d, J=5.2 Hz, 1H), 8.78 (s, 1H).

Preparation Example 420: (5-(4-chloropyridin-3-yl)-2,2-dimethyl-1,3-dioxolan-4-yl)methanol

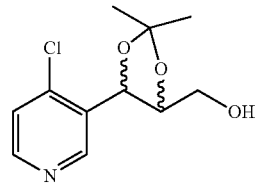 [SMILES: CC1(C)OC(CO)C(c2cnccc2Cl)O1]

The substantially same method as described in Preparation Example 415 was conducted, except that Ethyl 5-(4-chloropyridin-3-yl)-2,2-dimethyl-1,3-dioxolane-4-carboxylate (Preparation example 419) was used instead of Ethyl 5-(3-chloropyridin-4-yl)-2,2-dimethyl-1,3-dioxolane-4-carboxylate (Preparation example 414), to obtain the title compound (0.8 g, 70~90%).

$^1$H NMR (400 MHz, CDCl$_3$) δ 1.56 (s, 3H), 1.63 (s, 3H), 1.64 (s, 3H), 3.73~3.77 (m, 1H), 3.95~3.99 (m, 2H), 5.39 (d, J=8.4 Hz, 1H), 7.32 (d, J=5.6 Hz, 1H), 8.46 (d, J=5.2 Hz, 1H), 8.82 (s, 1H).

Preparation Example 421: (E)-ethyl 3-(pyrimidin-5-yl)acrylate

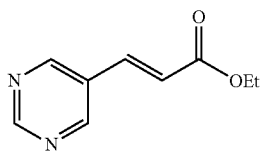 [SMILES: CCOC(=O)/C=C/c1cncnc1]

5-bromopyrimidine (5.0 g, 31.4 mmol) in DMF (75 mL) was added ethyl acrylate (9.5 mL, 94.4 mmol) at room temperature. Diisopropylamine (7.5 mL, 42.8 mmol), trimethyl phosphate (0.19 mL, 1.6 mmol), Pd(Pac)$_2$ (0.18 g, 0.78 mmol) were added. The reaction mixture was heated at 110°

C. for 2 hr. The reaction mixture was cooled to room temperature and quenched with H₂O then extracted with EA (Ethyl acetate). The aqueous layer was extracted with EA and separated. The combined organic layer was washed with H₂O, then dried over anhydrous magnesium sulfate (MgSO₄) and evaporated under reduced. The crude compound was purified by a silica gel column to produce the title compound (3.9 g, 70~90%).

¹H NMR (400 MHz, CDCl₃) δ 1.38 (t, J=6.8 Hz, 3H), 4.29~4.35 (m, 1H), 6.61 (d, J=17.2 Hz, 1H), 7.63 (d, J=16.4 Hz, 1H), 8.90 (s, 2H), 9.22 (s, 1H).

Preparation Example 422: Ethyl 3-(pyrimidin-5-yl)-2,3-dihydroxypropanoate

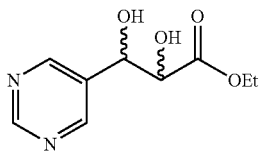 [SMILES: CCOC(=O)C(O)C(O)c1cncnc1]

The substantially same method as described in Preparation Example 418 was conducted, except that (E)-ethyl 3-(pyrimidin-5-yl)acrylate (Preparation example 421) was used instead of (E)-ethyl 3-(4-chloropyridin-3-yl)acrylate (Preparation example 417), to obtain the title compound (1.6 g, 40~60%).

¹H NMR (400 MHz, CDCl₃) δ 1.07~1.39 (m, 3H), 4.16~4.34 (m, 2H), 4.39 (s, 1H), 4.69 (s, 1H), 5.04 (s, 1H), 5.10 (s, 1H), 8.98 (s, 2H), 9.01 (s, 1H).

Preparation Example 423: Ethyl 2,2-dimethyl-5-(pyrimidin-5-yl)-1,3-dioxolane-4-carboxylate

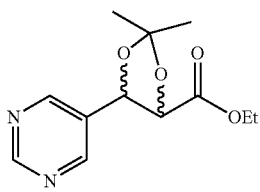 [SMILES: CCOC(=O)C1OC(C)(C)OC1c1cncnc1]

The substantially same method as described in Preparation Example 419 was conducted, except that Ethyl 3-(pyrimidin-5-yl)-2,3-dihydroxypropanoate (Preparation example 422) was used instead of Ethyl 3-(4-chloropyridin-3-yl)-2,3-dihydroxypropanoate (Preparation example 418), to obtain the title compound (0.97 g, 40~60%).

¹H NMR (400 MHz, CDCl₃) δ 1.30 (t, J=7.2 Hz, 3H), 1.55 (s, 3H), 1.61 (s, 3H), 4.25~4.32 (m, 1H), 4.35 (d, J=8.0 Hz, 1H), 5.18 (d, J=7.6 Hz, 1H), 8.82 (s, 2H), 9.20 (s, 1H).

Preparation Example 424: (2,2-dimethyl-5-(pyrimidin-5-yl)-1,3-dioxolan-4-yl)methanol

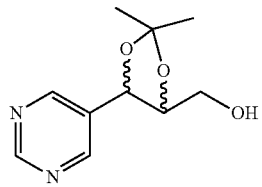

The substantially same method as described in Preparation Example 420 was conducted, except that Ethyl 2,2-dimethyl-5-(pyrimidin-5-yl)-1,3-dioxolane-4-carboxylate (Preparation example 423) was used instead of Ethyl 5-(4-chloropyridin-3-yl)-2,2-dimethyl-1,3-dioxolane-4-carboxylate (Preparation example 419), to obtain the title compound (0.65 g, 70~90%).

¹H NMR (400 MHz, CDCl₃) δ 1.53 (s, 3H), 1.56 (s, 3H), 2.75 (s, —OH), 3.68~3.73 (m, 1H), 3.69~3.64 (m, 1H), 3.89~3.93 (m, 2H), 5.0 (d, J=8.4 Hz, 1H), 8.79 (s, 2H), 9.18 (s, 1H).

Preparation Example 425: (E)-ethyl 3-(2-chloropyrimidin-5-yl)acrylate

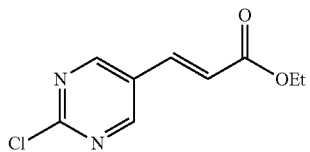 [SMILES: CCOC(=O)/C=C/c1cnc(Cl)nc1]

The substantially same method as described in Preparation Example 421 was conducted, except that 2-chloro-5-bromopyrimidine was used instead of 5-bromopyrimidine, to obtain the title compound (9.7 g, 50~70%).

¹H NMR (400 MHz, CDCl₃) δ 1.37 (t, J=6.8 Hz, 3H), 4.32 (qt, J=7.2 Hz, 2H), 6.59 (d, J=16.4 Hz, 1H), 7.60 (d, J=16.4 Hz, 1H), 8.77 (s, 2H).

Preparation Example 426: Ethyl 3-(2-chloropyrimidin-5-yl)-2,3-dihydroxypropanoate

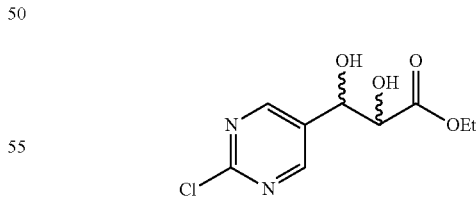

The substantially same method as described in Preparation Example 422 was conducted, except that (E)-ethyl 3-(2-chloropyrimidin-5-yl)acrylate (Preparation example 425) was used instead of (E)-ethyl 3-(pyrimidin-5-yl)acrylate (Preparation example 421), to obtain the title compound (2.1 g, 40~60%).

¹H NMR (400 MHz, CDCl₃) δ 1.33~1.37 (m, 3H), 2.97 (d, J=7.2 Hz, 1H), 3.31 (d, J=18.4 Hz, 1H), 4.34~4.55 (m, 3H), 5.10 (d, J=7.2 Hz, 1H), 8.72 (s, 2H).

Preparation Example 427: Ethyl 2,2-dimethyl-5-(2-chloropyrimidin-5-yl)-1,3-dioxolane-4-carboxylate

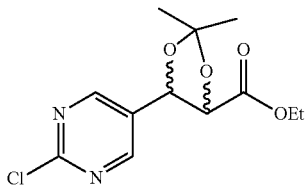 [SMILES: CCOC(=O)C1OC(C)(C)OC1c1cnc(Cl)nc1]

The substantially same method as described in Preparation Example 423 was conducted, except that Ethyl 3-(2-chloropyrimidin-5-yl)-2,3-dihydroxypropanoate (Preparation example 426) was used instead of Ethyl 3-(pyrimidin-5-yl)-2,3-dihydroxypropanoate (Preparation example 422), to obtain the title compound (0.98 g, 40~60%).

$^1$H NMR (400 MHz, CDCl$_3$) δ 1.32 (t, J=7.2 Hz, 3H), 1.55 (s, 3H), 1.60 (s, 3H), 4.27~4.34 (m, 3H), 5.19 (d, J=7.6 Hz, 1H), 8.71 (s, 2H).

Preparation Example 428: (2,2-dimethyl-5-(2-chloropyrimidin-5-yl)-1,3-dioxolan-4-yl)methanol

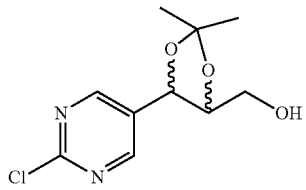 [SMILES: CC1(C)OC(CO)C(c2cnc(Cl)nc2)O1]

The substantially same method as described in Preparation Example 424 was conducted, except that Ethyl 2,2-dimethyl-5-(2-chloropyrimidin-5-yl)-1,3-dioxolane-4-carboxylate (Preparation example 427) was used instead of Ethyl 2,2-dimethyl-5-(pyrimidin-5-yl)-1,3-dioxolane-4-carboxylate (Preparation example 423), to obtain the title compound (0.71 g, 70~90%).

$^1$H NMR (400 MHz, CDCl$_3$) δ 1.54 (s, 3H), 1.56 (s, 3H), 2.21 (s, —OH), 3.71~3.76 (m, 1H), 3.69~3.64 (m, 1H), 3.88~3.96 (m, 2H), 5.02 (d, J=8.0 Hz, 1H), 8.68 (s, 2H).

Preparation Example 429: (1R,2S)-3-(benzyloxy)-1-(2-chlorophenyl)-1-hydroxypropan-2-yl acetate

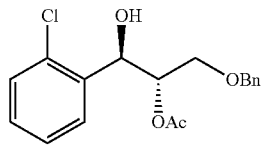 [SMILES: CC(=O)O[C@@H](COCc1ccccc1)[C@H](O)c1ccccc1Cl]

A regioisomer of acetate was separated and purified by conducting the silica gel column chromatography as described in Preparation example 376, to obtain the title compound (0.42 g, 10~30%).

$^1$H NMR (400 MHz, CDCl$_3$) δ 2.09 (s, 3H), 3.63~3.70 (m, 2H), 4.47~4.61 (m, 2H), 5.29~5.33 (m, 1H), 5.41 (t, J=5.0 Hz, 1H), 7.22~7.55 (m, 9H).

Preparation Example 430: (1R,2S)-3-(benzyloxy)-1-(2-chlorophenyl)propane-1,2-diol

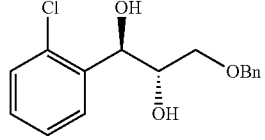 [SMILES: O[C@H](c1ccccc1Cl)[C@@H](O)COCc1ccccc1]

The substantially same method as described in Preparation Example 377 was conducted, except that (1R,2S)-3-(benzyloxy)-1-(2-chlorophenyl)-1-hydroxypropan-2-yl acetate (Preparation example 429) was used instead of (1S,2R)-3-(benzyloxy)-1-(2-chlorophenyl)-2-hydroxypropyl acetate (Preparation example 376), to obtain the title compound (0.31 g, 80~95%).

$^1$H NMR (400 MHz, CDCl$_3$) δ 3.02 (d, J=5.2 Hz, 1H), 3.55~3.42 (m, 3H, —OH), 4.18~4.13 (m, 1H), 4.46 (d, J=6.0 Hz, 2H), 5.28 (t, J=4.8 Hz, 1H), 7.35~7.19 (m, 8H), 7.50 (dd, J=1.2, 7.6 Hz, 1H).

Preparation Example 431: (4S,5R)-4-(benzyloxymethyl)-5-(2-chlorophenyl)-2,2-dimethyl-1,3-dioxolane

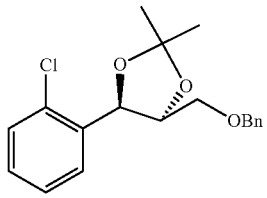 [SMILES: CC1(C)O[C@@H](COCc2ccccc2)[C@@H](c2ccccc2Cl)O1]

The substantially same method as described in Preparation example 373 was conducted, except that (1R,2S)-3-(benzyloxy)-1-(2-chlorophenyl)propane-1,2-diol (Preparation example 430) was used instead of that (±)-3-(benzyloxy)-1-(2-chlorophenyl)propane-1,2-diol (Preparation example 372), to obtain the title compound (0.84 g, 80~100%).

$^1$H NMR (400 MHz, CDCl$_3$) δ 1.53 (s, 3H), 1.66 (s, 3H), 3.14~3.06 (m, 2H), 4.26 (d, J=12.0 Hz, 2H), 4.83~4.78 (m, 1H), 5.63 (d, J=6.8 Hz, 1H), 7.35~7.16 (m, 8H), 7.61 (dd, J=1.6, 7.4 Hz, 1H).

Preparation Example 432: ((4S,5R)-5-(2-chlorophenyl)-2,2-dimethyl-1,3-dioxolan-4-yl)methanol

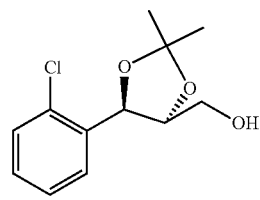 [SMILES: CC1(C)O[C@@H](CO)[C@@H](c2ccccc2Cl)O1]

The substantially same method as described in Preparation example 374 was conducted, except that ((4S,5R)-4-(benzyloxymethyl)-5-(2-chlorophenyl)-2,2-dimethyl-1,3-dioxolane (Preparation example 431) was used instead of that (±)-4-(benzyloxymethyl)-5-(2-chlorophenyl)-2,2-dimethyl-1,3-dioxolane (Preparation example 373), to obtain the title compound (0.82 g, 80~100%).

$^1$H NMR (400 MHz, CDCl$_3$) δ 1.66 (s, 3H), 1.53 (s, 3H), 3.14~3.06 (m, 2H), 4.26 (d, J=12.0 Hz, 2H), 4.83~4.78 (m, 1H), 5.63 (d, J=6.8 Hz, 1H), 7.35~7.16 (m, 8H), 7.61 (dd, J=1.6, 7.4 Hz, 1H).

Preparation Example 433: (2S,3R)-methyl-3-(2-chlorophenyl)-2,3-dihydroxypropanoate

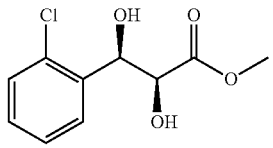

The substantially same method as described in Preparation example 3 was conducted, except that (E)-methyl-3-(2-chlorophenyl)acrylate (Preparation example 24) was used instead of that (E)-1-chloro-2-(3-(methoxymethoxy)prop-1-enyl)benzene (Preparation example 2), to obtain the title compound (14.2 g, 70~90%).

$^1$H NMR (400 MHz, CDCl$_3$) δ 2.79 (d, J=7.2 Hz, 1H), 3.13 (d, J=6.0 Hz, 1H), 3.86 (s, 3H), 4.50 (dd, J=2.4, 5.6 Hz, 1H), 5.51 (dd, J=2.4, 7.2 Hz, 1H), 7.62~7.26 (m, 4H).

TABLE 1

| | Example of sulfamate compound (A = Phenyl) | | | | | | | | |
|---|---|---|---|---|---|---|---|---|---|
| No | A = Phenyl | n | l | m | R$^1$ | R$^2$ | R$^3$ | R$^4$ | Chiral-1 | Chiral-2 |
| 1 | 2-Cl | 1 | 0 | 0 | Me | Me | H | H | R | R |
| 2 | 2-Cl | 1 | 0 | 0 | Me | Me | H | H | S | S |
| 3 | 2-Cl | 1 | 0 | 0 | Me | Me | H | H | Rac.(syn) | Rac.(syn) |
| 4 | 2-Cl | 1 | 0 | 0 | Me | Me | H | H | Rac.(anti) | Rac.(anti) |
| 5 | 2-Cl | 1 | 0 | 0 | Me | H | H | H | R | R |
| 6 | 2-Cl | 1 | 0 | 0 | Me | H | H | H | S | S |
| 7 | 2-Cl | 1 | 0 | 0 | Et | Et | H | H | R | R |
| 8 | 2-Cl | 1 | 0 | 0 | Et | Et | H | H | S | S |
| 9 | 2-Cl | 1 | 0 | 0 | Cyclopentyl | | H | H | R | R |
| 10 | 2-Cl | 1 | 0 | 0 | Cyclopentyl | | H | H | S | S |
| 11 | 2-Cl | 1 | 0 | 0 | Cyclohexyl | | H | H | R | R |
| 12 | 2-Cl | 1 | 0 | 0 | Cyclohexyl | | H | H | S | S |
| 13 | 2-Cl | 1 | 0 | 0 | Methylbenzene | | H | H | R | R |
| 14 | 2-Cl | 1 | 0 | 0 | Methylbenzene | | H | H | S | S |
| 15 | 2-F | 1 | 0 | 0 | Me | Me | H | H | R | R |
| 16 | 2-F | 1 | 0 | 0 | Me | Me | H | H | S | S |
| 17 | 2-F | 1 | 0 | 0 | Me | H | H | H | R | R |
| 18 | 2-F | 1 | 0 | 0 | Me | H | H | H | S | S |
| 19 | 2-F | 1 | 0 | 0 | Et | Et | H | H | R | R |
| 20 | 2-F | 1 | 0 | 0 | Et | Et | H | H | S | S |
| 21 | 2-F | 1 | 0 | 0 | Cyclopentyl | | H | H | R | R |
| 22 | 2-F | 1 | 0 | 0 | Cyclopentyl | | H | H | S | S |
| 23 | 2-F | 1 | 0 | 0 | Cyclohexyl | | H | H | R | R |
| 24 | 2-F | 1 | 0 | 0 | Cyclohexyl | | H | H | S | S |
| 25 | 2-F | 1 | 0 | 0 | Methylbenzene | | H | H | R | R |
| 26 | 2-F | 1 | 0 | 0 | Methylbenzene | | H | H | S | S |
| 27 | 2-I | 1 | 0 | 0 | Me | Me | H | H | R | R |
| 28 | 2-I | 1 | 0 | 0 | Me | Me | H | H | S | S |
| 29 | 2-I | 1 | 0 | 0 | Me | H | H | H | R | R |
| 30 | 2-I | 1 | 0 | 0 | Me | H | H | H | S | S |
| 31 | 2-I | 1 | 0 | 0 | Et | Et | H | H | R | R |
| 32 | 2-I | 1 | 0 | 0 | Et | Et | H | H | S | S |
| 33 | 2-I | 1 | 0 | 0 | Cyclopentyl | | H | H | R | R |
| 34 | 2-I | 1 | 0 | 0 | Cyclopentyl | | H | H | S | S |
| 35 | 2-I | 1 | 0 | 0 | Cyclohexyl | | H | H | R | R |
| 36 | 2-I | 1 | 0 | 0 | Cyclohexyl | | H | H | S | S |
| 37 | 2-I | 1 | 0 | 0 | Methylbenzene | | H | H | R | R |
| 38 | 2-I | 1 | 0 | 0 | Methylbenzene | | H | H | S | S |
| 39 | 2,4-Cl | 2 | 0 | 0 | Me | Me | H | H | R | R |
| 40 | 2,4-Cl | 2 | 0 | 0 | Me | Me | H | H | S | S |
| 41 | 2,4-Cl | 2 | 0 | 0 | Me | H | H | H | R | R |
| 42 | 2,4-Cl | 2 | 0 | 0 | Me | H | H | H | S | S |
| 43 | 2,4-Cl | 2 | 0 | 0 | Et | Et | H | H | R | R |
| 44 | 2,4-Cl | 2 | 0 | 0 | Et | Et | H | H | S | S |
| 45 | 2,4-Cl | 2 | 0 | 0 | Cyclopentyl | | H | H | R | R |
| 46 | 2,4-Cl | 2 | 0 | 0 | Cyclopentyl | | H | H | S | S |
| 47 | 2,4-Cl | 2 | 0 | 0 | Cyclohexyl | | H | H | R | R |
| 48 | 2,4-Cl | 2 | 0 | 0 | Cyclohexyl | | H | H | S | S |
| 49 | 2,4-Cl | 2 | 0 | 0 | Methylbenzene | | H | H | R | R |
| 50 | 2,4-Cl | 2 | 0 | 0 | Methylbenzene | | H | H | S | S |
| 51 | 2,6-Cl | 2 | 0 | 0 | Me | Me | H | H | R | R |
| 52 | 2,6-Cl | 2 | 0 | 0 | Me | Me | H | H | S | S |
| 53 | 2,6-Cl | 2 | 0 | 0 | Me | H | H | H | R | R |
| 54 | 2,6-Cl | 2 | 0 | 0 | Me | H | H | H | S | S |
| 55 | 2,6-Cl | 2 | 0 | 0 | Et | Et | H | H | R | R |
| 56 | 2,6-Cl | 2 | 0 | 0 | Et | Et | H | H | S | S |
| 57 | 2,6-Cl | 2 | 0 | 0 | Cyclopentyl | | H | H | R | R |
| 58 | 2,6-Cl | 2 | 0 | 0 | Cyclopentyl | | H | H | S | S |
| 59 | 2,6-Cl | 2 | 0 | 0 | Cyclohexyl | | H | H | R | R |

TABLE 1-continued

| | Example of sulfamate compound (A = Phenyl) | | | | | | | | | |
|---|---|---|---|---|---|---|---|---|---|---|
| No | A = Phenyl | n | l | m | $R^1$ | $R^2$ | $R^3$ | $R^4$ | Chiral-1 | Chiral-2 |
| 60 | 2,6-Cl | 2 | 0 | 0 | Cyclohexyl | H | H | H | S | S |
| 61 | 2,6-Cl | 2 | 0 | 0 | Methylbenzene | H | H | H | R | R |
| 62 | 2,6-Cl | 2 | 0 | 0 | Methylbenzene | H | H | H | S | S |
| 63 | 2-NH2 | 1 | 0 | 0 | Me | Me | H | H | R | R |
| 64 | 2-NH2 | 1 | 0 | 0 | Me | Me | H | H | S | S |
| 65* | 2-NH2 | 1 | 0 | 0 | Me | Me | H | H | R | R |
| 66* | 2-NH2 | 1 | 0 | 0 | Me | Me | H | H | S | S |
| 67 | 2-NH2 | 1 | 0 | 0 | Me | H | H | H | R | R |
| 68 | 2-NH2 | 1 | 0 | 0 | Me | H | H | H | S | S |
| 69 | 2-NH2 | 1 | 0 | 0 | Et | Et | H | H | R | R |
| 70 | 2-NH2 | 1 | 0 | 0 | Et | Et | H | H | S | S |
| 71 | 2-NH2 | 1 | 0 | 0 | Cyclopentyl | H | H | H | R | R |
| 72 | 2-NH2 | 1 | 0 | 0 | Cyclopentyl | H | H | H | S | S |
| 73 | 2-NH2 | 1 | 0 | 0 | Cyclohexyl | H | H | H | R | R |
| 74 | 2-NH2 | 1 | 0 | 0 | Cyclohexyl | H | H | H | S | S |
| 75 | 2-NH2 | 1 | 0 | 0 | Methylbenzene | H | H | H | R | R |
| 76 | 2-NH2 | 1 | 0 | 0 | Methylbenzene | H | H | H | S | S |
| 77 | 2-NO2 | 1 | 0 | 0 | Me | Me | H | H | R | R |
| 78 | 2-NO2 | 1 | 0 | 0 | Me | Me | H | H | S | S |
| 79 | 2-NO2 | 1 | 0 | 0 | Me | H | H | H | R | R |
| 80 | 2-NO2 | 1 | 0 | 0 | Me | H | H | H | S | S |
| 81 | 2-NO2 | 1 | 0 | 0 | Et | Et | H | H | R | R |
| 82 | 2-NO2 | 1 | 0 | 0 | Et | Et | H | H | S | S |
| 83 | 2-NO2 | 1 | 0 | 0 | Cyclopentyl | H | H | H | R | R |
| 84 | 2-NO2 | 1 | 0 | 0 | Cyclopentyl | H | H | H | S | S |
| 85 | 2-NO2 | 1 | 0 | 0 | Cyclohexyl | H | H | H | R | R |
| 86 | 2-NO2 | 1 | 0 | 0 | Cyclohexyl | H | H | H | S | S |
| 87 | 2-NO2 | 1 | 0 | 0 | Methylbenzene | H | H | H | R | R |
| 88 | 2-NO2 | 1 | 0 | 0 | Methylbenzene | H | H | H | S | S |
| 89 | 2-NO2 | 1 | 0 | 0 | Cyclocarbonyl | H | H | H | R | R |
| 90 | 2-NO2 | 1 | 0 | 0 | Cyclocarbonyl | H | H | H | S | S |
| 91 | 2-Me | 1 | 0 | 0 | Me | Me | H | H | R | R |
| 92 | 2-Me | 1 | 0 | 0 | Me | Me | H | H | S | S |
| 93 | 2-Me | 1 | 0 | 0 | Me | H | H | H | R | R |
| 94 | 2-Me | 1 | 0 | 0 | Me | H | H | H | S | S |
| 95 | 2-Me | 1 | 0 | 0 | Et | Et | H | H | R | R |
| 96 | 2-Me | 1 | 0 | 0 | Et | Et | H | H | S | S |
| 97 | 2-Me | 1 | 0 | 0 | Cyclopentyl | H | H | H | R | R |
| 98 | 2-Me | 1 | 0 | 0 | Cyclopentyl | H | H | H | S | S |
| 99 | 2-Me | 1 | 0 | 0 | Cyclohexyl | H | H | H | R | R |
| 100 | 2-Me | 1 | 0 | 0 | Cyclohexyl | H | H | H | S | S |
| 101 | 2-Me | 1 | 0 | 0 | Methylbenzene | H | H | H | R | R |
| 102 | 2-Me | 1 | 0 | 0 | Methylbenzene | H | H | H | S | S |
| 103 | 2-MeNH | 1 | 0 | 0 | Me | Me | Me | H | R | R |
| 104 | 2-MeNH | 1 | 0 | 0 | Me | Me | Me | H | S | S |
| 105 | H | 1 | 0 | 0 | Me | Me | H | H | R | R |
| 106 | H | 1 | 0 | 0 | Me | Me | H | H | S | S |
| 107 | H | 1 | 0 | 0 | Et | Et | H | H | R | R |
| 108 | H | 1 | 0 | 0 | Et | Et | H | H | S | S |
| 109 | H | 1 | 0 | 0 | Cyclopentyl | H | H | H | R | R |
| 110 | H | 1 | 0 | 0 | Cyclopentyl | H | H | H | S | S |
| 111 | H | 1 | 0 | 0 | Cyclohexyl | H | H | H | R | R |
| 112 | H | 1 | 0 | 0 | Cyclohexyl | H | H | H | S | S |
| 113 | H | 1 | 1 | 1 | Me | Me | H | H | R | R |
| 114 | H | 1 | 1 | 1 | Me | Me | H | H | S | S |
| 115 | H | 1 | 1 | 1 | Et | Et | H | H | R | R |
| 116 | H | 1 | 1 | 1 | Et | Et | H | H | S | S |
| 117 | H | 1 | 1 | 1 | Cyclopentyl | H | H | H | R | R |
| 118 | H | 1 | 1 | 1 | Cyclopentyl | H | H | H | S | S |
| 119 | H | 1 | 1 | 1 | Cyclohexyl | H | H | H | R | R |
| 120 | H | 1 | 1 | 1 | Cyclohexyl | H | H | H | S | S |
| 121 | H | 1 | 1 | 0 | Me | Me | H | H | R | R |
| 122 | H | 1 | 1 | 0 | Me | Me | H | H | S | S |
| 123 | H | 1 | 1 | 0 | Et | Et | H | H | R | R |
| 124 | H | 1 | 1 | 0 | Et | Et | H | H | S | S |
| 125 | H | 1 | 1 | 0 | Cyclopentyl | H | H | H | R | R |
| 126 | H | 1 | 1 | 0 | Cyclopentyl | H | H | H | S | S |
| 127 | H | 1 | 1 | 0 | Cyclohexyl | H | H | H | R | R |
| 128 | H | 1 | 1 | 0 | Cyclohexyl | H | H | H | S | S |
| 129 | H | 1 | 0 | 1 | Me | Me | H | H | R | R |
| 130 | H | 1 | 0 | 1 | Me | Me | H | H | S | S |
| 131 | H | 1 | 0 | 1 | Et | Et | H | H | R | R |
| 132 | H | 1 | 0 | 1 | Et | Et | H | H | S | S |
| 133 | H | 1 | 0 | 1 | Cyclopentyl | H | H | H | R | R |
| 134 | H | 1 | 0 | 1 | Cyclopentyl | H | H | H | S | S |

TABLE 1-continued

Example of sulfamate compound (A = Phenyl)

| No | A = Phenyl | n | l | m | R¹ | R² | R³ | R⁴ | Chiral-1 | Chiral-2 |
|---|---|---|---|---|---|---|---|---|---|---|
| 135 | H | 1 | 0 | 1 | Cyclohexyl | | H | H | R | R |
| 136 | H | 1 | 0 | 1 | Cyclohexyl | | H | H | S | S |
| 137 | 2-Cl | 1 | 1 | 1 | Me | Me | H | H | R | R |
| 138 | 2-Cl | 1 | 1 | 1 | Me | Me | H | H | S | S |
| 139 | 2-Cl | 1 | 1 | 1 | Et | Et | H | H | R | R |
| 140 | 2-Cl | 1 | 1 | 1 | Et | Et | H | H | S | S |
| 141 | 2-Cl | 1 | 1 | 1 | Cyclopentyl | | H | H | R | R |
| 142 | 2-Cl | 1 | 1 | 1 | Cyclopentyl | | H | H | S | S |
| 143 | 2-Cl | 1 | 1 | 1 | Cyclohexyl | | H | H | R | R |
| 144 | 2-Cl | 1 | 1 | 1 | Cyclohexyl | | H | H | S | S |
| 145 | 2-Cl | 1 | 1 | 0 | Me | Me | H | H | R | R |
| 146 | 2-Cl | 1 | 1 | 0 | Me | Me | H | H | S | S |
| 147 | 2-Cl | 1 | 1 | 0 | Et | Et | H | H | R | R |
| 148 | 2-Cl | 1 | 1 | 0 | Et | Et | H | H | S | S |
| 149 | 2-Cl | 1 | 1 | 0 | Cyclopentyl | | H | H | R | R |
| 150 | 2-Cl | 1 | 1 | 0 | Cyclopentyl | | H | H | S | S |
| 151 | 2-Cl | 1 | 1 | 0 | Cyclohexyl | | H | H | R | R |
| 152 | 2-Cl | 1 | 1 | 0 | Cyclohexyl | | H | H | S | S |
| 153 | 2-Cl | 1 | 0 | 1 | Me | Me | H | H | R | R |
| 154 | 2-Cl | 1 | 0 | 1 | Me | Me | H | H | S | S |
| 155 | 2-Cl | 1 | 0 | 1 | Et | Et | H | H | R | R |
| 156 | 2-Cl | 1 | 0 | 1 | Et | Et | H | H | S | S |
| 157 | 2-Cl | 1 | 0 | 1 | Cyclopentyl | | H | H | R | R |
| 158 | 2-Cl | 1 | 0 | 1 | Cyclopentyl | | H | H | S | S |
| 159 | 2-Cl | 1 | 0 | 1 | Cyclohexyl | | H | H | R | R |
| 160 | 2-Cl | 1 | 0 | 1 | Cyclohexyl | | H | H | S | S |
| 161 | 2-Cl | 1 | 0 | 0 | Me | Me | H | H | R | S |
| 162 | 2-Cl | 1 | 0 | 0 | Me | Me | H | H | S | R |
| 177* | 2-Cl | 1 | 0 | 0 | Me | Me | H | H | S | S |

*Sodium salt

TABLE 2

Example of sulfamate compound (A = Heterocyclic ring)

| No | A | X | n | l | m | R¹ | R² | R³ | R⁴ | Chiral-1 | Chiral-2 |
|---|---|---|---|---|---|---|---|---|---|---|---|
| 163 | Thiazole | 2,4-Cl | 2 | 0 | 0 | Me | Me | H | H | R | S |
| 164 | Thiazole | 2,4-Cl | 2 | 0 | 0 | Me | Me | H | H | S | R |
| 165 | Thiazole | 2-Cl | 1 | 0 | 0 | Me | Me | H | H | R | S |
| 166 | Thiazole | 2-Cl | 1 | 0 | 0 | Me | Me | H | H | S | R |
| 167 | Thiazole | 4-Me | 1 | 0 | 0 | Me | Me | H | H | R | S |
| 168 | Thiazole | 4-Me | 1 | 0 | 0 | Me | Me | H | H | S | R |
| 169 | Thiazole | 2-Cl, 4-Me | 2 | 0 | 0 | Me | Me | H | H | R | S |
| 170 | Thiazole | 2-Cl, 4-Me | 2 | 0 | 0 | Me | Me | H | H | S | R |
| 171 | Thiophene | H | 1 | 0 | 0 | Me | Me | H | H | S | S |
| 172 | Thiophene | 2-Cl | 1 | 0 | 0 | Me | Me | H | H | S | R |
| 173 | Pyridine | 3-Cl | 1 | 0 | 0 | Me | Me | H | H | Rac.(syn) | Rac.(syn) |
| 174 | Pyridine | 4-Cl | 1 | 0 | 0 | Me | Me | H | H | Rac.(syn) | Rac.(syn) |
| 175 | Pyrimidine | H | 1 | 0 | 0 | Me | Me | H | H | Rac.(syn) | Rac.(syn) |
| 176 | Pyrimidine | 2-Cl | 1 | 0 | 0 | Me | Me | H | H | Rac.(syn) | Rac.(syn) |
| 163 | Thiazole | 2,4-Cl | 2 | 0 | 0 | Me | Me | H | H | R | S |
| 164 | Thiazole | 2,4-Cl | 2 | 0 | 0 | Me | Me | H | H | S | R |
| 165 | Thiazole | 2-Cl | 1 | 0 | 0 | Me | Me | H | H | R | S |
| 166 | Thiazole | 2-Cl | 1 | 0 | 0 | Me | Me | H | H | S | R |
| 167 | Thiazole | 4-Me | 1 | 0 | 0 | Me | Me | H | H | R | S |
| 168 | Thiazole | 4-Me | 1 | 0 | 0 | Me | Me | H | H | S | R |
| 169 | Thiazole | 2-Cl, 4-Me | 2 | 0 | 0 | Me | Me | H | H | R | S |
| 170 | Thiazole | 2-Cl, 4-Me | 2 | 0 | 0 | Me | Me | H | H | S | R |
| 171 | Thiophene | H | 1 | 0 | 0 | Me | Me | H | H | S | S |
| 172 | Thiophene | 2-Cl | 1 | 0 | 0 | Me | Me | H | H | S | R |
| 173 | Pyridine | 3-Cl | 1 | 0 | 0 | Me | Me | H | H | Rac.(syn) | Rac.(syn) |
| 174 | Pyridine | 4-Cl | 1 | 0 | 0 | Me | Me | H | H | Rac.(syn) | Rac.(syn) |
| 175 | Pyrimidine | H | 1 | 0 | 0 | Me | Me | H | H | Rac.(syn) | Rac.(syn) |
| 176 | Pyrimidine | 2-Cl | 1 | 0 | 0 | Me | Me | H | H | Rac.(syn) | Rac.(syn) |

Example 1-1: ((4R,5R)-5-(2-chlorophenyl)-2,2-dimethyl-1,3-dioxolan-4-yl)methyl sulfamate

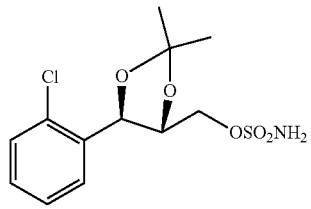

To a 100 mL flask, Acetonitrile (2.26 mL, 43.2 mmol) was added and cooled to 0° C. Chlorosulfonyl isocyanate (1.5 mL, 17.3 mmol), and formic acid (0.65 mL, 17.3 mmol) was added dropwise and stirred at room temperature for 6 hours. ((4R,5R)-5-(2-chlorophenyl)-2,2-dimethyl-1,3-dioxolan-4-yl)methanol (Preparation example 6, 1.05 g, 4.3 mmol) in N,N-dimethyl acetamide (13.2 mL, 142.7 mmol) was slowly added at 0° C. and stirred at room temperature for 1 hours. The reaction mixture was quenched with $H_2O$, extracted with EtOAc. and washed with $H_2O$. The organic layer was dried over anhydrous magnesium sulfate ($MgSO_4$), filtered and concentrated. The crude compound was purified by a silica gel column to produce the title compound (1.0 g, 50~80%).

$^1$H NMR (400 MHz, $CDCl_3$) δ 1.57 (s, 3H), 1.63 (s, 3H), 4.11~4.10 (m, 1H), 4.53~4.42 (m, 2H), 4.88 (s, 2H), 5.37 (d, J=8.4 Hz, 1H), 7.28~7.56 (m, 4H).

Example 1-2: ((4R,5R)-5-(2-chlorophenyl)-2,2-dimethyl-1,3-dioxolan-4-yl)methyl sulfamate To a 100 mL RB flask, ((4R,5R)-5-(2-chlorophenyl)-2,2-dimethyl-1,3-dioxolan-4-yl)methanol (Preparation example 6, 10.0 g, 41.2 mmol), 50 mL of toluene, 7.92 g (82.4 mmol) of sulfamide and 13.0 g (165 mmol) of pyridine were added at RT. The mixture was refluxed for 1.5 hr (bath temperature 135° C.). The reaction mixture cooled to room temperature then solution was extracted with 27.5 mL (82.4 mmol) of 3 N NaOH solution. The aqueous layer was washed with 50 mL of toluene. To the mixture 50 mL of methanol and 35 mL of water was added then acidified to pH 6.0 by slow adding acetic acid to give title compound (9.9 g, 60~80%).

According to the method described in Preparation example 1, the following compounds of Examples 2 to 64, 67 to 88, 91 to 102, 105 to 176 were prepared:

TABLE 3

Characteriztation of the examples of sulfamate compounds

| Example No. | Structure | Name | Starting material | $^1$H NMR (400 MHz) |
|---|---|---|---|---|
| 2 | 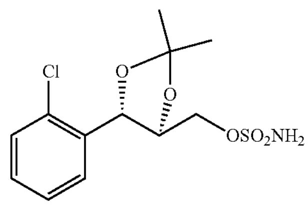 | ((4S,5S)-5-(2-chlorophenyl)-2,2-dimethyl-1,3-dioxolan-4-yl)methyl sulfamate | Preparation example 7, 27 | $^C$δ 1.59 (s, 3H), 1.05 (s, 3H), 4.12~4.07 (m, 1H), 4.54~4.42 (m, 2H), 4.91 (s, 2H), 5.37 (d, J = 8.8 Hz, 1H), 7.29~7.65 (m, 4H) |
| 3 | 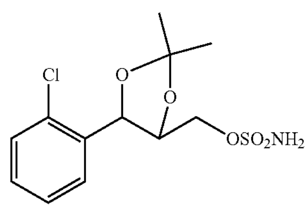 | (5-(2-chlorophenyl)-2,2-dimethyl-1,3-dioxolan-4-yl)methyl sulfamate(SS & RR mixture) | Preparation example 8 | $^C$δ 1.57 (s, 3H), 1.63 (s, 3H), 4.11~4.10 (m, 1H), 4.53~4.42 (m, 2H), 4.88 (s, 2H), 5.37 (d, J = 8.4 Hz, 1H), 7.28~7.65 (m, 4H) |
| 4 | 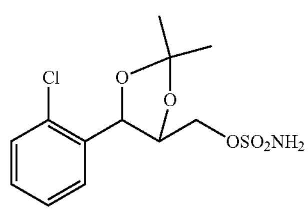 | (5-(2-chlorophenyl)-2,2-dimethyl-1,3-dioxolan-4-yl)methyl sulfamate(SS & RS mixture) | Preparation example 374 | $^C$δ 1.59 (s, 3H), 1.65 (s, 3H), 4.11~4.10 (m, 1H), 4.50~4.42 (m, 2H), 4.85 (s, 2H), 5.35 (d, J = 8.4 Hz, 1H), 7.28~7.65 (m, 4H) |
| 5 | 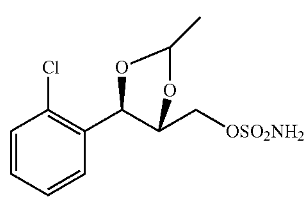 | ((4R,5R)-5-(2-chlorophenyl)-2-methyl-1,3-dioxolan-4-yl)methyl sulfamate | Preparation example 61 | $^D$δ 1.40 (d, J = 6.4 Hz, 3H), 4.22 (dt, J = 3.3, 7.0 Hz, 1H), 4.7 (d, J = 3.2 Hz, 2H), 5.08 (d, J = 7.0 Hz, 1H), 5.46 (m, J = 6.4 Hz, 1H), 7.26~7.40 (m, 3H), 7.49 (s, 2H), 7.61 (dd, J = 1.2, 7.6 Hz, 1H) |
| 6 | 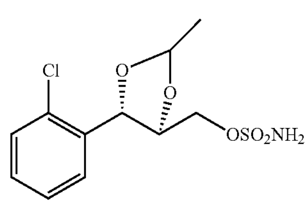 | ((4S,5S)-5-(2-chlorophenyl)-2-methyl-1,3-dioxolan-4-yl)methyl sulfamate | Preparation example 63 | $^D$δ 1.40 (d, J = 6.4 Hz, 3H), 4.22 (dt, J = 3.3, 7.0 Hz, 1H), 4.7 (d, J = 3.2 Hz, 2H), 5.08 (d, J = 7.0 Hz, 1H), 5.46 (m, J = 6.4 Hz, 1H), 7.26~7.40 (m, 3H), 7.49 (s, 2H), 7.61 (dd, J = 1.2, 7.6 Hz, 1H) |
| 7 | 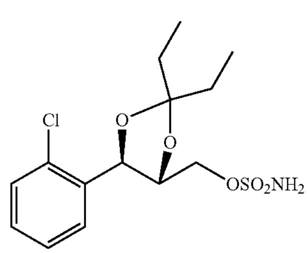 | ((4R,5R)-5-(2-chlorophenyl)-2,2-diethyl-1,3-dioxolan-4-yl)methyl sulfamate | Preparation example 65 | $^C$δ 1.59 (s, 10H), 4.17 (m, 3H), 4.98 (d, J = 8.4 Hz, 1H), 5.08 (s, 2H), 6.59 (t, J = 8.4 Hz, 1H), 6.68 (d, J = 8.4 Hz.1H), 7.04~7.56 (m, 4H) |

TABLE 3-continued

Characteriztation of the examples of sulfamate compounds

| Example No. | Structure | Name | Starting material | $^1$H NMR (400 MHz) |
|---|---|---|---|---|
| 8 | 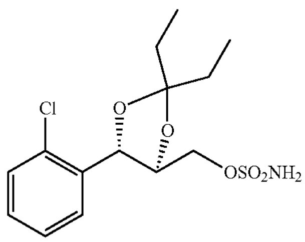 | ((4S,5S)-5-(2-chlorophenyl)-2,2-diethyl-1,3-dioxolan-4-yl)methyl sulfamate | Preparation example 67 | $^C$δ 1.59 (s, 10H), 4.17 (m, 3H), 4.98 (d, J = 8.4 Hz, 1H), 5.08 (s, 2H), 6.59 (t, J = 8.4 Hz, 1H), 6.68 (d, J = 8.4 Hz.1H), 7.04~7.56 (m, 4H) |
| 9 | 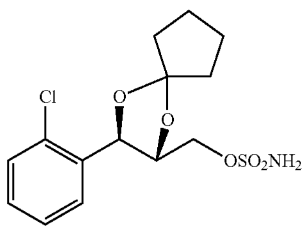 | ((2R,3R)-3-(2-chlorophenyl)-1,4-dioxaspiro[4,4]nonan-2-yl)methyl sulfamate | Preparation example 69 | $^D$δ 1.64~1.72 (m, 4H), 1.85~19.8 (m, 4H), 4.10~4.16 (m, 2H), 4.17~4.25 (m, 1H), 5.20 (d, J = 7.2 Hz, 1H), 7.34~7.62 (m, 6H) |
| 10 | 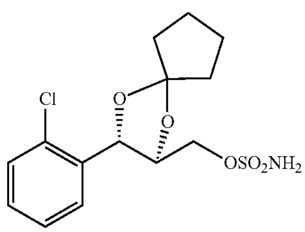 | ((2S,3S)-3-(2-chlorophenyl)-1,4-dioxaspiro[4,4]nonan-2-yl)methyl sulfamate | Preparation example 71 | $^D$δ 1.64~1.75 (m, 4H), 1.85~19.9 (m, 4H), 4.10~4.16 (m, 2H), 4.17~4.25 (m, 1H), 5.20 (d, J = 7.2 Hz, 1H), 7.34~7.62 (m, 6H) |
| 11 | 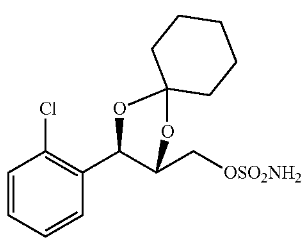 | ((2R,3R)-3-(2-chlorophenyl)-1,4-dioxaspiro[4,5]decan-2-yl)methyl sulfamate | Preparation example 73 | $^D$δ 1.51~1.67 (m, 10H), 4.11~4.23 (m, 3H), 4.98 (d, J = 8.0 Hz, 2H), 5.08 (s, 1H), 6.59 (t, J = 8.0 Hz, 1H), 6.68 (d, J = 8.0 Hz, 1H), 7.04~7.56 (m, 4H) |
| 12 | 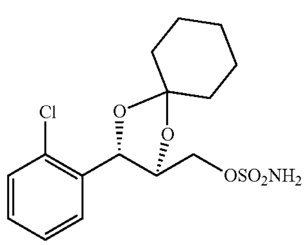 | ((2S,3S)-3-(2-chlorophenyl)-1,4-dioxaspiro[4,5]decan-2-yl)methyl sulfamate | Preparation example 75 | $^D$δ 1.51~1.67 (m, 10H), 4.11~4.23 (m, 3H), 4.98 (d, J = 8.0 Hz, 2H), 5.08 (s, 1H), 6.59 (t, J = 8.0 Hz, 1H), 6.68 (d, J = 8.0 Hz, 1H), 7.04~7.56 (m, 4H) |
| 13 | 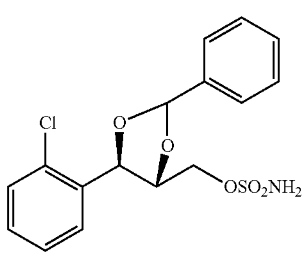 | ((4R,5R)-5-(2-chlorophenyl)-2-phenyl-1,3-dioxolan-4-yl)methyl sulfamate | Preparation example 77 | $^D$δ 4.25 (dt, J = 3.3, 5.7 Hz, 1H), 4.55 (d, J = 5.7 Hz, 1H), 4.75 (d, J = 3.3 Hz, 2H), 5.59 (m, 1H), 6.72~7.75 (m, 2H), 6.92~7.33 (m, 5H), 7.29 (m, 1H), 7.76 (m, 1H) |

TABLE 3-continued

Characteriztation of the examples of sulfamate compounds

| Example No. | Structure | Name | Starting material | $^1$H NMR (400 MHz) |
|---|---|---|---|---|
| 14 | 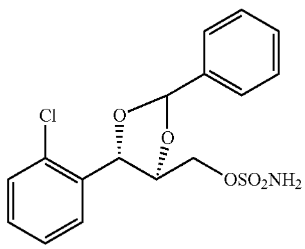 | ((4S,5S)-5-(2-chlorophenyl)-2-phenyl-1,3-dioxolan-4-yl)methyl sulfamate | Preparation example 79 | $^D$δ 4.28 (dt, J = 3.3, 5.7 Hz, 1H), 4.58 (d, J = 5.7 Hz, 1H), 4.75 (d, J = 3.3 Hz, 2H), 5.62 (m, 1H), 6.72~7.75 (m, 2H), 6.92~7.33 (m, 5H), 7.29 (m, 1H), 7.76 (m, 1H) |
| 15 | 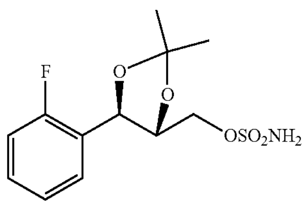 | ((4R,5R)-5-(2-fluorophenyl)-2,2-dimethyl-1,3-dioxolan-4-yl)methyl sulfamate | Preparation example 13 | $^D$δ 1.47 (d, J = 11.6 Hz, 6H), 3.35~3.94 (m, 1H), 4.02~4.20 (m, 1H), 4.23 (d, J = 2.0 Hz, 1H), 5.07 (d, J = 8.4 Hz, 1H), 7.21~7.58 (m, 4H) |
| 16 | 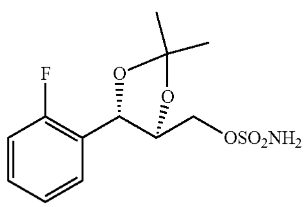 | ((4S,5S)-5-(2-fluorophenyl)-2,2-dimethyl-1,3-dioxolan-4-yl)methyl sulfamate | Preparation example 15 | $^D$δ 1.47 (d, J = 11.6 Hz, 6H), 3.35~3.94 (m, 1H), 4.02~4.20 (m, 1H), 4.23 (d, J = 2.0 Hz, 1H), 5.07 (d, J = 8.4 Hz, 1H), 7.21~7.58 (m, 4H) |
| 17 | 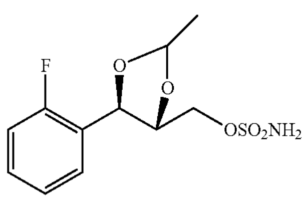 | ((4R,5R)-5-(2-fluorophenyl)-2-methyl-1,3-dioxolan-4-yl)methyl sulfamate | Preparation example 84 | $^D$δ 1.40 (d, J = 6.4 Hz, 3H), 4.7 (d, J = 3.2 Hz, 2H), 5.46 (m, J = 6.4 Hz, 1H), 4.22 (dt, J = 3.3, 7.0 Hz, 1H), 5.08 (d, J = 7.0 Hz, 1H), 7.26~7.40 (m, 3H), 7.49 (s, 2H), 7.61 (dd, J = 1.2, 7.6 Hz, 1H) |
| 18 | 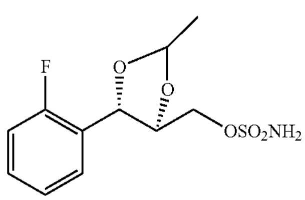 | ((4S,5S)-5-(2-fluorophenyl)-2-methyl-1,3-dioxolan-4-yl)methyl sulfamate | Preparation example 86 | $^D$δ 1.40 (d, J = 6.4 Hz, 3H), 4.7 (d, J = 3.2 Hz, 2H), 5.46 (m, J = 6.4 Hz, 1H), 4.22 (dt, J = 3.3, 7.0 Hz, 1H), 5.18 (d, J = 7.0 Hz, 1H), 7.26~7.40 (m, 3H), 7.52 (s, 2H), 7.61 (dd, J = 1.2, 7.6 Hz, 1H) |
| 19 | 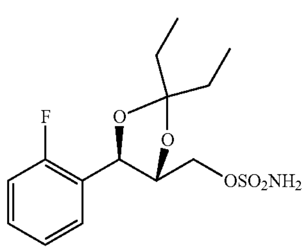 | ((4R,5R)-5-(2-fluorophenyl)-2,2-diethyl-1,3-dioxolan-4-yl) methyl sulfamate | Preparation example 88 | $^C$δ 1.59 (s, 10H), 4.17 (m, 3H), 4.98 (d, J = 8.4 Hz, 1H), 5.08 (s, 2H), 6.59 (t, J = 8.4 Hz, 1H), 6.68 (d, J = 8.4 Hz, 1H), 7.04~7.56 (m, 4H) |

TABLE 3-continued

Characteriztation of the examples of sulfamate compounds

| Example No. | Structure | Name | Starting material | $^1$H NMR (400 MHz) |
|---|---|---|---|---|
| 20 | 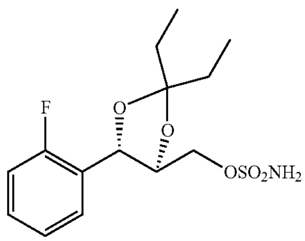 | ((4S,5S)-5-(2-fluorophenyl)-2,2-diethyl-1,3-dioxolan-4-yl) methyl sulfamate | Preparation example 90 | $^C$δ 1.59 (s, 10H), 4.14 (m, 3H), 4.98 (d, J = 8.4 Hz, 1H), 5.05 (s, 2H), 6.59 (t, J = 8.4 Hz, 1H), 6.65 (d, J = 8.4 Hz, 1H), 7.04~7.60 (m, 4H) |
| 21 | 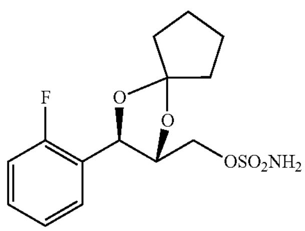 | ((2R,3R)-3-(2-fluorophenyl)-1,4-dioxaspiro[4,4]nonan-2-yl)methyl sulfamate | Preparation example 92 | $^D$δ 1.64~1.72 (m, 4H), 1.84~19.8 (m, 4H), 4.10~4.16 (m, 2H), 4.19~4.25 (m, 1H), 5.25 (d, J = 7.2 Hz, 1H), 7.34~7.62 (m, 6H) |
| 22 | 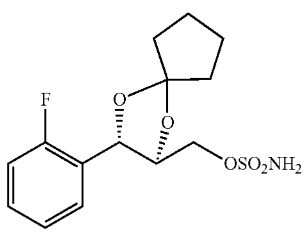 | ((2S,3S)-3-(2-fluorophenyl)-1,4-dioxaspiro[4,4]nonan-2-yl)methyl sulfamate | Preparation example 94 | $^D$δ 1.64~1.72 (m, 4H), 1.84~19.8 (m, 4H), 4.10~4.16 (m, 2H), 4.19~4.25 (m, 1H), 5.20 (d, J = 7.2 Hz, 1H), 7.34~7.62 (m, 6H) |
| 23 | 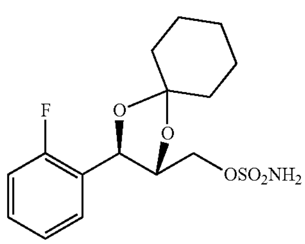 | ((2R,3R)-3-(2-fluorophenyl)-1,4-dioxaspiro[4,5]decan-2-yl)methyl sulfamate | Preparation example 96 | $^D$δ 1.51~1.67 (m, 10H), 4.11~4.23 (m, 3H), 4.98 (d, J = 8.0 Hz, 2H), 5.08 (s, 1H), 6.59 (t, J = 8.0 Hz, 1H), 6.68 (d, J = 8.0 Hz, 1H), 7.04~7.56 (m, 4H) |
| 24 | 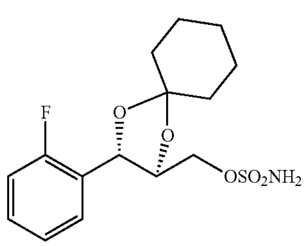 | ((2S,3S)-3-(2-fluorophenyl)-1,4-dioxaspiro[4,5]decan-2-yl)methyl sulfamate | Preparation example 98 | $^D$δ 1.51~1.67 (m, 10H), 4.11~4.23 (m, 3H), 4.98 (d, J = 8.0 Hz, 2H), 5.08 (s, 1H), 6.59 (t, J = 8.0 Hz, 1H), 6.68 (d, J = 8.0 Hz, 1H), 7.04~7.56 (m, 4H) |
| 25 | 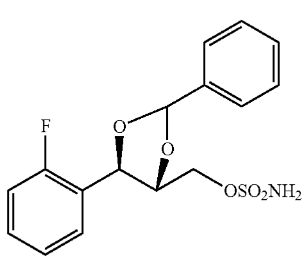 | ((4R,5R)-5-(2-fluorophenyl)-2-phenyl-1,3-dioxolan-4-yl)methyl sulfamate | Preparation example 100 | $^D$δ 4.25 (dt, J = 3.3, 5.7 Hz, 1H), 4.59 (d, J = 5.7 Hz, 1H), 4.75 (d, J = 3.3 Hz, 2H), 5.59 (m, 1H), 6.72~7.75 (m, 2H), 6.92~7.33 (m, 5H), 7.25 (m, 1H), 7.76 (m, 1H) |

TABLE 3-continued

Characteriztation of the examples of sulfamate compounds

| Example No. | Structure | Name | Starting material | ¹H NMR (400 MHz) |
|---|---|---|---|---|
| 26 | 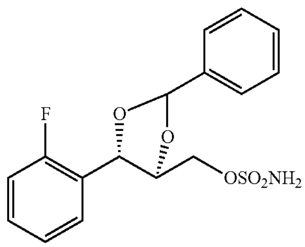 | ((4S,5S)-5-(2-fluorophenyl)-2-phenyl-1,3-dioxolan-4-yl)methyl sulfamate | Preparation example 102 | $^D$δ 4.25 (dt, J = 3.3, 5.7 Hz, 1H), 4.59 (d, J = 5.7 Hz, 1H), 4.75 (d, J = 3.3 Hz, 2H), 5.59 (m, 1H), 6.72~7.75 (m, 2H), 6.92~7.33 (m, 5H), 7.25 (m, 1H), 7.76 (m, 1H) |
| 27 | 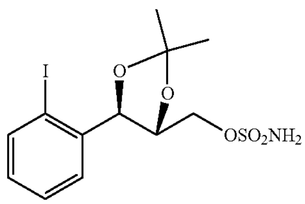 | ((4R,5R)-5-(2-iodophenyl)-2,2-dimethyl-1,3-dioxolan-4-yl)methyl sulfamate | Preparation example 21 | $^D$δ 1.55 (s, 3H), 1.47 (s, 3H) 4.21~4.11 (m, 3H), ). 5.10 (d, J7 = 7.6 Hz, 1H), 7.56~7.13 (m, 3H), 7.60 (s, 2H), 7.91 (d, J = 8.0 Hz, 1H) |
| 28 | 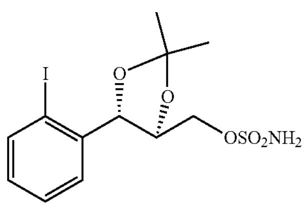 | ((4S,5S)-5-(2-iodophenyl)-2,2-dimethyl-1,3-dioxolan-4-yl)methyl sulfamate | Preparation example 23 | $^D$δ 1.55 (s, 3H), 1.47 (s, 3H) 4.21~4.11 (m, 3H), 5.10 (d, J = 7.6 Hz, 1H), 7.56~7.13 (m, 3H), 7.60 (s, 2H), 7.91 (d, J = 8.0 Hz, 1H) |
| 29 | 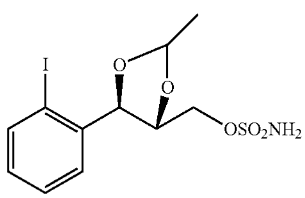 | ((4R,5R)-5-(2-iodophenyl)-2-methyl-1,3-dioxolan-4-yl)methyl sulfamate | Preparation example 107 | $^D$δ 1.40 (d, J = 6.4 Hz, 3H), 4.7 (d, J = 3.2 Hz, 2H), 5.46 (m, J = 6.4 Hz, 1H), 4.22 (dt, J = 3.3, 7.0 Hz, 1H), 5.10 (d, J = 7.0 Hz, 1H), 7.26~7.40 (m, 3H), 7.49 (s, 2H), 7.61 (dd, J = 1.2, 7.6 Hz, 1H) |
| 30 | 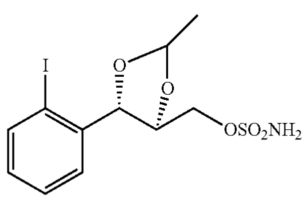 | ((4S,5S)-5-(2-iodophenyl)-2-methyl-1,3-dioxolan-4-yl)methyl sulfamate | Preparation example 109 | $^D$δ 1.40 (d, J = 6.4 Hz, 3H), 4.7 (d, J = 3.2 Hz, 2H), 5.46 (m, J = 6.4 Hz, 1H), 4.22 (dt, J = 3.3, 7.0 Hz, 1H), 5.08 (d, J = 7.0 Hz, 1H), 7.30~7.40 (m, 3H), 7.61 (s, 2H), 7.65 (dd, J = 1.2, 7.6 Hz, 1H) |
| 31 | 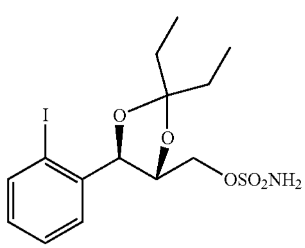 | ((4R,5R)-5-(2-iodophenyl)-2,2-diethyl-1,3-dioxolan-4-yl)methyl sulfamate | Preparation example 111 | $^C$δ 0.90 (t, J = 8.0 Hz, 6H), 1.59 (q, J = 8.0 Hz, 4H), 3.96~4.21 (m, 2H), 4.42 (q, J = 7.0 Hz, 1H), 4.88 (s, 2H), 5.17 (d, J = 7.0 Hz, 1H), 7.13~7.56 (m, 4H) |

TABLE 3-continued

Characteriztation of the examples of sulfamate compounds

| Example No. | Structure | Name | Starting material | $^1$H NMR (400 MHz) |
|---|---|---|---|---|
| 32 | 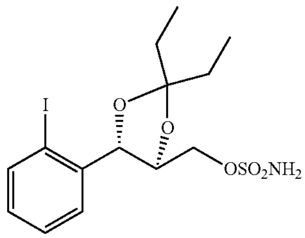 | ((4S,5S)-5-(2-iodophenyl)-2,2-diethyl-1,3-dioxolan-4-yl)methyl sulfamate | Preparation example 113 | $^C$δ 1.46~1.90 (m, 8H), 3.96~4.21 (m, 2H), 4.42 (q, J = 7.0 Hz, 1H), 4.88 (s, 2H), 5.17 (d, J = 7.0 Hz, 1H), 7.13~7.56 (m, 4H) |
| 33 | 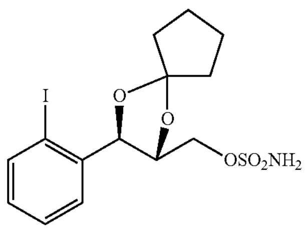 | ((2R,3R)-3-(2-iodophenyl)-1,4-dioxaspiro[4,4]nonan-2-yl)methyl sulfamate | Preparation example 115 | $^C$δ 1.46~1.90 (m, 8H), 3.96~4.21 (m, 2H), 4.42 (q, J = 7.0 Hz, 1H), 4.88 (s, 2H), 5.17 (d, J = 7.0 Hz, 1H), 7.13~7.56 (m, 4H) |
| 34 | 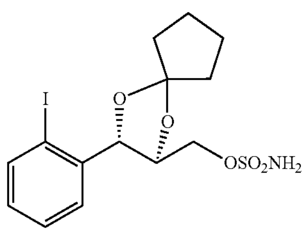 | ((2S,3S)-3-(2-iodophenyl)-1,4-dioxaspiro[4,4]nonan-2-yl)methyl sulfamate | Preparation example 117 | $^D$δ 1.46~1.90 (m, 8H), 3.96~4.21 (m, 2H), 4.42 (q, J = 7.0 Hz, 1H), 4.88 (s, 2H), 5.17 (d, J = 7.0 Hz, 1H), 7.13~7.59 (m, 4H) |
| 35 | 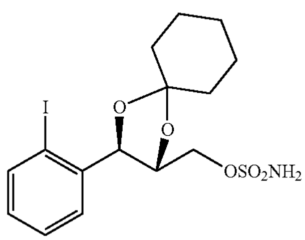 | ((2R,3R)-3-(2-iodophenyl)-1,4-dioxaspiro[4,5]decan-2-yl)methyl sulfamate | Preparation example 119 | $^D$δ 1.33~1.72 (m, 10H), 4.02~4.31 (m, 2H), 4.51 (q, J = 7.0 Hz, 1H), 4.97 (s, 2H), 5.25 (d, J = 7.0 Hz. 1H), 7.19~7.65 (m, 4H) |
| 36 | 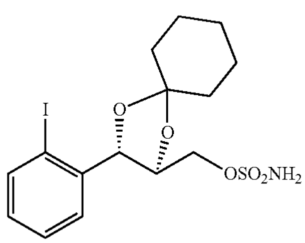 | ((2S,3S)-3-(2-iodophenyl)-1,4-dioxaspiro[4,5]decan-2-yl)methyl sulfamate | Preparation example 121 | $^D$δ 1.33~1.72 (m, 10H), 4.02~4.31 (m, 2H), 4.51 (q, J = 7.0 Hz, 1H), 4.97 (s, 2H), 5.25 (d, J = 7.0 Hz. 1H), 7.19~7.6 (m, 4H) |
| 37 | 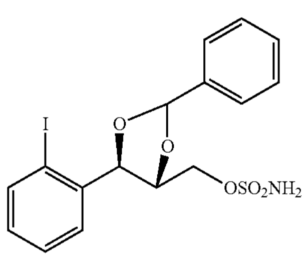 | ((4R,4R)-5-(2-iodophenyl)-2-phenyl-1,3-dioxolan-4-yl)methyl sulfamate | Preparation example 123 | $^D$δ 3.96~4.21 (m, 2H), 4.42 (q, J = 7.0 Hz, 1H), 4.92 (s, 2H), 5.20 (d, J = 7.0 Hz, 1H), 5.97 (s, 1H), 7.14~7.38 (m, 9H) |

TABLE 3-continued

Characteriztation of the examples of sulfamate compounds

| Example No. | Structure | Name | Starting material | $^1$H NMR (400 MHz) |
|---|---|---|---|---|
| 38 | 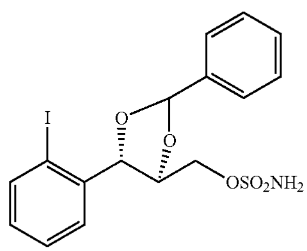 | ((4S,4S)-5-(2-iodophenyl)-2-phenyl-1,3-dioxolan-4-yl)methyl sulfamate | Preparation example 125 | $^D$δ 3.96~4.21 (m, 2H), 4.42 (q, J = 7.0 Hz, 1H), 4.92 (s, 2H), 5.20 (d, J = 7.0 Hz, 1H), 5.97 (s, 1H), 7.14~7.38 (m, 9H) |
| 39 | 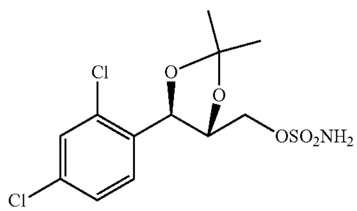 | ((4R,5R)-5-(2,4-dichlorophenyl)-2,2-dimethyl-1,3-dioxolan-4-yl)methyl sulfamate | Preparation example 38 | $^C$δ 1.27 (s, 6H), 3.90~4.15 (m, 2H), 4.37 (q, J = 7.0 Hz, 1H), 4.79 (s, 2H), 5.12 (d, J = 7.0 Hz, 1H), 7.29~7.42 (m, 2H), 7.79 (s, 1H) |
| 40 | 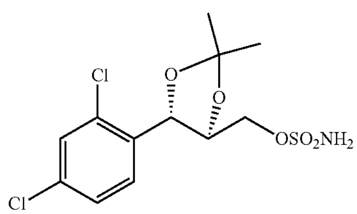 | ((4S,5S)-5-(2,4-dichlorophenyl)-2,2-dimethyl-1,3-dioxolan-4-yl)methyl sulfamate | Preparation example 31 | $^C$δ 1.27 (s, 6H), 3.90~4.15 (m, 2H), 4.37 (q, J = 7.0 Hz, 1H), 4.79 (s, 2H), 5.12 (d, J = 7.0 Hz, 1H), 7.29~7.42 (m, 2H), 7.79 (s, 1H) |
| 41 | 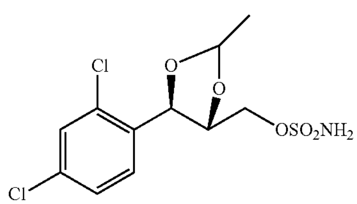 | ((4R,5R)-5-(2,4-dichlorophenyl)-2-methyl-1,3-dioxolan-4-yl)methyl sulfamate | Preparation example 127 | $^C$δ 1.40 (s, 3H), 3.81~4.08 (m, 2H), 4.25 (q, J = 7.0 Hz, 1H), 4.81 (s, 2H), 5.03 (q, J = 6.8 Hz, 1H), 5.12 (d, J = 7.0 Hz, 1H), 7.21~7.27 (m, 2H), 7.70 (s, 1H) |
| 42 | 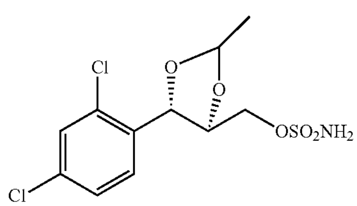 | ((4S,5S)-5-(2,4-dichlorophenyl)-2-methyl-1,3-dioxolan-4-yl)methyl sulfamate | Preparation example 129 | $^C$δ 1.40 (s, 3H), 3.81~4.08 (m, 2H), 4.25 (q, J = 7.0 Hz, 1H), 4.81 (s, 2H), 5.03 (q, J = 6.8 Hz, 1H), 5.12 (d, J = 7.0 Hz, 1H), 7.21~7.27 (m, 2H), 7.70 (s, 1H) |
| 43 | 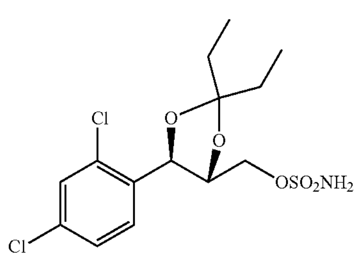 | ((4R,5R)-5-(2,4-dichlorophenyl)-2,2-diethyl-1,3-dioxolan-4-yl)methyl sulfamate | Preparation example 131 | $^C$δ 0.90 (t, J = 8.0 Hz, 6H), 1.59 (q, J = 8.0 Hz, 4H), 3.96~4.21 (m, 2H), 4.42 (q, J = 7.0 Hz, 1H), 4.88 (s, 2H), 5.17 (d, J = 7.0 Hz, 1H), 7.24~7.30 (m, 2H), 7.73 (s, 1H) |

TABLE 3-continued

Characteriztation of the examples of sulfamate compounds

| Example No. | Structure | Name | Starting material | $^1$H NMR (400 MHz) |
|---|---|---|---|---|
| 44 | 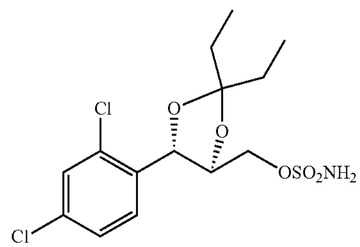 | ((4S,5S)-5-(2,4-dichlorophenyl)-2,2-diethyl-1,3-dioxolan-4-yl)methyl sulfamate | Preparation example 133 | $^C$δ 0.90 (t, J = 8.0 Hz, 6H), 1.59 (q, J = 8.0 Hz, 4H), 3.96~4.21 (m, 2H), 4.42 (q, J = 7.0 Hz, 1H), 4.88 (s, 2H), 5.17 (d, J = 7.0 Hz, 1H), 7.24~7.30 (m, 2H), 7.73 (s, 1H) |
| 45 | 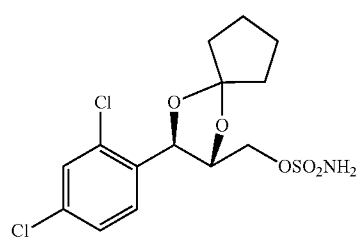 | ((2R,3R)-3-(2,4-dichlorophenyl)-1,4-dioxaspiro[4,4]nonan-2-yl)methyl sulfamate | Preparation example 135 | $^D$δ 1.46~1.90 (m, 8H), 3.79~4.05 (m, 2H), 4.25 (q, J = 7.0 Hz, 1H), 4.80 (s, 2H), 5.11 (d, J = 7.0 Hz, 1H), 7.28~7.34 (m, 2H), 7.76 (s, 1H) |
| 46 | 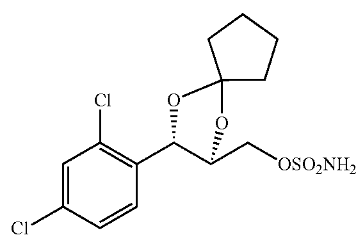 | ((2S,3S)-3-(2,4-dichlorophenyl)-1,4-dioxaspiro[4,4]nonan-2-yl)methyl sulfamate | Preparation example 137 | $^D$δ 1.46~1.90 (m, 8H), 3.79~4.05 (m, 2H), 4.25 (q, J = 7.0 Hz, 1H), 4.80 (s, 2H), 5.11 (d, J = 7.0 Hz, 1H), 7.28~7.34 (m, 2H), 7.76 (s, 1H) |
| 47 | 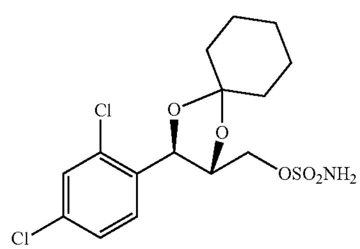 | ((2R,3R)-3-(2,4-dichlorophenyl)-1,4-dioxaspiro[4,5]decan-2-yl)methyl sulfamate | Preparation example 139 | $^D$δ 1.33~1.72 (m, 10H), 3.78~4.03 (m, 2H), 4.22 (q, J = 7.0 Hz, 1H), 4.78 (s, 2H), 5.07 (d, J~ 7.0 Hz, 1H), 7.26~7.32 (m, 2H), 7.77 (s, 1H) |
| 48 | 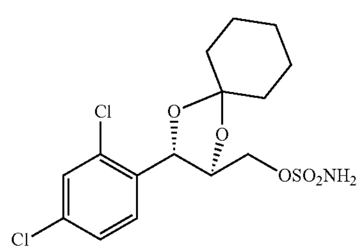 | ((2S,3S)-3-(2,4-dichlorophenyl)-1,4-dioxaspiro[4,5]decan-2-yl)methyl sulfamate | Preparation example 141 | $^D$δ 1.33~1.72 (m, 10H), 3.78~4.03 (m, 2H), 4.22 (q, J = 7.0 Hz, 1H), 4.78 (s, 2H), 5.07 (d, J~ 7.0 Hz, 1H), 7.26~7.32 (m, 2H), 7.77 (s, 1H) |
| 49 | 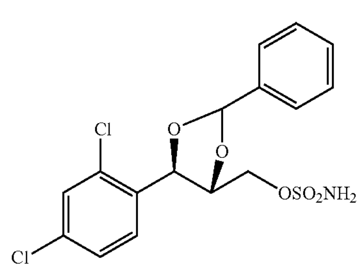 | ((4R,5R)-5-(2,4-dichlorophenyl)-2-phenyl-1,3-dioxolan-4-yl)methyl sulfamate | Preparation example 143 | $^D$δ 3.96~4.21 (m, 2H), 4.42 (q, J = 7.0 Hz, 1H), 4.88 (s, 2H), 5.17 (d, J = 7.0 Hz, 1H), 5.97 (s, 1.H), 7.14~7.39 (m, 8H) |

TABLE 3-continued

Characteriztation of the examples of sulfamate compounds

| Example No. | Structure | Name | Starting material | $^1$H NMR (400 MHz) |
|---|---|---|---|---|
| 50 | 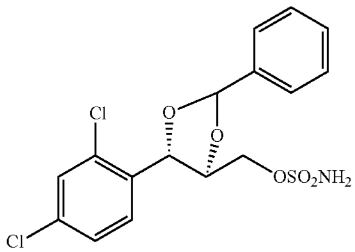 | ((4S,5S)-5-(2,4-dichlorophenyl)-2-phenyl-1,3-dioxolan-4-yl)methyl sulfamate | Preparation example 145 | $^D\delta$ 3.96~4.21 (m, 2H), 4.42 (q, J = 7.0 Hz, 1H), 4.88 (s, 2H), 5.17 (d, J = 7.0 Hz, 1H), 5.97 (s, 1.H), 7.14~7.39 (m, 8H) |
| 51 | 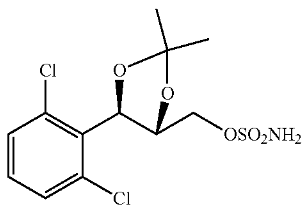 | ((4R,5R)-5-(2,6-dichlorophenyl)-2,2-dimethyl-1,3-dioxolan-4-yl)methyl sulfamate | Preparation example 41 | $^C\delta$ 1.27 (s, 6H), 3.96~4.21 (m, 2H), 4.42 (q, J = 7.0 Hz, 1H), 4.88 (s, 2H), 5.17 (d, J = 7.0 Hz, 1H), 7.45~7.58 (m, 3H) |
| 52 | 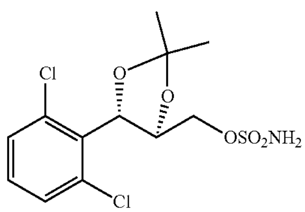 | ((4S,5S)-5-(2,6-dichlorophenyl)-2,2-dimethyl-1,3-dioxolan-4-yl)methyl sulfamate | Preparation example 35 | $^C\delta$ 1.27 (s, 6H), 3.96~4.21 (m, 2H), 4.42 (q, J = 7.0 Hz, 1H), 4.88 (s, 2H), 5.17 (d, J = 7.0 Hz, 1H), 7.45~7.58 (m, 3H) |
| 53 | 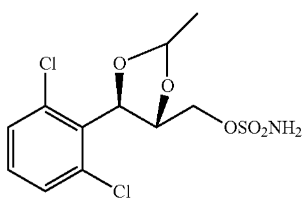 | ((4R,5R)-5-(2,6-dichlorophenyl)-2-methyl-1,3-dioxolan-4-yl)methyl sulfamate | Preparation example 147 | $^D\delta$ 1.40 (s, 3H), 3.88~4.13 (m, 2H), 4.42 (q, J = 7.0 Hz, 1H), 4.88 (s, 2H), 5.07 (q, J = 6.8 Hz, 1H), 5.21 (d, J = 7.0 Hz, 1H), 5.97 (s, 1H), 7.45~7.58 (m, 3H) |
| 54 | 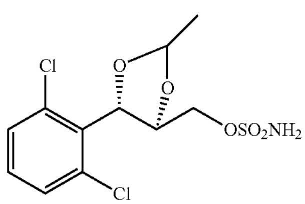 | ((4S,5S)-5-(2,6-dichlorophenyl)-2-methyl-1,3-dioxolan-4-yl)methyl sulfamate | Preparation example 149 | $^D\delta$ 1.40 (s, 3H), 3.88~4.13 (m, 2H), 4.42 (q, J = 7.0 Hz, 1H), 4.88 (s, 2H), 5.07 (q, J = 6.8 Hz, 1H), 5.21 (d, J = 7.0 Hz, 1H), 5.97 (s, 1H), 7.45~7.58 (m, 3H) |
| 55 | 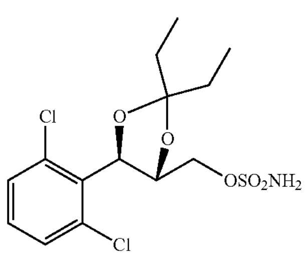 | ((4R,5R)-5-(2,6-dichlorophenyl)-2,2-diethyl-1,3-dioxolan-4-yl)methyl sulfamate | Preparation example 151 | $^C\delta$ 0.90 (t, J = 8.0 Hz, 6H), 1.59 (q, J = 8.0 Hz, 4H), 3.86~4.11 (m, 2H), 4.49 (q, J = 7.0 Hz, 1H), 4.88 (s, 2H), 5.15 (d, J = 7.0 Hz, 1H), 7.45~7.58 (m, 3H) |

TABLE 3-continued

Characteriztation of the examples of sulfamate compounds

| Example No. | Structure | Name | Starting material | $^1$H NMR (400 MHz) |
|---|---|---|---|---|
| 56 | 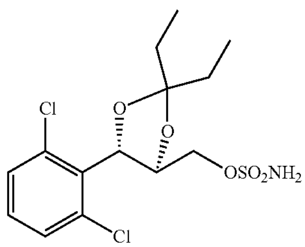 | ((4R,5R)-5-(2,6-dichlorophenyl)-2,2-diethyl-1,3-dioxolan-4-yl)methyl sulfamate | Preparation example 153 | $^C$δ 0.90 (t, J = 8.0 Hz, 6H), 1.59 (q, J = 8.0 Hz, 4H), 3.86~4.11 (m, 2H), 4.49 (q, J = 7.0 Hz, 1H), 4.88 (s, 2H), 5.15 (d, J = 7.0 Hz, 1H), 7.45~7.58 (m, 3H) |
| 57 | 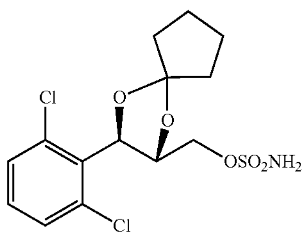 | ((2R,3R)-3-(2,6-dichlorophenyl)-1,4-dioxaspiro[4,4]nonan-2-yl)methyl sulfamate | Preparation example 155 | $^D$δ 1.46~1.90 (m, 8H), 3.98~4.24 (m, 2H), 4.45 (q, J = 7.0 Hz, 1H), 4.88 (s, 2H), 5.20 (d, J = 7.0 Hz, 1H), 7.45~7.58 (m, 3H) |
| 58 | 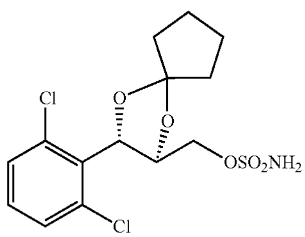 | ((2S,3S)-3-(2,6-dichlorophenyl)-1,4-dioxaspiro[4,4]nonan-2-yl)methyl sulfamate | Preparation example 157 | $^D$δ 1.46~1.90 (m, 8H), 3.98~4.24 (m, 2H), 4.45 (q, J = 7.0 Hz, 1H), 4.88 (s, 2H), 5.20 (d, J = 7.0 Hz, 1H), 7.45~7.58 (m, 3H) |
| 59 | 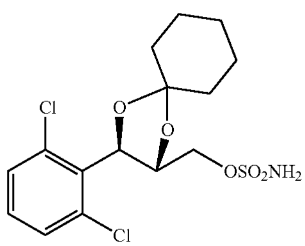 | ((2R,3R)-3-(2,6-dichlorophenyl)-1,4-dioxaspiro[4,5]decan-2-yl)methyl sulfamate | Preparation example 159 | $^D$δ 1.33~1.72 (m, 10H)-3.96~4.21 (m, 2H), 4.42 (q, J = 7.0 Hz, 1H), 4.88 (s, 2H), 5.17 (d, J = 7.0 Hz, 1H), 7.45~7.58 (m, 3H) |
| 60 | 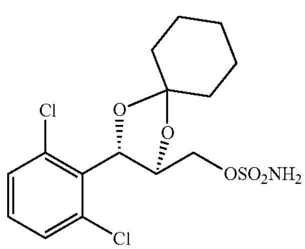 | ((2S,3S)-3-(2,6-dichlorophenyl)-1,4-dioxaspiro[4,5]decan-2-yl)methyl sulfamate | Preparation example 161 | $^D$δ 1.33~1.72 (m, 10H)-3.96~4.21 (m, 2H), 4.42 (q, J = 7.0 Hz, 1H), 4.88 (s, 2H), 5.17 (d, J = 7.0 Hz, 1H), 7.45~7.58 (m, 3H) |
| 61 | 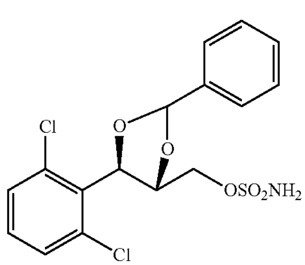 | ((4R,5R)-5-(2,6-dichlorophenyl)-2-phenyl-1,3-dioxolan-4-yl)methyl sulfamate | Preparation example 163 | $^D$δ 2.0 (s, 2H), 3.96~4.21 (m, 2H), 4.42 (dd, J = 7.0, 7.0 Hz, 1H), 5.17 (d, J = 7.0 Hz, 1H), 5.79 (s, 1H), 7.36~7.38 (m, 5H), 7.57~7.58 (m, 3H) |

TABLE 3-continued

Characteriztation of the examples of sulfamate compounds

| Example No. | Structure | Name | Starting material | $^1$H NMR (400 MHz) |
|---|---|---|---|---|
| 62 | 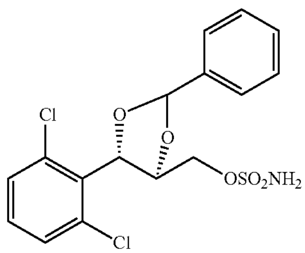 | ((4S,5S)-5-(2,6-dichlorophenyl)-2-phenyl-1,3-dioxolan-4-yl)methyl sulfamate | Preparation example 165 | $^D$δ 2.0 (s, 2H), 3.96~4.21 (m, 2H), 4.42 (dd, J = 7.0, 7.0 Hz, 1H), 5.17 (d, J = 7.0 Hz, 1H), 5.79 (s, 1H), 7.36~7.38 (m, 5H), 7.57~7.58 (m, 3H) |
| 63 | 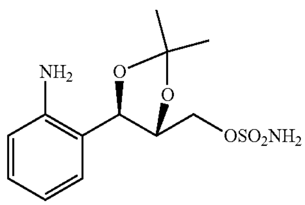 | ((4R,5R)-5-(2-aminophenyl)-2,2-dimethyl-1,3-dioxolan-4-yl)methyl sulfamate | Preparation example 47 | $^D$δ 1.27 (s, 6H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.73~7.13 (m, 4H) |
| 64 | 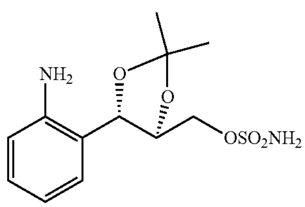 | ((4S,5S)-5-(2-aminophenyl)-2,2-dimethyl-1,3-dioxolan-4-yl)methyl sulfamate | Preparation example 51 | $^D$δ 1.27 (s, 6H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.73~7.13 (m, 4H) |
| 67 | 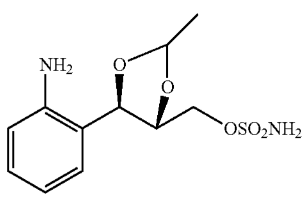 | ((4R,5R)-5-(2-aminophenyl)-2-methyl-1,3-dioxolan-4-yl)methyl sulfamate | Preparation example 206 | $^D$δ1.40 (d, J = 6.8 Hz, 3H), 2.0 (s, 2H), 3.96~4.21 (m, 2H), 4.42 (q, J = 7.0 Hz, 1H), 5.07 (q, J = 7.0 Hz. 1H), 5.17 (d, J = 7.0 Hz, 1H), 6.27 (s, 2H), 6.73~7.13 (m, 4H) |
| 68 | 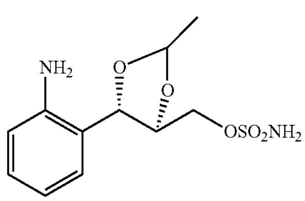 | ((4S,5S)-5-(2-aminophenyl)-2-methyl-1,3-dioxolan-4-yl)methyl sulfamate | Preparation example 207 | $^D$δ1.40 (d, J = 6.8 Hz, 3H), 2.0 (s, 2H), 3.96~4.21 (m, 2H), 4.42 (q, J = 7.0 Hz, 1H), 5.07 (q, J = 7.0 Hz. 1H), 5.17 (d, J = 7.0 Hz, 1H), 6.27 (s, 2H), 6.73~7.13 (m, 4H) |
| 69 | 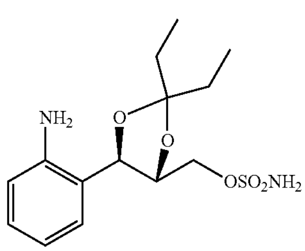 | ((4R,5R)-5-(2-aminophenyl)-2,2-diethyl-1,3-dioxolan-4-yl)methyl sulfamate | Preparation example 208 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.71~7.14 (m, 4H) |

TABLE 3-continued

Characteriztation of the examples of sulfamate compounds

| Example No. | Structure | Name | Starting material | $^1$H NMR (400 MHz) |
|---|---|---|---|---|
| 70 | 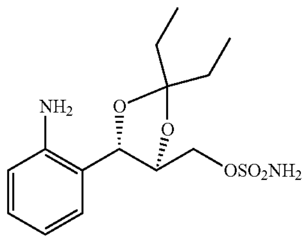 | ((4S,5S)-5-(2-aminophenyl)-2,2-diethyl-1,3-dioxolan-4-yl)methyl sulfamate | Preparation example 209 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.71~7.14 (m, 4H) |
| 71 | 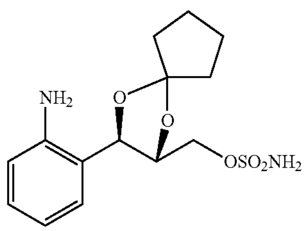 | ((2R,3R)-3-(2-aminophenyl)-1,4-dioxaspiro[4,4]nonan-2-yl)methyl sulfamate | Preparation example 210 | $^D$δ 1.46~1.56 (m, 6H), 1.65~1.90 (m, 2H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.70~7.11 (m, 4H) |
| 72 | 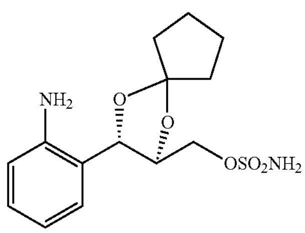 | ((2S,3S)-3-(2-aminophenyl)-1,4-dioxaspiro[4,4]nonan-2-yl)methyl sulfamate | Preparation example 211 | $^D$δ 1.46~1.56 (m, 6H), 1.65~1.90 (m, 2H), 2.0 (s, 2H), 3.96~4.21 (m, 2H), 4.42 (dt, J = 3.27, 7.02 Hz, 1H), 5.17 (d, J = 7.0 Hz, 1H), 6.27 (s, 2H), 6.70~7.11 (m, 4H) |
| 73 | 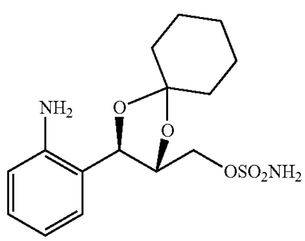 | ((2R,3R)-3-(2-aminophenyl)-1,4-dioxaspiro[4,5]decan-2-yl)methyl sulfamate | Preparation example 212 | $^D$δ 1.33~1.72 (m, 10H), 2.0 (s, 2H), 3.96~4.21 (m, 2H), 4.43 (dt, J = 3.27, 7.02 Hz, 1H), 5.17 (d, J = 7.0 Hz, 1H), 6.25 (s, 2H), 6.73~7.12 (m, 4H) |
| 74 | 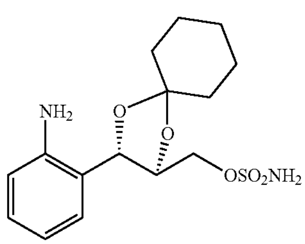 | ((2S,3S)-3-(2-aminophenyl)-1,4-dioxaspiro[4,5]decan-2-yl)methyl sulfamate | Preparation example 213 | $^D$δ 1.33~1.72 (m, 10H), 2.0 (s, 2H), 3.96~4.21 (m, 2H), 4.43 (dt, J = 3.27, 7.02 Hz, 1H), 5.17 (d, J = 7.0 Hz, 1H), 6.25 (s, 2H), 6.73~7.12 (m, 4H) |
| 75 | 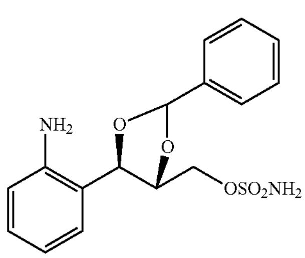 | ((4R,5R)-5-(2-aminophenyl)-2-phenyl-1,3-dioxolan-4-yl)methyl sulfamate | Preparation example 214 | $^D$δ 2.0 (s, 2H), 3.96~4.21 (m, 2H), 4.42 (dt, J = 3.27, 7.02 Hz, 1H), 5.17 (d, J = 7.0 Hz, 1H), 5.79 (s, 1H), 6.27 (s, 2H), 6.73~6.74 (m, 2H), 7.11~7.13 (m, 2H), 7.36~7.38 (m, 5H) |

TABLE 3-continued

Characteriztation of the examples of sulfamate compounds

| Example No. | Structure | Name | Starting material | $^1$H NMR (400 MHz) |
|---|---|---|---|---|
| 76 | 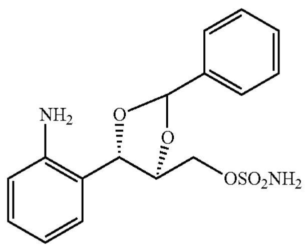 | ((4S,5S)-5-(2-aminophenyl)-2-phenyl-1,3-dioxolan-4-yl)methyl sulfamate | Preparation example 215 | $^D$δ 2.0 (s, 2H), 3.96~4.21 (m, 2H), 4.42 (dt, J = 3.27, 7.02 Hz, 1H), 5.17 (d, J = 7.0 Hz, 1H), 5.79 (s, 1H), 6.27 (s, 2H), 6.73~6.74 (m, 2H), 7.11~7.13 (m, 2H), 7.36~7.38 (m, 5H) |
| 77 | 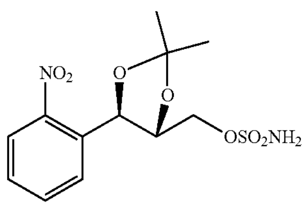 | ((4R,5R)-5-(2-nitrophenyl)-2,2-dimethyl-1,3-dioxolan-4-yl)methyl sulfamate | Preparation example 46 | $^D$δ 1.27 (s, 6H), 1.40 (s, 3H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 78 | 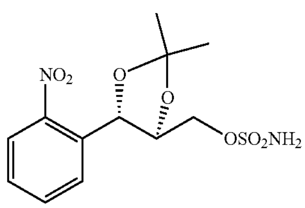 | ((4S,5S)-5-(2-nitrophenyl)-2,2-dimethyl-1,3-dioxolan-4-yl)methyl sulfamate | Preparation example 50 | $^D$δ 1.27 (s, 6H), 1.40 (s, 3H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 79 | 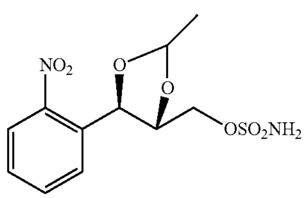 | ((4R,5R)-5-(2-nitrophenyl)-2-methyl-1,3-dioxolan-4-yl)methyl sulfamate | Preparation example 167 | $^D$δ 1.40 (d, J = 6.8 Hz, 3H), 2.0 (s, 2H), 3.96~4.21 (m, 2H), 4.42 (q, J = 7.0 Hz, 1H), 5.07 (q, J = 7.0 Hz, 1H), 5.17 (d, J = 7.0 Hz, 1H), 7.62~7.64 (m, 2H), 7.77~7.90 (m, 2H) |
| 80 | 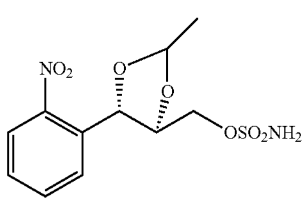 | ((4S,5S)-5-(2-nitrophenyl)-2-methyl-1,3-dioxolan-4-yl)methyl sulfamate | Preparation example 169 | $^D$δ 1.40 (d, J = 6.8 Hz, 3H), 2.0 (s, 2H), 3.96~4.21 (m, 2H), 4.42 (q, J = 7.0 Hz, 1H), 5.07 (q, J = 7.0 Hz, 1H), 5.17 (d, J = 7.0 Hz, 1H), 7.62~7.64 (m, 2H), 7.77~7.90 (m, 2H) |
| 81 | 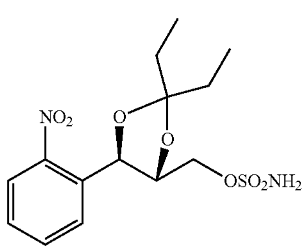 | ((4R,5R)-5-(2-nitrophenyl)-2,2-diethyl-1,3-dioxolan-4-yl)methyl sulfamate | Preparation example 171 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 82 | 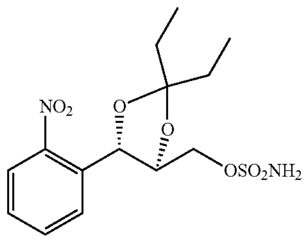 | ((4S,5S)-5-(2-nitrophenyl)-2,2-diethyl-1,3-dioxolan-4-yl)methyl sulfamate | Preparation example 173 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 83 | 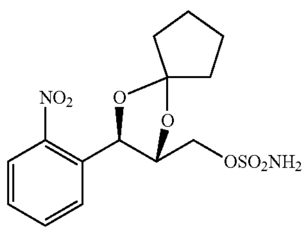 | ((2R,3R)-3-(2-nitrophenyl)-1,4-dioxaspiro[4,4]nonane-2-yl)methyl sulfamate | Preparation example 175 | $^D$δ 1.46~1.56 (m, 6H), 1.65~1.90 (m, 2H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 84 | 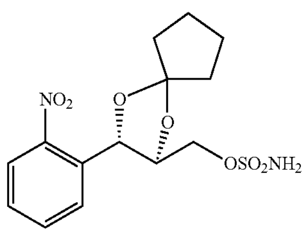 | ((2S,3S)-3-(2-nitrophenyl)-1,4-dioxaspiro[4,4]nonan-2-yl)methyl sulfamate | Preparation example 177 | $^D$δ 1.46~1.56 (m, 6H), 1.65~1.90 (m, 2H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 85 | 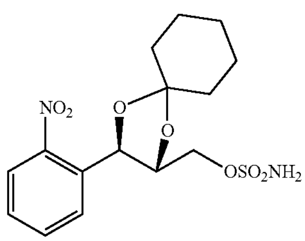 | ((2R,3R)-3-(2-nitrophenyl)-1,4-dioxaspiro[4,5]decan-2-yl)methyl sulfamate | Preparation example 179 | $^D$δ 1.33~1.72 (m, 10H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 86 | 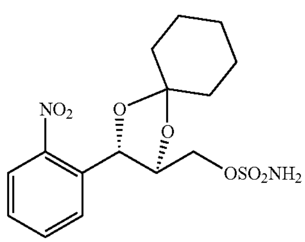 | ((2S,3S)-3-(2-nitrophenyl)-1,4-dioxaspiro[4,5]decan-2-yl)methyl sulfamate | Preparation example 181 | $^D$δ 1.33~1.72 (m, 10H), 2.0 (s, 2H), 3.96~4.21 (m, 2H), 4.42 (dt, J = 3.27, 7.02 Hz, 1H), 5.17 (d, J = 7.0 Hz, 1H), 7.62~7.64 (m, 2H), 7.77~7.90 (m, 2H) |
| 87 | 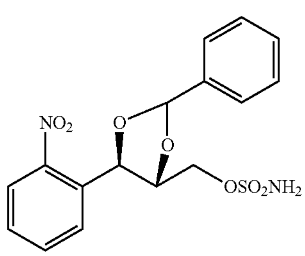 | ((4R,5R)-5-(2-nitrophenyl)-2-phenyl-1,3-dioxolan-4-yl)methyl sulfamate | Preparation example 183 | $^D$δ 2.0 (s, 2H), 3.96~4.21 (m, 2H), 4.42 (dt, J = 3.27, 7.02 Hz, 1H), 5.17 (d, J = 7.0 Hz, 1H), 5.79 (s, 1H), 6.73~6.74 (m, 2H), 7.11~7.13 (m, 2H), 7.36~7.38 (m, 5H) |

TABLE 3-continued

Characteriztation of the examples of sulfamate compounds

| Example No. | Structure | Name | Starting material | $^1$H NMR (400 MHz) |
|---|---|---|---|---|
| 88 | 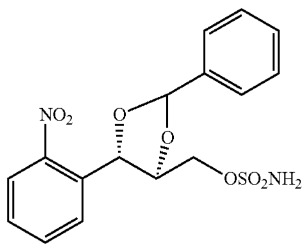 | ((4S,5S)-5-(2-nitrophenyl)-2-phenyl-1,3-dioxolan-4-yl)methyl sulfamate | Preparation example 185 | $^D$δ 2.0 (s, 2H), 3.96~4.21 (m, 2H), 4.42 (dt, J = 3.27, 7.02 Hz, 1H), 5.17 (d, J = 7.0 Hz, 1H), 5.79 (s, 1H), 6.73~6.74 (m, 2H), 7.11~7.13 (m, 2H), 7.36~7.38 (m, 5H) |
| 91 | 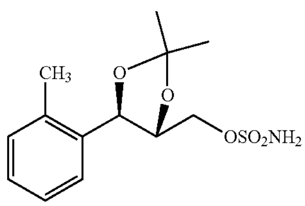 | ((4R,5R)-5-(2-methylphenyl)-2,2-dimethyl-1,3-dioxolan-4-yl)methyl sulfamate | Preparation example 56 | $^C$δ 1.38 (s, 3H), 1.40 (s, 3H), 2.24 (s, 3H), 4.29 (d, J = 3.3 Hz, 2H), 4.74 (dt, J = 3.3, 7.0 Hz, 1H), 5.06 (d, J = 7.0 Hz, 1H), 5.52 (s, 2H), 7.13~7.29 (m, 4H) |
| 92 | 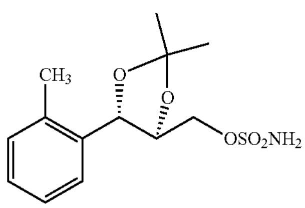 | ((4S,5S)-5-(2-methylphenyl)-2,2-dimethyl-1,3-dioxolan-4-yl)methyl sulfamate | Preparation example 59 | $^C$δ 1.38 (s, 3H), 1.40 (s, 3H), 2.24 (s, 3H), 4.29 (d, J = 3.3 Hz, 2H), 4.74 (dt, J = 3.3, 7.0 Hz, 1H), 5.06 (d, J = 7.0 Hz, 1H), 5.52 (s, 2H), 7.13~7.29 (m, 4H) |
| 93 | 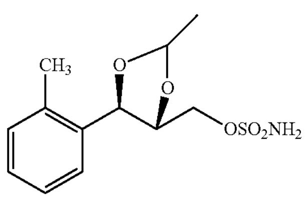 | ((4R,5R)-5-(2-methylphenyl)-2-methyl-1,3-dioxolan-4-yl)methyl sulfamate | Preparation example 187 | $^C$δ 1.40 (d, J = 6.4 Hz, 3H), 2.24 (s, 3H), 4.27 (dt, J = 3.3, 7.0 Hz, 1H), 4.70 (d, J = 3.3 Hz, 2H), 5.13 (d, J = 7.0 Hz, 1H), 5.40 (q, J = 6.4 Hz, 1H), 5.52 (s, 2H), 7.13~7.29 (m, 4H) |
| 94 | 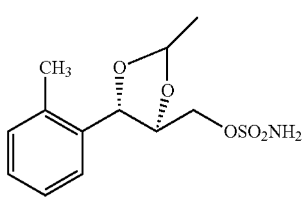 | ((4S,5S)-5-(2-methylphenyl)-2-methyl-1,3-dioxolan-4-yl)methyl sulfamate | Preparation example 189 | $^C$δ 1.40 (d, J = 6.4 Hz, 3H), 2.24 (s, 3H), 4.27 (dt, J = 3.3, 7.0 Hz, 1H), 4.70 (d, J = 3.3 Hz, 2H), 5.13 (d, J = 7.0 Hz, 1H), 5.40 (q, J = 6.4 Hz, 1H), 5.52 (s, 2H), 7.13~7.29 (m, 4H) |
| 95 | 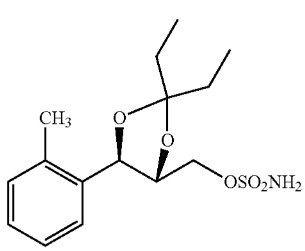 | ((4R,5R)-5-(2-methylphenyl)-2,2-diethyl-1,3-dioxolan-4-yl)methyl sulfamate | Preparation example 191 | $^C$δ 1.05 (t, J = 6.8 Hz, 3H), 1.15 (t, J = 6.8 Hz, 3H), 1.77~1.85 (m, 4H), 2.24 (s, 3H), 4.35 (d, J = 3.3 Hz, 2H), 4.75 (dt, J = 3.3, 7.0 Hz, 1H), 5.10 (d, J = 7.0 Hz, 1H), 5.52 (s, 2H), 7.18~7.30 (m, 4H) |

TABLE 3-continued

Characteriztation of the examples of sulfamate compounds

| Example No. | Structure | Name | Starting material | $^1$H NMR (400 MHz) |
|---|---|---|---|---|
| 96 | 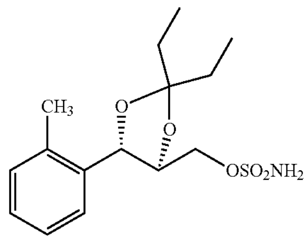 | ((4S,5S)-5-(2-methylphenyl)-2,2-diethyl-1,3-dioxolan-4-yl)methyl sulfamate | Preparation example 193 | $^c$δ 1.05 (t, J = 6.8 Hz, 3H), 1.15 (t, J = 6.8 Hz, 3H), 1.77~1.85 (m, 4H), 2.24 (s, 3H), 4.35 (d, J = 3.3 Hz, 2H), 4.75 (dt, J = 3.3, 7.0 Hz, 1H), 5.10 (d, J = 7.0 Hz, 1H), 5.52 (s, 2H), 7.18~7.30 (m, 4H) |
| 97 | 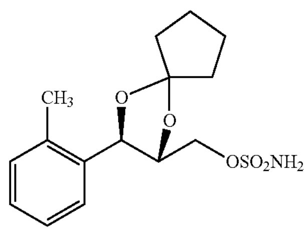 | ((2R,3R)-3-(2-methylphenyl)-1,4-dioxaspiro[4,4]nonane-2-yl)methyl sulfamate | Preparation example 195 | $^c$δ 1.60~1.70 (m, 4H), 1.74~1.99 (m, 4H), 2.24 (s, 3H), 4.75 (d, J = 3.3 Hz, 2H), 4.36 (dt, J = 3.3, 7.1 Hz, 1H), 5.13 (d, J = 7.0 Hz, 1H), 5.52 (s, 2H), 7.13~7.30 (m, 4H) |
| 98 | 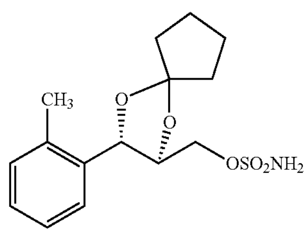 | ((2S,3S)-3-(2-methylphenyl)-1,4-dioxaspiro[4,4]nonane-2-yl)methyl sulfamate | Preparation example 197 | $^c$δ 1.60~1.70 (m, 4H), 1.74~1.99 (m, 4H), 2.24 (s, 3H), 4.75 (d, J = 3.3 Hz, 2H), 4.36 (dt, J = 3.3, 7.1 Hz, 1H), 5.13 (d, J = 7.0 Hz, 1H), 5.52 (s, 2H), 7.13~7.30 (m, 4H) |
| 99 | 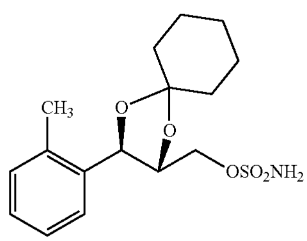 | ((2R,3R)-3-(2-methylphenyl)-1,4-dioxaspiro[4,5]decan-2-yl)methyl sulfamate | Preparation example 199 | $^c$δ 1.40~1.49 (m, 2H), 1.53~1.60 (m, 4H), 1.61~2.09 (m, 4H), 2.24 (s, 3H), 4.23 (d, J = 3.3 Hz, 2H), 4.75 (dt, J = 3.3, 7.0 Hz, 1H), 5.10 (d, J = 7.0 Hz, 1H), 5.62 (s, 2H), 7.13~7.30 (m, 4H) |
| 100 | 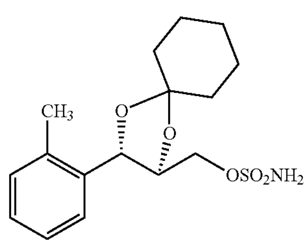 | ((2S,3S)-3-(2-methylphenyl)-1,4-dioxaspiro[4,5]decan-2-yl)methyl sulfamate | Preparation example 201 | $^c$δ 1.40~1.49 (m, 2H), 1.53~1.60 (m, 4H), 1.61~2.09 (m, 4H), 2.24 (s, 3H), 4.23 (d, J = 3.3 Hz, 2H), 4.75 (dt, J = 3.3, 7.0 Hz, 1H), 5.10 (d, J = 7.0 Hz, 1H), 5.62 (s, 2H), 7.13~7.30 (m, 4H) |
| 101 | 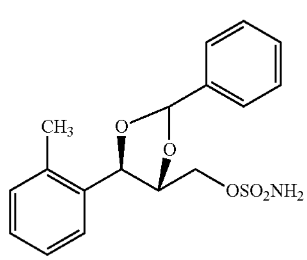 | ((4R,5R)-5-(2-methylphenyl)-2-phenyl-1,3-dioxolan-4-yl)methyl sulfamate | Preparation example 203 | $^c$δ 2.24 (s, 3H), 4.35 (d, J = 3.3 Hz, 2H), 4.64 (d, J = 5.7 Hz, 1H), 4.75 (dt, J = 3.3, 5.7 Hz, 1H), 5.59 (m, 1H), 5.78 (s, 2H), 7.13~7.29 (m, 4H), 7.33 (ddt, J = 1.5, 7.5, 7.7 Hz, 1H), 7.40~7.75 (m, 4H) |

TABLE 3-continued

Characteriztation of the examples of sulfamate compounds

| Example No. | Structure | Name | Starting material | $^1$H NMR (400 MHz) |
|---|---|---|---|---|
| 102 | 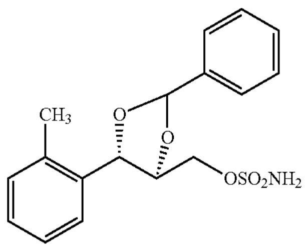 | ((4S,5S)-5-(2-methylphenyl)-2-phenyl-1,3-dioxolan-4-yl)methyl sulfamate | Preparation example 205 | $^C$δ 2.24 (s, 3H), 4.35 (d, J = 3.3 Hz, 2H), 4.64 (d, J = 5.7 Hz, 1H), 4.75 (dt, J = 3.3, 5.7 Hz, 1H), 5.59 (m, 1H), 5.78 (s, 2H), 7.13~7.29 (m, 4H), 7.33 (ddt, J = 1.5, 7.5, 7.7 Hz, 1H), 7.40~7.75 (m, 4H) |
| 105 | 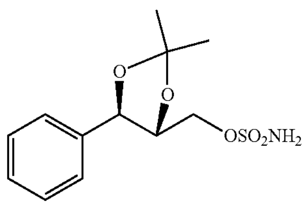 | ((4R,5R)-5-phenyl-2,2-dimethyl-1,3-dioxolan-4-yl)methyl sulfamate | Preparation example 219 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 106 | 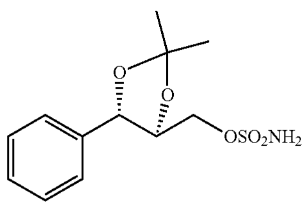 | ((4S,5S)-5-phenyl-2,2-dimethyl-1,3-dioxolan-4-yl)methyl sulfamate | Preparation example 222 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 107 | 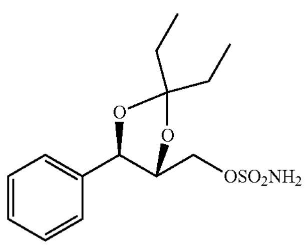 | ((4R,5R)-5-phenyl-2,2-dimethyl-1,3-dioxolan-4-yl)methyl sulfamate | Preparation example 224 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 108 | 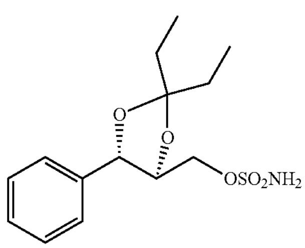 | ((4S,5S)-5-phenyl-2,2-dimethyl-1,3-dioxolan-4-yl)methyl sulfamate | Preparation example 226 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 109 | 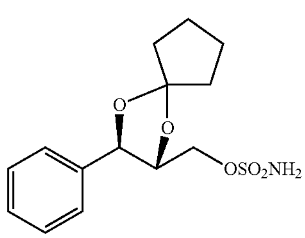 | ((2R,3R)-3-phenyl-1,4-dioxaspiro[4,4]nonan-2-yl)methyl sulfamate | Preparation example 228 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 110 | 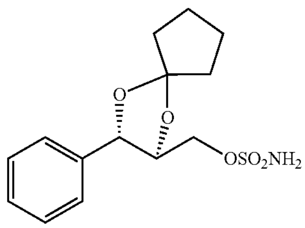 | ((2S,3S)-3-phenyl-1,4-dioxaspiro[4,4]nonan-2-yl)methyl sulfamate | Preparation example 230 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 111 | 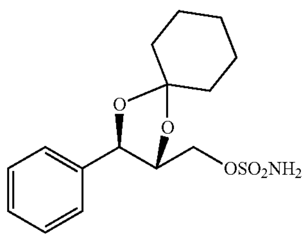 | ((2R,3R)-3-phenyl-1,4-dioxaspiro[4,5]decan-2-yl)methyl sulfamate | Preparation example 232 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 112 | 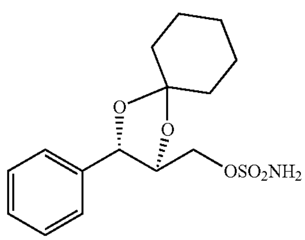 | ((2S,3S)-3-phenyl-1,4-dioxaspiro[4,5]decan-2-yl)methyl sulfamate | Preparation example 234 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 113 | 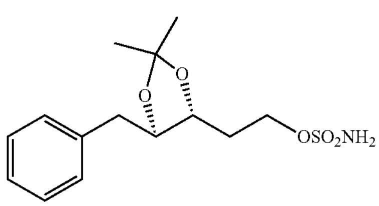 | 2-((4R,5R)-5-benzyl-2,2-dimethyl-1,3-dioxolan-4-yl)ethyl sulfamate | Preparation example 244 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 114 | 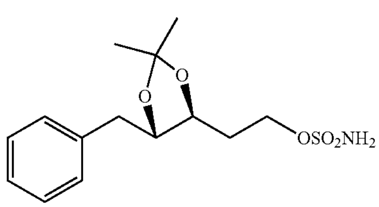 | 2-((4S,5S)-5-benzyl-2,2-dimethyl-1,3-dioxolan-4-yl)ethyl sulfamate | Preparation example 241 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 115 | 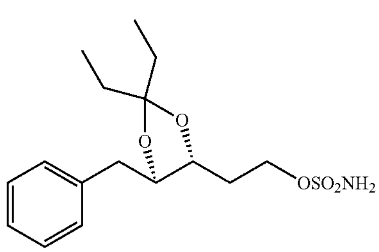 | 2-((4R,5R)-5-benzyl-2,2-diethyl-1,3-dioxolan-4-yl)ethyl sulfamate | Preparation example 250 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 116 | 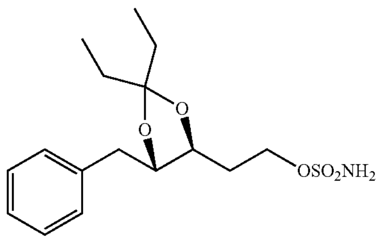 | 2-((4S,5S)-5-benzyl-2,2-dimethyl-1,3-dioxolan-4-yl)ethyl sulfamate | Preparation example 247 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 117 | 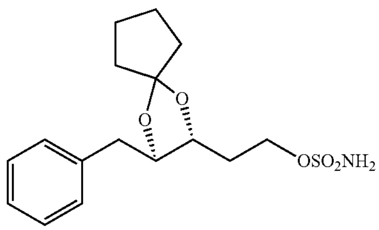 | 2-((2R,3R)-3-benzyl-1,4-dioxaspiro[4,4]nonan-2-yl)ethyl sulfamate | Preparation example 254 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 118 | 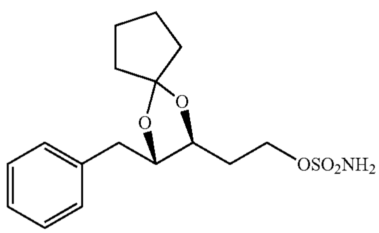 | 2-((2S,3S)-3-benzyl-1,4-dioxaspiro[4,4]nonan-2-yl)ethyl sulfamate | Preparation example 252 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 119 | 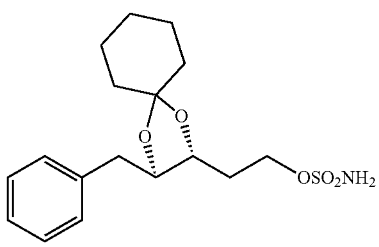 | 2-((2R,3R)-3-benzyl-1,4-dioxaspiro[4,5]decan-2-yl)ethyl sulfamate | Preparation example 258 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 120 | 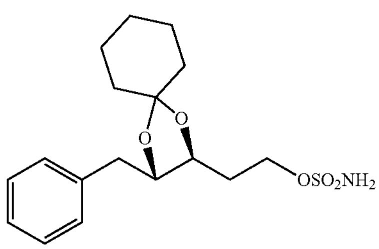 | 2-((2S,3S)-3-benzyl-1,4-dioxaspiro[4,5]decane-2-yl)ethyl sulfamate | Preparation example 256 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 121 | 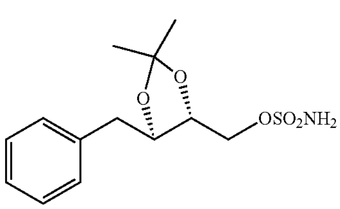 | ((4R,5R)-5-benzyl-2,2-dimethyl-1,3-dioxolan-4-yl)methyl sulfamate | Preparation example 271 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 122 | 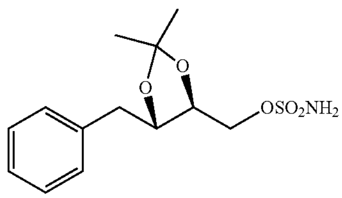 | ((4S,5S)-5-benzyl-2,2-dimethyl-1,3-dioxolan-4-yl)methyl sulfamate | Preparation example 262 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 123 | 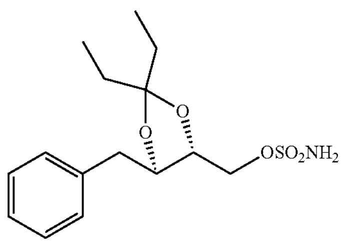 | ((4R,5R)-5-benzyl-2,2-diethyl-1,3-dioxolan-4-yl)methyl sulfamate | Preparation example 273 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 124 | 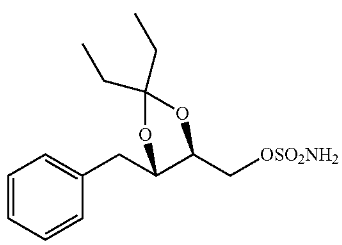 | ((4S,5S)-5-benzyl-2,2-diethyl-1,3-dioxolan-4-yl)methyl sulfamate | Preparation example 264 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 125 | 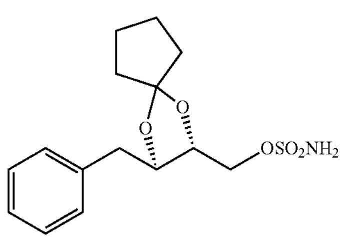 | ((2R,3R)-3-benzyl-1,4-dioxaspiro[4,4]nonan-2-yl)methyl sulfamate | Preparation example 275 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 126 | 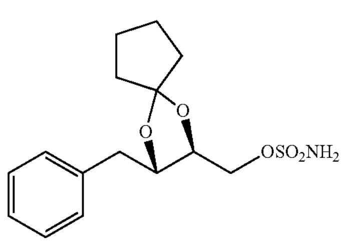 | ((2S,3S)-3-benzyl-1,4-dioxaspiro[4,4]nonan-2-yl)methyl sulfamate | Preparation example 266 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 127 | 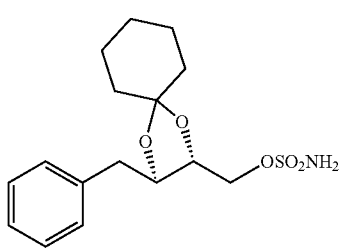 | ((2R,3R)-3-benzyl-1,4-dioxaspiro[4,5]decan-2-yl)methyl sulfamate | Preparation example 277 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | ¹H NMR (400 MHz) |
|---|---|---|---|---|
| 128 | 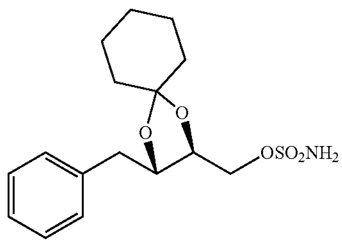 | ((2S,3S)-3-benzyl-1,4-dioxaspiro[4,5]decan-2-yl)methyl sulfamate | Preparation example 268 | [D]δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 129 | 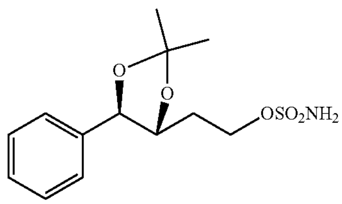 | 2-((4R,5R)-5-phenyl-2,2-dimethyl-1,3-dioxolan-4-yl)ethyl sulfamate | Preparation example 285 | [D]δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 130 | 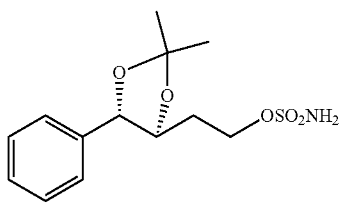 | 2-((4S,5S)-5-phenyl-2,2-dimethyl-1,3-dioxolan-4-yl)ethyl sulfamate | Preparation example 289 | [D]δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 131 | 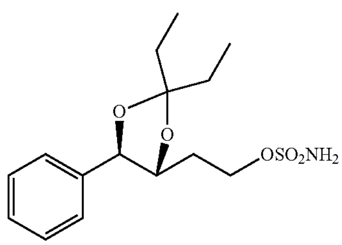 | 2-((4R,5R)-5-phenyl-2,2-diethyl-1,3-dioxolan-4-yl)ethyl sulfamate | Preparation example 291 | [C]δ 0.90 (t, J = 8.0 Hz, 6.H), 1.59 (q, J = 8.0 Hz, 4H), 2.0 (s, 2H), 3.96~4.21 (m, 2H), 4.42 (dt J = 3.3, 7.0 Hz, 1H), 5.17 (d, J = 7.0 Hz, 1H), 7.62~7.64 (m, 2H), 7.77~7.90 (m, 2H) |
| 132 | 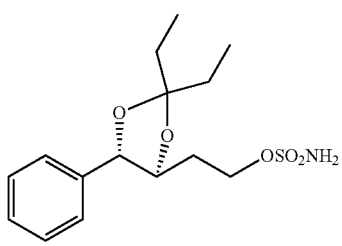 | 2-((4S,5S)-5-phenyl-2,2-diethyl-1,3-dioxolan-4-yl)ethyl sulfamate | Preparation example 297 | [C]δ 0.90 (t, J = 8.0 Hz, 6.H), 1.59 (q, J = 8.0 Hz, 4H), 2.0 (s, 2H), 3.96~4.21 (m, 2H), 4.42 (dt J = 3.3, 7.0 Hz, 1H), 5.17 (d, J = 7.0 Hz, 1H), 7.62~7.64 (m, 2H), 7.77~7.90 (m, 2H) |
| 133 | 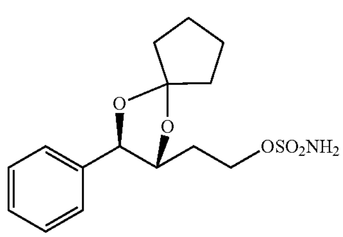 | 2-((2R,3R)-3-phenyl-1,4-dioxaspiro[4,4]nonan-2-yl)ethyl sulfamate | Preparation example 293 | [D]δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 134 | 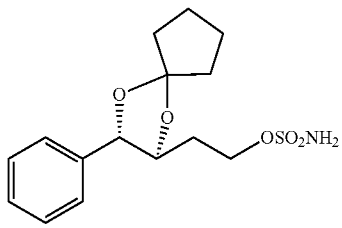 | 2-((2S,3S)-3-phenyl-1,4-dioxaspiro[4,4]nonan-2-yl)ethyl sulfamate | Preparation example 299 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 135 | 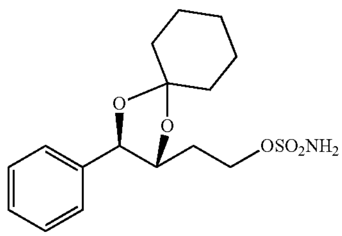 | 2-((2R,3R)-3-phenyl-1,4-dioxaspiro[4,5]decan-2-yl)ethyl sulfamate | Preparation example 295 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 136 | 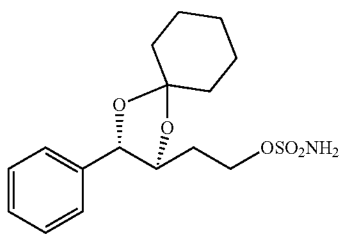 | 2-((2S,3S)-3-phenyl-1,4-dioxaspiro[4,5]decan-2-yl)ethyl sulfamate | Preparation example 301 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 137 | 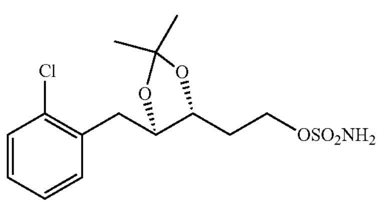 | 2-((4R,5R)-5-(2-chlorobenzyl)-2,2-dimethyl-1,3-dioxolan-4-yl)ethyl sulfamate | Preparation example 311 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 138 | 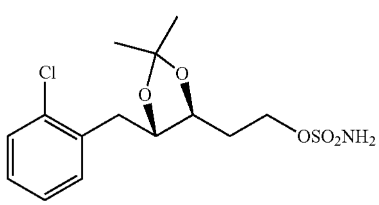 | 2-((4S,5S)-5-(2-chlorobenzyl)-2,2-dimethyl-1,3-dioxolan-4-yl)ethyl sulfamate | Preparation example 308 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 139 | 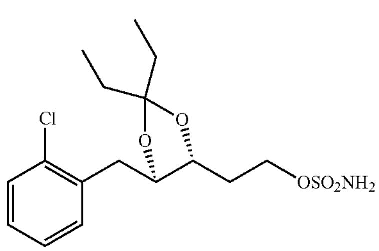 | 2-((4R,5R)-5-(2-chlorobenzyl)-2,2-diethyl-1,3-dioxolan-4-yl)ethyl sulfamate | Preparation example 317 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | ¹H NMR (400 MHz) |
|---|---|---|---|---|
| 140 | 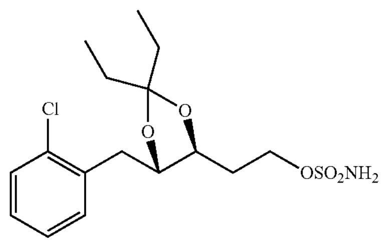 | 2-((4S,5S)-5-(2-chlorobenzyl)-2,2-diethyl-1,3-dioxolan-4-yl)ethyl sulfamate | Preparation example 314 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 141 | 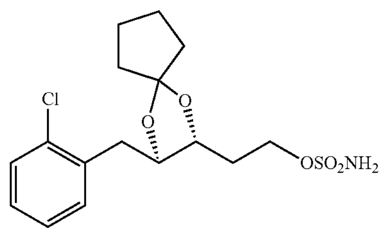 | 2-((2R,3R)-3-(2-chlorobenzyl)-1,4-dioxaspiro[4,4]nonan-2-yl)ethyl sulfamate | Preparation example 321 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 142 | 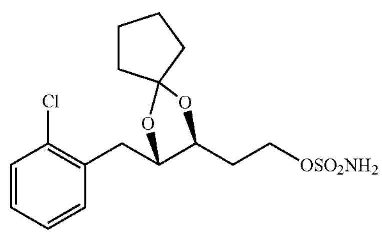 | 2-((2S,3S)-3-(2-chlorobenzyl)-1,4-dioxaspiro[4,4]nonan-2-yl)ethyl sulfamate | Preparation example 319 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 143 | 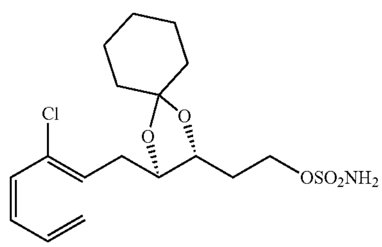 | 2-((2R,3R)-3-(2-chlorobenzyl)-1,4-dioxaspiro[4,5]decan-2-yl)ethyl sulfamate | Preparation example 325 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz,1H), 7.62~7.64 (m, 2H), 7.77~7.90 (m, 2H) |
| 144 | 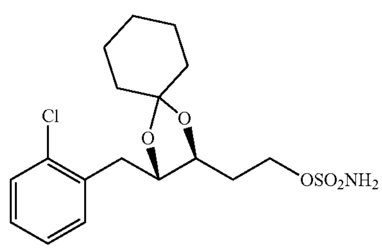 | 2-((2S,3S)-3-(2-chlorobenzyl)-1,4-dioxaspiro[4,5]decan-2-yl)ethyl sulfamate | Preparation example 323 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 145 | 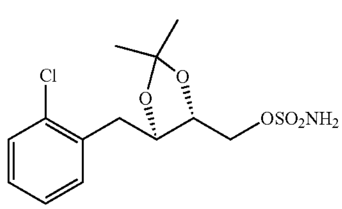 | ((4R,5R)-5-(2-chlorobenzyl)-2,2-dimethyl-1,3-dioxolan-4-yl)methyl sulfamate | Preparation example 338 | $^D$δ 1.27 (s, 6H), 1.40 (s, 3H), 2.0 (s,2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 146 | 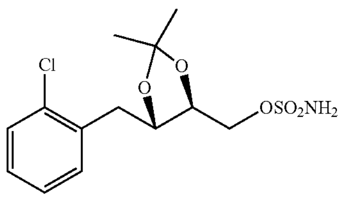 | ((4S,5S)-5-(2-chlorobenzyl)-2,2-dimethyl-1,3-dioxolan-4-yl)methyl sulfamate | Preparation example 329 | $^D$δ 1.27 (s, 6H), 1.40 (s, 3H), 2.0 (s,2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 147 | 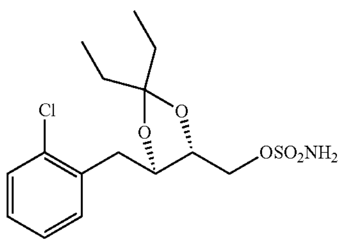 | ((4R,5R)-5-(2-chlorobenzyl)-2,2-diethyl-1,3-dioxolan-4-yl)methyl sulfamate | Preparation example 340 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 148 | 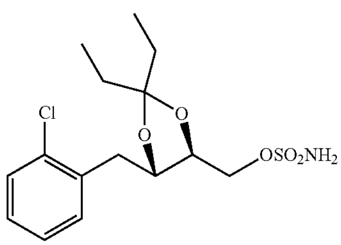 | ((4S,5S)-5-(2-chlorobenzyl)-2,2-diethyl-1,3-dioxolan-4-yl)methyl sulfamate | Preparation example 331 | $^C$δ 0.90 (t, J = 8.0 Hz, 6H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 149 | 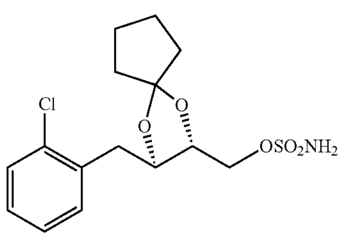 | ((2R,3R)-3-(2-chlorobenzyl)-1,4-dioxaspiro[4,4]nonan-2-yl)methyl sulfamate | Preparation example 342 | $^D$δ 1.46~1.56 (m, 6H), 1.65~1.90 (m, 2H), 2.0 (s, 2H), 3.96~4.21 (m, 2H), 4.42 (dt, 3.3, 7.0 Hz, 1H), 5.17 (d, J = 7.0 Hz, 1H), 7.62~7.64 (m, 2H), 7.77~7.90 (m, 2H) |
| 150 | 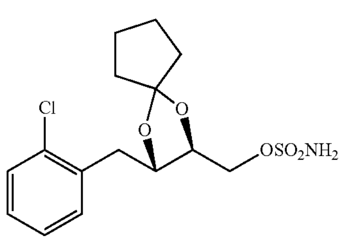 | ((2S,3S)-3-(2-chlorobenzyl)-1,4-dioxaspiro[4,4]nonan-2-yl)methyl sulfamate | Preparation example 333 | $^D$δ 1.46~1.56 (m, 6H), 1.65~1.90 (m, 2H), 2.0 (s, 2H), 3.96~4.21 (m, 2H), 4.42 (dt, 3.3, 7.0 Hz, 1H), 5.17 (d, J = 7.0 Hz, 1H), 7.62~7.64 (m, 2H), 7.77~7.90 (m, 2H) |
| 151 | 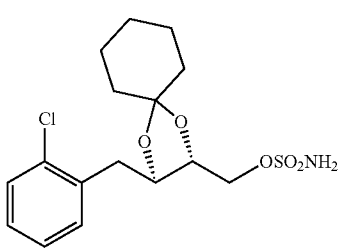 | ((2R,3R)-3-(2-chlorobenzyl)-1,4-dioxaspiro[4,5]decan-2-yl)methyl sulfamate | Preparation example 344 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 1.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 152 | 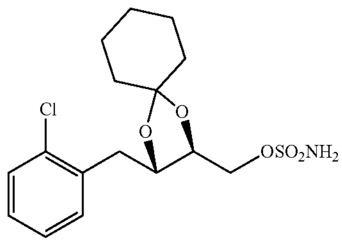 | ((2S,3S)-3-(2-chlorobenzyl)-1,4-dioxaspiro[4,5]decan-2-yl)methyl sulfamate | Preparation example 335 | $^D$δ 1.33~1.72 (m, 10H), 2.0 (s, 2H), 3.96~4.21 (m, 2H), 4.42 (dt, J = 3.3, 7.0 Hz, 1H), 5.17 (d, J = 1.0 Hz, 1H), 7.62~7.64 (m, 2H), 7.77~7.90 (m, 2H) |
| 153 | 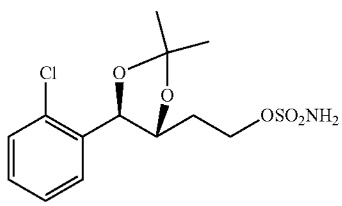 | 2-((4R,5R)-5-(2-chlorophenyl)-2,2-dimethyl-1,3-dioxolan-4-yl)ethyl sulfamate | Preparation example 352 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 154 | 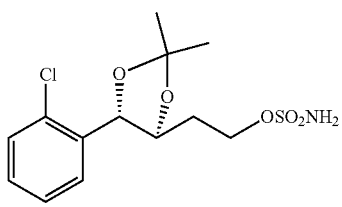 | 2-((4S,5S)-5-(2-chlorophenyl)-2,2-dimethyl-1,3-dioxolan-4-yl)ethyl sulfamate | Preparation example 356 | $^D$δ 1.27 (s, 6H), 1.40 (s, 3H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 155 | 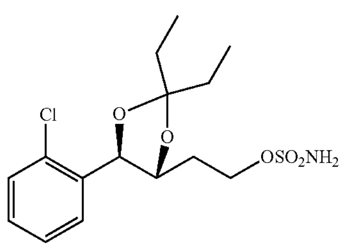 | 2-((4R,5R)-5-(2-chlorophenyl)-2,2-diethyl-1,3-dioxolan-4-yl)ethyl sulfamate | Preparation example 358 | $^C$δ 0.90 (t, J = 8.0 Hz, 6.H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 1.0 Hz, 1H), 7.62~7.64 (m, 2H), 7.77~7.90 (m, 2H) |
| 156 | 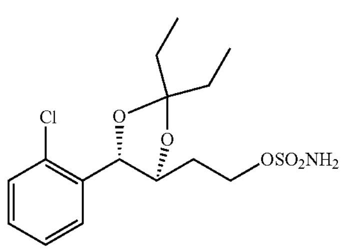 | 2-((4S,5S)-5-(2-chlorophenyl)-2,2-diethyl-1,3-dioxolan-4-yl)ethyl sulfamate | Preparation example 364 | $^C$δ 0.90 (t, J = 8.0 Hz, 6.H), 1.59 (q, J = 8.0 Hz, 4H), 2.0 (s, 2H), 3.96~4.21 (m, 2H), 4.42 (dt, J = 3.3, 7.0 Hz, 1H), 5.17 (d, J = 1.0 Hz, 1H), 7.62~7.64 (m, 2H), 7.77~7.90 (m, 2H) |
| 157 | 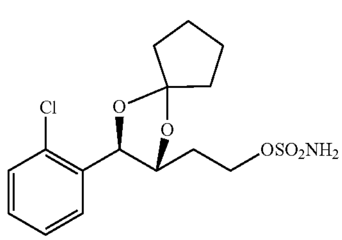 | 2-((2R,3R)-3-(2-chlorophenyl)-1,4-dioxaspiro[4,4]nonan-2-yl)ethyl sulfamate | Preparation example 360 | $^D$δ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, 7.0 Hz, 1H), 7.62~7.64 (m, 2H), 7.77~7.90 (m, 2H) |

TABLE 3-continued

Characteriztation of the examples of sulfamate compounds

| Example No. | Structure | Name | Starting material | $^1$H NMR (400 MHz) |
|---|---|---|---|---|
| 158 | 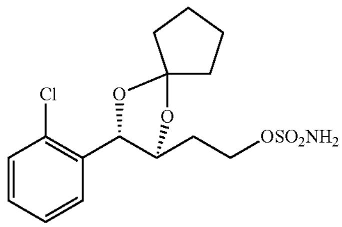 | 2-((2S,3S)-3-(2-chlorophenyl)-1,4-dioxaspiro[4,4]nonan-2-yl)ethyl sulfamate | Preparation example 366 | $^D\delta$ 1.46~1.56 (m, 6H), 1.65~1.90 (m, 2H), 2.0 (s, 2H), 3.96~4.21 (m, 2H), 4.42 (dt, J = 3.3, 7.0 Hz, 1H), 5.17 (d, 7.0 Hz, 1H), 7.62~7.64 (m, 2H), 7.77~7.90 (m, 2H) |
| 159 | 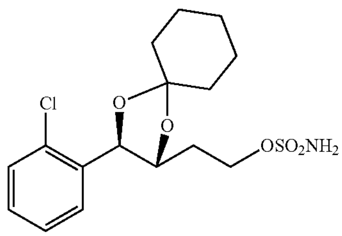 | 2-((2R,3R)-3-(2-chlorophenyl)-1,4-dioxaspiro[4,5]decan-2-yl)ethyl sulfamate | Preparation example 362 | $^D\delta$ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 160 | 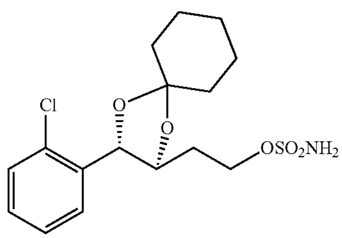 | 2-((2S,3S)-3-(2-chlorophenyl)-1,4-dioxaspiro[4,5]decan-2-yl)ethyl sulfamate | Preparation example 368 | $^D\delta$ 1.33~1.72 (m, 10H), 2.0 (s, 2H), 3.96~4.21 (m, 2H), 4.42 (dt, J = 3.3, 7.0 Hz, 1H), 5.17 (d, J = 7.0 Hz, 1H), 7.62~7.64 (m, 2H), 7.77~7.90 (m, 2H) |
| 161 | 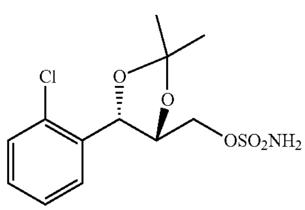 | ((4R,5S)-5-(2-chlorophenyl)-2,2-dimethyl-1,3-dioxolan-4-yl)methyl sulfamate | Preparation example 379 | $^C\delta$ 1.53 (s, 3H), 1.66 (s, 3H), 3.14~3.06 (m, 2H), 4.26 (d, J = 12.0 Hz, 2H), 4.83~4.78 (m, 1H), 5.63 (d, J = 6.8 Hz, 1H), 7.35~7.16 (m, 8H), 7.61 (dd, J = 1.6, 7.4 Hz, 1H) |
| 162 | 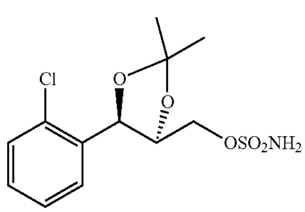 | ((4S,5R)-5-(2-chlorophenyl)-2,2-dimethyl-1,3-dioxolan-4-yl)methyl sulfamate | Preparation example 432 | $^C\delta$ 1.58 (s, 3H), 1.70 (s, 3H), 3.68~3.88 (m, 2H), 4.61 (s, 2H), 4.88~4.93 (m, 1H), 5.64 (d, J = 6.8 Hz, 1H), 7.29~7.66 (m, 4H) |
| 163 | 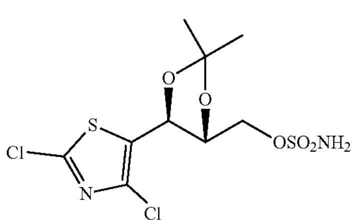 | ((4R,5S)-5-(2,4-dichlorothiazol-5-yl)-2,2-dimethyl-1,3-dioxolan-4-yl)methyl sulfamate | Preparation example 383 | $^D\delta$ 1.44 (s, 3H), 1.45 (s, 3H), 4.21~4.24 (m, 1H), 4.25~4.27 (m, 2H), 5.17 (d, J = 7.6 Hz, 1H), 7.64 (brs, 2H) |

TABLE 3-continued

Characteriztation of the examples of sulfamate compounds

| Example No. | Structure | Name | Starting material | $^1$H NMR (400 MHz) |
|---|---|---|---|---|
| 164 | 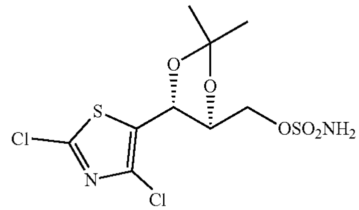 | ((4S,5R)-5-(2,4-dichlorothiazol-5-yl)-2,2-dimethyl-1,3-dioxolan-4-yl)methyl sulfamate | Preparation example 386 | $^D\delta$ 1.44 (s, 3H), 1.45 (s, 3H), 4.21~4.24 (m, 1H), 4.25~4.27 (m, 2H), 5.17 (d, J = 7.6 Hz, 1H), 7.64 (brs, 2H) |
| 165 | 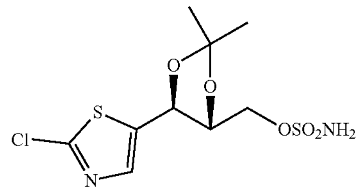 | ((4R,5S)-5-(2-chlorothiazol-5-yl)-2,2-dimethyl-1,3-dioxolan-4-yl)methyl-sulfamate | Preparation example 390 | $^D\delta$ 1.42 (s, 3H), 1,43 (s, 3H), 4.16~4.19 (m, 1H), 4.20~4.22 (m, 2H), 5.20 (d, J = 8.4 Hz, 1H), 7.65 (brs, 2H), 7.74 (s, 1H) |
| 166 | 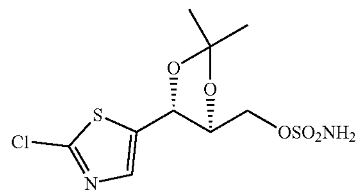 | ((4R,5S)-5-(2-chlorothiazol-5-yl)-2,2-dimethyl-1,3-dioxolan-4-yl)methyl-sulfamate | Preparation example 393 | $^D\delta$ 1.42 (s, 3H), 1,43 (s, 3H), 4.16~4.19 (m, 1H), 4.20~4.22 (m, 2H), 5.20 (d, J = 8.4 Hz, 1H), 7.65 (brs, 2H), 7.74 (s, 1H) |
| 167 | 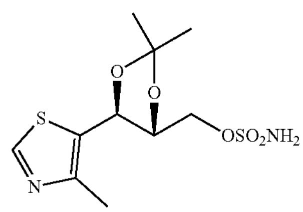 | ((4R,5S)-2,2-dimethyl-5-(4-methylthiazol-5-yl)-1,3-dioxolan-4-yl)methylsulfamate | Preparation example 397 | $^D\delta$ 1.43 (s, 3H), 1.47 (s, 3H), 2.39 (s, 3H), 4.06~4.10 (m, 1H), 4.13 (d, J = 4.0 Hz. 2H), 5.27 (d, J = 8.0 Hz, 1H), 7.62 (brs, 2H), 9.04 (s, 1H) |
| 168 | 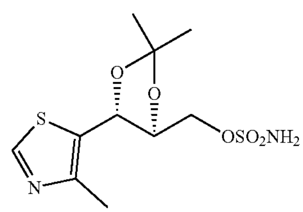 | ((4S,5R)-2,2-dimethyl-5-(4-methylthiazol-5-yl)-1,3-dioxolan-4-yl)methylsulfamate | Preparation example 400 | $^D\delta$ 1.42 (s, 3H), 1.47 (s, 3H), 2.39 (s, 3H), 4.06~4.11 (m, 1H), 4.13 (d, J = 4.0 Hz. 2H), 5.27 (d, J = 8.0 Hz, 1H), 7.62 (brs, 2H), 9.04 (s, 1H) |
| 169 | 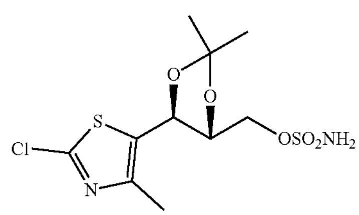 | ((4R,5S)-2,2-dimethyl-5-(2-chloro-4-methylthiazol-5-yl)-1,3-dioxolan-4-yl)methylsulfamate | Preparation example 401 | $^D\delta$ 1.43 (S, 3H), 1.44 (s, 3H), 2.33 (s, 3H), 4.11~4.25 (m, 1H), 4.15 (d, J = 4.4 Hz. 2H), 5.22 (d, J = 8.0 Hz, 1H), 7.62 (brs, 2H) |
| 170 | 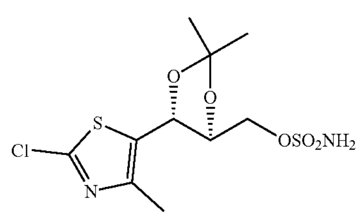 | ((4S,5R)-2,2-dimethyl-5-(2-chloro-4-methylthiazol-5-yl)-1,3-dioxolan-4-yl)methylsulfamate | Preparation example 402 | $^D\delta$ 1.43 (S, 3H), 1.44 (s, 3H), 2.33 (s, 3H), 4.11~4.25 (m, 1H), 4.15 (d, J = 4.4 Hz. 2H), 5.22 (d, J = 8.0 Hz, 1H), 7.62 (brs, 2H) |

TABLE 3-continued

Characteriztation of the examples of sulfamate compounds

| Example No. | Structure | Name | Starting material | $^1$H NMR (400 MHz) |
|---|---|---|---|---|
| 171 | 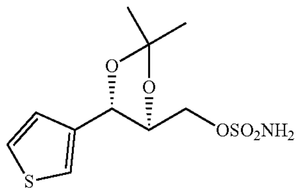 | ((4S,5S)-2,2-dimethyl-5-(thiophen-3-yl)-1,3-dioxolan-4-yl)methylsulfamate | Preparation example 406 | $^D$δ 1.41 (s, 3H), 1.45 (s, 3H), 4.05~4.15 (m, 2H), 4.54~4.71 (m, 1H), 4.94 (d, J = 7.6 Hz, 1H), 7.03 (d, J = 3.6 Hz, 1H), 7.14 (s, 1H), 7.22 (brs, 2H), 7.42 (d, J = 3.6 Hz, 1H) |
| 172 | 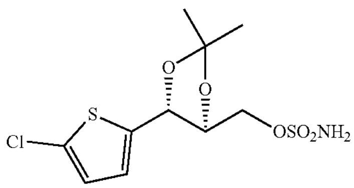 | ((4S,5R)-2,2-dimethyl-5-(5-chlorothiphen-2-yl)-1,3-dioxolan-4-yl)methylsulfamate | Preparation example 410 | $^D$δ 1.51 (s, 3H), 1.54 (s, 3H), 4.11~4.14 (m, 2H), 4.16~4.18 (m, 1H), 5.10 (d, J = 7.6 Hz, 1H), 7.05 (dd, J = 3.6, 10.0 Hz, 2H), 7.63 (brs, 2H) |
| 173 | 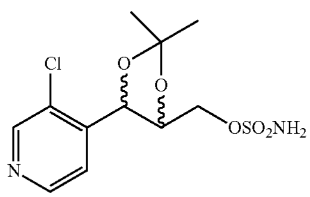 | (5-(3-chloropyridin-4-yl)-2,2-dimethyl-1,3-dioxolan-4-yl)methylsulfamate | Preparation example 415 | $^D$δ 1.39 (s, 3H), 1.48 (s, 3H), 4.16-4.21 (m, 2H), 4.27~4.22 (m, 1H), 5.23 (d, J = 8.0 Hz, 1H), 7.37 (brs, 2H), 7.62 (d, J = 4.0 Hz, 1H), 8.59 (d, J = 4.0 Hz, 1H), 8.66 (s, 1H) |
| 174 | 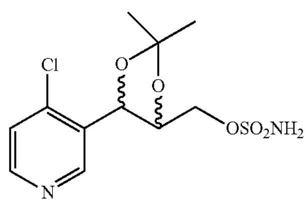 | (5-(4-chloropyridin-3-yl)-2,2-dimethyl-1,3-dioxolan-4-yl)methylsulfamate | Preparation example 420 | $^D$δ 1.47 (s, 3H), 1.54 (s, 3H), 4.23~4.30 (m, 2H), 4.40 (s, 1H), 5.25 (d, J = 8.0 Hz, 1H), 7.58 (brs, 2H), 7.59 (s, 1H), 8.53 (d, J = 5.2 Hz, 1H), 8.75 (s, 1H) |
| 175 | 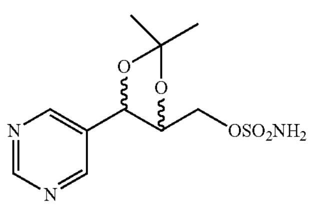 | 2,2-dimethyl-5-(pyrimidin-5-yl)-1,3-dioxolan-4-yl)methylsulfamate | Preparation example 424 | $^C$δ 1.32 (s, 3H), 1.35 (s, 3H), 3.86~3.90 (m, 1H), 4.06~4.14 (m, 2H), 4.82 (d, J = 8.0 Hz, 2H), 6.92 (brs, 2H), 8.63 (s, 2H), 8.95 (s, 1H) |
| 176 | 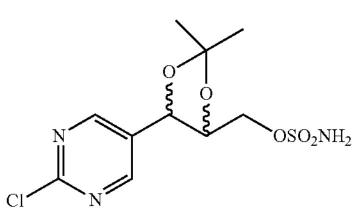 | (2,2-dimethyl-5-(2-chloropyrimidin-5-yl)-1,3-dioxolan-4-yl)methylsulfamate | Preparation example 428 | $^C$δ 1.29 (s, 3H), 1.33 (s, 3H), 3.86~3.90 (m, 1H), 4.10~4.18 (m, 2H), 4.62 (d, J = 8.0 Hz, 2H), 6.92 (brs, 2H), 8.67 (s, 2H) |

Example 65: Sodium ((((4R,5R)-5-(2-aminophenyl)-2,2-dimethyl-1,3-dioxolan-4-yl)methyl sulfonyl)amide

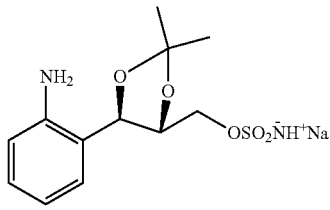

To stirred solution of ((4R,5R)-5-(2-aminophenyl)-2,2-dimethyl-1,3-dioxolan-4-yl)methyl sulfamate (Example 63, 5.5 g) in distilled water (55 mL) was added 1 N NaOH (23 mL) then heated. After 30 min, the resulting mixture cooled to room temperature and concentrated under reduced pressure. The crude product in EA (ethyl acetate, 16.5 mL) was slowly added to Ether (200 mL) at low temperature. The precipitate was filtered off, washed with Hexane, and dried under vacuum to obtain the title compound (4.7 g, 65~85%).

$^1$H NMR (400 MHz, DMSO-$d_6$) δ 1.42 (s, 3H), 1.46 (s, 3H), 3.79~3.81 (m, 2H), 3.99~4.00 (m, 1H), 4.94 (d, J=8.4 Hz, 1H), 6.59~7.16 (m, 4H).

Example 66: Sodium ((((4S,5S)-5-(2-aminophenyl)-2,2-dimethyl-1,3-dioxolan-4-yl)methyl sulfonyl)amide

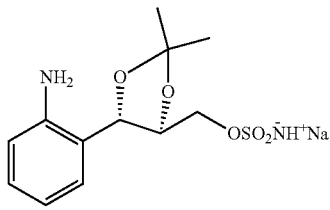

The substantially same method as described in example 65 was conducted, except that ((4R,5R)-5-(2-aminophenyl)-2,2-dimethyl-1,3-dioxolan-4-yl)methyl sulfamate (Example 64) was used instead of ((4R,5R)-5-(2-aminophenyl)-2,2-dimethyl-1,3-dioxolan-4-yl)methyl sulfamate (Example 63), to obtain the title compound (4.23 g, 65~85%).

$^1$H NMR (400 MHz, DMSO-$d_6$) δ 1.42 (s, 3H), 1.46 (s, 3H), 3.79~3.81 (m, 2H), 3.99~4.00 (m, 1H), 4.94 (d, J=8.4 Hz, 1H), 6.59~7.16 (m, 4H).

Example 89: ((4R,5R)-5-(2-nitrophenyl)-2-oxo-1,3-dioxolan-4-yl)methyl sulfamate

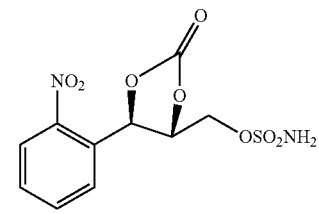

To a stirred solution of ((4R,5R)-5-(2-nitrophenyl)-2,2-dimethyl-1,3-dioxolan-4-yl)methyl sulfamate (Example 77, 5.2 g, 16 mmol) in EtOAc (50 mL) was added 3 N HCl (24.6 mL, 80 mmol) at room temperature. The mixture was stirred for 5 h. The resulting mixture was diluted with EtOAc, washed with sat. NaHCO$_3$, dried over MgSO$_4$, filtered, and concentrated under reduced pressure. The crude product stirred in THF (35 mL) was added CDI (2.9 g, 17.9 mmol) at room temperature. The mixture was stirred for 1 h. The resulting mixture was diluted with EtOAc, washed with water, dried over MgSO$_4$, filtered, and concentrated under reduced pressure. The crude product was purified by SiO$_2$ gel column chromatography to produce the title compound (2.6 g, 60~80%).

$^1$H NMR (400 MHz, CDCl$_3$) δ 2.0 (s, 2H), 4.08~4.33 (m, 2H), 4.72 (dt, J=3.3, 7.0 Hz, 1H), 5.47 (d, J=7.0 Hz, 1H), 7.62~7.64 (m, 2H), 7.77~7.90 (m, 2H).

Example 90: ((4S,5S)-5-(2-nitrophenyl)-2-oxo-1,3-dioxolan-4-yl)methyl sulfamate

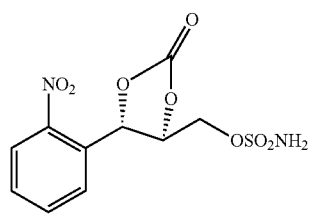

The substantially same method as described in example 89 was conducted, except that ((4S,5S)-5-(2-nitrophenyl)-2,2-dimethyl-1,3-dioxolan-4-yl)methyl sulfamate (Example 78) was used instead of ((4R,5R)-5-(2-nitrophenyl)-2,2-dimethyl-1,3-dioxolan-4-yl)methyl sulfamate (Example 77), to obtain the title compound (0.9 g, 50~80%).

$^1$H NMR (400 MHz, CDCl$_3$) δ 2.0 (s, 2H), 4.08~4.33 (m, 2H), 4.72 (dt, J=3.3, 7.0 Hz, 1H), 5.47 (d, J=7.0 Hz, 1H), 7.62~7.64 (m, 2H), 7.77~7.90 (m, 2H).

Example 103: ((4R,5R)-5-(2-methylaminophenyl)-2,2-dimethyl-1,3-dioxolan-4-yl)methyl methylsulfamate

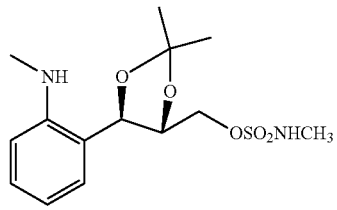

To a stirred solution of ((4R,5R)-5-(2-aminophenyl)-2,2-dimethyl-1,3-dioxolan-4-yl)methyl sulfamate (Example 63, 0.68 g, 2.25 mmol) and benzotriazole (0.27 g, 2.25 mmol) in EtOH (10 mL) was slowly added formaldehyde (10 wt % in H$_2$O, 0.62 mL, 2.25 mmol) and NaBH$_4$ (0.085 g, 2.25 mmol) at 0° C. The resulting mixture was diluted with EtOAc, washed with water, dried over MgSO$_4$, filtered, and concentrated under reduced pressure. The crude product was purified by SiO₂ gel column chromatography to obtain the title compound (0.3 g, 30~50%).

¹H NMR (400 MHz, CDCl₃) δ 1.40 (s, 6H), 2.62 (s, 3H), 2.96 (s, 3H), 4.25 (dt, J=3.3, 7.0 Hz, 1H), 4.75 (d, J=3.3 Hz, 2H), 4.84 (d, J=7.0 Hz, 1H), 6.99~7.20 (m, 4H).

Example 104: ((4S,5S)-5-(2-methylaminophenyl)-2,2-dimethyl-1,3-dioxolan-4-yl)methyl methylsulfamate

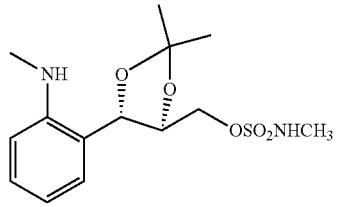

The substantially same method as described in example 103 was conducted, except that ((4S,5S)-5-(2-aminophenyl)-2,2-dimethyl-1,3-dioxolan-4-yl)methyl sulfamate (Example 64) was used instead of ((4R,5R)-5-(2-aminophenyl)-2,2-dimethyl-1,3-dioxolan-4-yl)methyl sulfamate (Example 63), to obtain the title compound (0.5 g, 50~80%).

¹H NMR (400 MHz, CDCl₃) δ 1.40 (s, 6H), 2.62 (s, 3H), 2.96 (s, 3H), 4.25 (dt, J=3.3, 7.0 Hz, 1H), 4.75 (d, J=3.3 Hz, 2H), 4.84 (d, J=7.0 Hz, 1H), 6.99~7.20 (m, 4H).

Example 177: sodium ((((4S,5S)-5-(2-chlorophenyl)-2,2-dimethyl-1,3-dioxolan-4-yl)methoxy)sulfonyl)amide

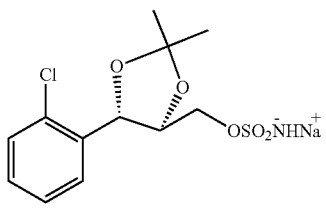

To a stirred solution of ((4S,5S)-5-(2-chlorophenyl)-2,2-dimethyl-1,3-dioxolan-4-yl)methyl sulfamate (Example 2, 5.0 g, 15.5 mmol) in a mixture of MTBE and IPA (50 mL, 3:1, v/v) was added 6 N NaOH aqueous solution (2.5 mL, 14.2 mmol) at room temperature then stirred for 1 hr at 0° C. The resulting mixture was removed solvent. The concentrated residue was added a mixture of H₂O and IPA (15 mL, 1:2, v/v) at room temperature then stirred for 30 min. The mixture was added MTBE (75 mL) then stirred for 1 hr at 0° C. Solid product was filtered and air-dried to give a title compound. (4.76 g, 70~90%).

Water content: 1.54%, MP: 1% 67.6~67.7° C. $2^{nd}$ 126.9° C.

¹H NMR (400 MHz, DMSO-d₆) δ 1.43 (s, 3H), 1.50 (s, 3H), 3.77 (dd, J=7.2, 11.2 Hz, 1H), 3.87 (dd, J=2.8, 11.2 Hz, 1H), 3.99~4.03 (m, 1H), 5.09 (d, J=8.4 Hz, 1H), 7.35~7.47 (m, 3H), 7.61 (dd, J=1.8, 7.4 Hz, 1H).

Biological Experimental Example 1: Open Field Test

This test is based on anxiety behaviors of rodents in the central area of an open field. When a mouse stayed in the central area for a longer period of time, it was deemed that there were more anti-stress, anti-depressant and anti-anxiety effects. ICR male mice (30 g to 35 g) were purchased from Orient Bio Korea Co. (Korea) and allowed to acclimatize for 1 week before being tested in a controlled animal facility (temperature 22±2° C., humidity 55±5%). When treatment began, the weight of the animals was 35±5 g. The test compound for oral administration was dissolved in 30% PEG400 and administered at a dose per body weight of 10 mL/kg 60 minutes before testing. The test compound for intraperitoneal administration was dissolved in 20% Tween80 and administered at a dose per body weight of 10 mL/kg 60 minutes before testing. The control group was provided with a corresponding vehicle. The open field was measured and analyzed by OPTO-VARIMEX instrument (Columbus Instruments, USA). The mouse was placed in the center of the open field, and its behavior was measured for 10 minutes. The open field was divided into 16 equal parts, and the middle area was established as the central area. Locomotor activity was measured using a spontaneous momentum (distance moved in cm), and measurement of anxiety behavior was obtained using the time spent in the central area as an index. In the open field experiment, when the time during which the mouse stayed in the central area was longer, it was evaluated that the symptoms of anxiety were alleviated, and when the time was shorter, the mouse was evaluated to have symptoms of anxiety (Reference; Prut L, Belzung C. 2003. The open field as a paradigm to measure the effects of drugs on anxiety-like behaviors: a review. *Eur J Pharmacol*. February 28; 463(1-3):3-33.).

As confirmed in Table 4, mice in the group treated with the compound of the present invention had an increased spontaneous momentum compared to those in the control group, and it can be seen that the time of staying in the central area was significantly increased, exhibiting excellent anti-stress, anti-depressant and anti-anxiety effects.

TABLE 4

Measurement results of anti-anxiety activity of compound in open-field test (mice)

| Compound (Example No.) | Administration route | Administration dose(mg/kg) | Spontaneous momentum(cm)/10 minutes | | Time of staying in central area (sec.)/10 minutes | |
|---|---|---|---|---|---|---|
| | | | Treatment | Control | Treatment | Control |
| 2 | Oral | 10 | 4997.3 ± 491.6 | 3751.8 ± 466.3 | 36.6 ± 4.6** | 19.0 ± 1.5 |
| | | 30 | 5033.5 ± 233.8 | | 44.7 ± 3.5** | |
| | Intraperitoneal | 10 | 5038.2 ± 455.9 | 3962.8 ± 521.2 | 31.6 ± 2.7 | 20.9 ± 4.1 |
| | | 30 | 4249.4 ± 402.4 | | 35.6 ± 3.1** | |

Biological Experimental Example 2: Light Dark Choice Test

The light-dark choice test is a model for anxiety-like behavior. This test is based on innate aversion of rodents to brightly lit areas and their voluntary exploration behaviors for light stress factors, that is, new environments and light. ICR male mice (30 g to 35 g) were purchased from Orient Bio Korea Co. (Korea) and allowed to acclimatize for 1 week before being tested in a controlled animal facility (temperature 22±2° C., humidity 55±5%). When treatment began, the weight of the animals was 35±5% g. The test compound for oral administration was dissolved in 30% PEG400 and administered at a dose per body weight of 10 mL/kg 60 minutes before testing. The test compound for intraperitoneal administration was dissolved in 20% Tween80 and administered at a dose per body weight of 10 mL/kg 60 minutes before testing. The control group was provided with a corresponding vehicle. An acryl box (45 cm×27 cm×27 cm) was composed of 2 chambers (white color: ⅔ of the box, black color: ⅓ of the box) connected by an opening (7.5 cm×7.5 cm) located at the bottom surface of the center of a partition wall. Each mouse was placed in the white part of the box and allowed to roam freely for a 5-minute session. At the end of the session, mice were returned to their habitat cage, and the experimental box was cleanly wiped with a 70% alcohol solution. All experiments were videotaped. After testing, all video recordings were analyzed. The obtained results are shown in Table 5 below (Reference; Bourin, M., Hascoet, M. 2003. The mouse light/dark box test. European Journal of Pharmacology, 463, 55-65. Bouwknecht, J A., Paylor, R. 2002. Behavioral and physiological mouse assays for anxiety: a survey in nine mouse strains. *Behavioural Brain Research*, 136, 489-501.).

As confirmed in Table 5, since the mice in the group treated with the compound of the present invention had a significant increase in the duration time in the white box compared to those in the control group, it can be seen that the anti-anxiety activity was increased. In addition, the anti-anxiety activity was increased as the dose was increased.

TABLE 5

Measurement results of anti-anxiety activity of compound in light-dark choice test (mouse)

| Compound (Example No.) | Administration route | Administration dose(mg/kg) | White box duration time (sec.)/5 minutes | |
|---|---|---|---|---|
| | | | Treatment | Control |
| 2 | Oral | 10 | 136.4 ± 4.2** | 98.5 ± 4.8 |
| | | 30 | 140.0 ± 12.3** | |
| | | 40 | 193.1 ± 8.7** | |
| | Intra-peritoneal | 10 | 189.0 ± 10.8** | 126.9 ± 6.4 |
| | | 30 | 208.1 ± 13.2*** | |
| | | 40 | 219.2 ± 13.3*** | |

Biological Experimental Example 3: Forced Swim Test

In order to determine the anti-depressant effect in rodents, the forced swim test was performed with rats and mice. The forced swim test causes an immobile state by forcing an animal to swim in a confined space. It reflects a state of despair giving up evading such a circumstance. ICR male mice (25 g to 30 g) and Wistar male rats (240 g to 260 g) were purchased from Samtako Bio Korea Co. (Korea) and allowed to acclimatize for 1 week before being tested in a controlled animal facility (temperature 22±2° C., humidity 55±5%). The test compound was dissolved in 20% Tween80 and administered orally 60 minutes before testing. The control group was provided with a corresponding vehicle. Water at 25±1° C. was filled up to 15 cm of a 19 cm circular cylinder for mice and was filled up to 30 cm of a 40 cm circular cylinder for rats to be performed such that the animal's tail did not touch the bottom of the cylinders. 15 minutes of forced swimming was performed a day before the experiment. On the day of the experiment, the animal was placed in the cylinder 60 minutes after the administration of the compound and was videotaped for 6 minutes. In the recorded videos, time during which the animal placed its head on the water and remained still without movement was measured based on the remaining 4 minutes excluding the first 2 minutes. It was evaluated that the lower the value of the immobile posture time, the greater the anti-depressant action (Reference; Porsolt R D, Le Pichon M. Jalfre M. 1997. Depression: a new animal model sensitive to antidepressant treatments. *Nature*. April 21; 266(5604):730-2.).

As shown in Table 6, it can be seen that in both of the mouse and rat models, the time to take an immobile posture was significantly decreased in the group treated with the compound of the present invention compared to the control group, and thus the anti-depressant activity was increased. In addition, as the administration dose was increased, the anti-depressant activity was increased.

TABLE 6

Measurement results of anti-depressant activity of compound in forced swim test

| Compound (Example No.) | Animal | Administration dose(mg/kg) | Immobile posture time (sec.)/4 minutes | |
|---|---|---|---|---|
| | | | Treatment | Control |
| 2 | Mouse | 10 | 105.7 ± 6.9** | 154.5 ± 5.1 |
| | | 20 | 80.5 ± 8.6** | |
| | | 40 | 61.2 ± 20.1** | |
| | Rat | 5 | 160.7 ± 3.8 | 173.1 ± 3.0 |
| | | 10 | 117.3 ± 12.2** | |
| | | 20 | 51.0 ± 11.6** | |

Statistical Analysis

The result was shown as the standard error of measurement (SEM) of mean value t mean value. Behavioral data were analyzed by one-way ANOVA. For statistical significance, a value of <0.05 was taken (*p<0.001, p=0.001~0.01, *p=0.01~0.05). Data management and statistics were performed using the Prism software of Windows version 4 (GraphPad Softward Co., San Diego, CA, USA).

Based on the results of Table 7, the ED50 value of the compound of Example 2 was calculated and shown in Table 7, and after 30 mg/kg and 60 mg/kg of the compounds of the other remaining examples were administered based on TD50 values to perform the forced swim tests, respectively, the administration doses with protected efficacy and protection % at the corresponding administration doses were shown in Table 7. That is, for the remaining compounds excluding the compound of Example 2, values were shown in the form of "administration dose (protection %)." As shown in Table 7, it was confirmed that all of the test compounds exhibited protective activity for anti-depressant efficacy.

TABLE 7

| Example No. | mFST | rFST |
|---|---|---|
| 2 | 23.51(po) | 13.31 (po) |
| 10 | 60 (19.0%, 1 hr) | |
| 40 | 30 (64.2%, 1 hr) | |
| 57 | 30 (61.6%, 1 hr) | |
| 72 | 60 (54.3%, 1 hr) | |
| 90 | 60 (60.4%, 1 hr) | |
| 92 | 30 (47.0%, 1 hr) | |
| 106 | 60 (24.5%, 1 hr) | |
| 110 | 60 (39.3%, 1 hr) | |
| 114 | 60 (36.4%, 1 hr) | |
| 118 | 60 (35.3%, 1 hr) | |
| 122 | 30 (46.9%, 1 hr) | |
| 126 | 60 (43.0%, 1 hr) | |
| 130 | 30 (57.5%, 1 hr) | |
| 134 | 30 (63.0%, 1 hr) | |
| 138 | 60 (60.2%, 1 hr) | |
| 142 | 60 (45.9%, 1 hr) | |
| 146 | 60 (65.1%, 1 hr) | |
| 150 | 60 (56.9%, 1 hr) | |
| 154 | 60 (38.9%, 1 hr) | |
| 158 | 30 (51.6%, 1 hr) | |
| 164 | 60 (44.9%, 1 hr) | |
| 166 | 60 (53.3%, 1 hr) | |

Biological Experimental Example 4: PPD (Chronic CORT Induced PPD Model)

In order to confirm the effect on postpartum depression in rats, the forced swim test was conducted after chronic administration of corticosterone, a depression-causing substance, to rats that gave birth. The forced swim test causes an immobile state by forcing an animal to swim in a confined space. It reflects a state of despair giving up evading such a circumstance. Rats on the 15$^{th}$ day of pregnancy were purchased from Koatech (Korea) and allowed to acclimatize for 1 week before being tested in a controlled animal facility (temperature 22±2° C., humidity 55±5%). Corticosterone, which is a substance that causes depression, was dissolved in sesame oil and 5% ethanol and subcutaneously administered once a day for 23 days from the day after the rat's labor. The forced swim test was conducted to confirm depression and efficacy. The test compound was dissolved in 20% Tween 80 and intraperitoneally administered 15 minutes before testing. The control group was provided with a corresponding vehicle. Water at 25±1° C. was filled up to 30 cm in a 40 cm circular cylinder for rats such that the tail of the animal did not touch the bottom of the cylinder. 15 minutes of forced swimming was performed a day before the experiment. On the day of the experiment, the animal was placed in the cylinder 15 minutes after the administration of the compound and was videotaped for 6 minutes. In the recorded videos, the time during which the animal placed its head on the water and remained still without movement was measured based on the remaining 4 minutes excluding the first 2 minutes. It was evaluated that the lower the value of the immobile posture time, the greater the anti-depressant action (Reference; S. Brummelte et al. Chronic corticosterone during pregnancy and affects maternal care, cell proliferation and depressive-like behavior in the dam. *Hormones and Behavior* 58 (2010) 769~779, Porsolt R D, Le Pichon M, Jalfre M. 1997. Depression: a new animal model sensitive to anti-depressant treatments. *Nature.* April 21; 266 (5604):730~2.).

As shown in Table 8, since the rats in the group treated with the compound of the present invention had a significant decrease in the time to take an immobile posture compared to those in the control group, it was confirmed that the anti-depressant activity was increased.

TABLE 8

Measurement results of anti-depressant activity of compound for postpartum depression in forced swim test

| Compound (Example No.) | Animal | Administration dose (mg/kg) | Immobile posture time (sec.)/4 minutes | | |
|---|---|---|---|---|---|
| | | | Treatment | Control | Normal |
| 2 | Rat | 30 | 5.07 ± 1.49(***) | 20.67 ± 3.54(†) | 12.81 ± 2.54 |

Statistical Analysis

The result was shown as the standard error of measurement (SEM) of mean value±mean value. Behavioral data were analyzed by one-way ANOVA. For statistical significance, a value of <0.05 was taken (*: control group vs treatment group, ***p<0.001, †: normal group vs control group, †p=0.01~0.05). Data management and statistics were performed using the Prism software of Windows version 4 (GraphPad Softward Co., San Diego, CA, USA).

The invention claimed is:
1. A method for treating a psychiatric disorder in a subject, comprising:
   selecting a subject having a psychiatric disorder; and
   administering to the subject a pharmaceutical composition comprising a sulfamate derivative compound of Chemical Formula I or a pharmaceutically acceptable salt thereof:

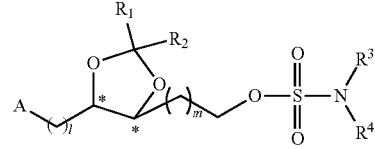

[Chemical Formula I]

wherein
   $R^1$ and $R^2$ are each independently selected from the group consisting of hydrogen, $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group;
   A is an aryl moiety or a heterocyclic moiety optionally substituted by one or more substituents selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen;
   $R^3$ and $R^4$ are each independently hydrogen or $C_1$-$C_3$ alkyl;
   l and m are each independently an integer of 0~4; and
   the psychiatric disorder is selected from the group consisting of anxiety disorder, mood disorder, somatoform disorder, dissociative disorder, psychotic disorder, personality disorder, sexual disorder, sexual identity disorder, substance-related disorder, eating disorder, sleep disorder, impulse control disorder and adjustment disorder.

2. The method according to claim 1, wherein A is the aryl moiety representing a $C_6$-$C_{10}$ aryl group.

3. The method according to claim 1, wherein A is the heterocyclic moiety representing a $C_3$-$C_{10}$ heterocyclic group.

4. The method according to claim 1, wherein A is phenyl optionally substituted by one or more substituents selected from the group consisting of hydrogen, halogen, $C_1$-$C_5$ alkyl, nitro, amine and $C_1$-$C_5$ alkyl amine or $C_3$-$C_{10}$ heterocyclic group optionally substituted by one or more substituents selected from the group consisting of hydrogen, halogen, $C_1$-$C_5$ alkyl and $C_6$-$C_{10}$ aryl.

5. The method according to claim 4, wherein A is selected from the group consisting of:

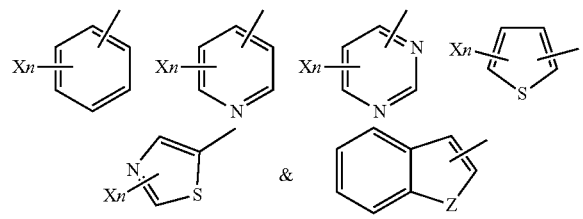

wherein each X is independently selected from the group consisting of halogen, nitro, amine and $C_1$-$C_5$ alkyl;
n is an integer of 0~5; and
Z is selected from the group consisting of S, O and NH.

6. The method according to claim 5, wherein n is an integer of 0~2.

7. The method according to claim 1, wherein $R^3$ and $R^4$ are each independently hydrogen or methyl.

8. The method according to claim 1, wherein 1 and m are each independently an integer of 0~2.

9. The method according to claim 1, wherein the compound is selected from the group consisting of:

(1) (5-(2-chlorophenyl)-2,2-dimethyl-1,3-dioxolan-4-yl) methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl) methyl sulfamate;
(4) (3-(2-chlorophenyl)-1,4-dioxaspiro[4,4]nonan-2-yl) methyl sulfamate;
(5) (3-(2-chlorophenyl)-1,4-dioxaspiro[4,5]decan-2-yl) methyl sulfamate;
(6) (5-(2-chlorophenyl)-2-phenyl-1,3-dioxolan-4-yl) methyl sulfamate;
(7) (5-(2-fluorophenyl)-2,2-dimethyl-1,3-dioxolan-4-yl) methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl) methyl sulfamate;
(10) (3-(2-fluorophenyl)-1,4-dioxaspiro[4,4]nonan-2-yl) methyl sulfamate;
(11) (3-(2-fluorophenyl)-1,4-dioxaspiro[4,5]decan-2-yl) methyl sulfamate;
(12) (5-(2-fluorophenyl)-2-phenyl-1,3-dioxolan-4-yl) methyl sulfamate;
(13) (5-(2-iodophenyl)-2,2-dimethyl-1,3-dioxolan-4-yl) methyl sulfamate;
(14) (5-(2-iodophenyl)-2-methyl-1,3-dioxolan-4-yl) methyl sulfamate;
(15) (5-(2-iodophenyl)-2,2-diethyl-1,3-dioxolan-4-yl) methyl sulfamate;
(16) (3-(2-iodophenyl)-1,4-dioxaspiro[4,4]nonan-2-yl) methyl sulfamate;
(17) (3-(2-iodophenyl)-1,4-dioxaspiro[4,5]decan-2-yl) methyl sulfamate;
(18) (5-(2-iodophenyl)-2-phenyl-1,3-dioxolan-4-yl) methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl) methyl sulfamate;
(21) (5-(2,4-dichlorophenyl)-2,2-diethyl-1,3-dioxolan-4-yl)methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl)methyl sulfamate;
(24) (5-(2,4-dichlorophenyl)-2-phenyl-1,3-dioxolan-4-yl) methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl) methyl sulfamate;
(27) (5-(2,6-dichlorophenyl)-2,2-diethyl-1,3-dioxolan-4-yl)methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl)methyl sulfamate;
(30) (5-(2,6-dichlorophenyl)-2-phenyl-1,3-dioxolan-4-yl) methyl sulfamate;
(31) (5-(2-aminophenyl)-2,2-dimethyl-1,3-dioxolan-4-yl) methyl sulfamate;
(32) (5-(2-aminophenyl)-2-methyl-1,3-dioxolan-4-yl) methyl sulfamate;
(33) (5-(2-aminophenyl)-2,2-diethyl-1,3-dioxolan-4-yl) methyl sulfamate;
(34) (3-(2-aminophenyl)-1,4-dioxaspiro[4,4]nonan-2-yl) methyl sulfamate;
(35) (3-(2-aminophenyl)-1,4-dioxaspiro[4,5]decan-2-yl) methyl sulfamate;
(36) (5-(2-aminophenyl)-2-phenyl-1,3-dioxolan-4-yl) methyl sulfamate;
(37) (5-(2-nitrophenyl)-2,2-dimethyl-1,3-dioxolan-4-yl) methyl sulfamate;
(38) (5-(2-nitrophenyl)-2-methyl-1,3-dioxolan-4-yl) methyl sulfamate;
(39) (5-(2-nitrophenyl)-2,2-diethyl-1,3-dioxolan-4-yl) methyl sulfamate;
(40) (3-(2-nitrophenyl)-1,4-dioxaspiro[4,4]nonan-2-yl) methyl sulfamate;
(41) (3-(2-nitrophenyl)-1,4-dioxaspiro[4,5]decan-2-yl) methyl sulfamate;
(42) (5-(2-nitrophenyl)-2-phenyl-1,3-dioxolan-4-yl) methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl)methyl sulfamate;
(45) (5-(2-methylphenyl)-2-methyl-1,3-dioxolan-4-yl) methyl sulfamate;
(46) (5-(2-methylphenyl)-2,2-diethyl-1,3-dioxolan-4-yl) methyl sulfamate;
(47) (3-(2-methylphenyl)-1,4-dioxaspiro[4,4]nonan-2-yl) methyl sulfamate;

(48) (3-(2-methylphenyl)-1,4-dioxaspiro[4,5]decan-2-yl)methyl sulfamate;
(49) (5-(2-methylphenyl)-2-phenyl-1,3-dioxolan-4-yl)methyl sulfamate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;
(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;
(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 2-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl)ethyl sulfamate;
(68) 2-(5-(2-chlorobenzyl)-2,2-diethyl-1,3-dioxolan-4-yl)ethyl sulfamate;
(69) 2-(3-(2-chlorobenzyl)-1,4-dioxaspiro[4,4]nonan-2-yl)ethyl sulfamate;
(70) 2-(3-(2-chlorobenzyl)-1,4-dioxaspiro[4,5]decan-2-yl)ethyl sulfamate;
(71) (5-(2-chlorobenzyl)-2,2-dimethyl-1,3-dioxolan-4-yl)methyl sulfamate;
(72) (5-(2-chlorobenzyl)-2,2-diethyl-1,3-dioxolan-4-yl)methyl sulfamate;
(73) (3-(2-chlorobenzyl)-1,4-dioxaspiro[4,4]nonan-2-yl)methyl sulfamate;
(74) (3-(2-chlorobenzyl)-1,4-dioxaspiro[4,5]decan-2-yl)methyl sulfamate;
(75) 2-(5-(2-chlorophenyl)-2,2-dimethyl-1,3-dioxolan-4-yl)ethyl sulfamate;
(76) 2-(5-(2-chlorophenyl)-2,2-diethyl-1,3-dioxolan-4-yl)ethyl sulfamate;
(77) 2-(3-(2-chlorophenyl)-1,4-dioxaspiro[4,4]nonan-2-yl)ethyl sulfamate;
(78) 2-(3-(2-chlorophenyl)-1,4-dioxaspiro[4,5]decan-2-yl)ethyl sulfamate;
(79) (5-(2,4-dichlorothiazol-5-yl)-2,2-dimethyl-1,3-dioxolan-4-yl)methyl sulfamate;
(80) (5-(2-chlorothiazol-5-yl)-2,2-dimethyl-1,3-dioxolan-4-yl)methylsulfamate;
(81) (2,2-di methyl-5-(4-methylthiazol-5-yl)-1,3-dioxolan-4-yl)methyl sulfamate;
(82) (2,2-dimethyl-5-(2-chloro-4-methylthiazol-5-yl)-1,3-dioxolan-4-yl)methylsulfamate;
(83) (2,2-dimethyl-5-(thiophen-3-yl)-1,3-dioxolan-4-yl)methyl sulfamate;
(84) (2,2-dimethyl-5-(5-chlorothiophen-2-yl)-1,3-dioxolan-4-yl)methylsulfamate;
(85) (5-(3-chloropyridin-4-yl)-2,2-dimethyl-1,3-dioxolan-4-yl)methylsulfamate;
(86) (5-(4-chloropyridin-3-yl)-2,2-dimethyl-1,3-dioxolan-4-yl)methylsulfamate;
(87) (2,2-dimethyl-5-(pyrimidin-5-yl)-1,3-dioxolan-4-yl)methylsulfamate; and
(88) (2,2-dimethyl-5-(2-chloropyrimidin-5-yl)-1,3-dioxolan-4-yl)methylsulfamate.

10. The method according to claim 1, wherein the compound is in the form of a racemate, an enantiomer, a diastereomer, a mixture of enantiomers, or a mixture of diastereomers.

11. The method according to claim 1, wherein the pharmaceutically acceptable salt is produced by reacting the compound with an inorganic acid, an organic acid, an amino acid, sulfonic acid, an alkali metal or ammonium ion.

12. The method according to claim 1, wherein:
the anxiety disorder is generalized anxiety disorder, phobia, panic disorder, obsessive compulsive disorder or post traumatic stress disorder (PTSD);
the mood disorder is depressive disorder or bipolar disorder;
the somatoform disorder is somatization disorder, conversion disorder, pain disorder, hypochondria or body dysmorphic disorder;
the dissociative disorder is dissociative amnesia or dissociative identity disorder;
the psychotic disorder is schizophrenia, schizoaffective disorder or delusional disorder;
the personality disorder is schizoid personality disorder, borderline personality disorder or obsessive-compulsive personality disorder;
the substance-related disorder is disorder of being addicted to addictive substances including alcohol, tobacco or drugs;
the eating disorder is anorexia nervosa or bulimia nervosa;
the sleep disorder is sleep disturbance or dyssomnia; and
the impulse-control disorder is intermittent explosive disorder, gambling disorder, arsonism or trichotillomania.

13. The method according to claim 12, wherein the depressive disorder is major depressive disorder, dysthymic disorder, persistent depressive disorder, premenstrual dysphoric disorder or postpartum depression.

* * * * *